US012617771B2

(12) United States Patent
Liu et al.

(10) Patent No.: US 12,617,771 B2
(45) Date of Patent: May 5, 2026

(54) DIPHENYLPYRAZOLE COMPOUND, AND PREPARATION METHOD THEREFOR AND APPLICATION THEREOF

(71) Applicant: NORTHWEST A&F UNIVERSITY, Yangling (CN)

(72) Inventors: Jiyuan Liu, Yangling (CN); Yalin Zhang, Yangling (CN)

(73) Assignee: NORTHWEST A&F UNIVERSITY, Yangling (CN)

( * ) Notice: Subject to any disclaimer, the term of this patent is extended or adjusted under 35 U.S.C. 154(b) by 397 days.

(21) Appl. No.: 18/259,861

(22) PCT Filed: Jul. 12, 2021

(86) PCT No.: PCT/CN2021/105643
§ 371 (c)(1),
(2) Date: Jun. 29, 2023

(87) PCT Pub. No.: WO2022/147993
PCT Pub. Date: Jul. 14, 2022

(65) Prior Publication Data
US 2024/0083871 A1 Mar. 14, 2024

(30) Foreign Application Priority Data
Jan. 5, 2021 (CN) ......................... 202110005578.6
Jul. 6, 2021 (CN) ......................... 202110760647.4

(51) Int. Cl.

| | |
|---|---|
| ***A01N 43/56*** | (2006.01) |
| ***A01N 43/78*** | (2006.01) |
| ***A01P 7/04*** | (2006.01) |
| ***C07D 231/10*** | (2006.01) |
| ***C07D 401/12*** | (2006.01) |
| ***C07D 403/12*** | (2006.01) |
| ***C07D 405/12*** | (2006.01) |
| ***C07D 417/12*** | (2006.01) |

(52) U.S. Cl.
CPC ........... *C07D 401/12* (2013.01); *A01N 43/56* (2013.01); *A01N 43/78* (2013.01); *A01P 7/04* (2021.08); *C07D 231/10* (2013.01); *C07D 403/12* (2013.01); *C07D 405/12* (2013.01); *C07D 417/12* (2013.01)

(58) Field of Classification Search
CPC .. C07D 401/12; C07D 231/10; C07D 403/12; C07D 405/12; C07D 417/12; C07D 231/14; A01N 43/56; A01N 43/78; A01N 43/58; A01P 7/04
See application file for complete search history.

(56) References Cited

U.S. PATENT DOCUMENTS

| | | | |
|---|---|---|---|
| 9,765,052 | B2 | 9/2017 | Kaiser et al. |
| 2016/0031863 | A1 | 2/2016 | Dominguez et al. |

FOREIGN PATENT DOCUMENTS

| | | | | |
|---|---|---|---|---|
| CN | 1654456 A | | 8/2005 | |
| CN | 1654457 A | | 8/2005 | |
| CN | 103483313 A | | 1/2014 | |
| CN | 105968092 A | | 9/2016 | |
| WO | WO2017087218 | * | 5/2017 | ........... C07D 405/12 |

OTHER PUBLICATIONS

Pubchem (SID 370676293 entry, Available date May 25, 2018).*
International Search Report issued in International Application No. PCT/CN2021/105643; mailed Oct. 12, 2021; 7 pgs.
First Office Action issued in Chinese Application No. 202110760647.4; mailed May 23, 2023; 8 pgs.
STN Registry; CAS RN 875156-62-0, 1H-Pyrazole-5-carboxylic acid, 1,3-diphenyl-, 2-benzoylhydrazide (CA Index Name); entered Feb. 24, 2006; 29 pgs.
Zhou, Yunyun et al.; Synthesis and insecticidal activity study of novel anthranilic diamides analogs containing a diacylhydrazine bridge as effective Ca 2+ modulators; Chemical Biology & Drug Design, 2018; vol. 92, No. 5, pp. 1914-1919.
STN Registry; CAS RN 1240813-76-6; 1H-Pyrazole-5-carboxylic acid, 1,3-diphenyl-, 2-[3-[(dimethylamino)sulfonyl]benzoyl]hydrazide (Ca Index Name); entered Sep. 14, 2010; 22 pgs.
STN Registry; CAS RN 2636891-44-4, 4-Pyridinecarboxylic acid, 1,2-dihydro-2-oxo-, 2-[(1,3-diphenyl-1H-pyrazol-5-yl) carbonyl]hydrazide (CA Index Name); entered Apr. 23, 2021; 1 pg.
Hearing Notice issued in Indian Patent Application No. 202317046741; mailed Nov. 17, 2025; 4 pages.

* cited by examiner

*Primary Examiner* — Robert H Havlin
(74) *Attorney, Agent, or Firm* — HAUPTMAN HAM, LLP

(57) ABSTRACT

Provided is a diphenylpyrazole-based compound of following formula (I), or its pesticidally acceptable salts, which is a novel inhibitor targeting pest GSTs, has broad inhibitory activities against GSTs in various pests, and can effectively delay the metabolism of insecticides by GSTs in pests, thereby reducing the metabolic resistance of pests to insecticides, and is suitable for use as a synergist for insecticides.

Formula (I)

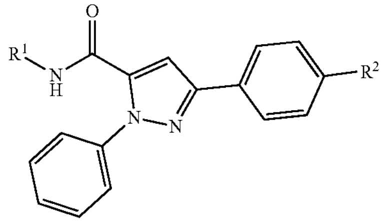

20 Claims, 24 Drawing Sheets

DIPHENYLPYRAZOLE COMPOUND, AND PREPARATION METHOD THEREFOR AND APPLICATION THEREOF

RELATED APPLICATIONS

The present application is a U.S. National Phase of International Application Number PCT/CN2021/105643 filed Jul. 12, 2021, and claims priority to Chinese Application Number 202110005578.6, filed Jan. 5, 2021, and Chinese Application Number 202110760647.4 filed Jul. 6, 2021.

TECHNICAL FIELD

The present invention relates to the technical field of insecticides, in particular to diphenylpyrazole-based compounds, the preparation method therefor and use thereof.

BACKGROUND ART

Insecticides have long been the primary means of agricultural pest control. Among many insecticides, the ryanodine receptor modulator represented by chlorantraniliprole and the voltage-dependent sodium ion channel blocker represented by indoxacarb have novel structure, unique mechanism of action, quick effect, wide insecticidal spectrum, and environmental friendliness. Thus they have received widespread attention and become a popular variety of insecticides. Chlorantraniliprole belongs to the diamide-based insecticides, and indoxacarb belongs to the oxadiazine-based insecticides. Both types of insecticides can control most pests with chewing mouthparts, particularly, they have good control effects on Pyralidae (*Cnaphalocrocis medinalis, Pyrausta nubilalis, Maruca vitrata Fabricius*, etc.), Carposinidae (*Carposina sasakii*, etc.), Noctuidae (*Spodoptera frugiperda, Helicoverpa armigera, Spodoptera litura*, etc.), Tortricidae (*Cydia pomonella, Grapholita molesta*, etc.), Gelechiidae (*Pectinophora gossypiella*, etc.), Plutellidae (*Plutella xylostella* etc.), Pieridae (*Pieris rapae*, etc.), Gracilariidae (*Lithocolletis ringoniella Mats*., etc.), etc. of Lepidoptera, and they also have high activity against Coleoptera (*Leptinotarsa decemlineata*, etc.), Diptera (*Liriomyza sativae Blanchard*, etc.), Isoptera (Termite) pests.

The market for diamide-based and oxadiazine-based insecticides has grown rapidly in recent years, and still has a large potential for future growth. The most widely used of these two classes of insecticides are chlorantraniliprole and indoxacarb. In 2019, chlorantraniliprole took the leading position in the global insecticide market, with global sales of US$1.581 billion; indoxacarb's also reached US$206 million. However, with the widespread use of these two insecticides, a variety of pests have developed varying degrees of resistance to them, which has become the main limiting factor for both insecticides. Resistance monitoring shows that the population of *Plutella xylostella* in the field has developed a high level of resistance to chlorantraniliprole, and the population resistance in some areas has even reached more than 1000 times; the resistance to indoxacarb is generally more than 10 times, and resistance of some population is more than 100 times. The intensification of insecticide resistance not only seriously affects the life cycle of pesticides, but also leads to an increase in the frequency and dosage of pesticides use, resulting in huge economic losses. Effective control of pest resistance has become an urgent problem in crop protection worldwide.

The resistance mechanisms of pests to insecticides can be basically classified into three categories: metabolic resistance, penetration resistance and target resistance, of which metabolic resistance mediated by detoxification enzymes is more common. Many studies have shown that, glutathione S-transferases (GSTs), as an important detoxification enzyme system in insects, can participate in insects' resistance against commonly used insecticides, such as organochlorines, organophosphates, pyrethroids, neonicotinoids, diamides and abamectin through gene mutation, increased activity, and up-regulated expression. For example, silencing LmGSTs5 and LmGSTu1 in *Locusta migratoria* significantly increased the sensitivity of its nymphs to malathion and chlorpyrifos. There is also evidence that insect GSTs can directly metabolize a variety of insecticides. For example, the recombinant protein from *Helicoverpa armigera* HaGST-8 has good metabolic activity to chlorpyrifos, dichlorvos and cypermethrin.

GSTs play an important role in the occurrence and development of pest resistance, and reducing their activity will significantly reduce the resistance of pests. Compounds such as S-Hexyl glutathione (GTX) and diethyl maleate (DEM) have been reported to increase control effects by inhibiting GSTs activity and delaying the metabolism of insecticides by pests. As inhibitors of GSTs, these compounds usually have no insecticidal activity by themselves, but when mixed with insecticides, they can significantly improve the toxicity or efficacy of insecticides, and are important pesticide synergists. The research and development of GSTs-targeted inhibitors can not only improve the control of insecticides, but also delay or reduce insecticide resistance and prolong the life cycle of insecticides, which is of great significance to the management of insecticide resistance.

SUMMARY OF THE INVENTION

The present invention provides a novel inhibitor targeting pest GSTs. The inhibitor has broad inhibitory activities against GSTs in various pests, and can effectively delay the in vivo metabolism of insecticides by GSTs in pests, thereby reducing the metabolic resistance of pests to insecticides. The inhibitor effectively decreases the resistance of resistant strains of *Plutella xylostella* to ryanodine receptor modulators represented by chlorantraniliprole and voltage-dependent sodium ion channel blockers represented by indoxacarb, making it suitable for use as a synergist for insecticides.

It is an object of the present invention to provide a diphenylpyrazole-based compound of following formula (I), or its pesticidally acceptable salts.

It is another object of the present invention to provide a method for preparing the diphenylpyrazole-based compound of following formula (I), or its pesticidally acceptable salts.

It is another object of the present invention to provide use of the diphenylpyrazole-based compound of following formula (I), or its pesticidally acceptable salts in the preparation of pesticides (for example, preferably synergist for insecticides).

The present invention provides a diphenylpyrazole-based compound of following formula (I), or its pesticidally acceptable salts, Formula (I)

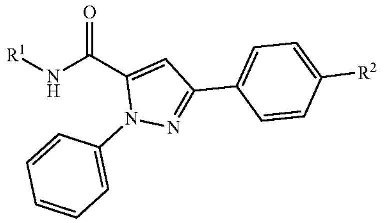

wherein $R^1$ can be:

(1) an amido group —NH—CH(O) which is unsubstituted or substituted by one or more of the following substituents;

(a) —$C_{1\sim6}$ alkyl-$R^3$, —$C_{3\sim8}$ cycloalkyl-$R^3$, —$C_{2\sim6}$ alkenyl-$R^3$, —$C_{2\sim6}$ alkynyl-$R^3$, —NH—$R^3$, —$N(R^3)_2$, —C(O)—$R^3$, —NH—$C_{1\sim6}$ alkyl-$R^3$, —$C_{1\sim6}$ alkyl-NH—$R^3$, —$C_{1\sim6}$ alkyl-$N(R^3)_2$, —$C_{1\sim6}$ alkyl-$OR^3$, —$C_{3\sim8}$ cycloalkyl-$OR^3$, —$OC_{1\sim6}$ alkyl-$R^3$, —$C_{1\sim6}$ alkyl-$OC_{1\sim6}$ alkyl-$R^3$, —C(O)—NH—$R^3$, —C(O)—$N(R^3)_2$, —NH—C(O)—$R^3$, —$C_{1\sim6}$ alkyl-NH—C(O)—$R^3$, —$C_{1\sim6}$ alkyl-NH—C(O)—$OR^3$, —NH—C(O)—$C_{1\sim6}$ alkyl-$R^3$, —NH—C(O)—$C_{1\sim6}$ alkyl-$OR^3$, —C(O)—NH—$C_{1\sim6}$ alkyl-$R^3$ or —$C_{1\sim6}$ alkyl-$SR^3$;

$R^3$ is each independently selected from: H, O, S, ═NH, amino, halogen, cyano, —$C_{1\sim6}$ alkyl, —$C_{3\sim8}$ cycloalkyl, —S—$C_{1\sim6}$ alkyl, —S—OH, —$SO_2$—$C_{1\sim6}$ alkyl, -6~14 membered aryl, -5~14 membered heterocyclic group, -5~14 membered heteroaryl and -adamantyl; $R^3$ is unsubstituted or substituted by one or more of the following substituents: O, —OH, halogen, cyano, nitro, —CH(O), amino, —$C_{1\sim6}$ alkyl, —$C_{2\sim6}$ alkenyl, —$C_{2\sim6}$ alkynyl, —$OC_{1\sim6}$ alkyl, nitro, sulfonic acid group, —$C_{1\sim6}$ alkyl-halogen, —$C_{1\sim6}$ alkyl-HS, —$C_{1\sim6}$ alkyl-$NH_3^+$, —$C_{1\sim6}$ alkyl-OH, —$C_{1\sim6}$ alkyl-NH—$C_{1\sim6}$ alkyl, or —$C_{1\sim6}$ alkyl-$N(C_{1\sim6}\ alkyl)_2$;

(b) -6~14 membered aryl, -5~14 membered heterocyclic group or -5~14 membered heteroaryl;

the 6~14 membered aryl, the 5~14 membered heterocyclic group or the 5~14 membered heteroaryl is unsubstituted or substituted by one or more of the following substituents: O, —OH, halogen, cyano, nitro, —CH(O), amino, —$C_{1\sim6}$ alkyl, —$OC_{1\sim6}$ alkyl, —$C_{1\sim6}$ alkyl-NH—$C_{1\sim6}$ alkyl, —$C_{1\sim6}$ alkyl-$N(C_{1\sim6}\ alkyl)_2$, —C(O)—$OC_{1\sim6}$ alkyl, —NH—C(O)—$C_{1\sim6}$ alkyl, —$SO_2$—$C_{1\sim6}$ alkyl, —$SO_2$—$NH_2$, —$SO_2$—NH—$C_{1\sim6}$ alkyl, —$SO_2$—$N(C_{1\sim6}\ alkyl)_2$, -6~14 membered aryl, -5~14 membered heterocyclic group, or -5~14 membered heteroaryl;

(2) N atom and C atom of the amido group —NH—CH(O) are connected to form a ring structure via —$C_{3\sim6}$ alkylene-, —NH—$C_{2\sim6}$ alkylene-, —NH—C(O)—$C_{1\sim6}$ alkylene-, —$C_{1\sim6}$ alkylene-NH—C(O)—, —NH—$C_{1\sim6}$ alkylene-C(O)— or —$C_{1\sim6}$ alkylene-C(O)—; the ring structure is optionally substituted by one or more of the following substituents: —$C_{1\sim6}$ alkyl, —$C_{3\sim8}$ cycloalkyl, —$C_{3\sim8}$ cycloalkyl-$C_{1\sim6}$ alkyl, —$OC_{1\sim6}$ alkyl, -6~14 membered aryl, -5~14 membered heterocyclic group, -5~14 membered heteroaryl, —$C_{1\sim6}$ alkyl-6~14 membered aryl, —$C_{1\sim6}$ alkyl-5~14 membered heterocyclic group, —$C_{1\sim6}$ alkyl-5~14 membered heteroaryl or trifluoroethyl; the 6~14 membered aryl, the 5~14 membered heterocyclic group and the 5~14 membered heteroaryl are optionally substituted by —$OC_{1\sim6}$ alkyl; or, the ring structure is further combined with 5~8 membered aryl, 5~8 membered heterocyclic group or 5~8 membered heteroaryl to fuse into a fused ring.

the heterocyclic group (including 5~14 members, 5~10 members and 5~8 members) contains 1~4 heteroatoms selected from N, S and O; the heteroaryl (including 5~14 members, 5~10 members and 5~8 members) contains 1~4 heteroatoms selected from N, S and O.

$R^2$ can be: —H, -halogen, -amino, —$NO_2$, —CF, —$C_{1\sim6}$ alkyl, —$C_{1\sim6}$ alkyl-OH, —O—$R^4$, —C(O)—$R^4$, —C(O)—$NH_2$, —NH—C(O)—$R^4$, —C(O)—O—$R^4$ or —C(O)—O—$N(R^4)_2$; $R^4$ can be: H or $C_{1\sim6}$ alkyl.

The substituent of the amide group is connected to the N atom of the amino group and/or connected to the C atom of the carbonyl group; and when there are two substituents, the two substituents may be the same or different.

The term "halogen" refers to fluorine, chlorine, bromine or iodine as a substituent. When a halogen atom is used as a substituent, the number of substitutions is one or more, including 1, 2 or 3, etc.

The term "alkyl" refers to a straight-chain or branched-chain alkyl group derived from an alkane by removing one hydrogen atom.

The term "alkenyl" refers to a straight-chain or branched-chain or cyclic alkenyl group containing carbon-carbon double bond.

The term "alkynyl" refers to a straight-chain or branched-chain or cyclic alkynyl group containing carbon-carbon triple bond.

The term "cycloalkyl" is a fully hydrogenated non-aromatic ring composed of mono-, bi- or tri-cyclic rings. Thus, a cycloalkyl can typically be a monocyclic ring containing 3 to 7 ring atoms. Examples include, but are not limited to, cyclopropyl, cyclobutyl, cyclopentyl, and cyclohexyl. Also, "cycloalkyl" includes bridged bicycloalkyl systems.

The term "alkyloxy" refers to a group derived from "alkyl" by connecting through —O— to other moieties.

The term "aryl" refers to a cyclic aromatic group whose ring atoms are carbon atoms, including single-ring aryl and condensed-ring aryl. A single-ring aryl refers to a fully unsaturated aryl, and a condensed-ring aryl refers to a cyclic group formed by two or more ring structures sharing two adjacent carbon atoms with each other, and at least one ring is fully unsaturated aromatic ring.

The term "heterocyclic group" refers to a saturated or unsaturated non-aromatic group consisting of 1 to 3 rings containing 1, 2, 3 or 4 heteroatoms (N, O or S).

The term "heteroaryl" refers to an aromatic ring structure, including monocyclic heteroaryl and condensed ring heteroaryl. wherein at least one of the ring atoms is a heteroatom (N, O or S) and the remaining ring atoms are independently selected from carbon, oxygen, nitrogen and sulfur.

Preferably, $R^1$ can be:

(1) an amido group —NH—CH(O) which is substituted by one or more of the following substituents, (a) —$C_{1\sim3}$ alkyl-$R^3$, —$C_{3\sim6}$ cycloalkyl-$R^3$, —$C_{2\sim5}$ alkenyl-$R^3$, —$C_{1\sim3}$ alkyl-NH—$R^3$, —$C_{1\sim3}$ alkyl-O—$R^3$, or —O—$C_{1\sim3}$ alkyl-$R^3$; $R^3$ are each independently selected from: H, O, S, ═NH, amino, halogen, cyano, —$C_{1\sim3}$ alkyl, —$C_{3\sim6}$ cycloalkyl, -6~14 membered aryl, -5~14 membered heterocyclic group, or -5~14 membered heteroaryl; $R^3$ is unsubstituted or substituted by one or more of the following substituents: O, —OH, halogen, cyano, nitro, —CH(O), —S—OH, amino, —$C_{1\sim3}$ alkyl, —$C_{2\sim5}$ alkenyl, —$C_{2\sim5}$ alkynyl, —$OC_{1\sim3}$ alkyl, nitro, sulfonic acid group, —$C_{1\sim3}$ alkyl-halogen or —$C_{1\sim3}$ alkyl-OH;

(b) -6~14 membered aryl, -5~14 membered heterocyclic group or -5~14 membered heteroaryl; the 6~14 membered aryl, the 5~14 membered heterocyclic group or the 5~14 membered heteroaryl is unsubstituted or substituted by one or more of the following substituents: O, —OH, halogen, cyano, nitro, —CH (O), amino, —$C_{1\sim3}$ alkyl, —$OC_{1\sim3}$ alkyl, —$C_{1\sim3}$ alkyl-NH—$C_{1\sim3}$ alkyl, —$C_{1\sim3}$ alkyl-N($C_{1\sim3}$ alkyl)$_2$, —C(O)—$OC_{1\sim3}$ alkyl, —NH—C(O)—$C_{1\sim3}$ alkyl, —$SO_2$—$C_{1\sim3}$ alkyl, —$S_2$—$NH_2$, —$SO_2$—NH—$C_{1\sim3}$ alkyl, or —$SO_2$—N($C_{1\sim3}$ alkyl)$_2$;

(2) N atom and C atom of the amido group —NH—CH (O) are connected to form a ring structure via —$C_{3\sim6}$ alkylene-, —NH—$C_{2\sim4}$ alkylene-, —NH—C(O)—$C_{1\sim3}$ alkylene-, —$C_{1\sim3}$ alkylene-NH—C(O)—, —NH—$C_{1\sim3}$ alkylene-C(O)— or —$C_{1\sim3}$ alkylene-C (O)—; the ring structure is optionally substituted by the following substituents: —$C_{1\sim3}$ alkyl, —$C_{3\sim6}$ cycloalkyl, —$C_{3\sim6}$ cycloalkyl-$C_{1\sim3}$ alkyl, -6~14 membered aryl, -5~14 membered heterocyclic group, -5~14 membered heteroaryl, —$C_{1\sim3}$ alkyl-6~14 membered aryl, —$C_{1\sim3}$ alkyl-5~14 membered heterocyclic group, —$C_{1\sim3}$ alkyl-5~14 membered heteroaryl, or trifluoroethyl; the 6~14 membered aryl, the 5~14 membered heterocyclic group and the 5~14 membered heteroaryl are optionally substituted by —$OC_{1\sim3}$ alkyl;

the heterocyclic group contains 1~3 heteroatoms selected from N, S and O; the heteroaryl contains 1~3 heteroatoms selected from N, S and O.

$R^2$ is: —H or halogen.

more preferably, $R^1$ can be:

(1) —NH—C(O)—$C_{1\sim3}$ alkyl-$R^3$; $R^3$ is selected from: -6~10 membered aryl, -5~10 membered heterocyclic group, -5~10 membered heteroaryl; $R^3$ is unsubstituted or substituted by one or more of the following substituents: O, —OH, halogen, cyano, nitro, —CH(O), —S—OH, amino, —$C_{1\sim3}$ alkyl, —$OC_{1\sim3}$ alkyl, nitro, sulfonic acid group, —$C_{1\sim3}$ alkyl-halogen, —$C_{1\sim3}$ alkyl-HS, —$C_{1\sim3}$ alkyl-$NH_3$ or —$C_{1\sim3}$ alkyl-OH;

(2) —NH—C(O)-6~10 membered aryl, —NH—C(O)-5~10 membered heterocyclic group or —NH—C(O)-5~10 membered heteroaryl; the 6~10-membered aryl, the 5~10-membered heterocyclic group or the 5~10-membered heteroaryl is unsubstituted or substituted by one or more of the following substituents: O, —OH, halogen, cyano, nitro, —CH(O), amino, —$C_{1\sim3}$ alkyl or —$OC_{1\sim3}$ alkyl;

The heterocyclic group contains 1~3 heteroatoms selected from N, S and O; the heteroaryl contains 1~3 heteroatoms selected from N, S and O;

$R^2$ can be: —H.

Specifically, $R^1$ can be:

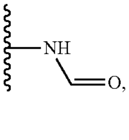,
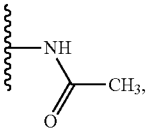,
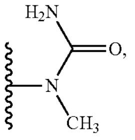

-continued

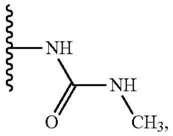
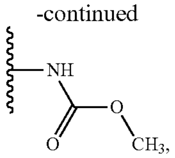
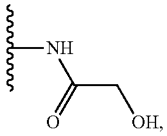
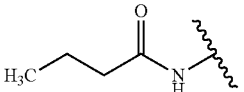,
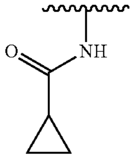,
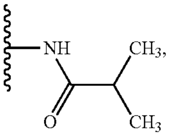
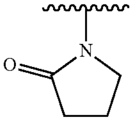,
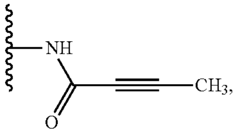
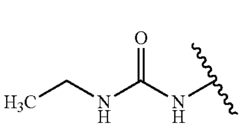,
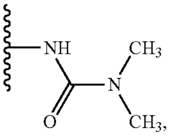
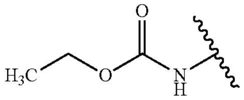,
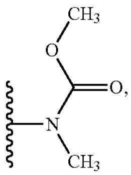
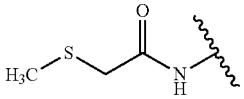,
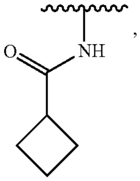,
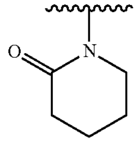,
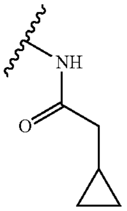,
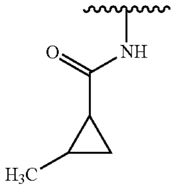,
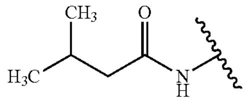,
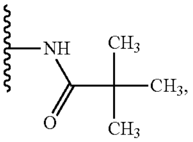
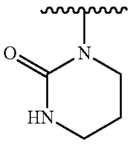,
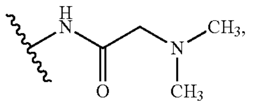
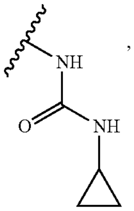,
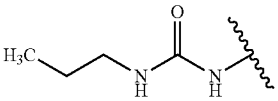,
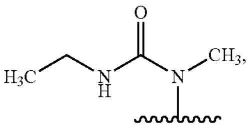

-continued
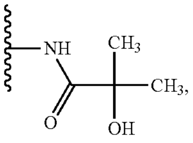 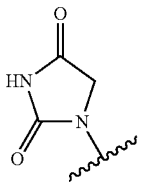, 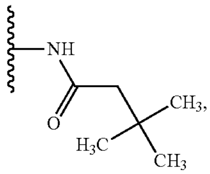
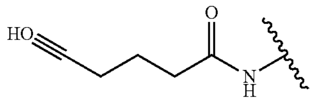, 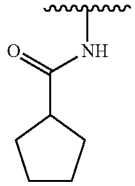,
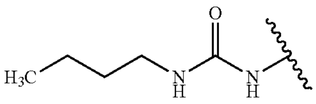, 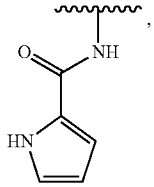,
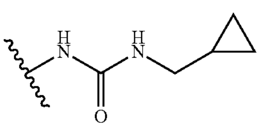, 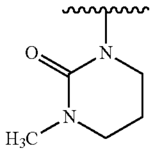,
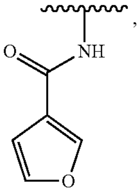, 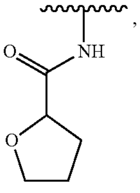, 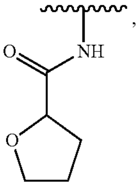,
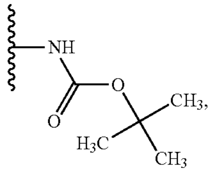
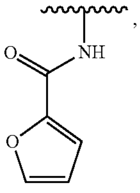, 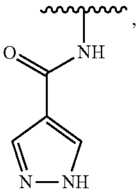, 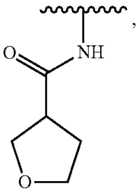,
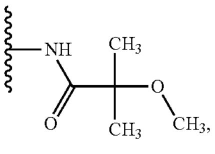 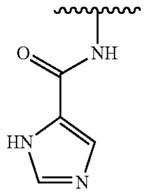, 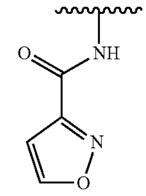,
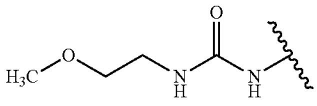, 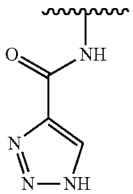,
-continued
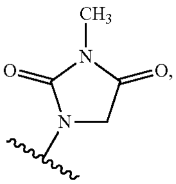 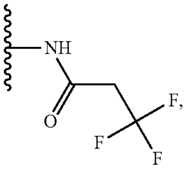 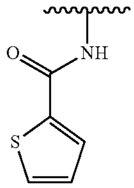,
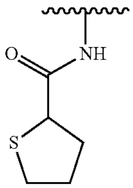, 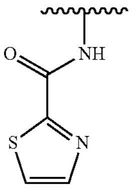, 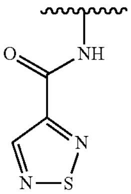,
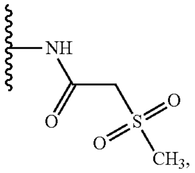 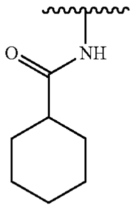, 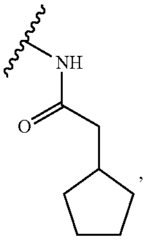,
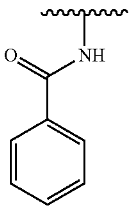, 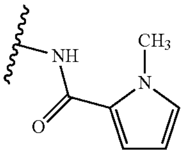, 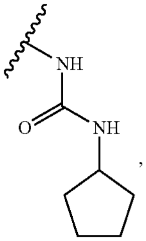,
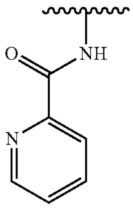, 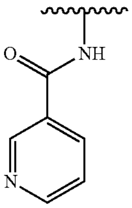, 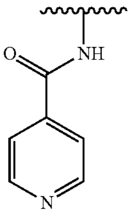,
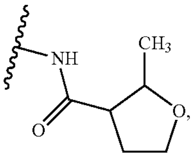 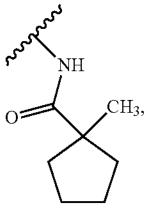 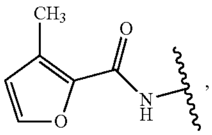,
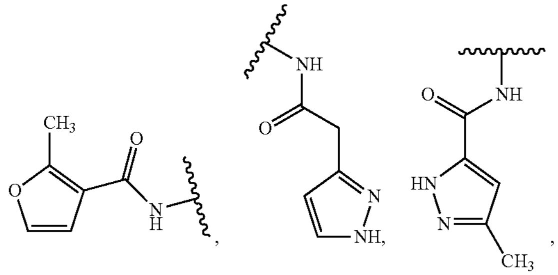

-continued
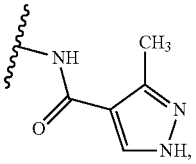
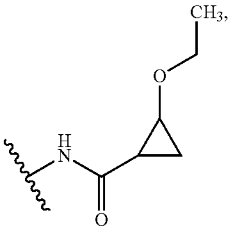
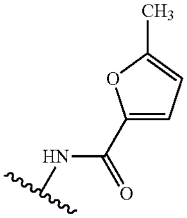,
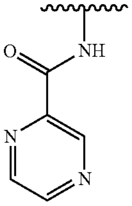,
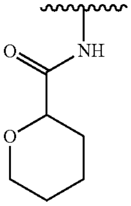,
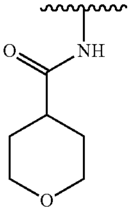,
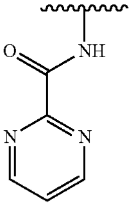,
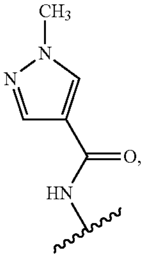
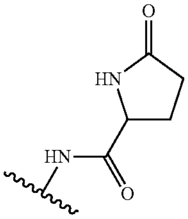,
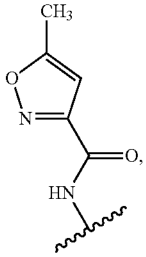
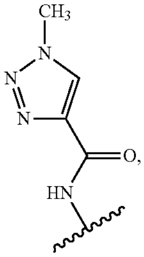
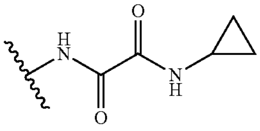,
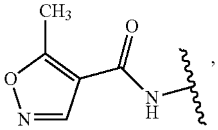,
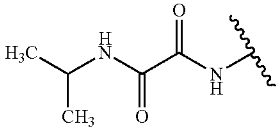,
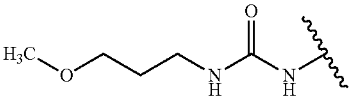,
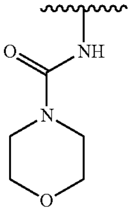,
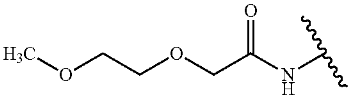,
-continued
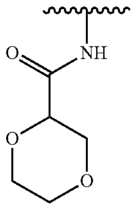,
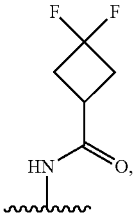
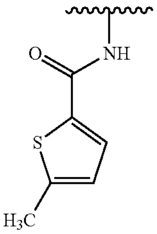,
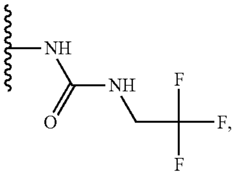
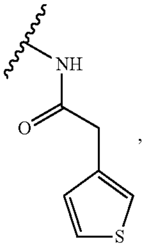,
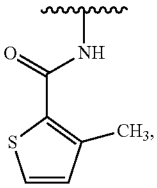
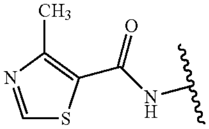,
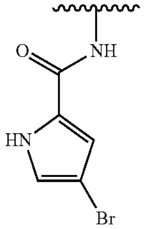,
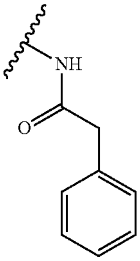,
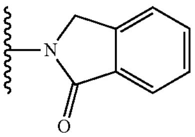,
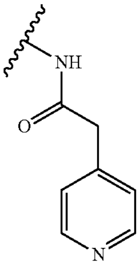,
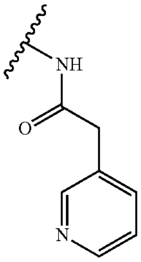,
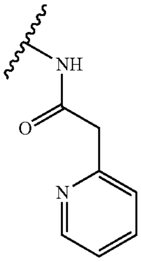,
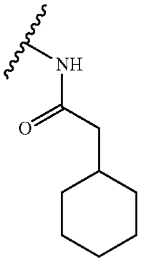,
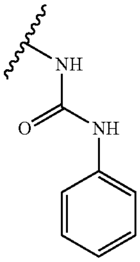,
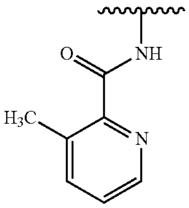,
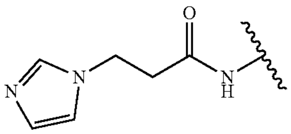,
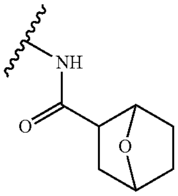, -continued
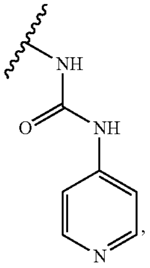,
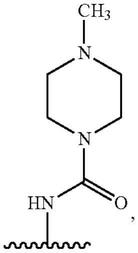,
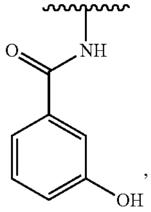,
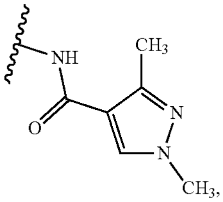,
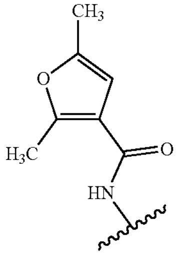,
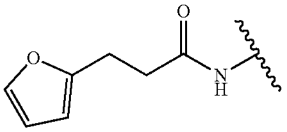,
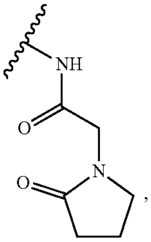,
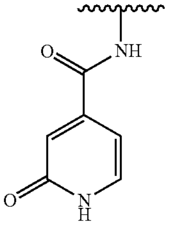,
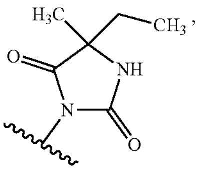,
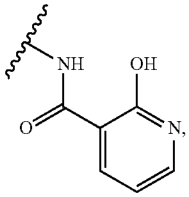,
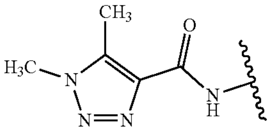,
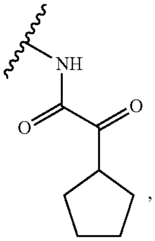,
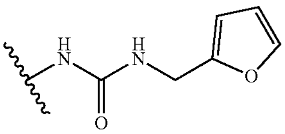,
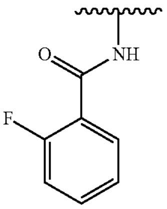,
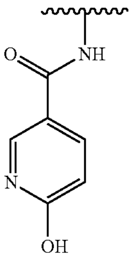,
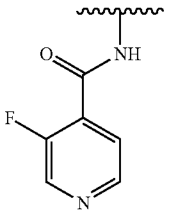,
-continued
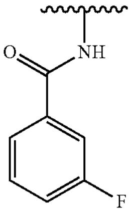,
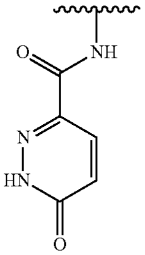,
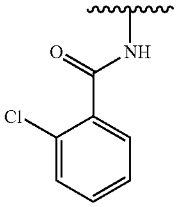,
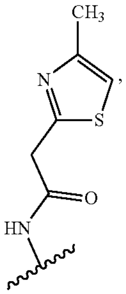,
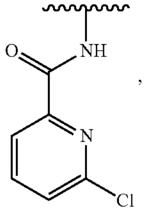,
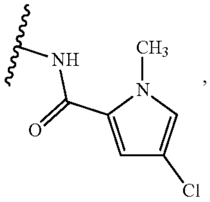,
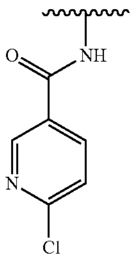,
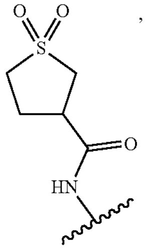,
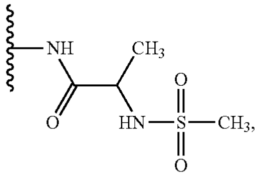,
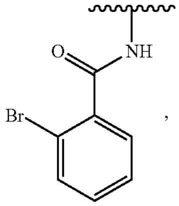,
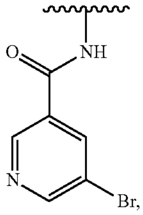,
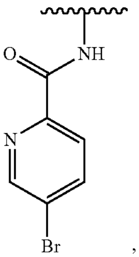,
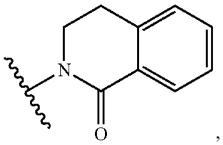,
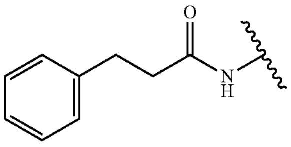,
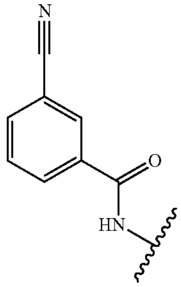,
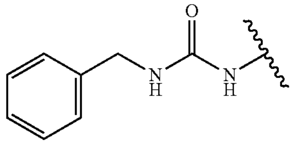, -continued
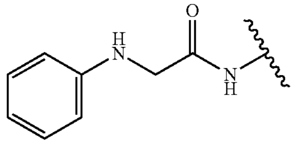,
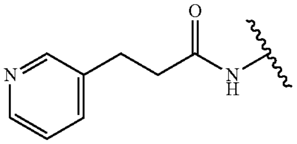,
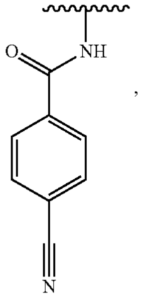,
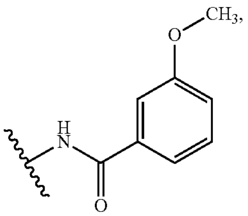
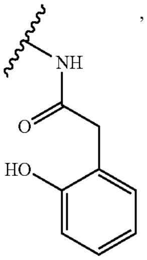,
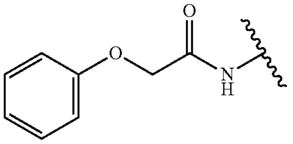,
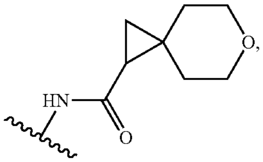
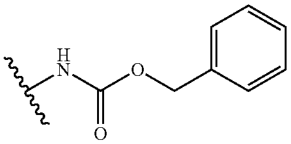,
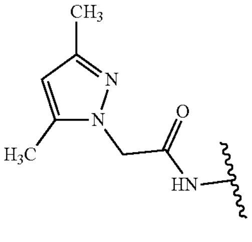,
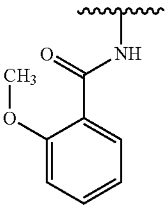,
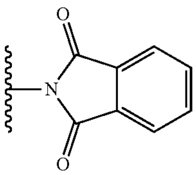,
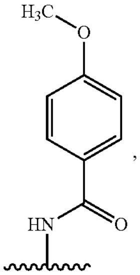,
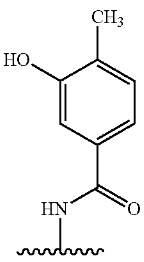,
-continued
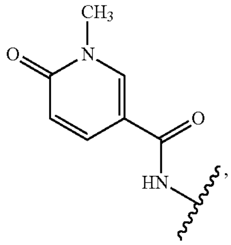,
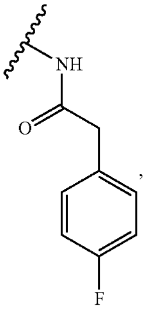,
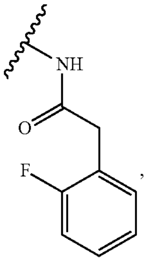,
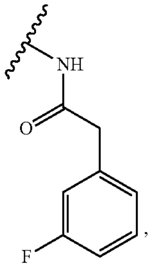,
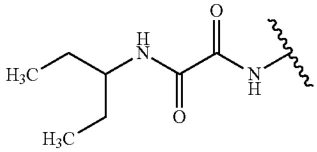,
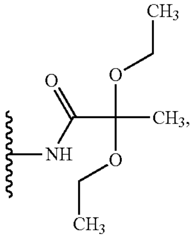
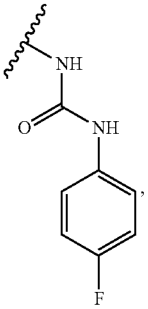
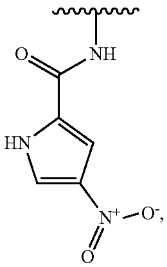
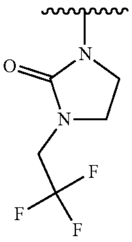,
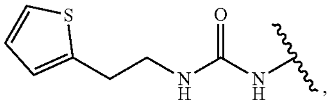,
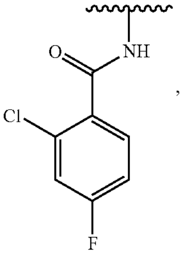,
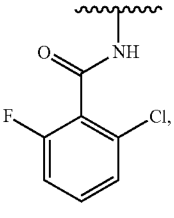
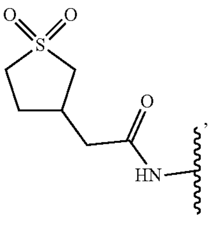

-continued
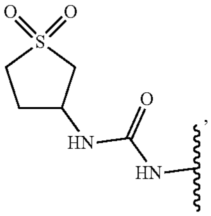,
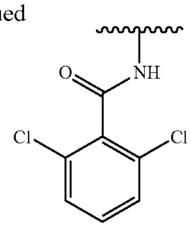,
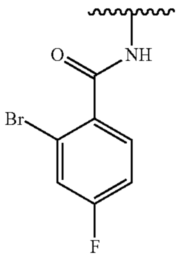,
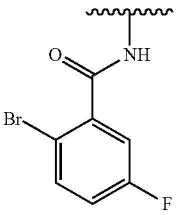,
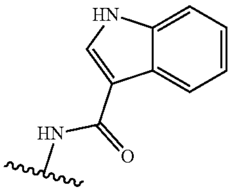,
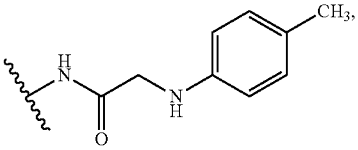,
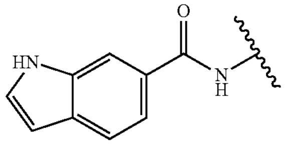,
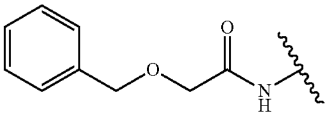,
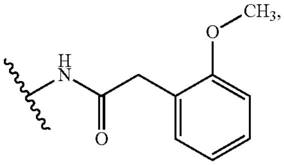,
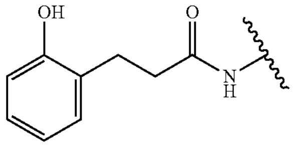,
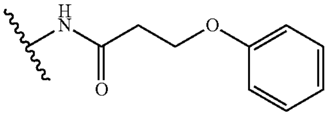,
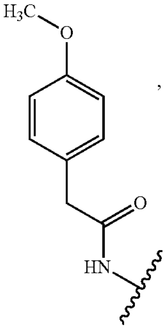,
-continued
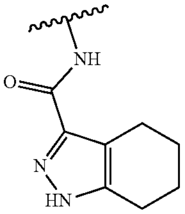,
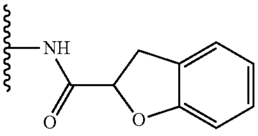,
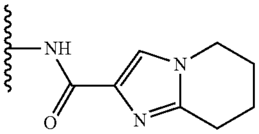,
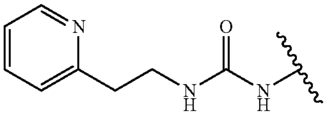,
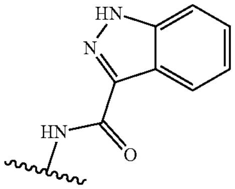,
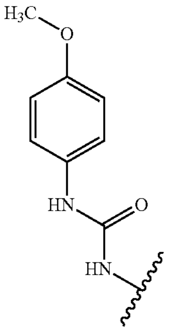,
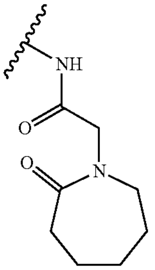,
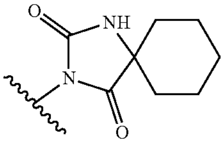,
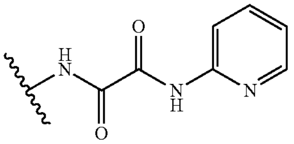,
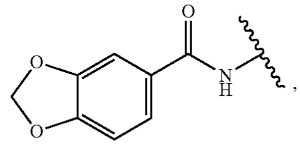,
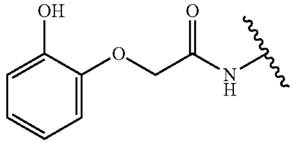,
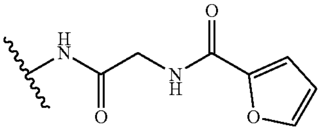, -continued
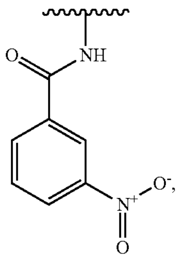,
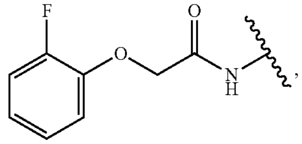,
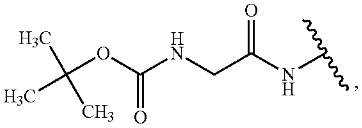,
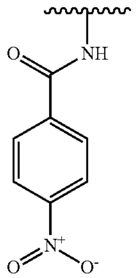,
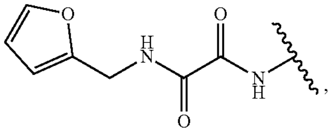,
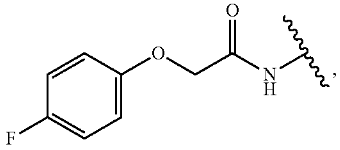,
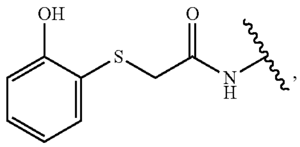,
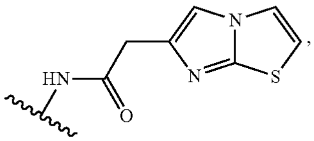,
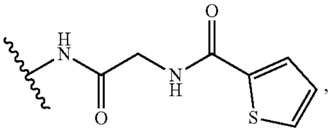,
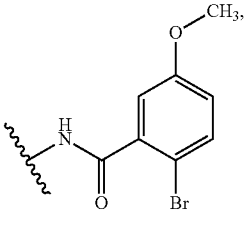,
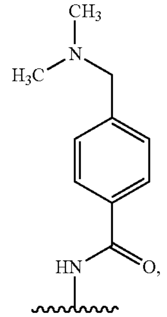,
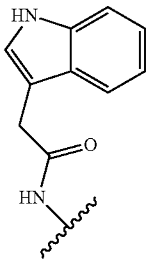,
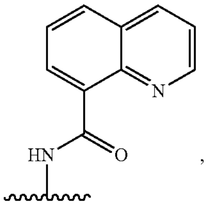,
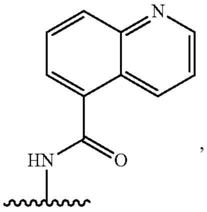,
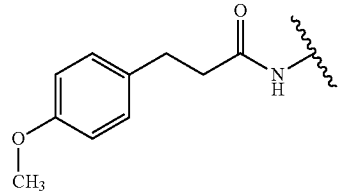,
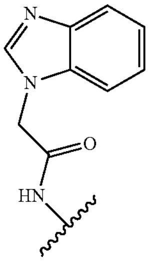,
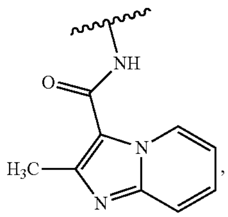,
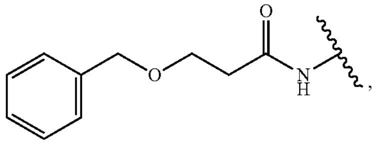,
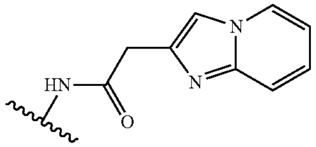,
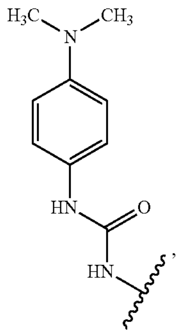,
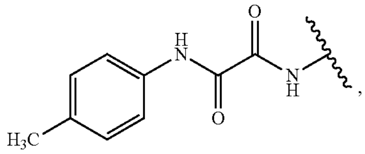,
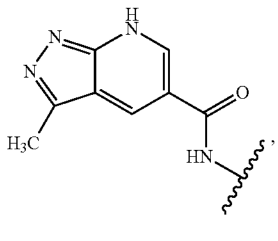, -continued
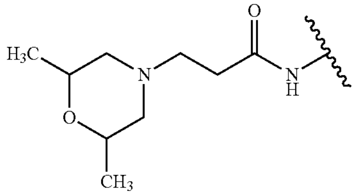,
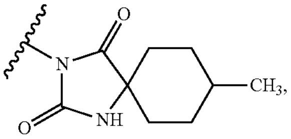,
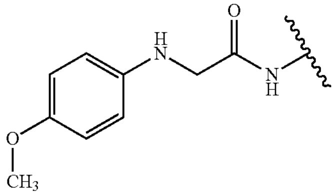,
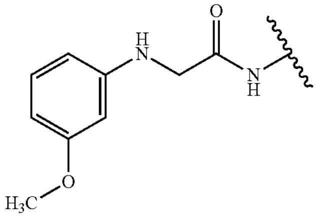,
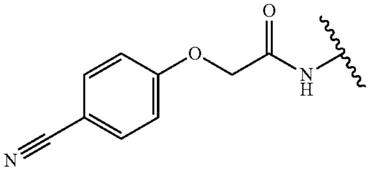,
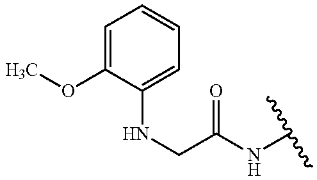,
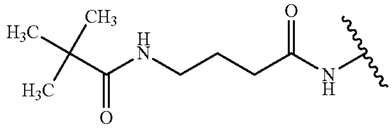,
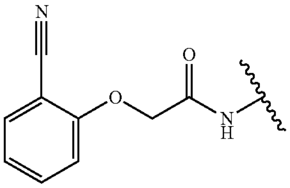,
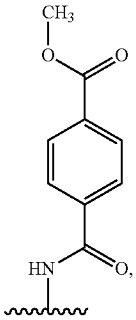,
-continued
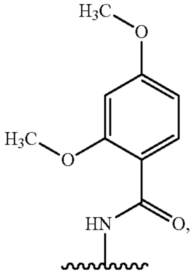,
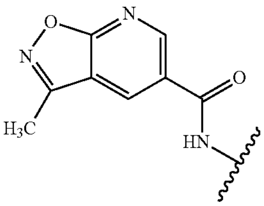,
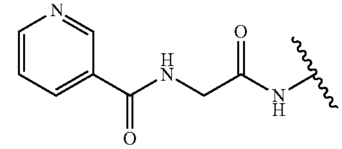,
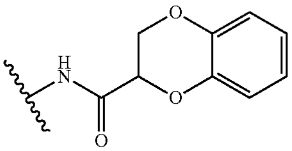,
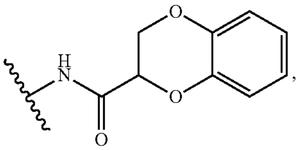,
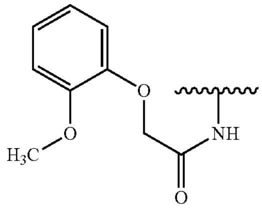,
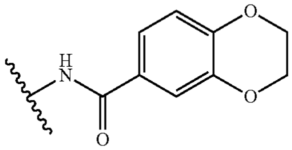,
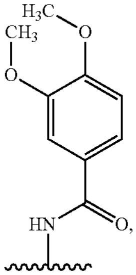,
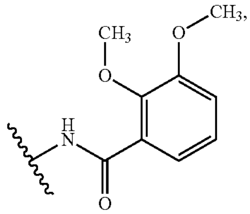,
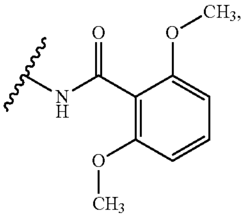,
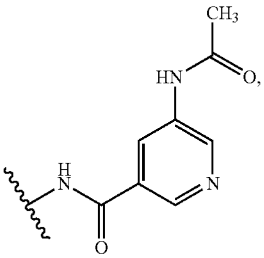,
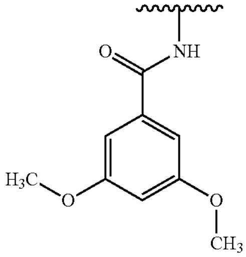,
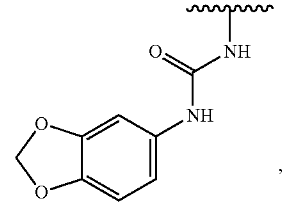, -continued
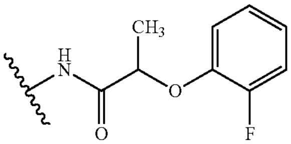,
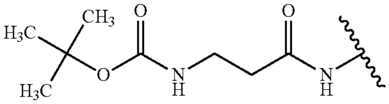,
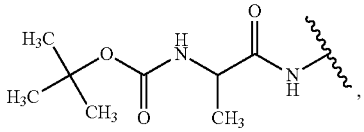,
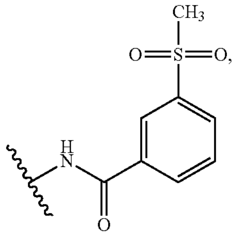 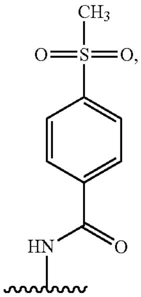 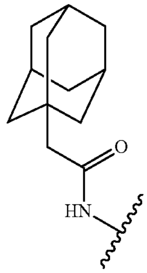,
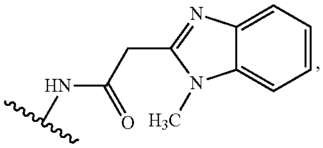, 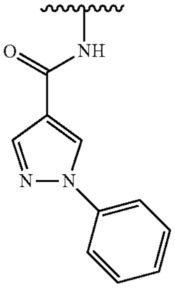,
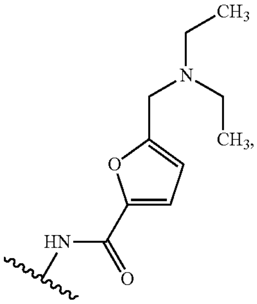 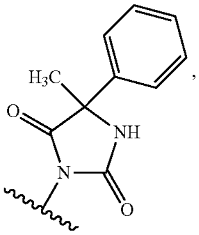,
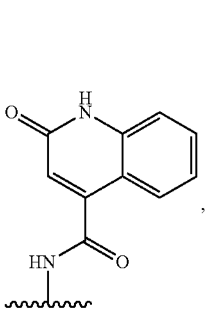, 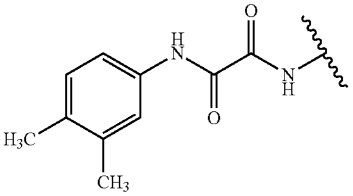,
-continued
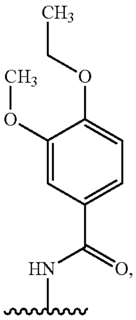 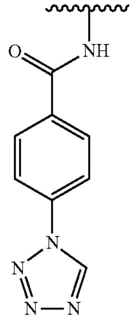, 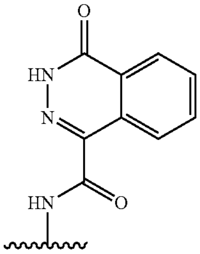,
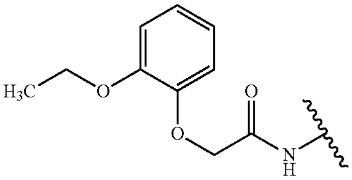, 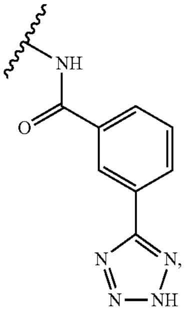
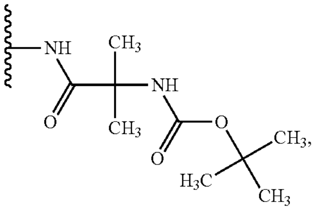 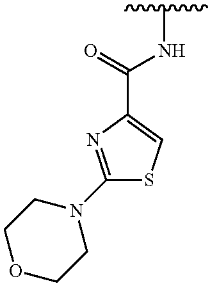,
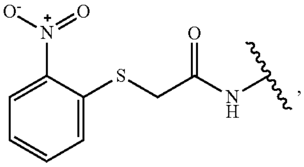, 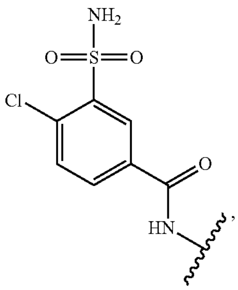
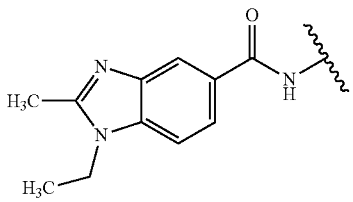, 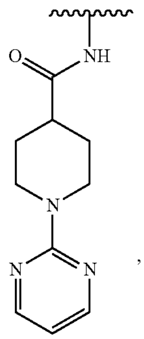, -continued
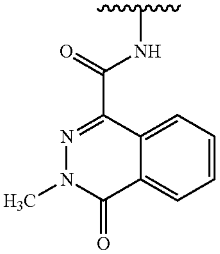,
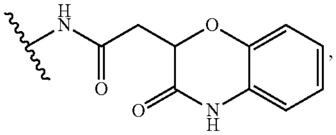,
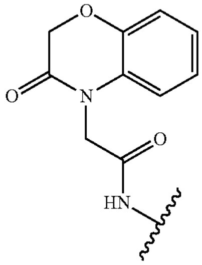,
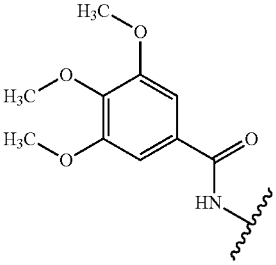,
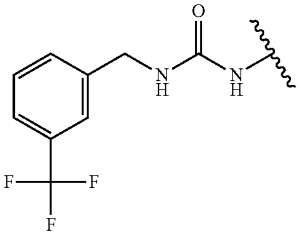,
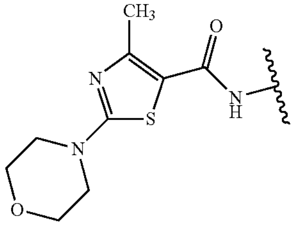,
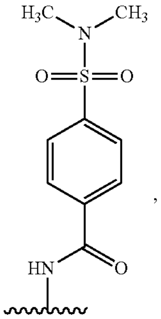,
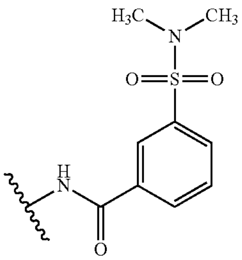,
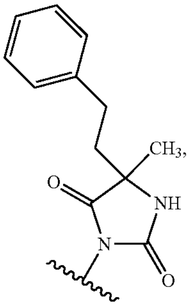
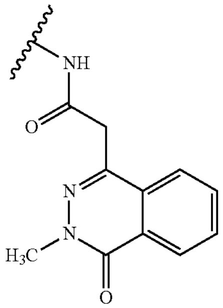,
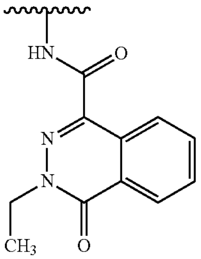,
-continued
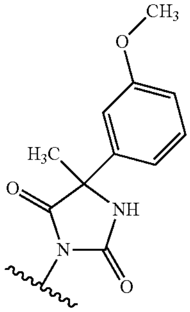,
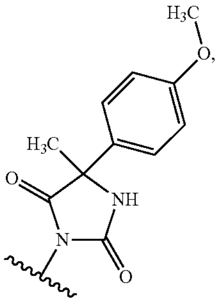
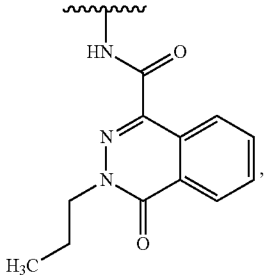,
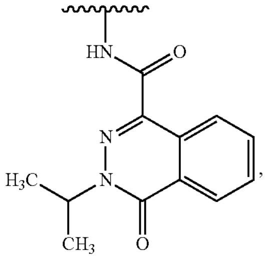,
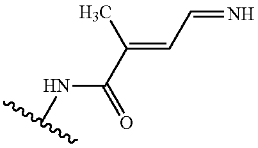,
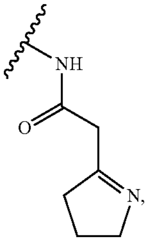
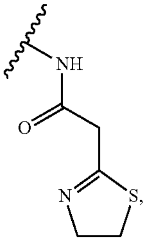
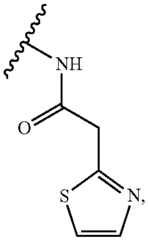
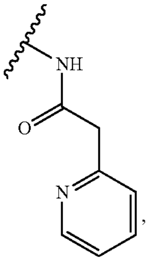,
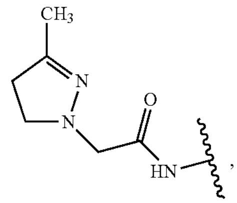,
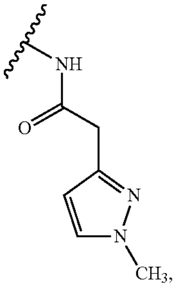
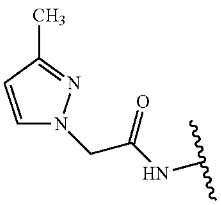,
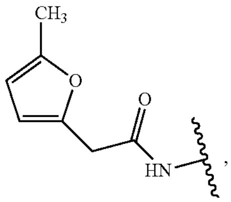,
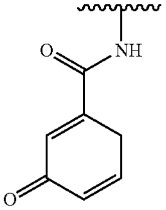, -continued
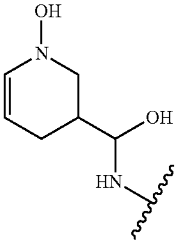, 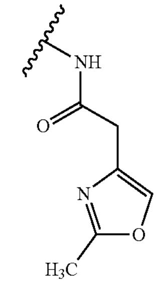, 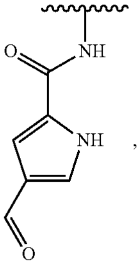,
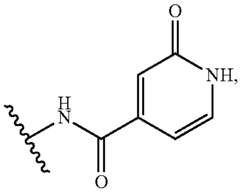 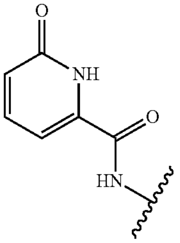,
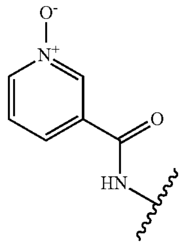, 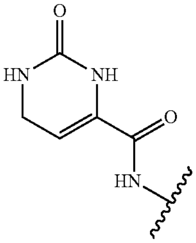,
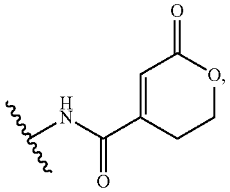 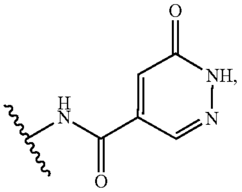
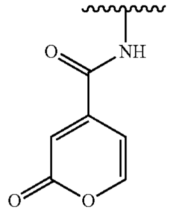, 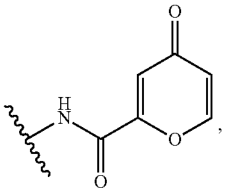
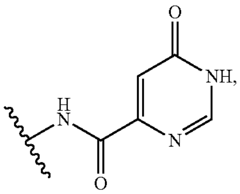 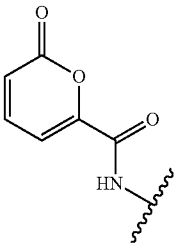,
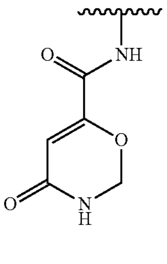, 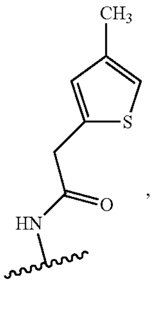, 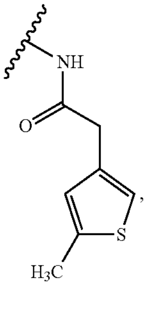
-continued
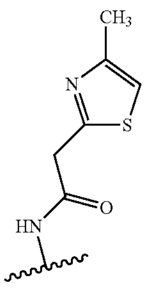, 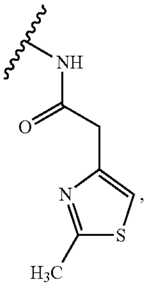
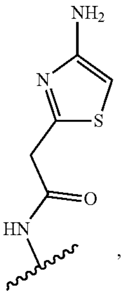, 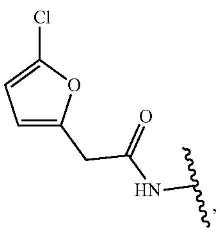 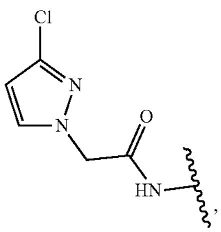
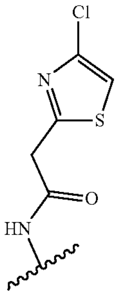, 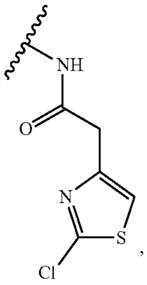, 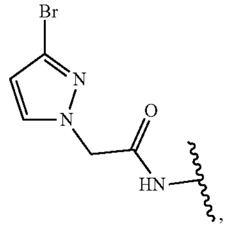
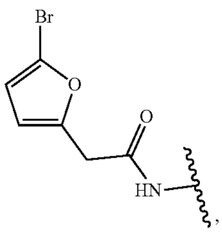 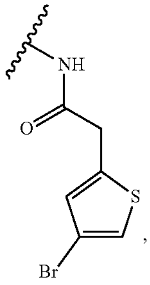, 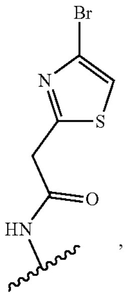,
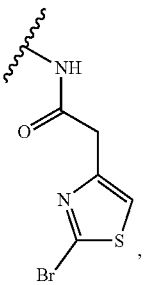, 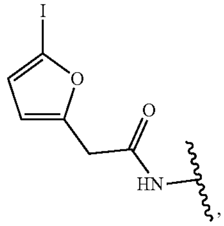 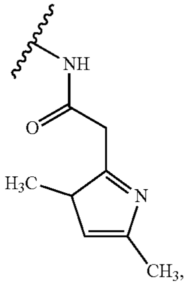

-continued
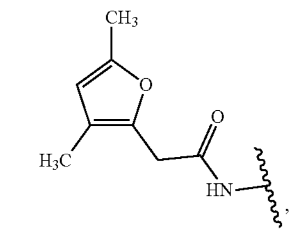
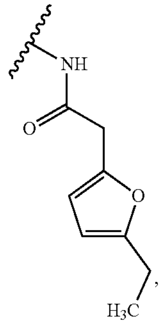
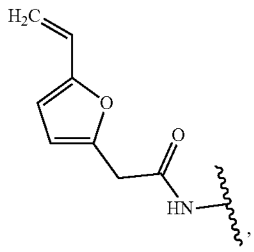
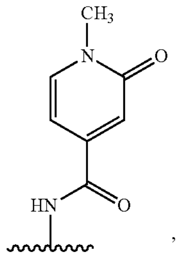
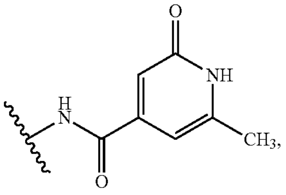
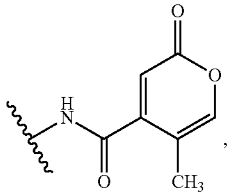
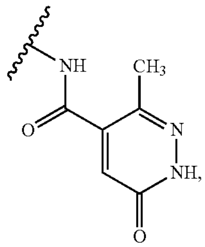
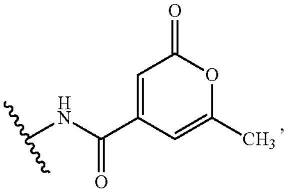
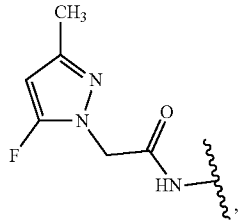
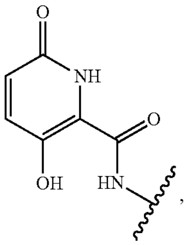
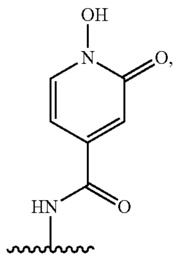
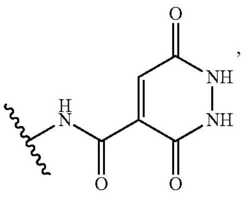
-continued
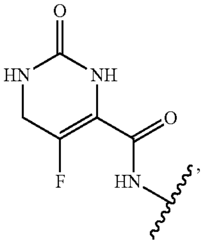
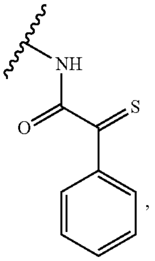
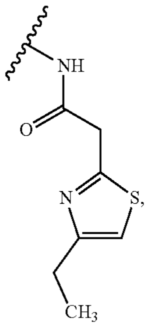
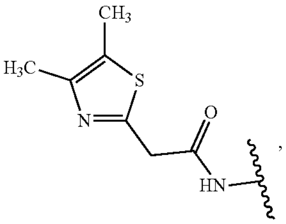
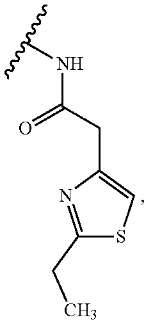
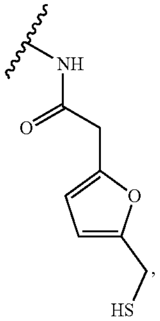
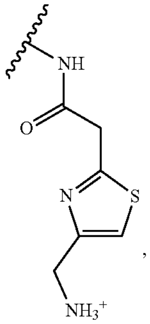
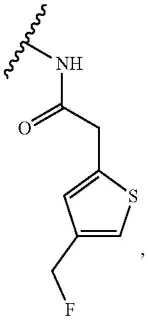
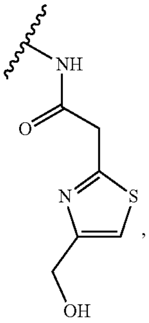
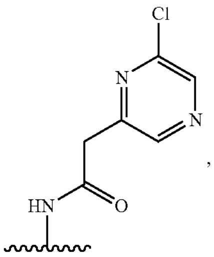
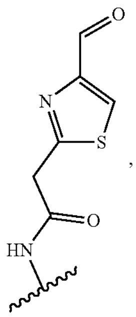
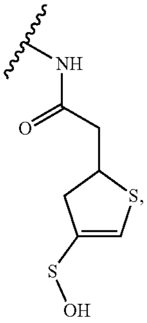
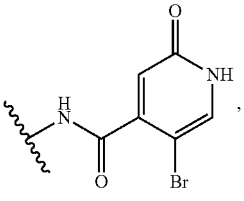

-continued
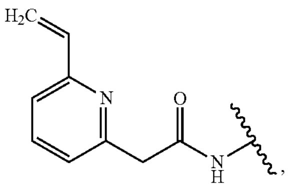,
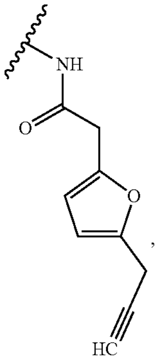,
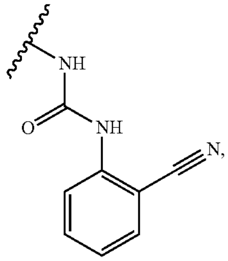,
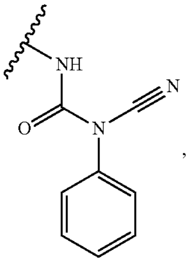,
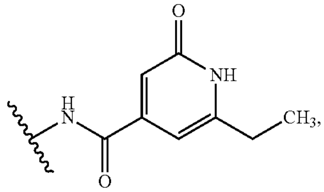,
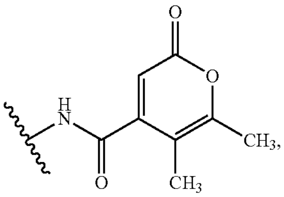,
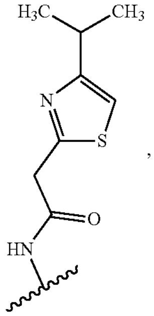,
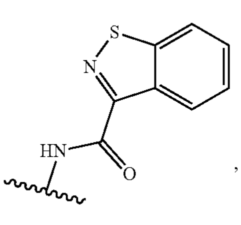,
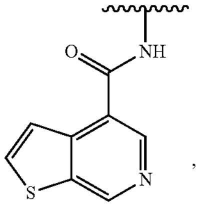,
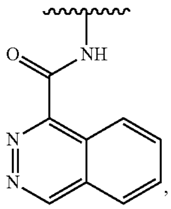,
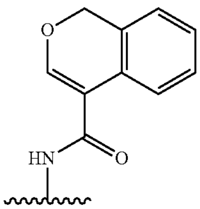,
-continued
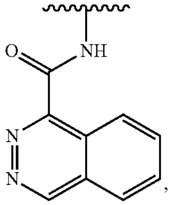,
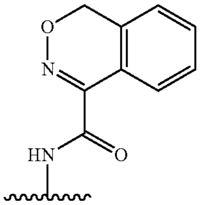,
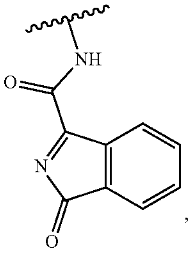,
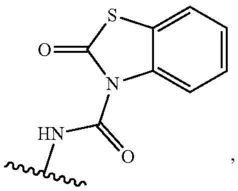,
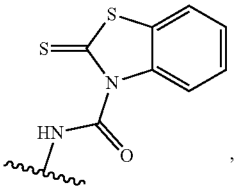,
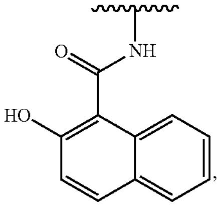,
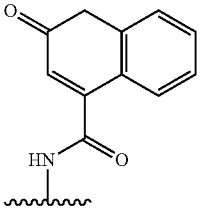,
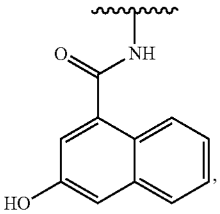,
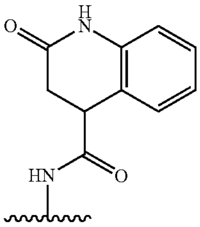,
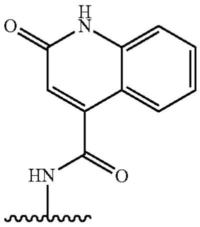,
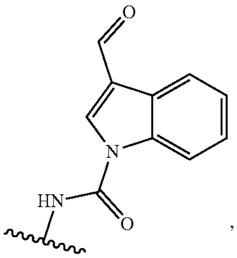,
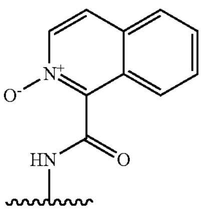,
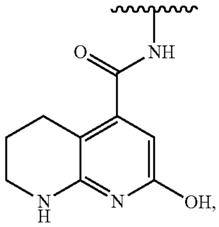,
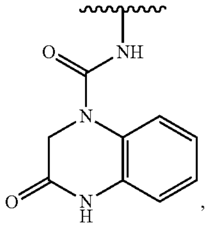, -continued
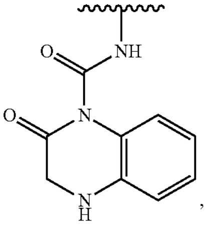,
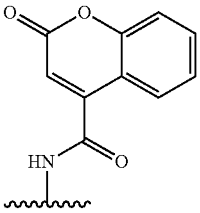,
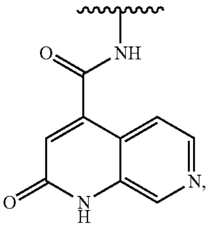
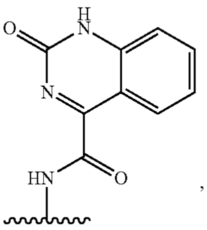,
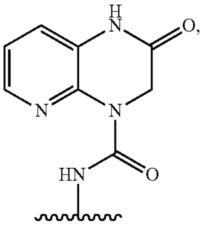
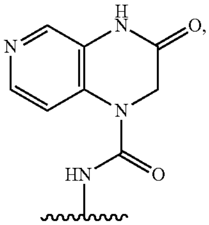
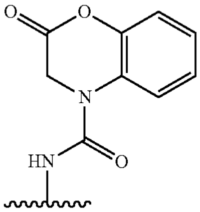,
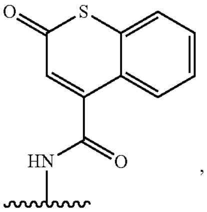,
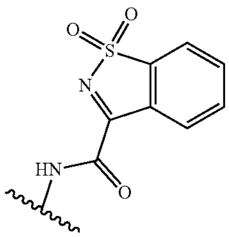,
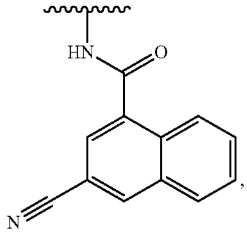
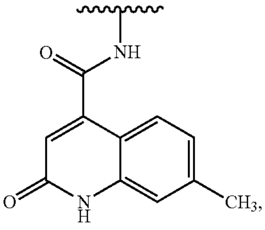
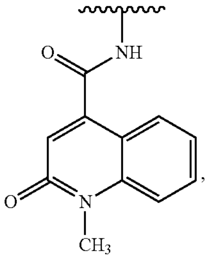
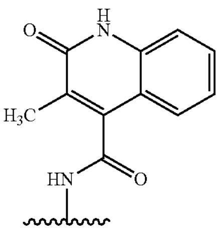,
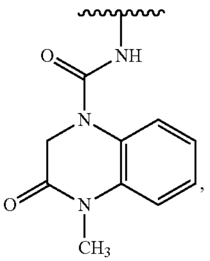
-continued
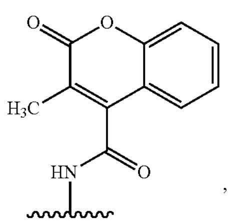,
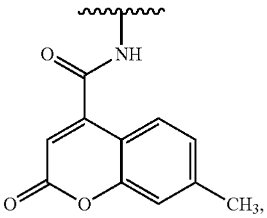
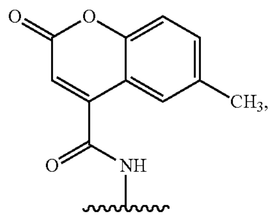
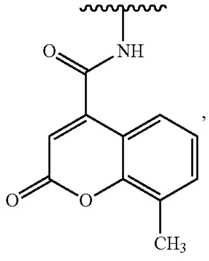,
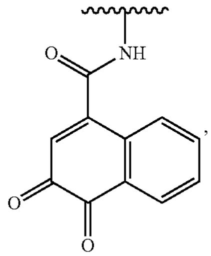
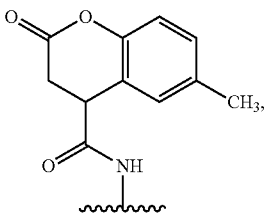
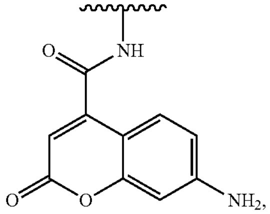
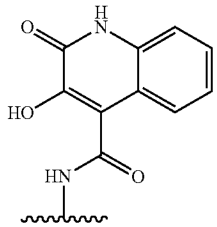,
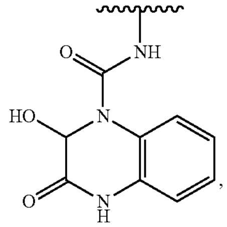
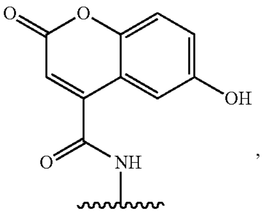,
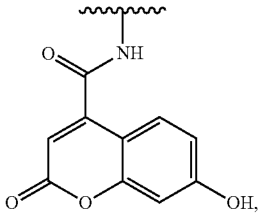
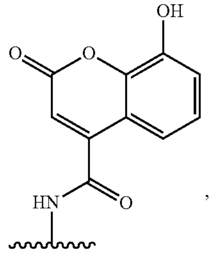, -continued
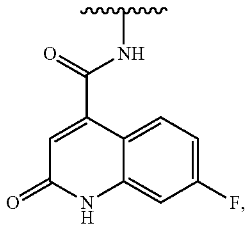
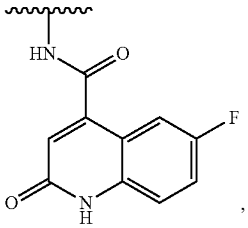
,
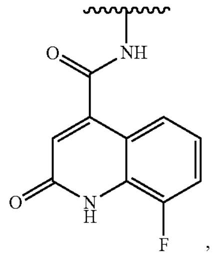
,
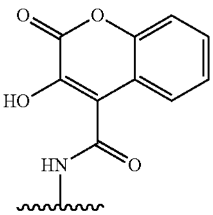
,
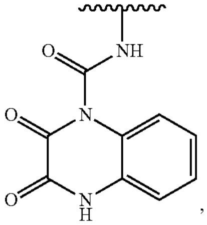
,
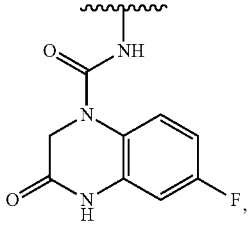
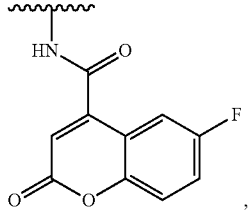
,
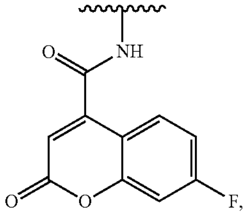
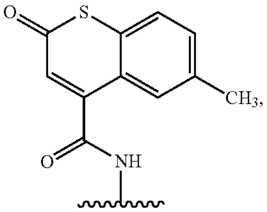
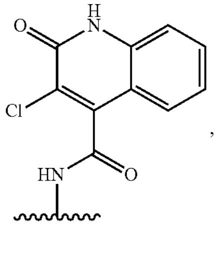
,
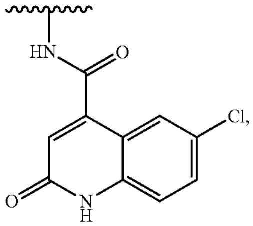
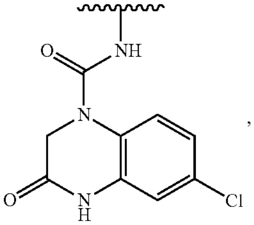
,
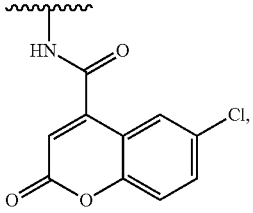
,
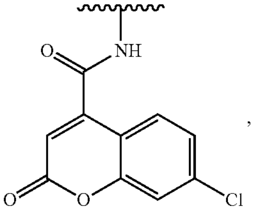
-continued
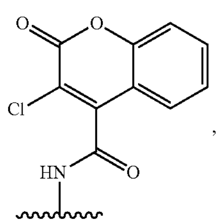
,
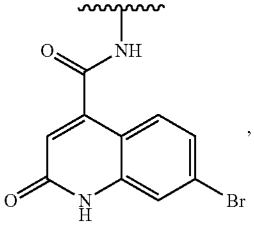
,
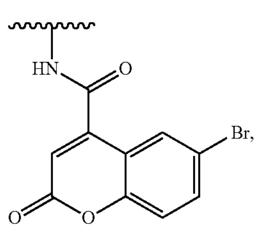
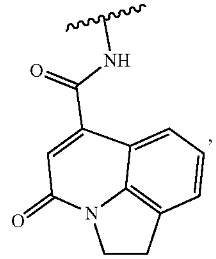
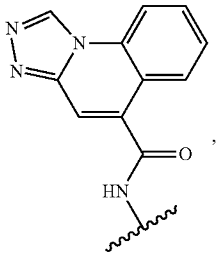
,
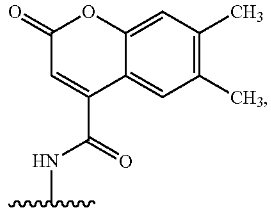
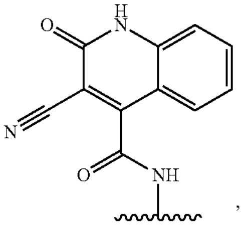
,
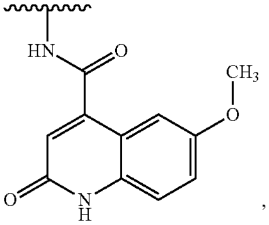
,
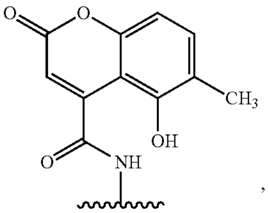
,
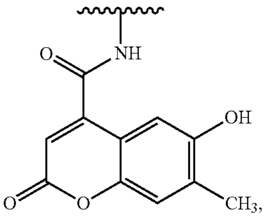
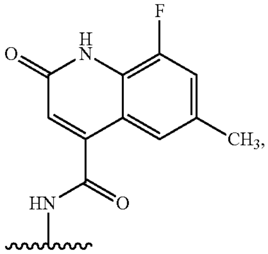
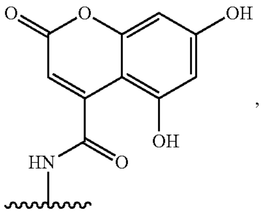
,
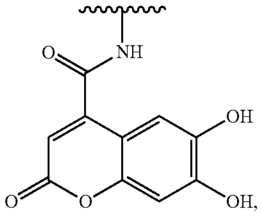
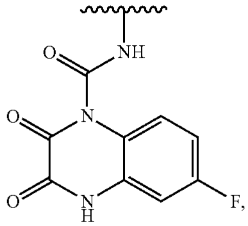

-continued
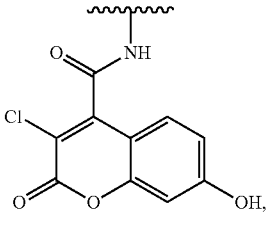
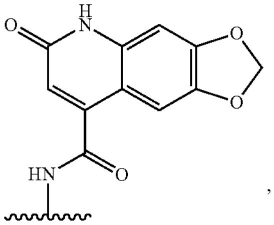
,
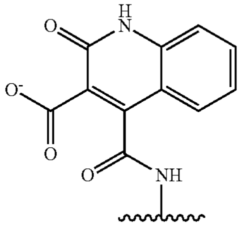
,
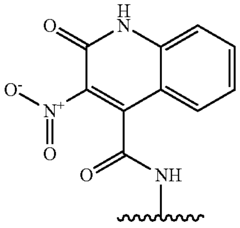
, or
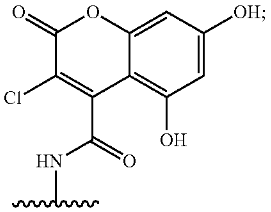
Preferably, $R^1$ can be specifically:
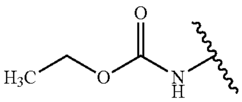
,
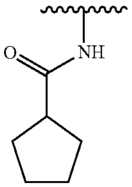
,
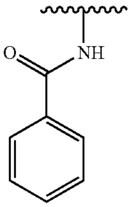
,
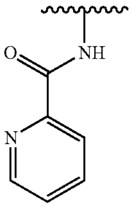
,
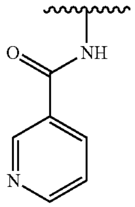
,
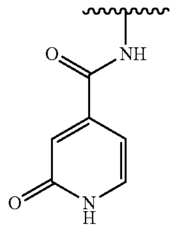
,
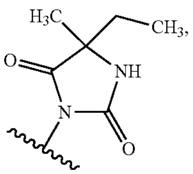
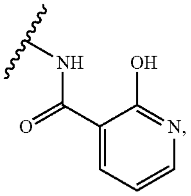
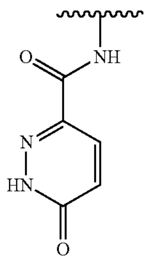
,
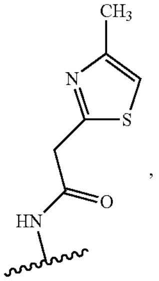
,
-continued
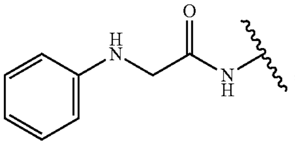
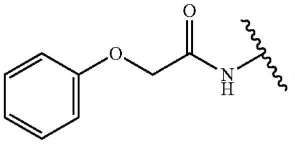
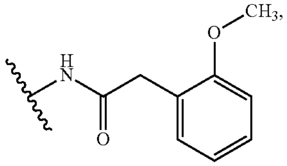
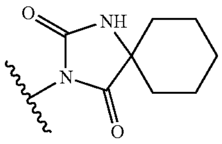
,
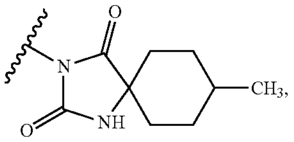
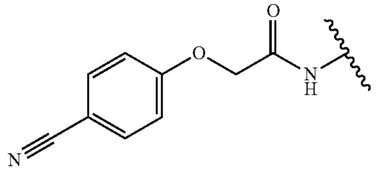
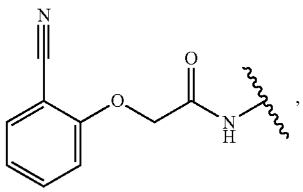
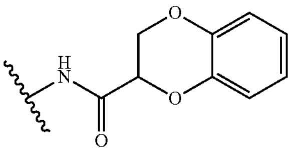
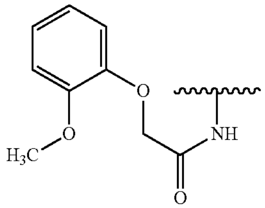
,
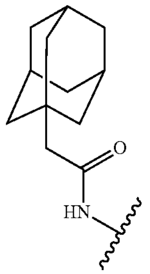
,
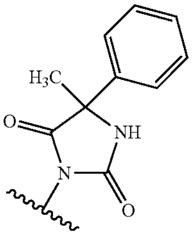
,
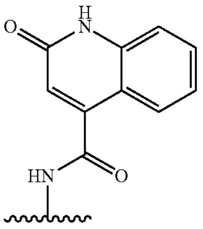
, -continued
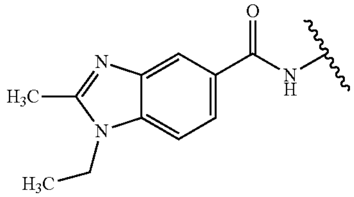
,
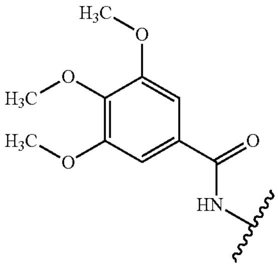
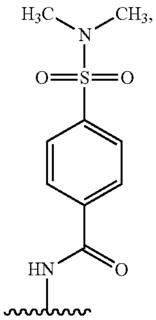
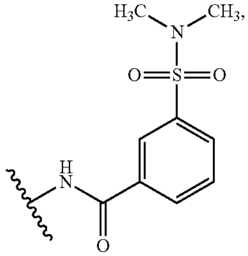
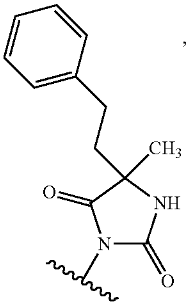
,
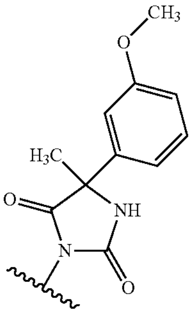
,
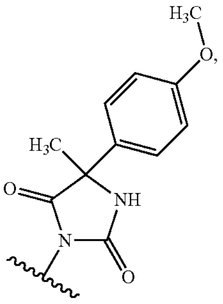
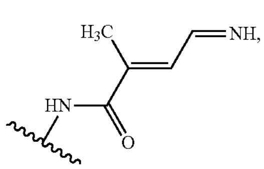
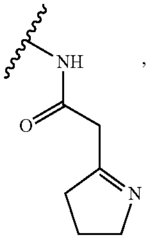
,
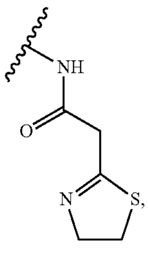
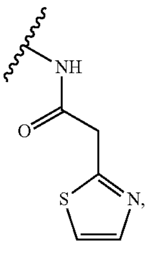
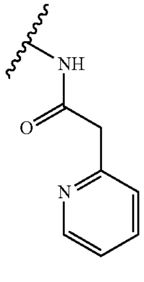
,
-continued
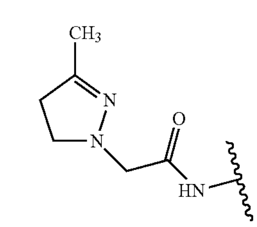
,
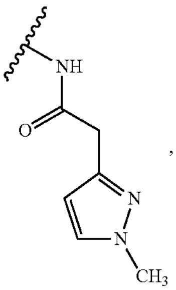
,
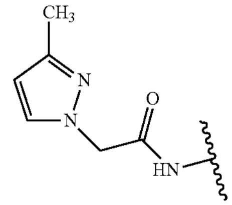
,
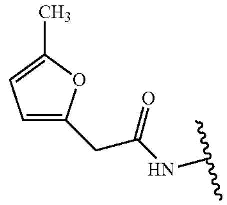
,
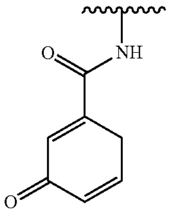
,
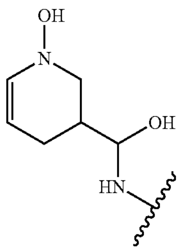
,
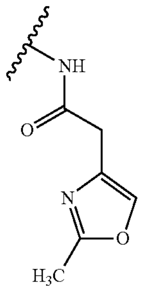
,
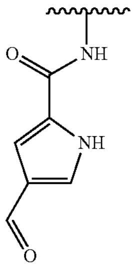
,
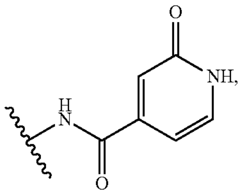
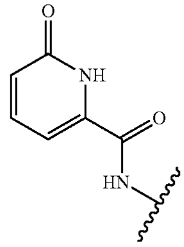
,
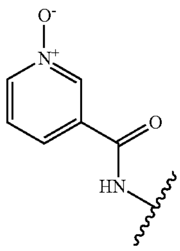
,
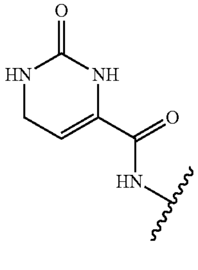
,
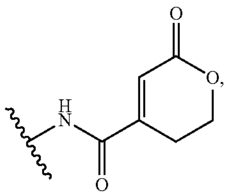

-continued
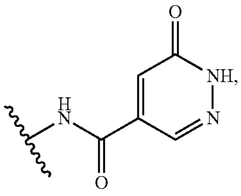
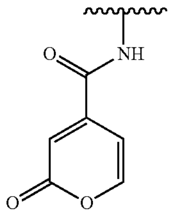
,
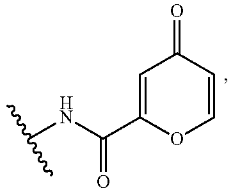
,
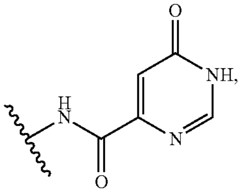
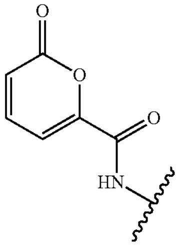
,
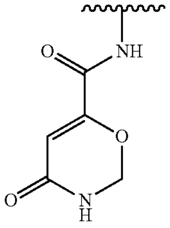
,
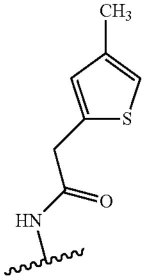
,
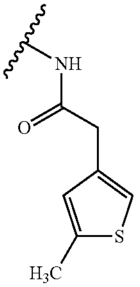
,
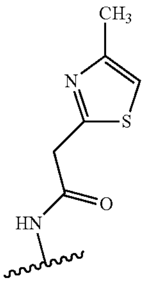
,
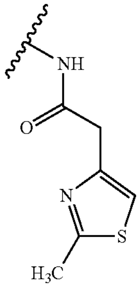
,
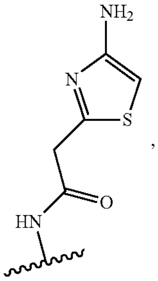
,
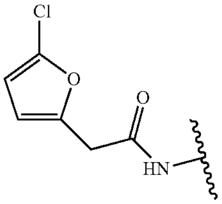
,
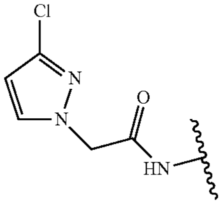
,
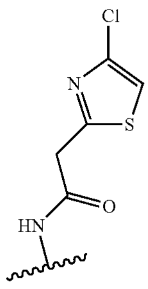
,
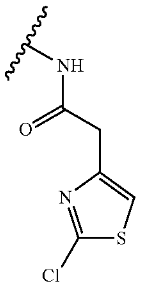
,
-continued
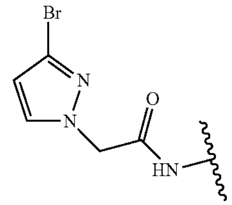
,
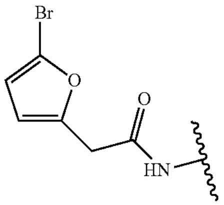
,
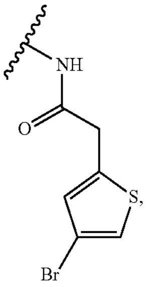
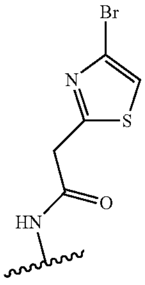
,
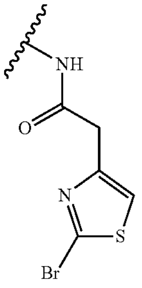
,
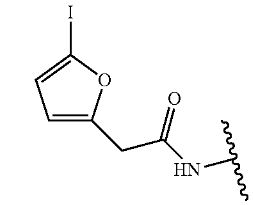
,
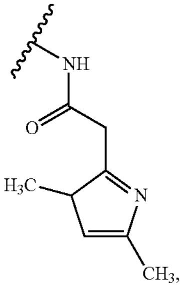
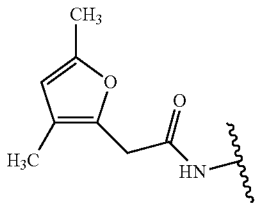
,
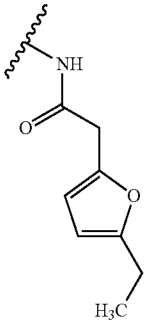
,
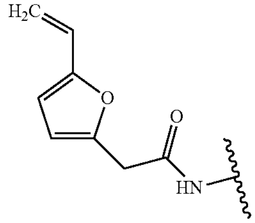
,
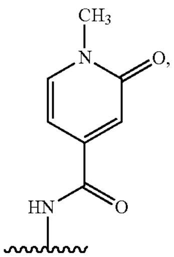
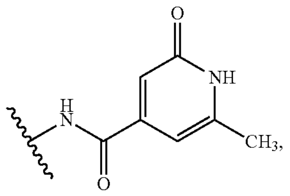
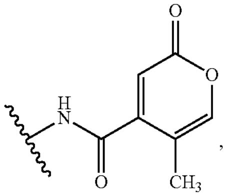
, -continued
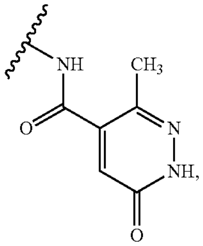
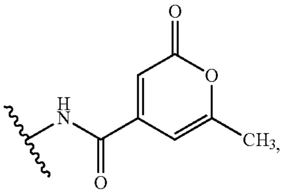
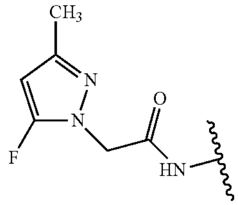
,
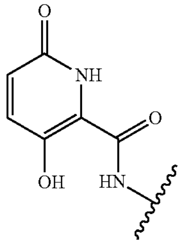
,
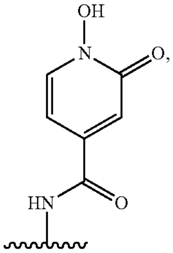
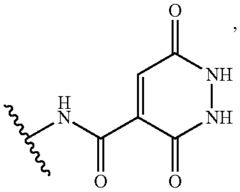
,
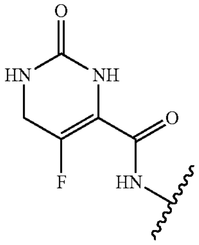
,
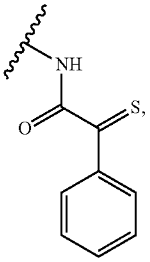
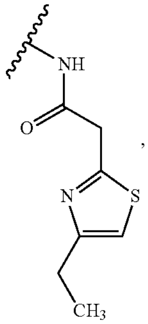
,
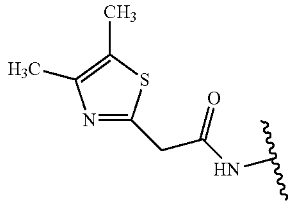
,
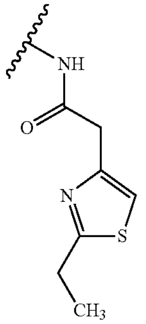
,
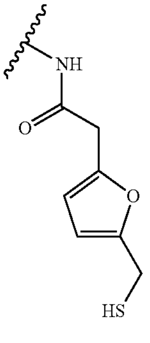
,
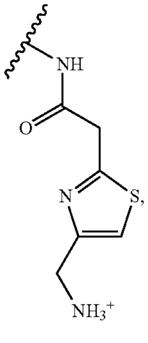
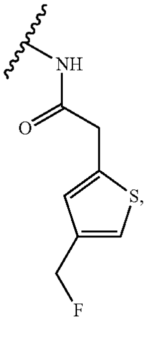
-continued
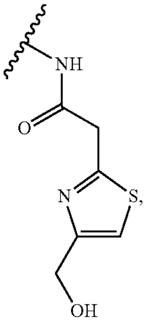
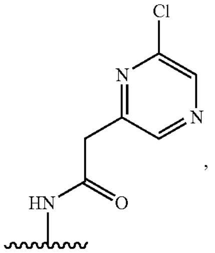
,
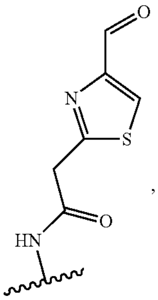
,
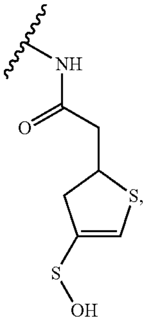
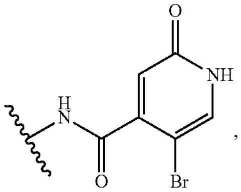
,
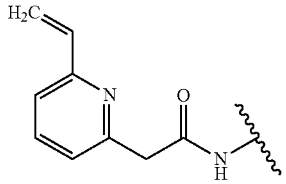
,
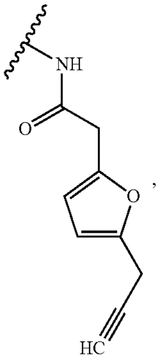
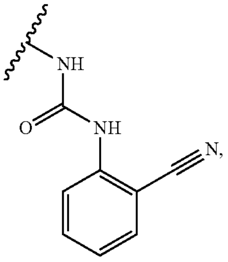
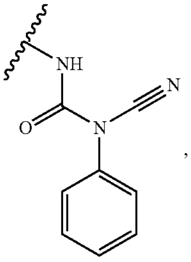
,
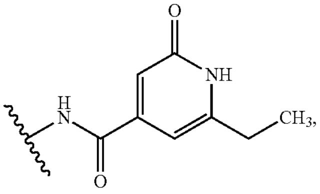

-continued
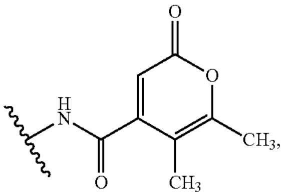
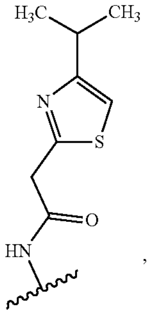
,
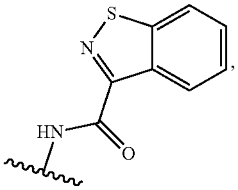
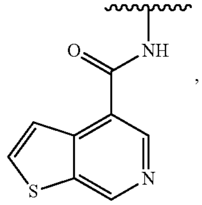
,
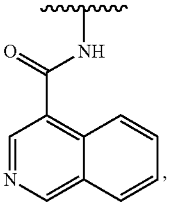
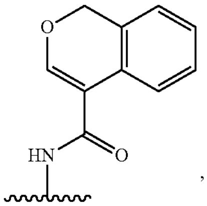
,
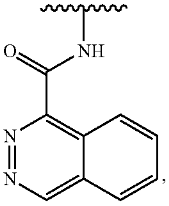
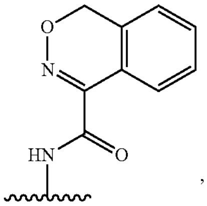
,
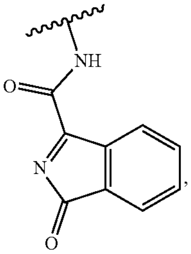
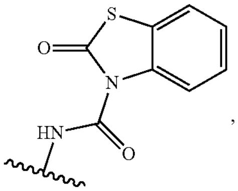
,
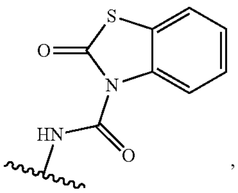
,
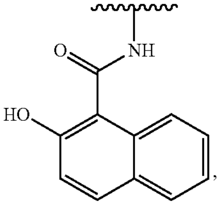
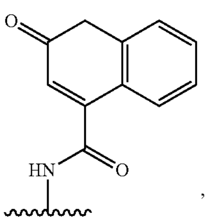
,
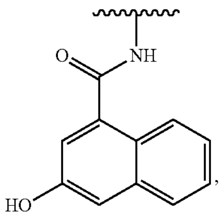
-continued
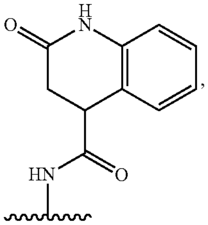
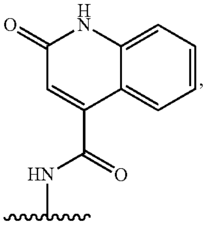
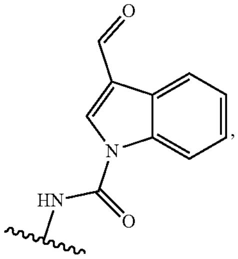
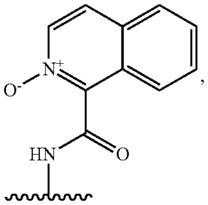
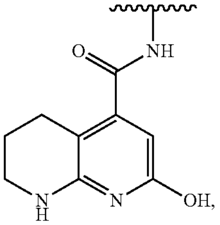
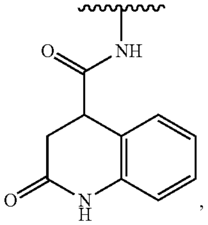
,
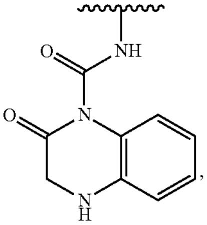
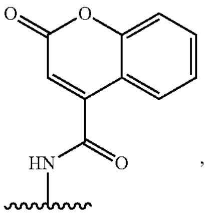
,
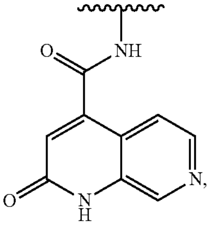
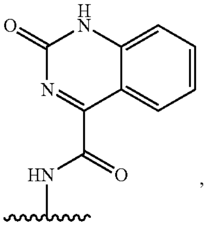
,
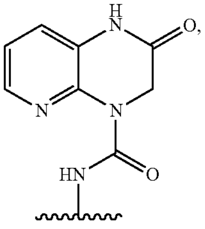
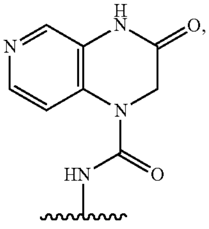
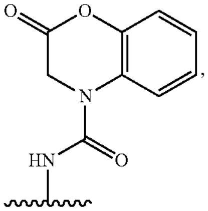
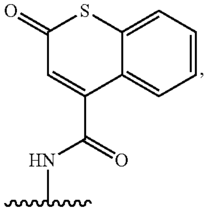

-continued
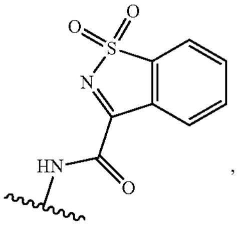
,
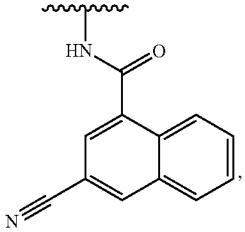
,
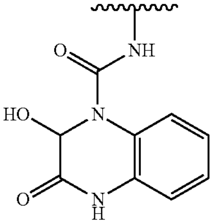
,
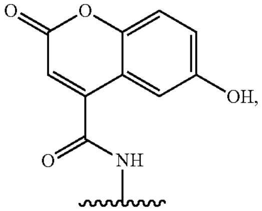
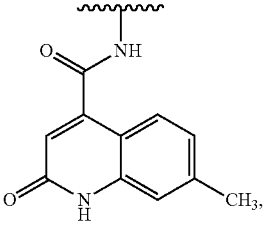
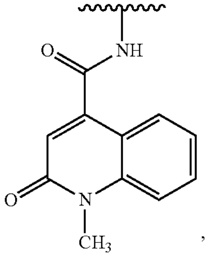
,
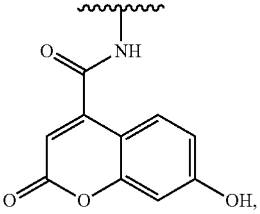
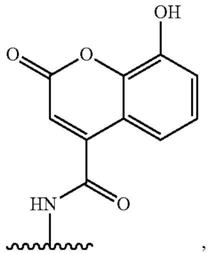
,
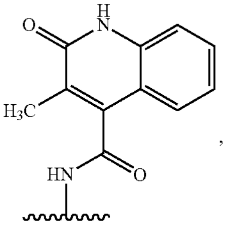
,
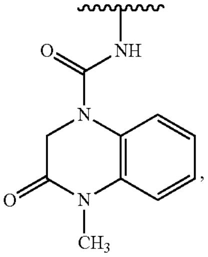
,
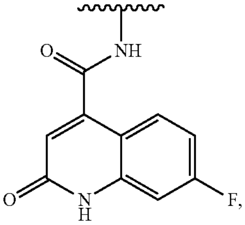
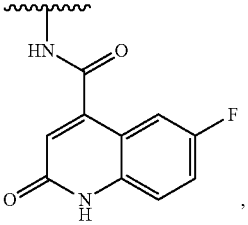
,
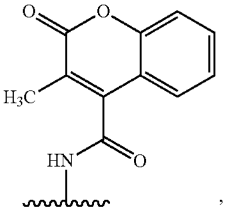
,
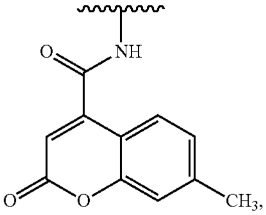
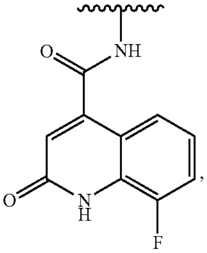
,
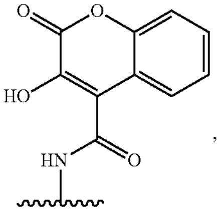
,
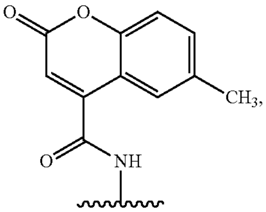
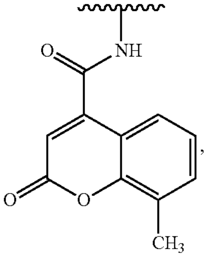
,
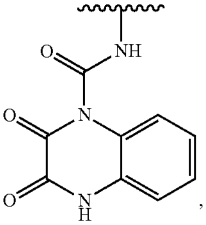
,
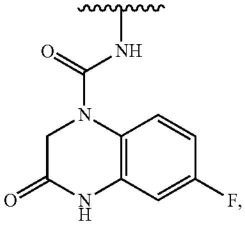
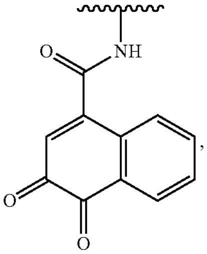
,
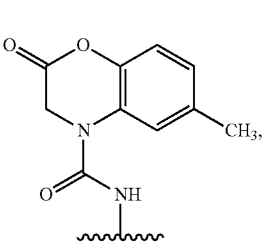
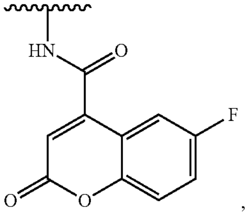
,
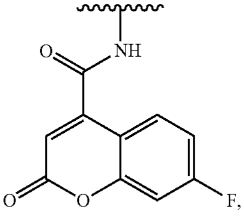
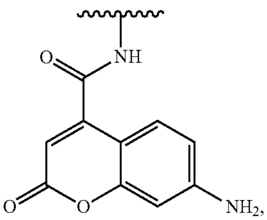
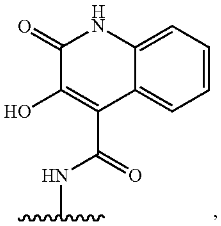
,
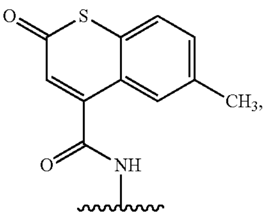
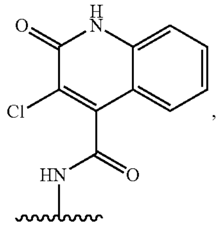
, -continued
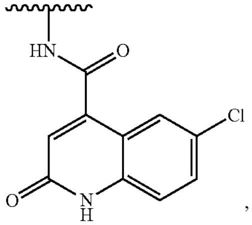
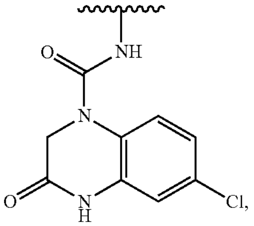
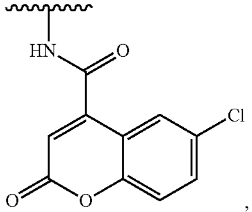
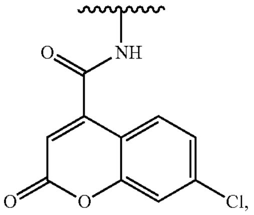
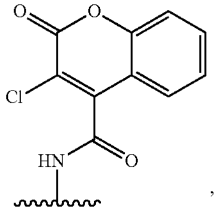
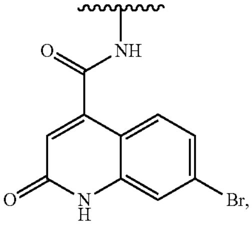
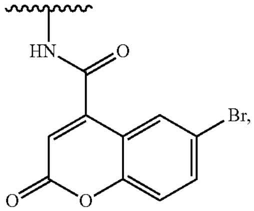
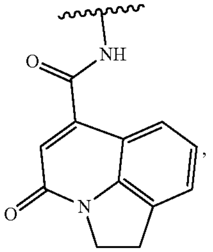
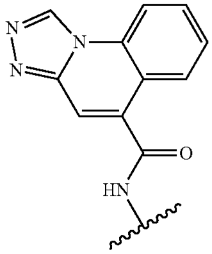
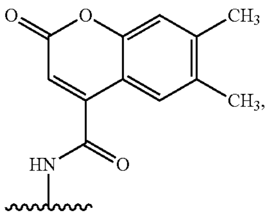
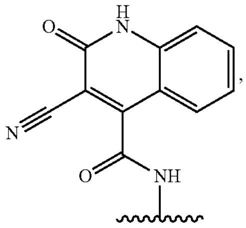
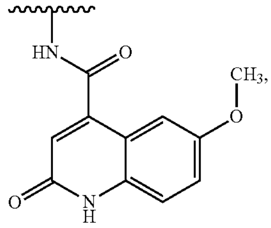
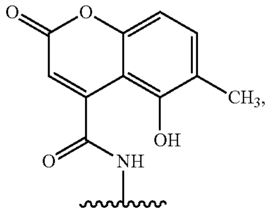
-continued
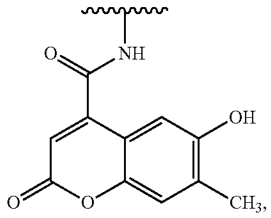
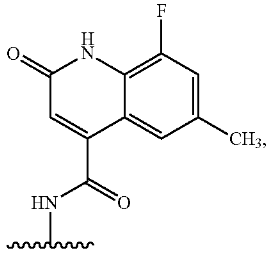
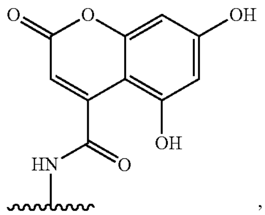
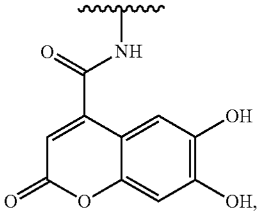
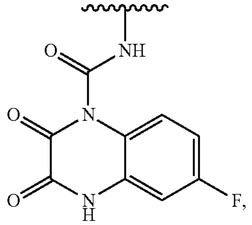
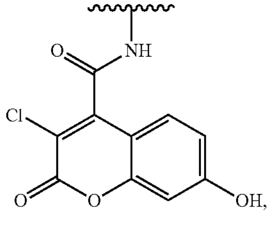
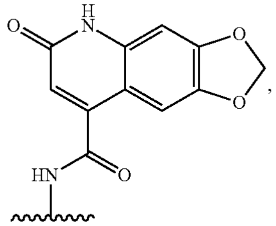
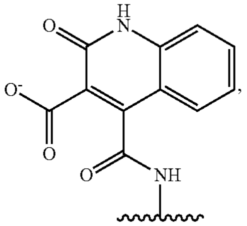
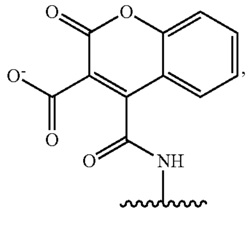
or
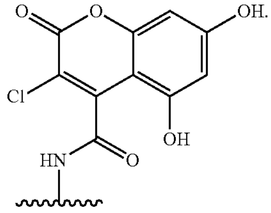

Further preferably, $R^1$ can be specifically:
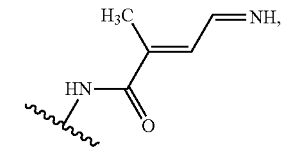
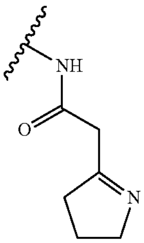
,
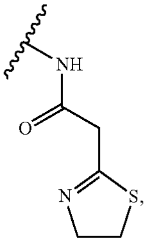
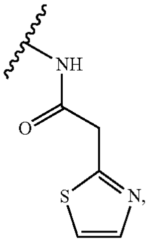
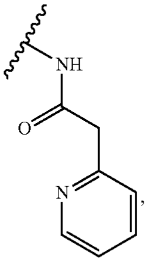
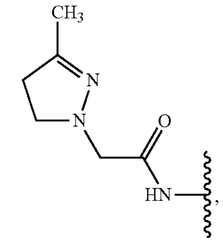
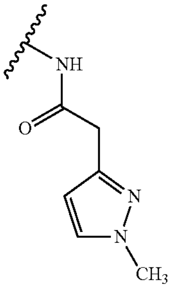
,
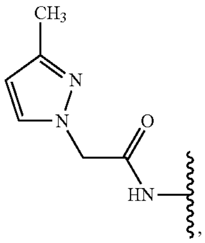
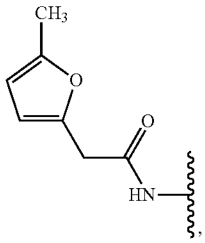
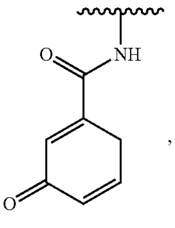
,
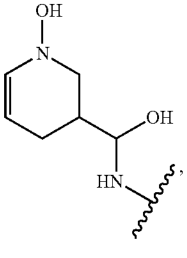
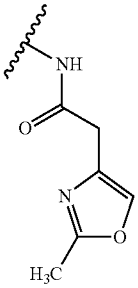
,
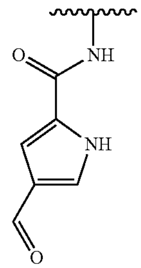
,
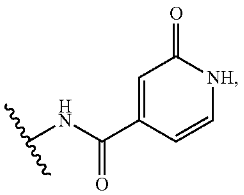
-continued
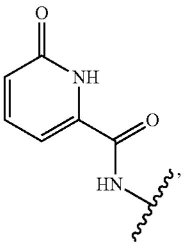
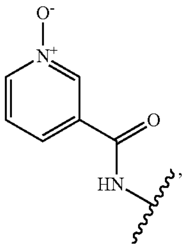
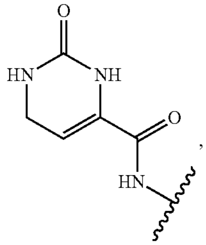
,
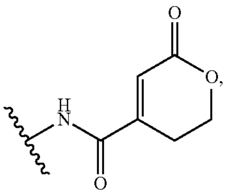
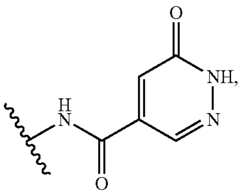
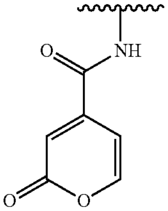
,
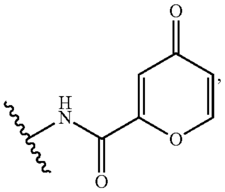
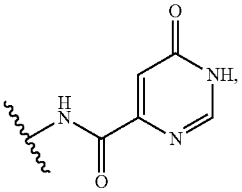
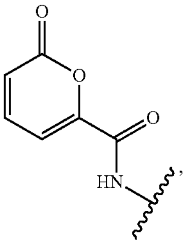
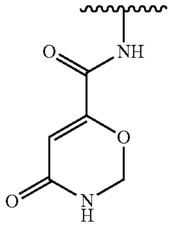
,
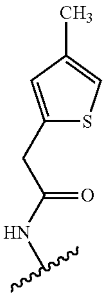
,
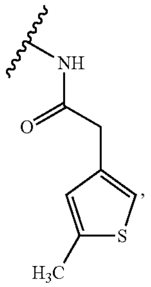
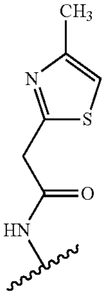
,
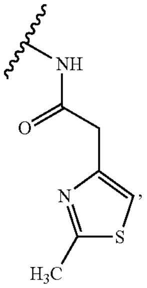

-continued
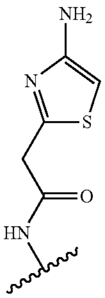,
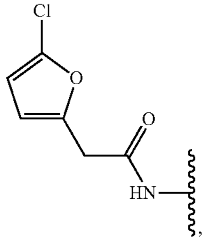,
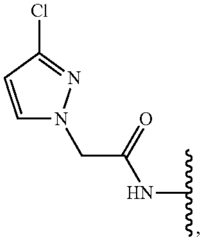,
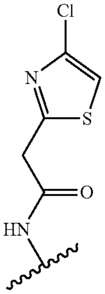,
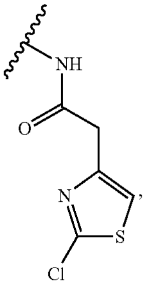,
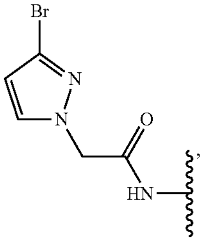,
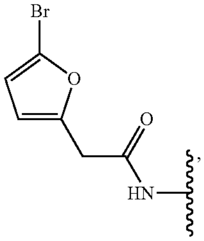,
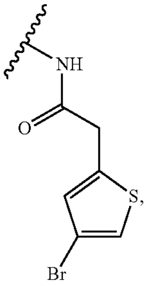,
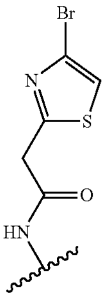,
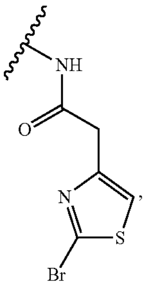,
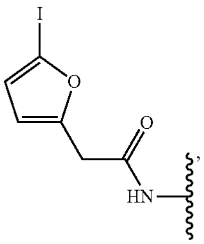,
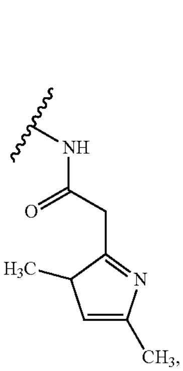,
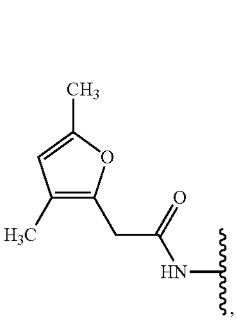,
-continued
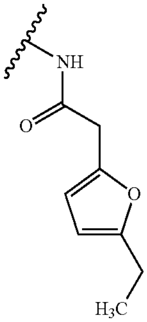,
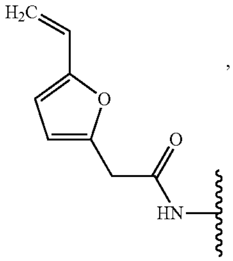,
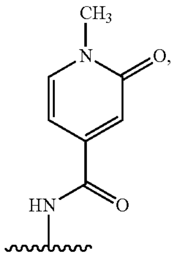,
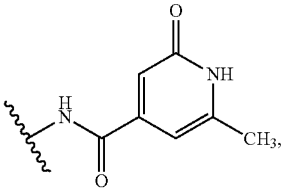,
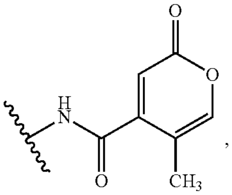,
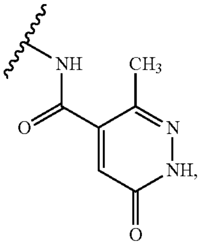,
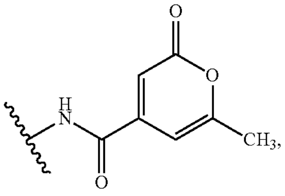,
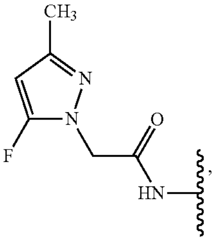,
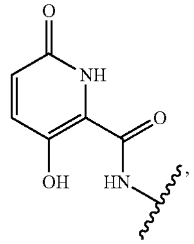,
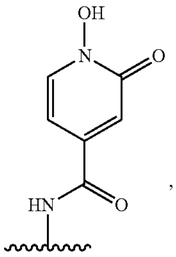,
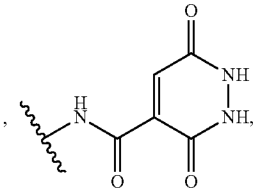,
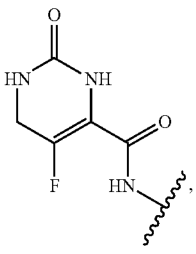,
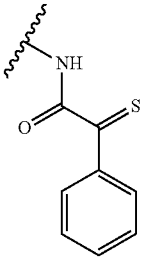,
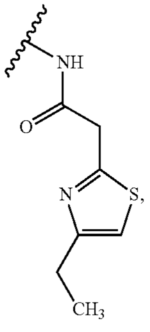

-continued
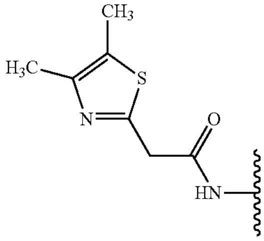,
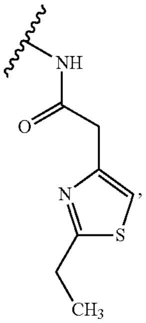
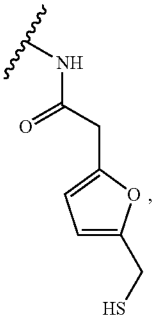
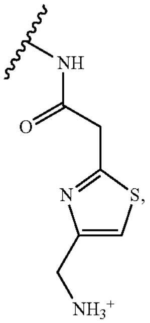
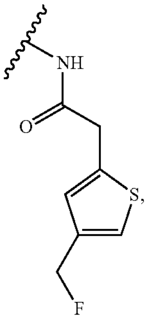
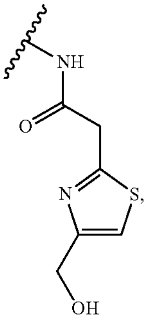
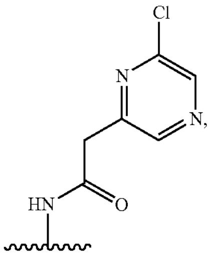
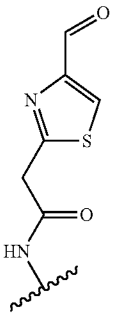,
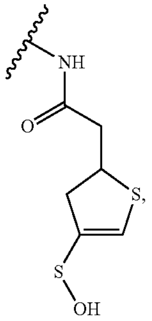
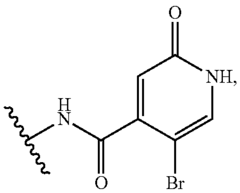
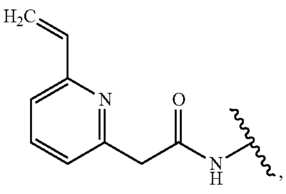
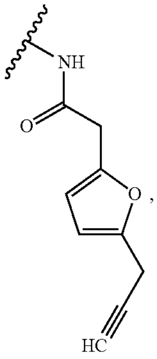
-continued
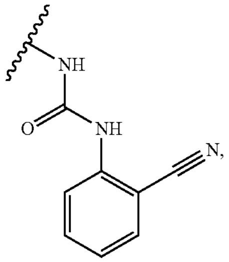
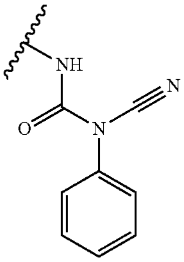,
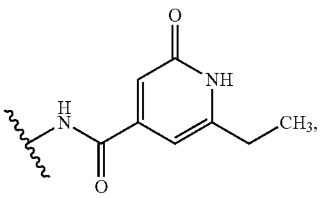
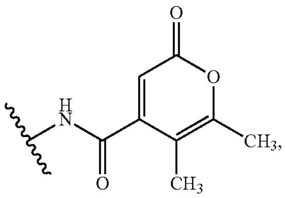
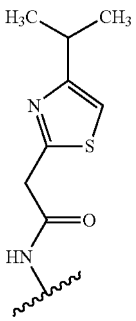,
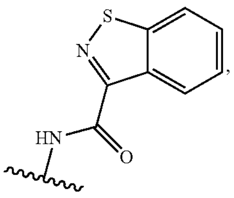
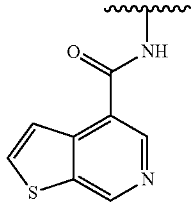,
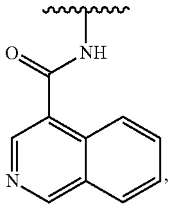
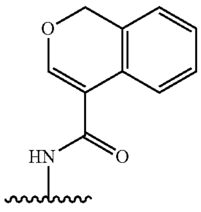,
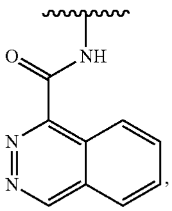
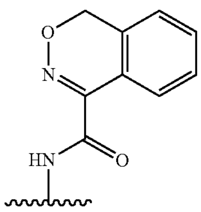,
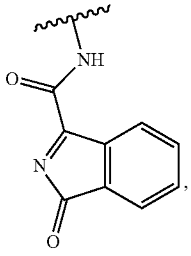
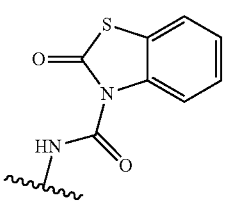, -continued
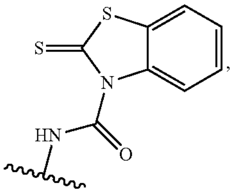,
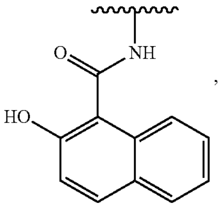,
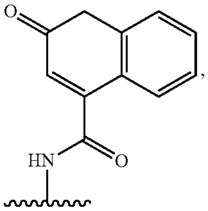,
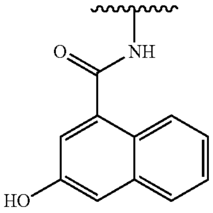,
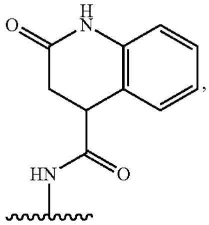,
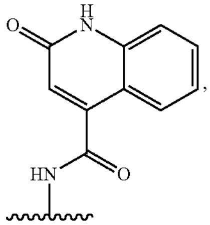,
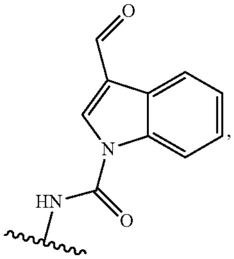,
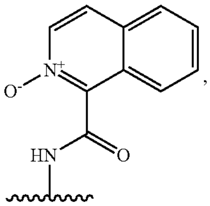,
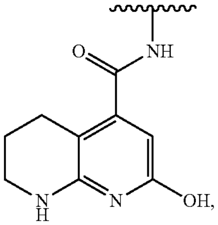,
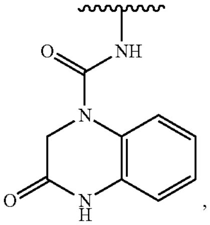,
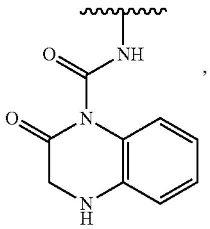,
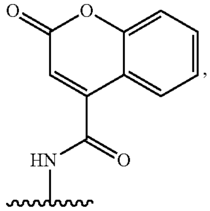,
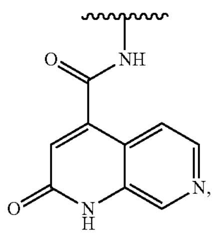,
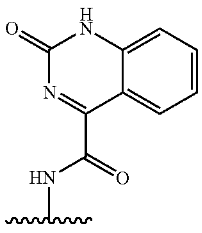,
-continued
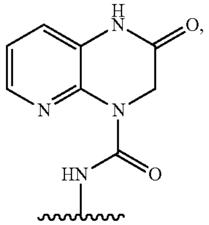
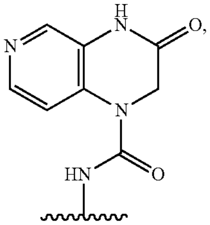
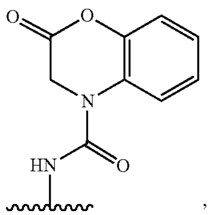,
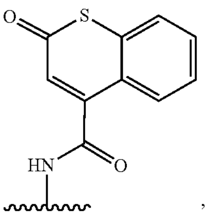,
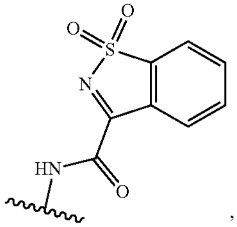,
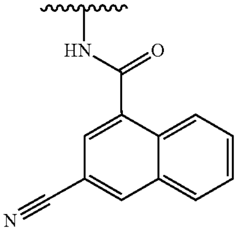,
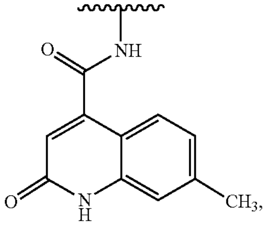,
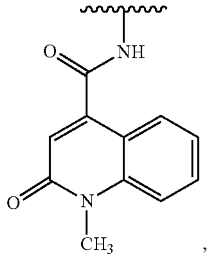,
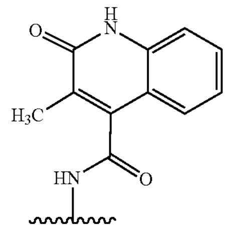,
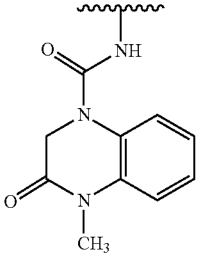,
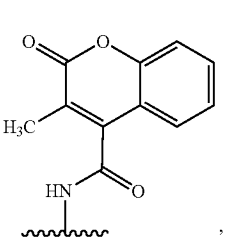,
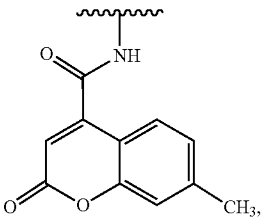

-continued
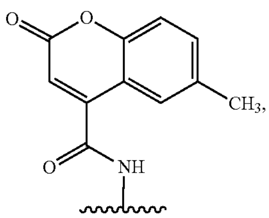
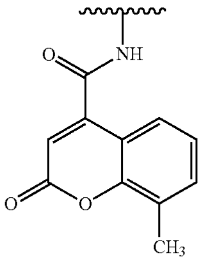
,
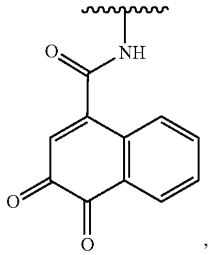
,
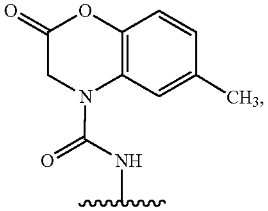
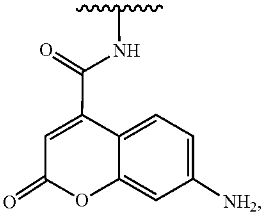
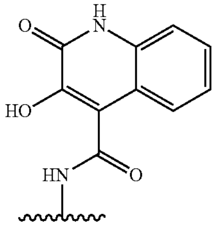
,
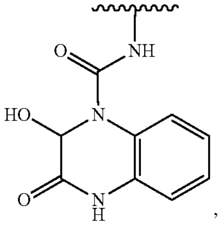
,
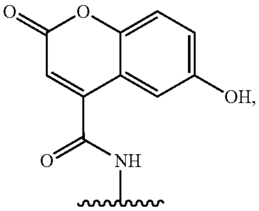
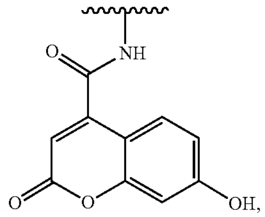
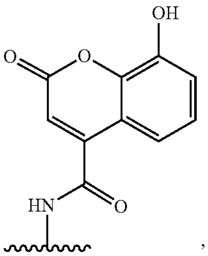
,
-continued
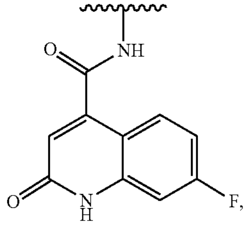
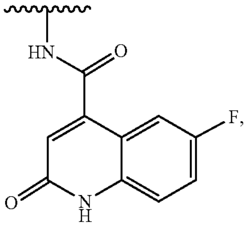
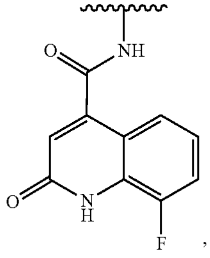
,
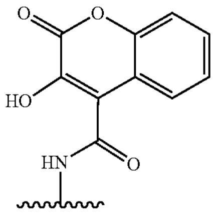
,
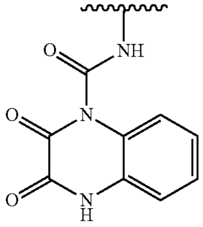
,
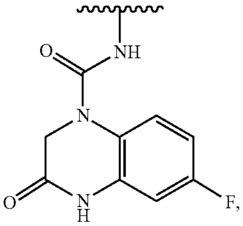
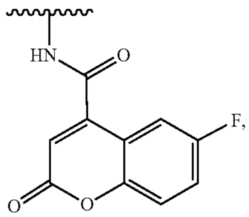
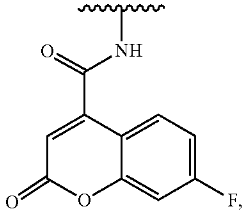
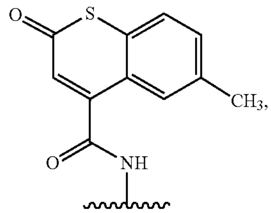
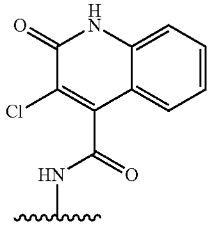
,
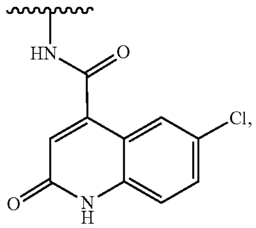
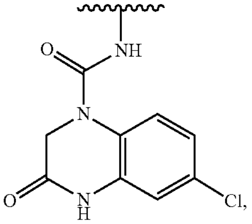

-continued
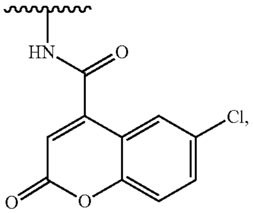
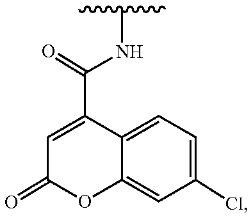
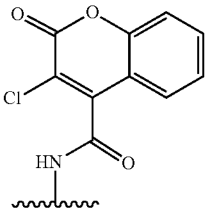
,
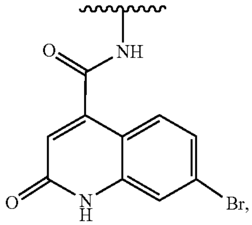
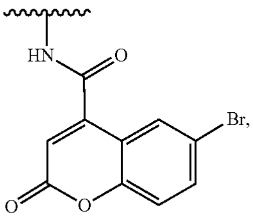
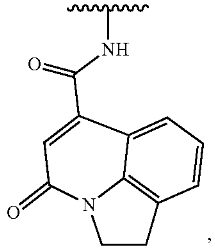
,
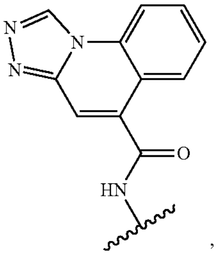
,
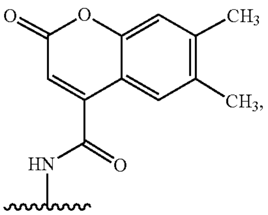
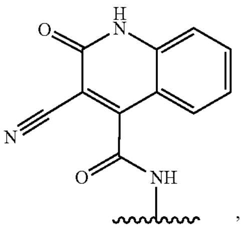
,
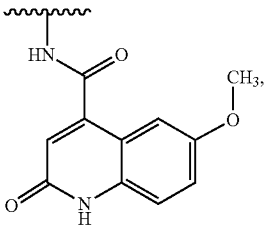
-continued
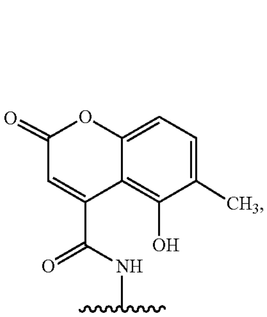
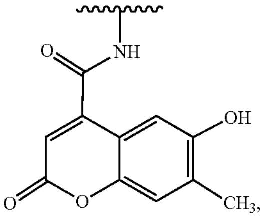
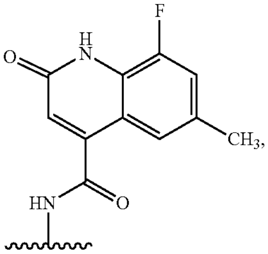
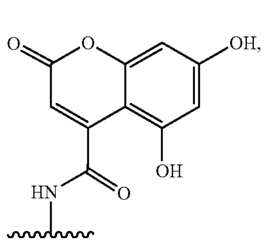
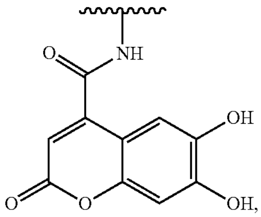
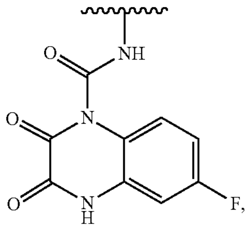
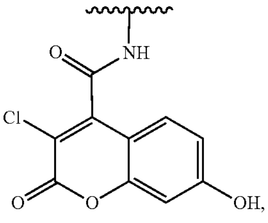
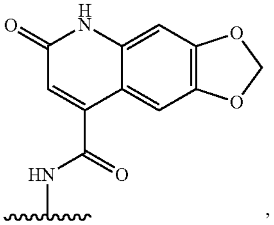
,
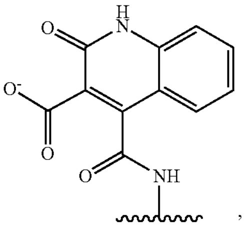
,
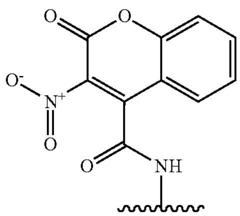
, or
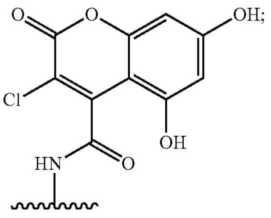

Further preferably, $R^1$ can be specifically:
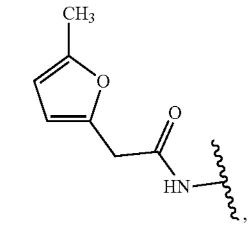, 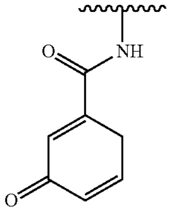,
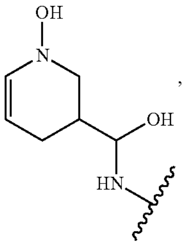, 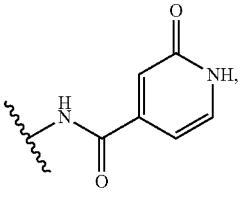
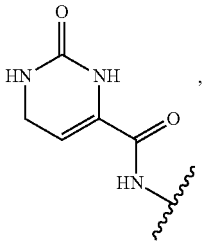, 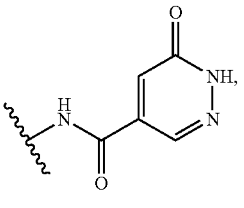
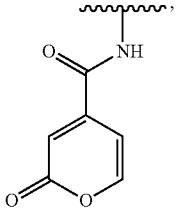, 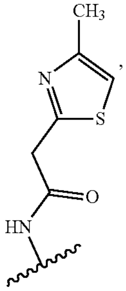, 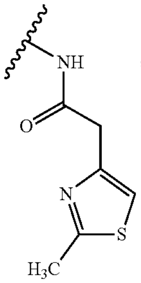,
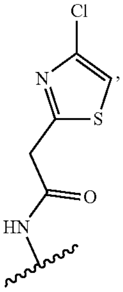, 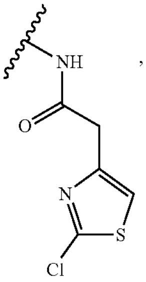, 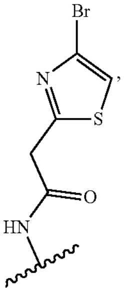
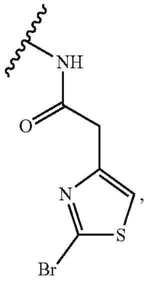 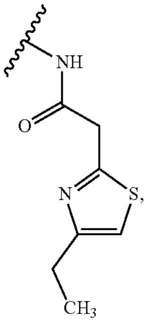 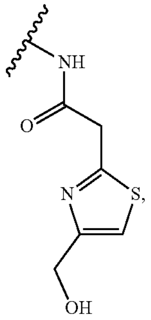
-continued
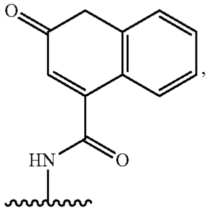 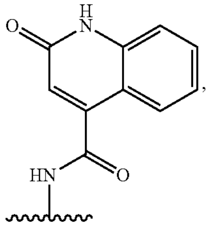
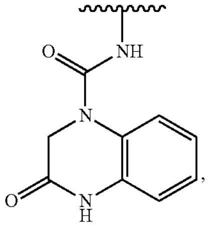 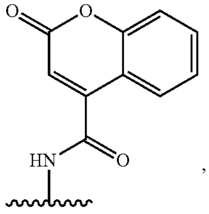,
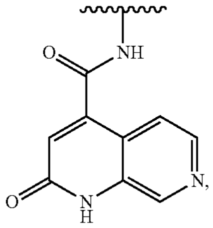 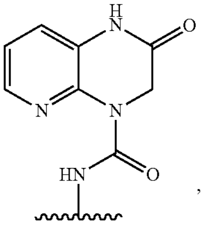,
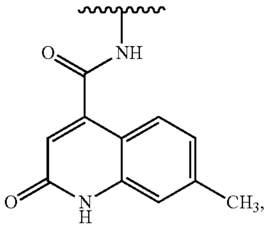 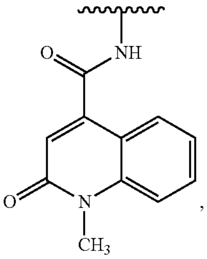,
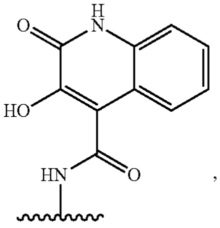, 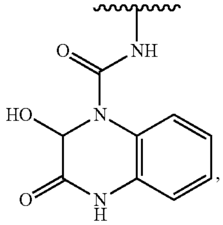
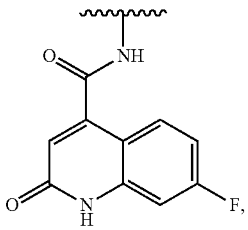 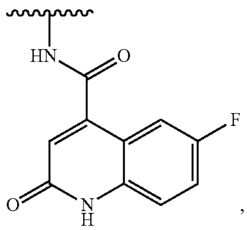, -continued

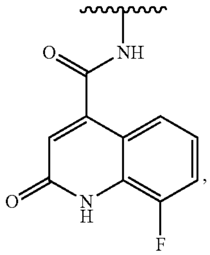
,
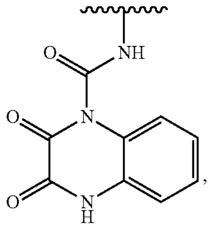
,
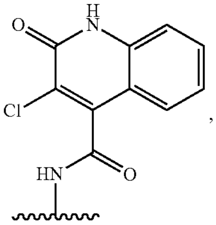
, or
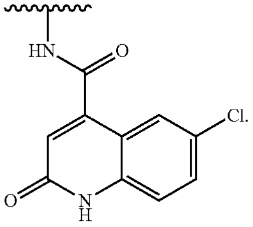

Further preferably, $R^1$ can be specifically:

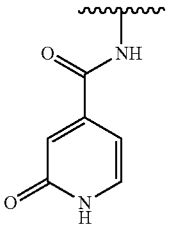
,
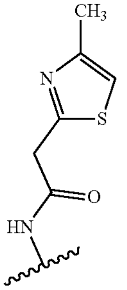
, or
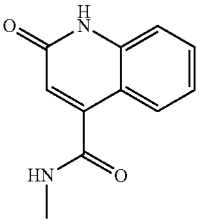
.

In a specific embodiment, the diphenylpyrazole-based compound of following formula (I) or its pesticidally acceptable salts is the following compound or its pesticidally acceptable salts:

| Name | Structure | Number |
|---|---|---|
| N'-(1,3-diphenyl-1H-pyrazol-5-yl-carbonyl)-2-oxo-1,2-dihydropyridinyl-4-carbohydrazide | 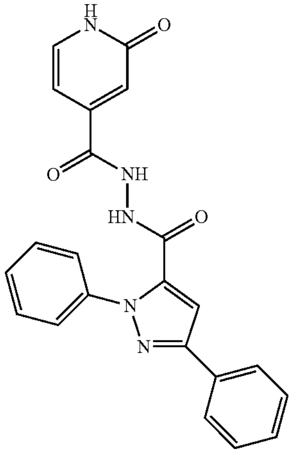 [SMILES: O=C(NNC(=O)c1cc(-c2ccccc2)nn1-c1ccccc1)c1cc[nH]c(=O)c1] | PXG1 |
| N'-[2-(4-methyl-1,3-thiazol-2-yl)acetyl]-1,3-diphenyl-1H-pyrazol-5-yl-carbohydrazide | 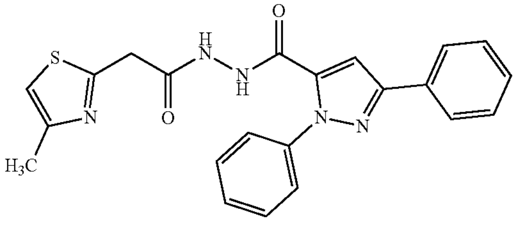 [SMILES: Cc1csc(CC(=O)NNC(=O)c2cc(-c3ccccc3)nn2-c2ccccc2)n1] | PXG2 |
| N'-(1,3-diphenyl-1H-pyrazol-5-yl-carbonyl)-2-(phenylamino) acetohydrazide | 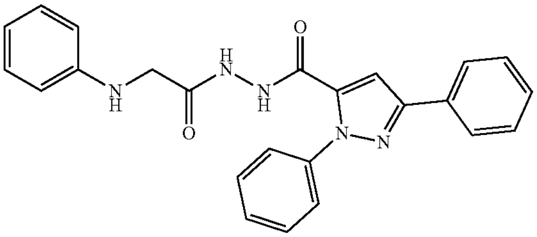 [SMILES: O=C(CNc1ccccc1)NNC(=O)c1cc(-c2ccccc2)nn1-c1ccccc1] | PXG3 |

-continued
| Name | Structure | Number |
|---|---|---|
| N'-(1,3-diphenyl-1H-pyrazol-5-yl-carbonyl)-3,4,5-trimethoxybenzohydrazine | 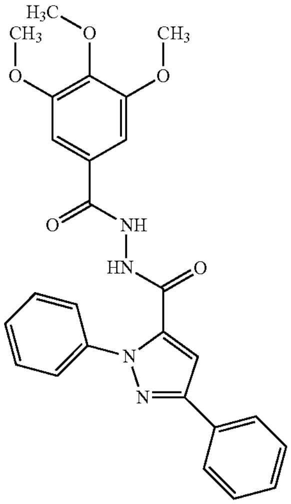 [SMILES: COc1cc(C(=O)NNC(=O)c2cc(-c3ccccc3)nn2-c2ccccc2)cc(OC)c1OC] | PXG4 |
| N'-(1,3-diphenyl-1H-pyrazol-5-yl-carbonyl)-2-phenoxyacetohydrazide | 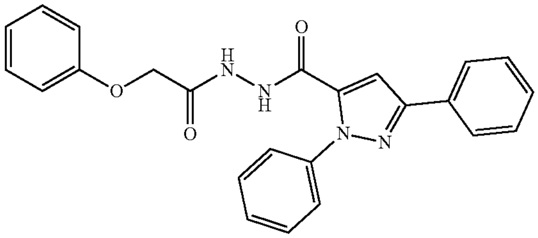 [SMILES: O=C(COc1ccccc1)NNC(=O)c1cc(-c2ccccc2)nn1-c1ccccc1] | PXG5 |
| N-{2,4-dioxa-1,3-diazaspiro[4.5]dec-3-yl}-1,3-diphenyl-1H-pyrazol-5-yl-carboxamide | 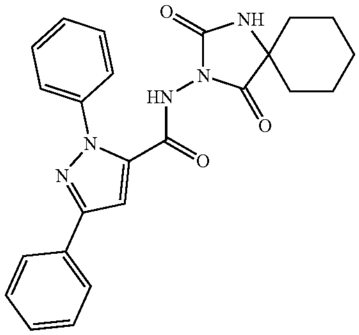 [SMILES: O=C(NN1C(=O)NC2(CCCCC2)C1=O)c1cc(-c2ccccc2)nn1-c1ccccc1] | PXG6 |
| N'-[3-(4-chlorophenyl)-1-phenyl-1H-pyrazol-5-yl-carbonyl]pyridin-3-yl-carbohydrazide | 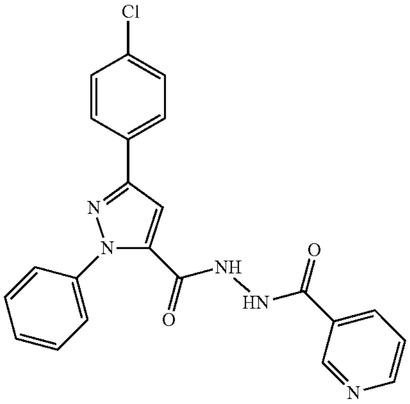 [SMILES: O=C(NNC(=O)c1cc(-c2ccc(Cl)cc2)nn1-c1ccccc1)c1cccnc1] | PXG7 |

-continued
| Name | Structure | Number |
|---|---|---|
| (2S)-N'-(1,3-diphenyl-1H-pyrazol-5-yl-carbonyl)-2,3-dihydro-1,4-benzodioxin-2-yl-carbohydrazide | 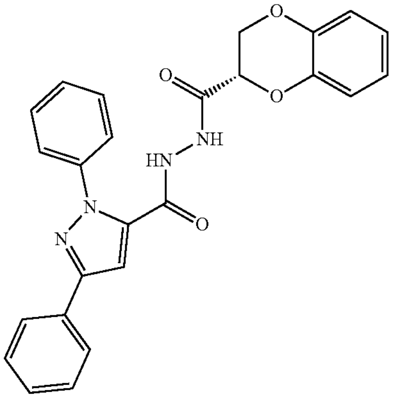 [SMILES: O=C(NNC(=O)[C@@H]1COc2ccccc2O1)c1cc(-c2ccccc2)nn1-c1ccccc1] | PXG8 |
| 3-[N'-(1,3-diphenyl-1H-pyrazol-5-yl-carbonyl) hydrazinocarbonyl]-N,N-dimethylphenyl-1-sulfonamide | 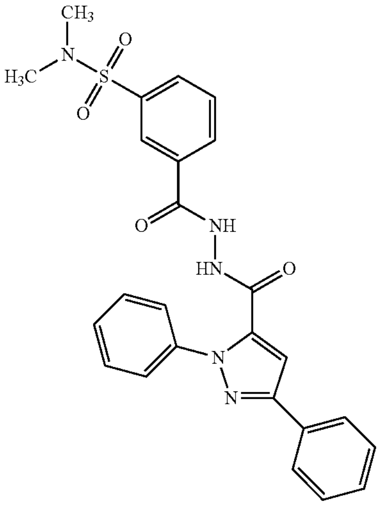 [SMILES: CN(C)S(=O)(=O)c1cccc(C(=O)NNC(=O)c2cc(-c3ccccc3)nn2-c2ccccc2)c1] | PXG9 |
| N'-(1,3-diphenyl-1H-pyrazol-5-yl-carbonyl)-2-(2-methoxyphenyl) acetohydrazide | 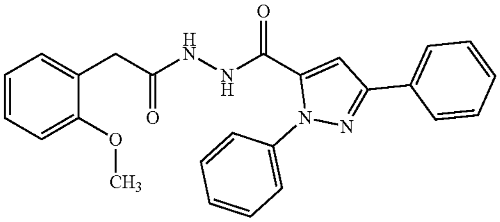 [SMILES: COc1ccccc1CC(=O)NNC(=O)c1cc(-c2ccccc2)nn1-c1ccccc1] | PXG10 |
| N'-(1,3-diphenyl-1H-pyrazol-5-yl-carbonyl) benzohydrazine | 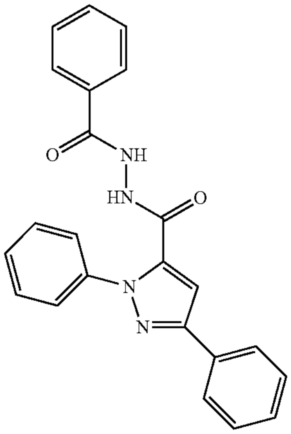 [SMILES: O=C(NNC(=O)c1cc(-c2ccccc2)nn1-c1ccccc1)c1ccccc1] | PXG11 |

-continued
| Name | Structure | Number |
|---|---|---|
| N-(4-methyl-2,5-dioxo-4-phenylimidazolin-1-yl)-1,3-diphenyl-1H-pyrazol-5-yl-carboxamide | 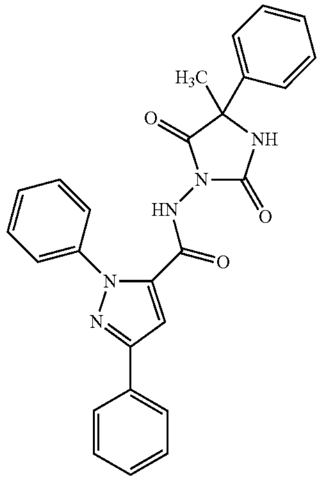 [SMILES: CC1(c2ccccc2)NC(=O)N(NC(=O)c2cc(-c3ccccc3)nn2-c2ccccc2)C1=O] | PXG12 |
| N-(4-ethyl-4-methyl-2,5-dioxaimidazolin-1-yl)-1,3-diphenyl-1H-pyrazol-5-yl-carboxamide | 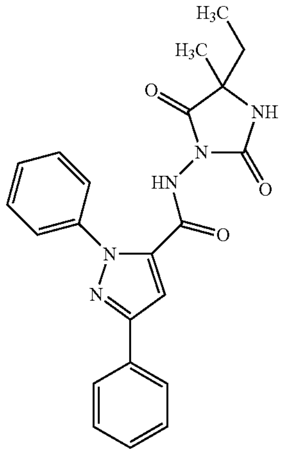 [SMILES: CCC1(C)NC(=O)N(NC(=O)c2cc(-c3ccccc3)nn2-c2ccccc2)C1=O] | PXG13 |
| N-[4-(4-methoxyphenyl)-4-methyl-2,5-dioxaimidazolin-1-yl]-1,3-diphenyl-1H-pyrazol-5-yl-carboxamide | 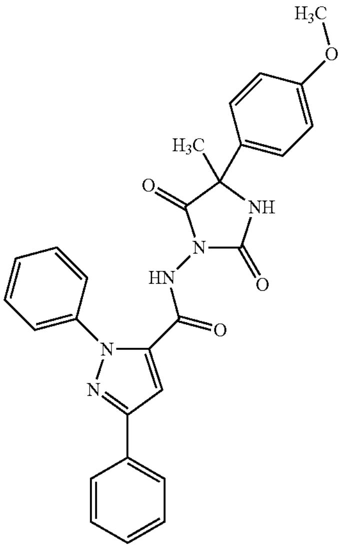 [SMILES: COc1ccc(C2(C)NC(=O)N(NC(=O)c3cc(-c4ccccc4)nn3-c3ccccc3)C2=O)cc1] | PXG14 |

-continued
| Name | Structure | Number |
|---|---|---|
| N-[4-methyl-2,5-dioxo-4-(2-phenylethyl)imidazolin-1-yl]-1,3-diphenyl-1H-pyrazol-5-yl-carboxamide | 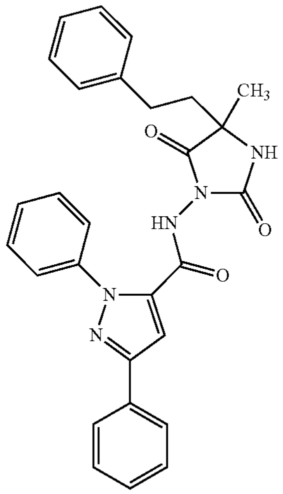 [SMILES: CC1(CCc2ccccc2)NC(=O)N(NC(=O)c2cc(-c3ccccc3)nn2-c2ccccc2)C1=O] | PXG15 |
| N-{8-methyl-2,4-dioxo-1,3-diazaspiro[4.5]dec-3-yl}-1,3-diphenyl-1H-pyrazol-5-yl-carboxamide | 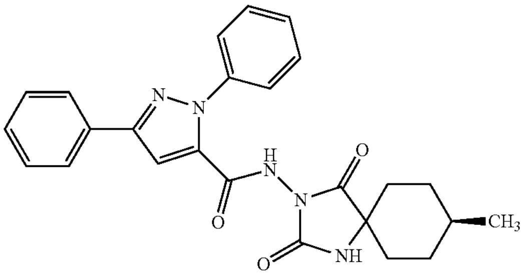 | PXG16 |
| N-[4-(3-methoxyphenyl)-4-methyl-2,5-dioxaimidazolin-1-yl]-1,3-diphenyl-1H-pyrazol-5-yl-carboxamide | 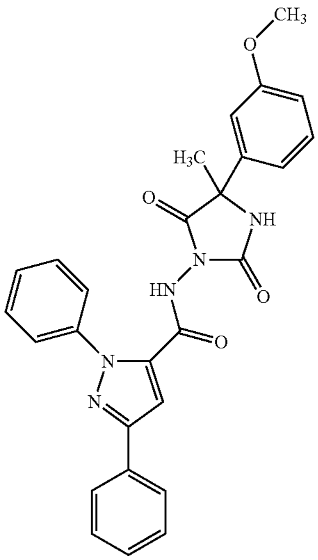 [SMILES: COc1cccc(C2(C)NC(=O)N(NC(=O)c3cc(-c4ccccc4)nn3-c3ccccc3)C2=O)c1] | PXG17 |
| N'-(1,3-diphenyl-1H-pyrazol-5-yl-carbonyl)-2-(2-methoxyphenoxy)acetohydrazide | 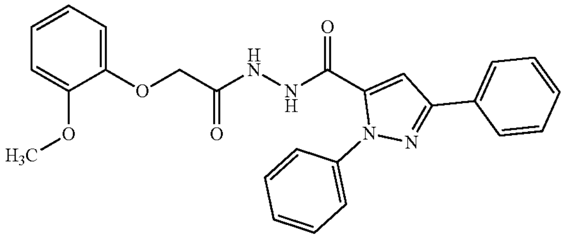 [SMILES: COc1ccccc1OCC(=O)NNC(=O)c1cc(-c2ccccc2)nn1-c1ccccc1] | PXG18 |

-continued
| Name | Structure | Number |
| --- | --- | --- |
| 2-(4-cyanophenoxy)-N'-(1,3-diphenyl-1H-pyrazol-5-yl-carbonyl)acetohydrazide | 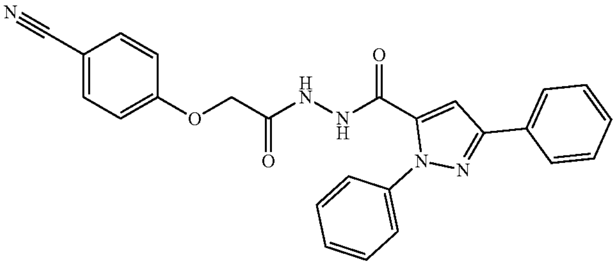 [SMILES: N#Cc1ccc(OCC(=O)NNC(=O)c2cc(-c3ccccc3)nn2-c2ccccc2)cc1] | PXG19 |
| N'-[3-(4-chlorophenyl)-1-phenyl-1H-pyrazol-5-yl-carbonyl]pyridin-2-yl-carbohydrazide | 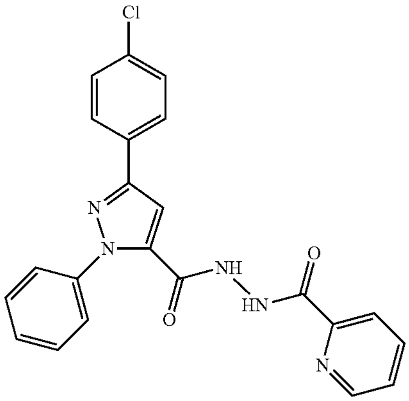 [SMILES: O=C(NNC(=O)c1cc(-c2ccc(Cl)cc2)nn1-c1ccccc1)c1ccccn1] | PXG20 |
| N'-(1-ethyl-2-methyl-1H-1,3-benzodiazol-5-yl-carbonyl)-1,3-diphenyl-1H-pyrazol-5-yl-carbohydrazide | 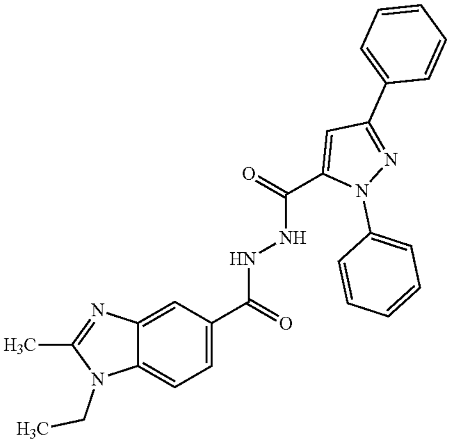 [SMILES: CCn1c(C)nc2cc(C(=O)NNC(=O)c3cc(-c4ccccc4)nn3-c3ccccc3)ccc21] | PXG21 |
| N'-(1,3-diphenyl-1H-pyrazol-5-yl-carbonyl)-2-oxo-1,2-dihydroquinoline-4-yl-carbohydrazide | 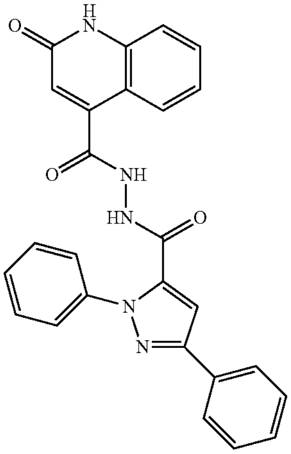 [SMILES: O=C(NNC(=O)c1cc(-c2ccccc2)nn1-c1ccccc1)c1cc(=O)[nH]c2ccccc12] | PXG22 |

-continued
| Name | Structure | Number |
| --- | --- | --- |
| 2-(2-cyanophenoxy)-N'-(1,3-diphenyl-1H-pyrazol-5-yl-carbonyl)acetohydrazide | 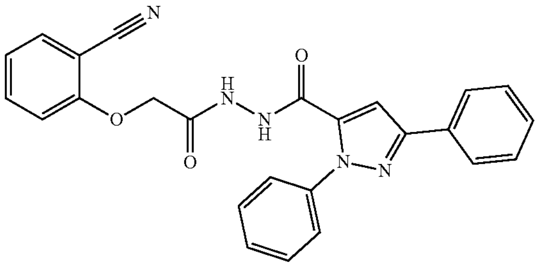 [SMILES: N#Cc1ccccc1OCC(=O)NNC(=O)c1cc(-c2ccccc2)nn1-c1ccccc1] | PXG23 |
| N'-(ethoxycarbonyl)-1,3-diphenyl-1H-pyrazol-5-yl-carbohydrazide | 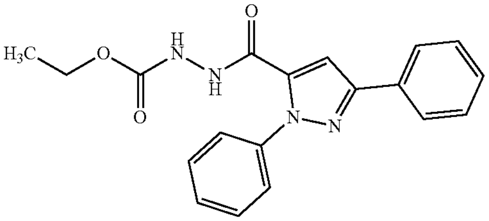 [SMILES: CCOC(=O)NNC(=O)c1cc(-c2ccccc2)nn1-c1ccccc1] | PXG24 |
| N'-(1,3-diphenyl-1H-pyrazol-5-yl-carbonyl)-2-hydroxypyridin-3-yl-carbohydrazide | 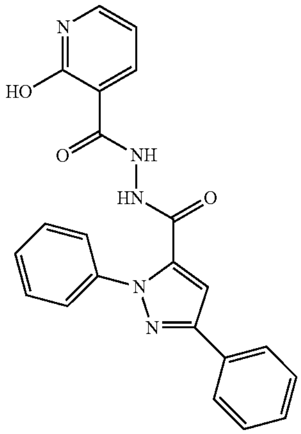 [SMILES: O=C(NNC(=O)c1cc(-c2ccccc2)nn1-c1ccccc1)c1cccnc1O] | PXG25 |
| N'-(1,3-diphenyl-1H-pyrazol-5-yl-carbonyl)-2-[(3r)-adamantan-1-yl]acetohydrazide | 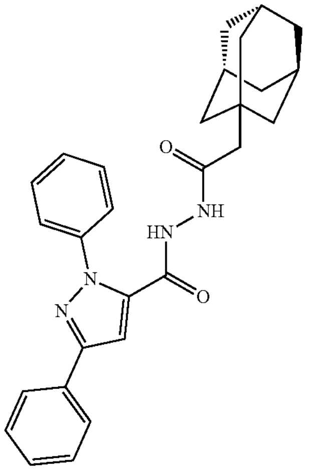 [SMILES: O=C(CC12C[C@H]3C[C@H](C1)C[C@@H](C2)C3)NNC(=O)c1cc(-c2ccccc2)nn1-c1ccccc1] | PXG26 |

-continued
| Name | Structure | Number |
| --- | --- | --- |
| N'-(1,3-diphenyl-1H-pyrazol-5-yl-carbonyl)-6-oxo-1,6-dihydropyridazin-3-yl-carbohydrazide | 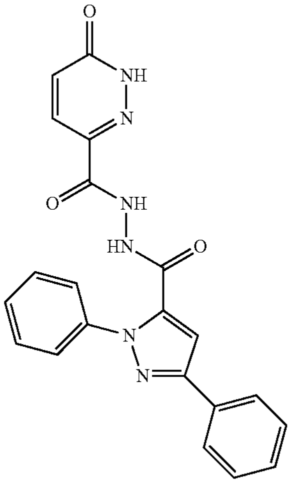 [SMILES: O=C(NNC(=O)c1cc(-c2ccccc2)nn1-c1ccccc1)c1ccc(=O)[nH]n1] | PXG27 |
| N'-(1,3-diphenyl-1H-pyrazol-5-yl-carbonyl) cyclopentyl carbohydrazide | 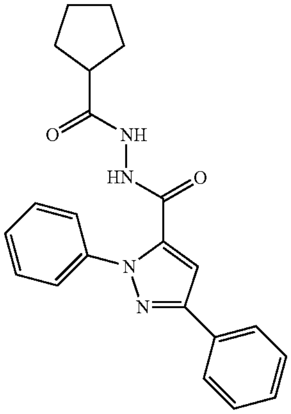 [SMILES: O=C(NNC(=O)C1CCCC1)c1cc(-c2ccccc2)nn1-c1ccccc1] | PXG28 |
| 4-[N'-(1,3-diphenyl-1H-pyrazol-5-yl-carbonyl) hydrazinocarbonyl]-N,N-dimethyl phenyl-1-sulfonamide | 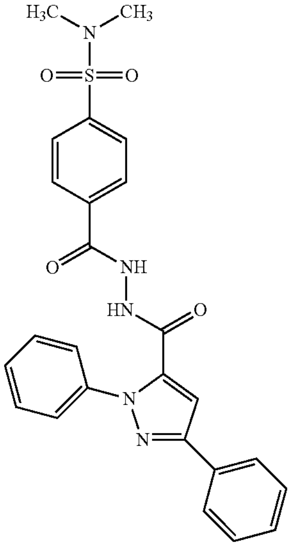 [SMILES: CN(C)S(=O)(=O)c1ccc(C(=O)NNC(=O)c2cc(-c3ccccc3)nn2-c2ccccc2)cc1] | PXG29 |

In the most preferably specific embodiment, the diphenylpyrazole-based compound of following formula (I) or its pesticidally acceptable salts is the following compound or its pesticidally acceptable salts:

| Structure | Number |
|---|---|
| 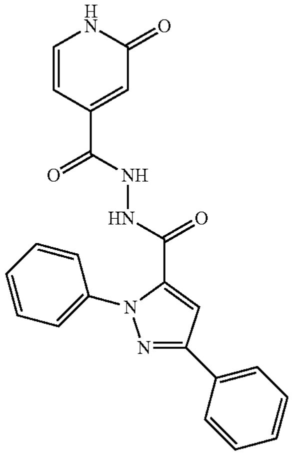 [SMILES: O=C(NNC(=O)c1cc(-c2ccccc2)nn1-c1ccccc1)c1cc[nH]c(=O)c1] | PXG1 |
| 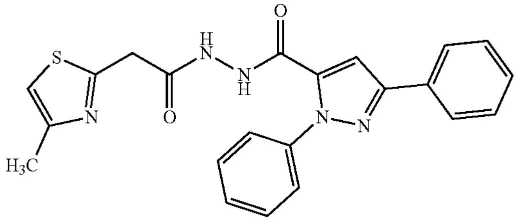 [SMILES: Cc1csc(CC(=O)NNC(=O)c2cc(-c3ccccc3)nn2-c2ccccc2)n1] | PXG2 |
| 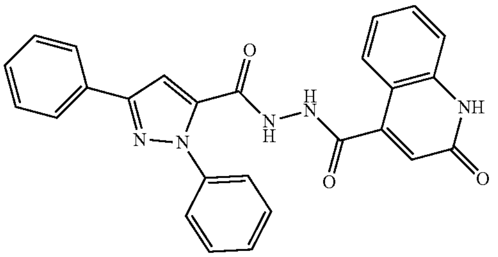 [SMILES: O=C(NNC(=O)c1cc(-c2ccccc2)nn1-c1ccccc1)c1cc(=O)[nH]c2ccccc12] | PXG22 |

The present invention provides a method for preparing a diphenylpyrazole-based compound of following formula (I), or its pesticidally acceptable salts, which includes steps of:

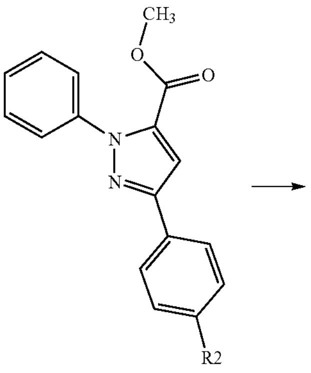

A

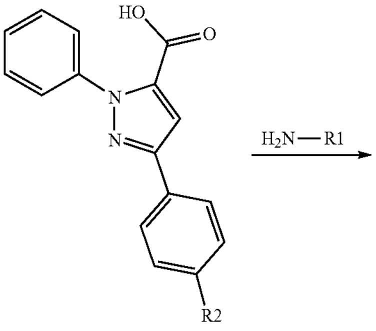

B

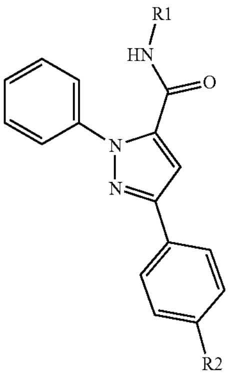

(I)

hydrolyzing compound A to its carboxylic acid form compound B, and then condensing compound B and compound $H_2N—R^1$ to compound (I) through a condensing agent in a solvent by adding an organic base or an inorganic base, under stirring at room temperature or heating; wherein $R^1$ and $R^2$ are defined as above;

or,

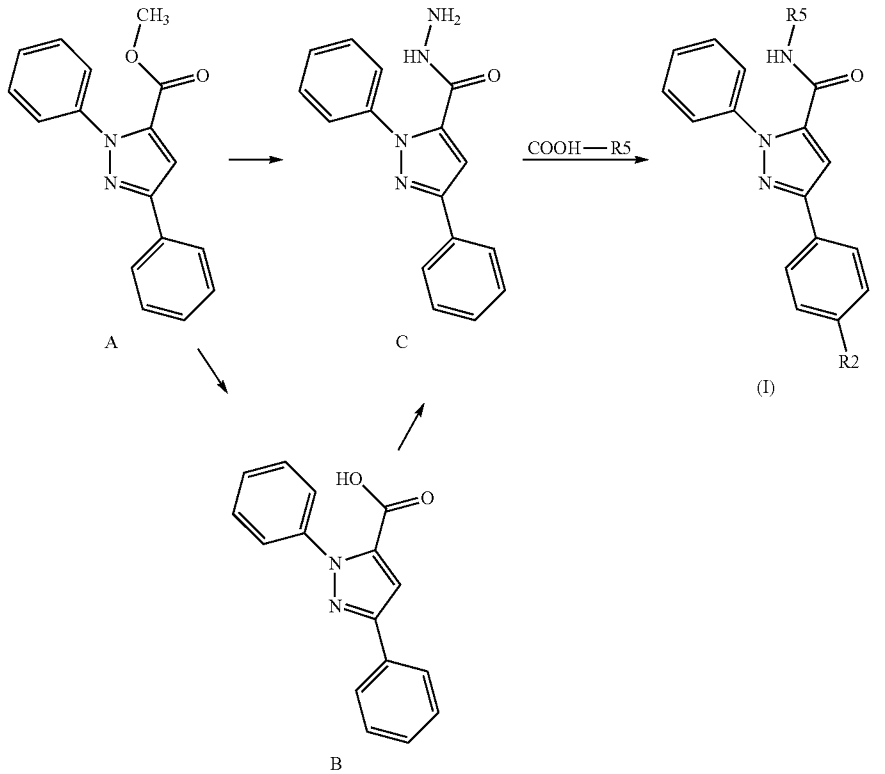

reacting compound A with hydrazine hydrate to give hydrazide compound C, or hydrolyzing compound A to compound B, then reacting compound B with hydrazine hydrate to give hydrazide compound C, and then condensing compound C and compound COOH—$R^5$ to compound (I) through a condensing agent in a solvent by adding an organic base or an inorganic base, under stirring at room temperature or heating; wherein $R^2$ is defined as above, and $R^5$ is: (a) —$C_{1\sim6}$ alkyl-$R^3$, —$C_{3\sim8}$ cycloalkyl-$R^3$, —$C_{2\sim6}$ alkenyl-$R^3$, —$C_{2\sim6}$ alkynyl-$R^3$, —NH—$R^3$, —$N(R^3)_2$, —C(O)—$R^3$, —NH—$C_{1\sim6}$ alkyl-$R^3$, —$C_{1\sim6}$ alkyl-NH—$R^3$, —$C_{1\sim6}$ alkyl-N$(R^3)_2$, —$C_{1\sim6}$ alkyl-$OR^3$, —$C_{3\sim8}$ cycloalkyl-O—$R^3$, —O—$C_{1\sim6}$ alkyl-$R^3$, —$C_{1\sim6}$ alkyl-O—$C_{1\sim6}$ alkyl-$R^3$, —C(O)—NH—$R^3$, —C(O)—$N(R^3)_2$, —NH—C(O)—$R^3$, —$C_{1\sim6}$ alkyl-NH—C(O)—$R^3$, —$C_{1\sim6}$ alkyl-NH—C(O)—O—$R^3$, —NH—C(O)—$C_{1\sim6}$ alkyl-$R^3$, —NH—C(O)—$C_{1\sim6}$ alkyl-O—$R^3$, —C(O)—NH—$C_{1\sim6}$ alkyl-$R^3$ or —$C_{1\sim6}$ alkyl-S—$R^3$;

$R^3$ is each independently selected from: H, O, S, =NH, amino, halogen, cyano, —$C_{1\sim6}$ alkyl, —$C_{3\sim8}$ cycloalkyl, —S—$C_{1\sim6}$ alkyl, —S—OH, —$SO_2$—$C_{1\sim6}$ alkyl, -6~14 membered aryl, -5~14 membered heterocyclic group, -5~14 membered heteroaryl and -adamantyl; $R^3$ is unsubstituted or substituted by one or more of the following substituents: O, —OH, halogen, cyano, nitro, —CH(O), amino, —$C_{1\sim6}$ alkyl, —$C_{2\sim6}$ alkenyl, —$C_{2\sim6}$ alkynyl, —O—$C_{1\sim6}$ alkyl, nitro, sulfonic acid group, —$C_{1\sim6}$ alkyl-halogen, —$C_{1\sim6}$ alkyl-HS, —$C_{1\sim6}$ alkyl-$NH_3^+$, —$C_{1\sim6}$ alkyl-OH, —$C_{1\sim6}$ alkyl-NH—$C_{1\sim6}$ alkyl or —$C_{1\sim6}$ alkyl-N$(C_{1\sim6}$ alkyl$)_2$; (b) -6~14 membered aryl, -5~14 membered heterocyclic group or -5~14 membered heteroaryl; said 6~14 membered aryl, said 5~14 membered heterocyclic group or said 5~14 membered heteroaryl is unsubstituted or substituted by one or more of the following substituents: O, —OH, halogen, cyano, nitro, —CH(O), amino, —$C_{1\sim6}$ alkyl, —O—$C_{1\sim6}$ alkyl, —$C_{1\sim6}$ alkyl-NH—$C_{1\sim6}$ alkyl, —$C_{1\sim6}$ alkyl-N$(C_{1\sim6}$ alkyl$)_2$, —C(O)—O—$C_{1\sim6}$ alkyl, —NH—C(O)—$C_{1\sim6}$ alkyl, —$SO_2$—$C_{1\sim6}$ alkyl, —$SO_2$—$NH_2$, —$SO_2$—NH—$C_{1\sim6}$ alkyl, —$SO_2$—N$(C_{1\sim6}$ alkyl$)_2$, -6~14 membered aryl, -5~14 membered heterocyclic group, or -5~14 membered heteroaryl; said heterocyclic group contains 1~4 heteroatoms selected from N, S and O; said heteroaryl contains 1 to 4 heteroatoms selected from N, S and O.

The condensing agents include, but are not limited to: active esters, carbodiimides, onium salts, organic phosphorus, and other condensing agents.

The solvents include, but are not limited to: N,N-dimethylformamide, dichloromethane, acetonitrile, and tetrahydrofuran.

The organic bases include, but are not limited to: triethylamine, diisopropylethylamine and the like.

The inorganic base includes but not limited to: sodium carbonate, potassium carbonate, sodium hydroxide, sodium bicarbonate and the like.

The synthesis of Compound A was carried out according to reference (*J. Org. Chem.* 2010, 75, 3, 984-987).

The present invention provides a composition comprising a diphenylpyrazole-based compound of following formula (I), or its pesticidally acceptable salts, and pesticidally acceptable excipients.

Preferably, the composition contains one or more insecticides.

The present invention also provides use of the diphenylpyrazole-based compound of following formula (I), or its pesticidally acceptable salts in preparation of GSTs inhibitors.

Preferably, the GSTs include: PxGSTδ1, PxGSTε3, PxGSTσ1, PxGSTσ2, PxGSTω4, PxGSTθ1, PxGSTζ1 and PxGSTμ1; preferably, the GSTs include: PxGSTδ1, PxGSTσ1, PxGSTσ2 and PxGSTε3; more preferably, the GSTs include: PxGSTδ1 and PxGSTε3.

The present invention also provides use of the diphenylpyrazole-based compound of following formula (I), or its pesticidally acceptable salts in the preparation of pesticides, preferably insecticide synergists.

The insecticide synergist delays or reduces pest resistance to insecticides.

The insecticides include: ryanodine receptor modulator insecticides (for example, diamide insecticides); voltage-dependent sodium ion channel blocker insecticides (for example: oxadiazine insecticides).

Specifically, the insecticides include: chlorantraniliprole and indoxacarb.

The pests include: field crop pests and economic crop pests.

Specifically, the pest include: *Plutella xylostella, Mythimna separata, Pyrausta nubilalis, Chilo suppressalis, Nilaparvata lugens, Spodoptera frugiperda, Helicoverpa armigera, Carposina sasakii*, and *Spodoptera litura.*

The present invention provides a class of insect GSTs inhibitors with novel structures. It is found that the compounds with such structures have broad inhibitory activity on GSTs in insects, and significantly improve the sensitivity of resistant pest strains to various insecticides and the effectiveness of insecticides. The compounds play an important role in managing the insecticide resistance of pests.

DETAILED EMBODIMENTS

Figure 1:
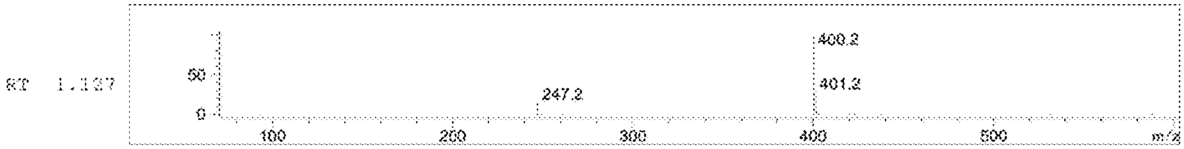
FIG. 1 is the mass spectrogram of the compound PXG1 prepared in the present invention.

The present invention will be described below through examples, but the present invention is not limited thereto. The experimental methods shown in the following examples are conventional methods unless otherwise specified. The reagents and materials shown are all commercially available.

Preparation Example 1 Preparation of Compound PXG1

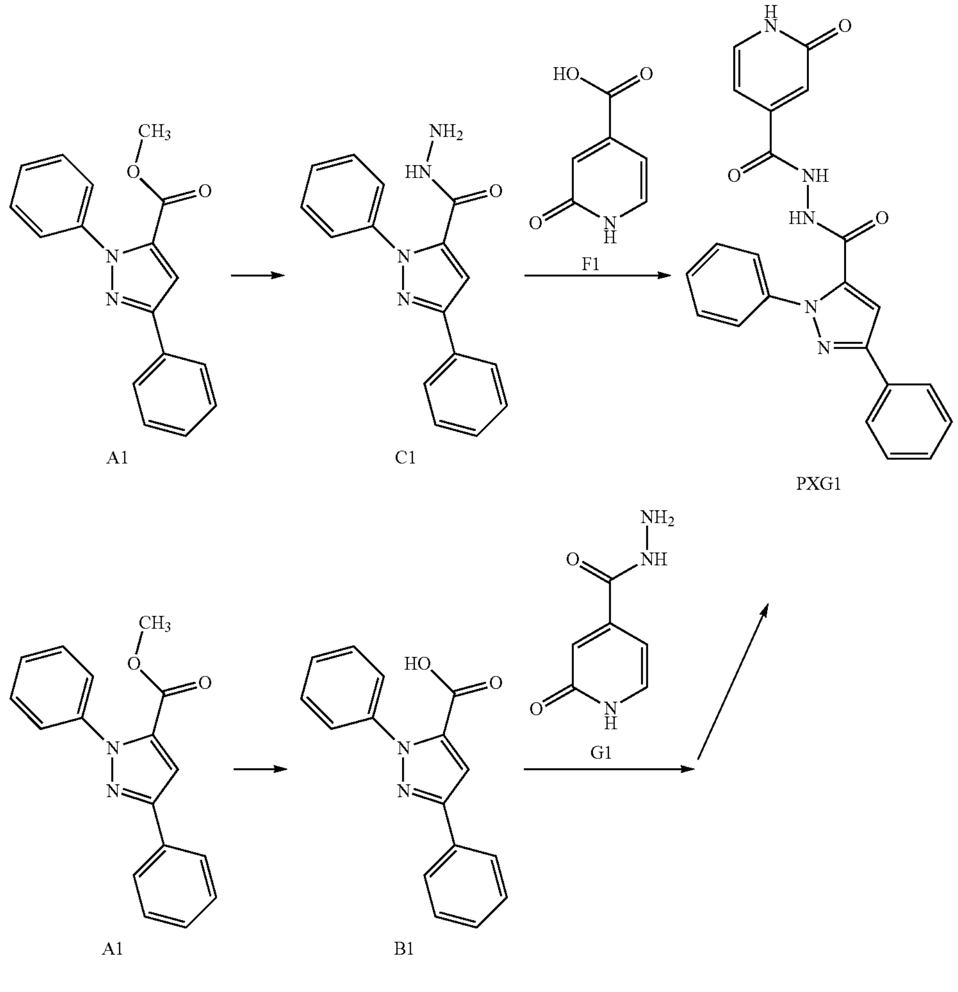

A1

C1

F1

PXG1

A1

B1

G1

Method 1:

(1) Preparation of hydrazide compound C1: 10 g of compound A1 (A1 was prepared by reference to *J. Org. Chem.* 2010, 75, 3, 984-987; HNMR (400 MHz, $CDCl_3$): δ 3.83 (s, 3H), 7.33-7.36 (m, 2H), 7.41-7.50 (m, 7H), 7.87 (m, 2H). the same below), 100 ml of absolute ethanol, 20 ml of hydrazine hydrate was first added into 100 ml three-necked flask, heated to reflux overnight, cooled and filtered by suction to obtain 9.5 g of compound C1, yield 95%.

(2) Compound F1 (carboxylic acid) (2.5 g, 1 eq), DMF (10 ml), EDCI (4.14 g, 1.2 eq), potassium carbonate (6.21 g, 2.5 eq) were added into 100 ml three-necked flask, stirred for 10 minutes and then added with compound C1 (hydrazide) (5.5 g, 1.1 eq), stirred overnight at room temperature, the reaction was monitored by TLC until completion. The resultant was diluted with water, the formed precipitate was filtered off and dried, the crude compound was purified by reverse phase HPLC without additional treatment with the eluent methanol-water, the selected fractions were combined and concentrated to obtain the target product PXG1.

Or, method 2:

(1) Preparation of compound B1: 10 g of compound A1, 100 ml of absolute ethanol, 28.7 ml (2 eq) of 10% NaOH was first put into 100 ml three-necked flask, heated to reflux for 5 hours, the reaction was completely cooled, and was adjusted to pH=2-3 with 10% hydrochloric acid, filtered by suction to obtain 8 g of compound B1, yield 85%.

(2) Compound B1 (carboxylic acid) (6.5 g, 1 eq), DMF (10 ml), EDCI (5.75 g, 1.2 eq), potassium carbonate (8.63 g, 2.5 eq) were added into 100 ml three-necked flask, stirred for 10 minutes and then added with compound G1 (hydrazide) (4.21 g, 1.1 eq), stirred overnight at room temperature, the reaction was monitored by TLC until completion. The resultant was diluted with water, the formed precipitate was filtered off and dried, the crude compound was purified by reverse phase HPLC without additional treatment with the eluent methanol-water, the selected fractions were combined and concentrated to obtain the target product PXG1.

MS(ES-API) cacld. for $C_{22}H_{17}N_5O_3$ found 400.2 $[M+1]^+$. (FIG. 1)

Preparation Example 2 Preparation of Compound PXG2

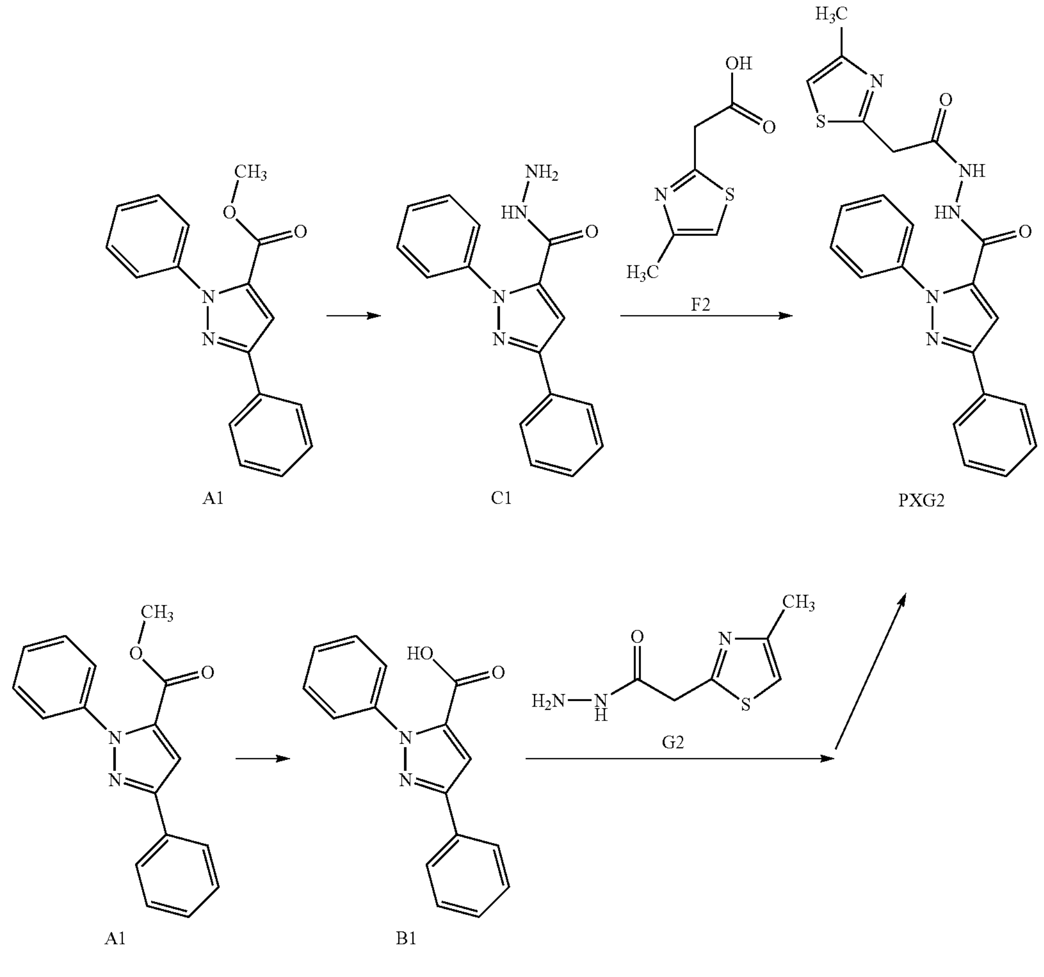

A1

C1

PXG2

A1

B1

Method 1: Compound PXG2 was prepared using the same method and steps as in Preparation Example 1, except that compound F2 (carboxylic acid) (2.83 g, 1 eq) was added into the 100 ml three-neck flask in step (2). Or, Method 2: Compound PXG2 was prepared using the same method and steps as in Preparation Example 1, except that compound G2 (hydrazide) (4.70 g, 1.1 eq) was added after stirring for 10 minutes in step (2).

Figure 2:
FIG. 2 is the mass spectrogram of the compound PXG2 prepared in the present invention.

MS(ES-API) cacld. for $C_{22}H_{19}N_5O_2S$ found 418.2 $[M+1]^+$. (FIG. 2)

Preparation Example 3 Preparation of Compound PXG3

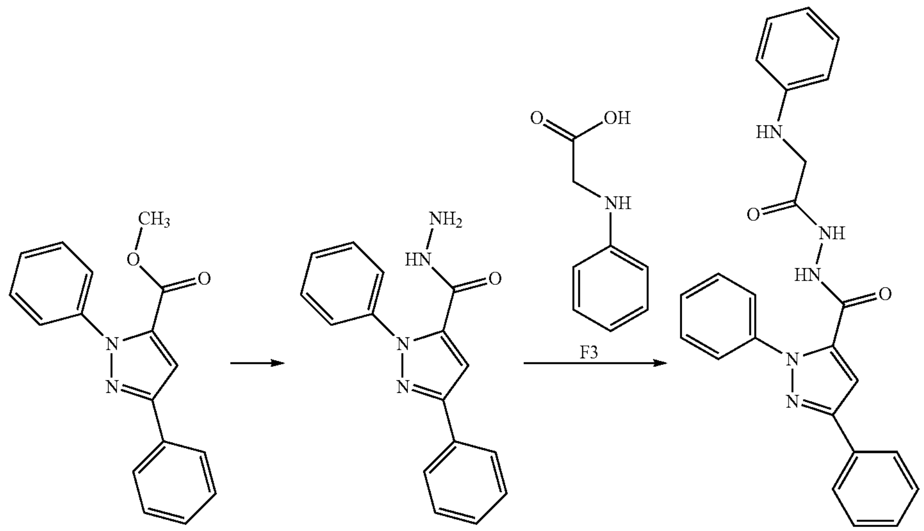

A1 C1 PXG3

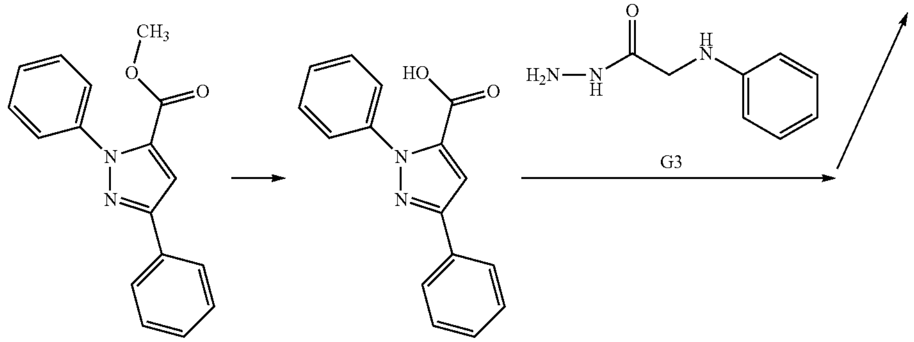

A1 B1

Method 1: Compound PXG3 was prepared using the same method and steps as in Preparation Example 1, except that compound F3 (carboxylic acid) (2.72 g, 1 eq) was added into the 100 ml three-neck flask in step (2). Or, Method 2: Compound PXG3 was prepared using the same method and steps as in Preparation Example 1, except that compound G3 (hydrazide) (4.54 g, 1.1 eq) was added after stirring for 10 minutes in step (2).

Figure 3:
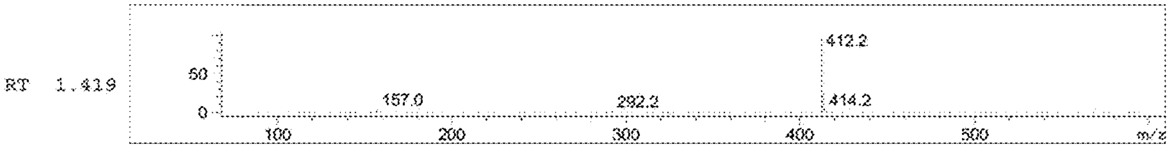
FIG. 3 is the mass spectrogram of the compound PXG3 prepared in the present invention.
Figure 4:
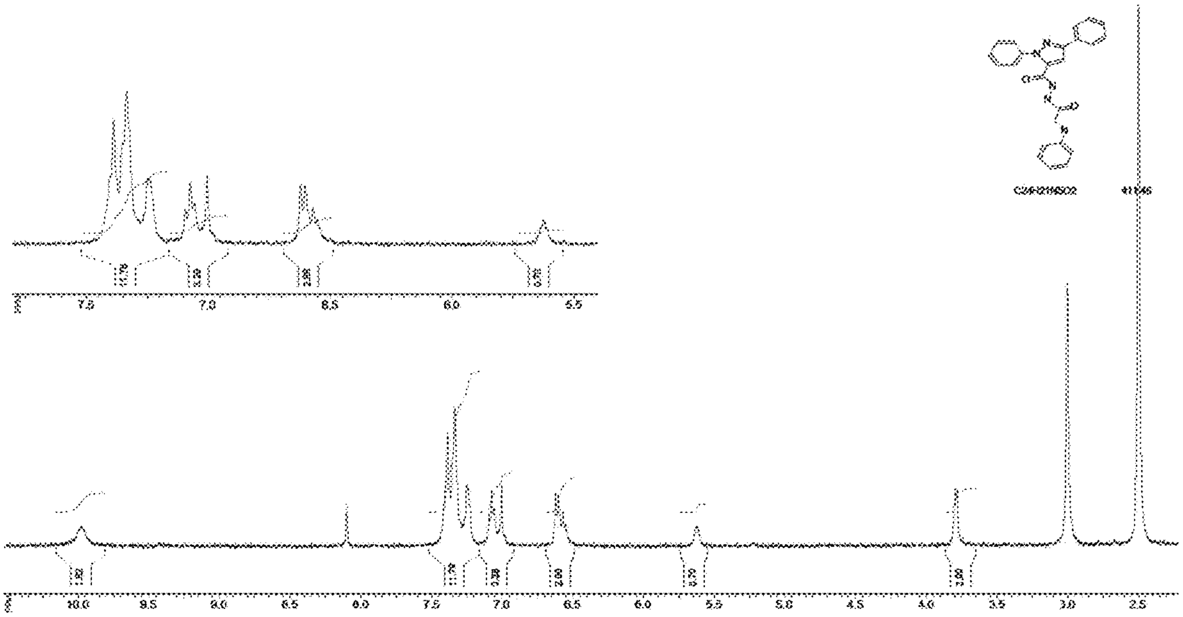
FIG. 4 is the $^1$H-NMR spectrogram of the compound PXG3 prepared in the present invention dissolved in deuterated DMSO.

MS(ES-API) cacld. for $C_{24}H_{21}N_5O_2$ found 412.2 $[M+1]^+$. (FIG. 3); HNMR (400 MHz, DMSO): δ 3.6 (s, 2H), 2.45 (m, 5H), 5.65 (s, 1H), 6.6 (m, 3H), 7.05-7.2 (m, 3H), 7.4-7.5 (m, 12H), 10.0 (s, 2H). (FIG. 4)

Preparation Example 4 Preparation of Compound PXG4

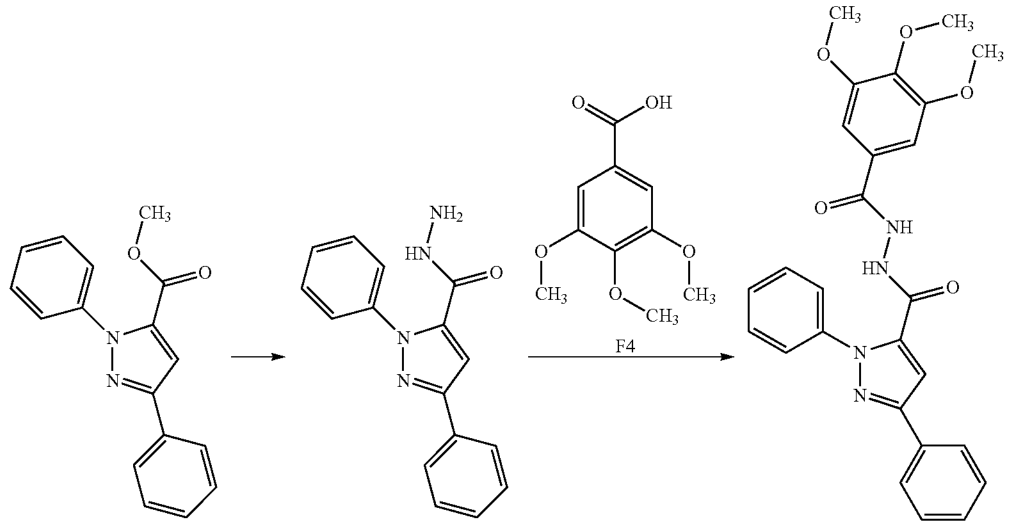

A1 C1 PXG4

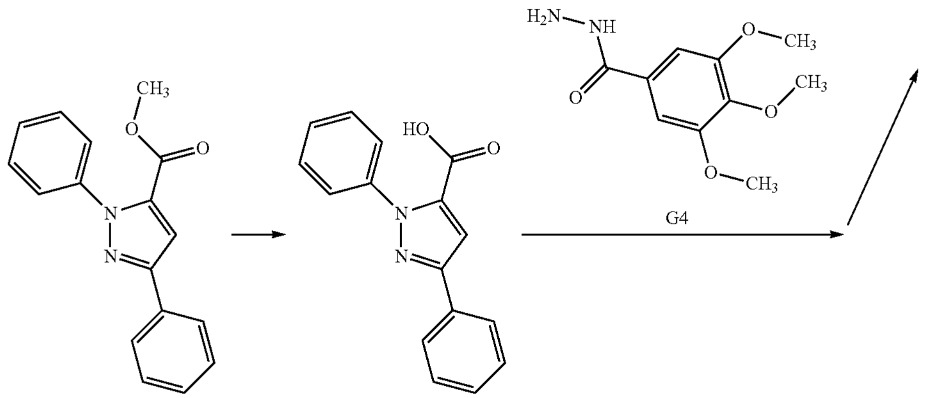

A1 B1

Method 1: Compound PXG4 was prepared using the same method and steps as in Preparation Example 1, except that compound F4 (carboxylic acid) (3.81 g, 1 eq) was added into the 100 ml three-neck flask in step (2). Or, Method 2: Compound PXG4 was prepared using the same method and steps as in Preparation Example 1, except that compound G4 (hydrazide) (6.22 g, 1.1 eq) was added after stirring for 10 minutes in step (2).

Figure 5:
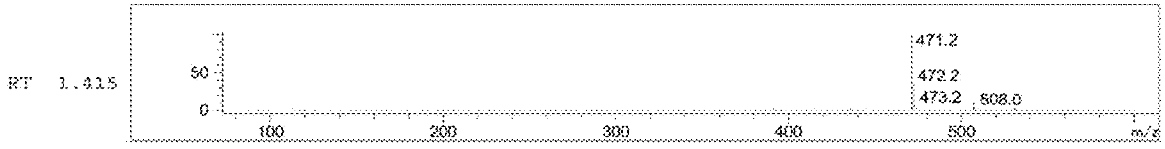
FIG. 5 is the mass spectrogram of the compound PXG4 prepared in the present invention.
Figure 6:
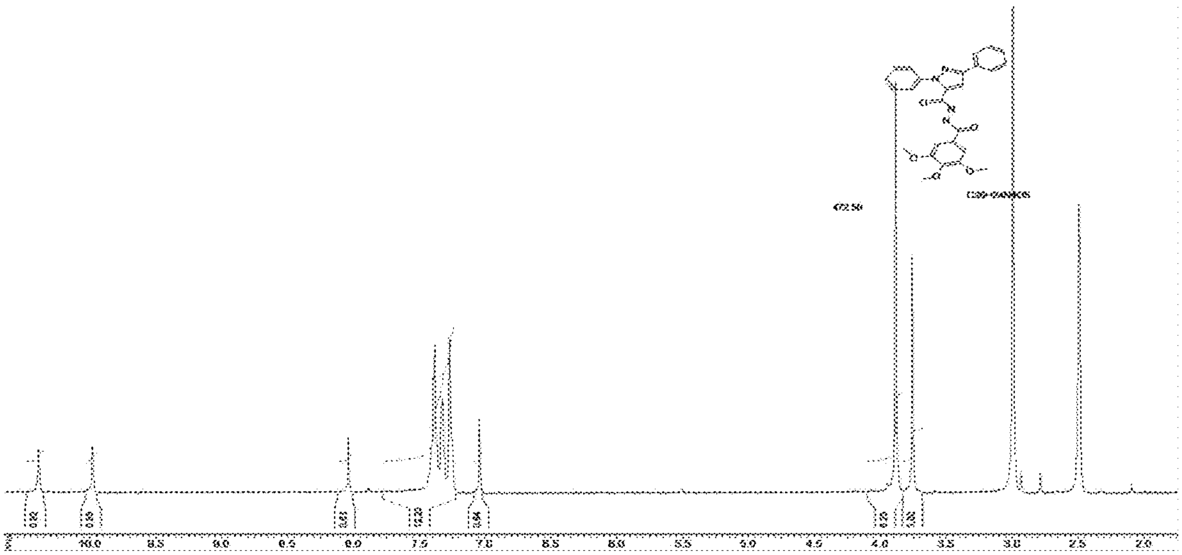
FIG. 6 is the $^1$H-NMR spectrogram of the compound PXG4 prepared in the present invention dissolved in deuterated DMSO.

MS(ES-API) cacld. for $C_{26}H_{24}N_4O_5$ found 473.2 $[M+1]^+$. (FIG. 5); HNMR (400 MHz, DMSO): δ 3.75 (s, 3H), 3.9 (s, 6H), 7.05 (s, 1H), 7.2-7.5 (m, 12H), 8.05 (s, 1H), 10.0 (s, 1H), 10.4 (s, 1H). (FIG. 6)

Preparation Example 5 Preparation of Compound PXG5

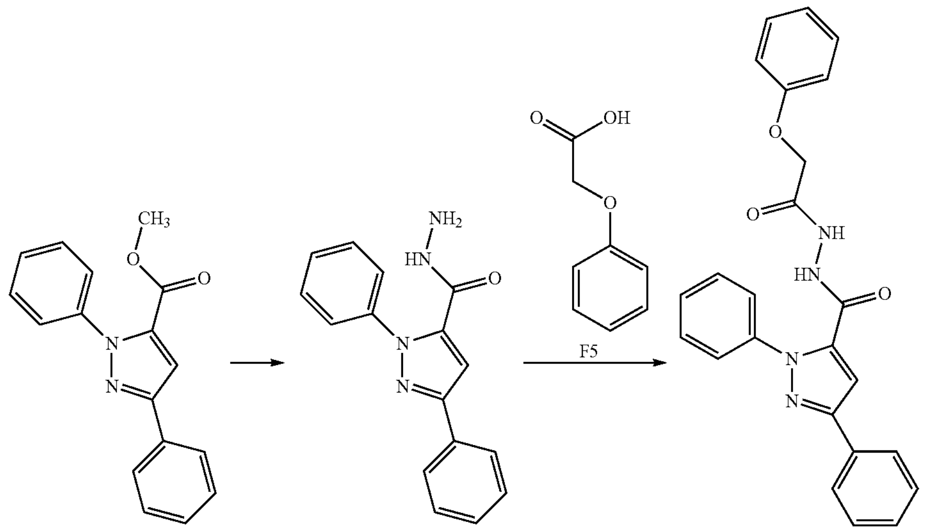

A1 C1 PXG5

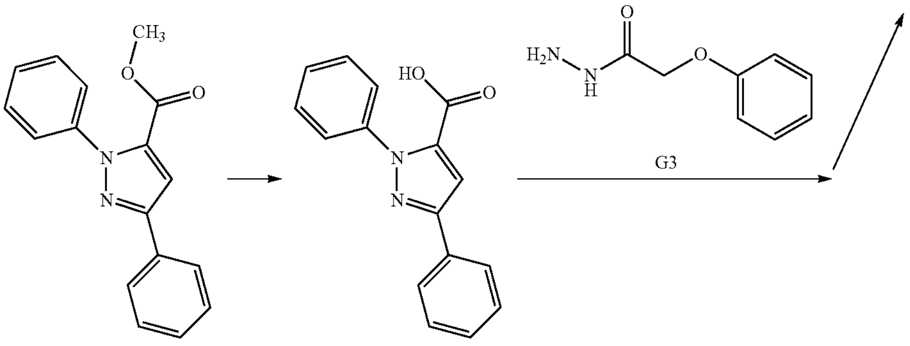

A1 B1

Method 1: Compound PXG5 was prepared using the same method and steps as in Preparation Example 1, except that compound F5 (carboxylic acid) (2.74 g, 1 eq) was added into the 100 ml three-neck flask in step (2). Or, Method 2: Compound PXG5 was prepared using the same method and steps as in Preparation Example 1, except that compound G5 (hydrazide) (4.57 g, 1.1 eq) was added after stirring for 10 minutes in step (2).

Figure 7:
FIG. 7 is the mass spectrogram of the compound PXG5 prepared in the present invention.

MS(ES-API) cacld. for $C_{24}H_{20}N_4O_3$ found 413.2 $[M+1]^+$. (FIG. 7)

Preparation Example 6 Preparation of Compound PXG6

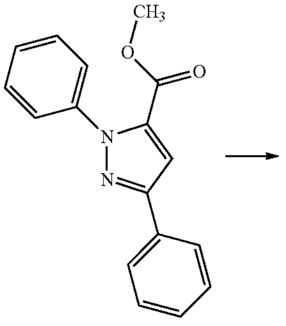

A1

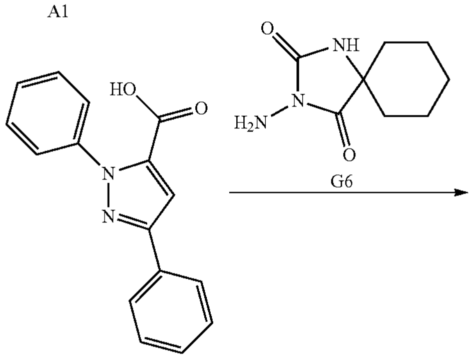

B1

-continued

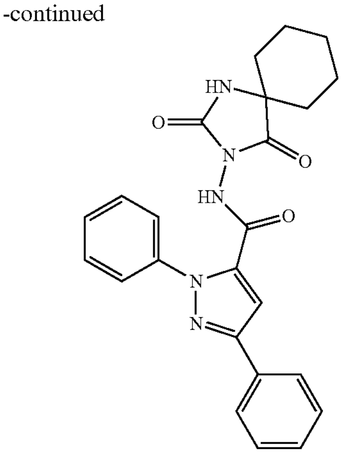

PXG6

Method 1: Compound PXG6 was prepared using the same method and steps as in Preparation Example 1, except that compound G6 (hydrazide) (5.04 g, 1 eq) was added into the 100 ml three-neck flask in step (2).

Figure 8:
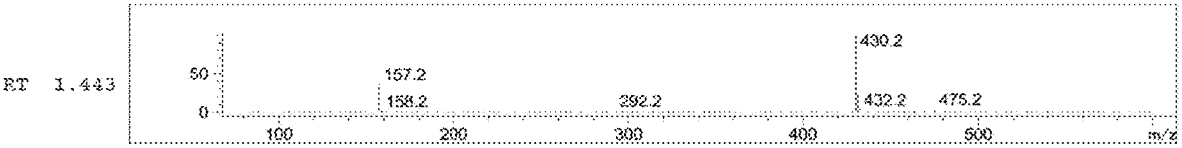
FIG. 8 is the mass spectrogram of the compound PXG6 prepared in the present invention.
Figure 9:
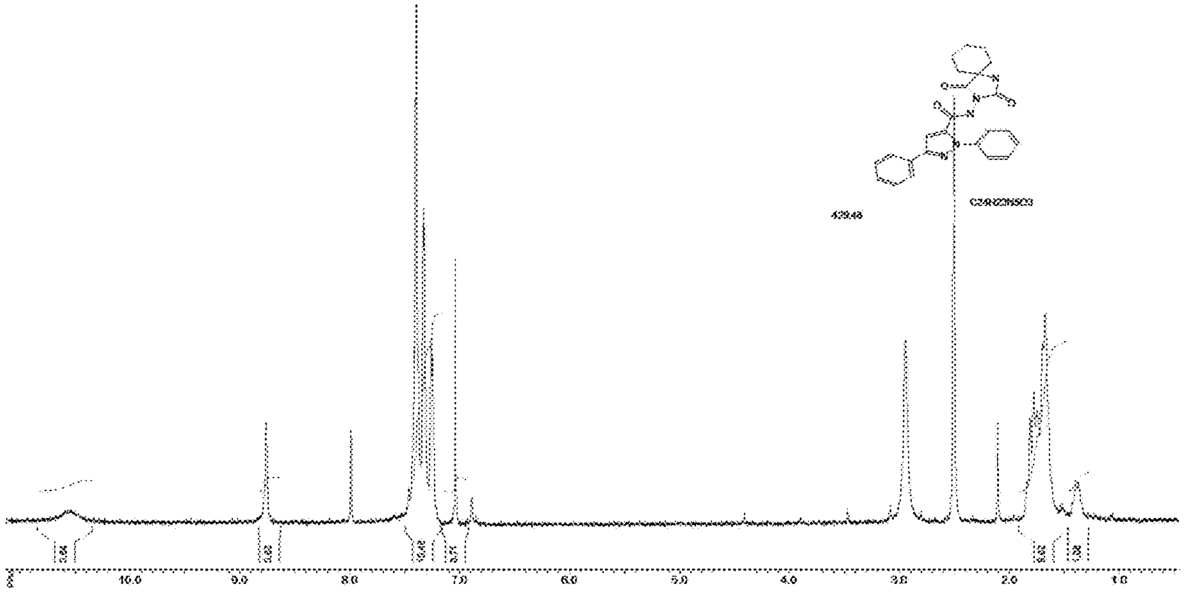
FIG. 9 is the $^1$H-NMR spectrogram of the compound PXG6 prepared in the present invention dissolved in deuterated DMSO.

MS(ES-API) cacld. for $C_{24}H_{23}N_5O_3$ found 430.2 [M+1]+. (FIG. 8); HNMR (400 MHz, DMSO): δ 1.4 (m, 1H), 1.5-1.9 (m, 9H), 7.05 (s, 1H), 7.2-7.4 (m, 10H), 8.8 (s, 1H), 10.6 (s, 1H). (FIG. 9)

Preparation Example 7 Preparation of Compound PXG7

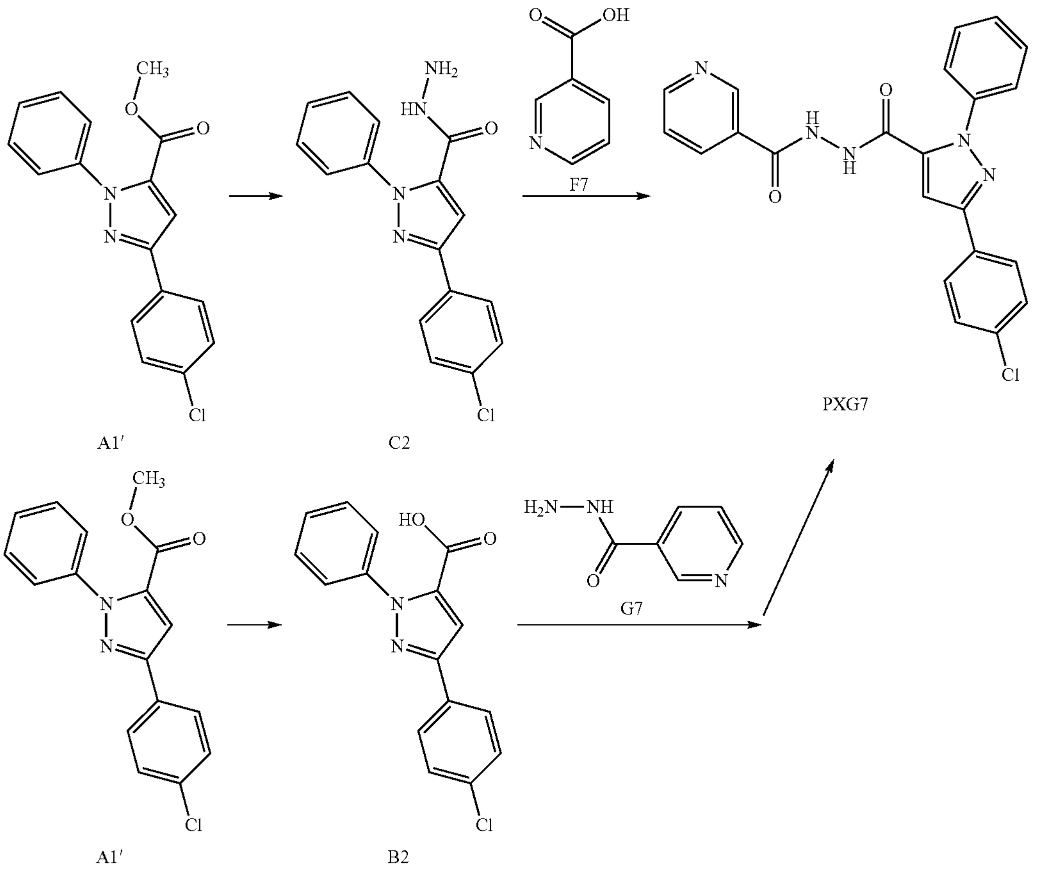

Method 1:

(1) Preparation of hydrazide compound C2: 10 g of compound A2 (A2 was prepared by reference to *J Org. Chem.* 2010, 75, 3, 984-987), 100 ml of absolute ethanol, 20 ml of hydrazine hydrate was first added into 100 ml three-necked flask, heated to reflux overnight, cooled and filtered by suction to obtain 7.5 g of compound C2, yield 75%.

(2) Compound F7 (carboxylic acid) (2.10 g, 1 eq), DMF (10 ml), EDCI (4.14 g, 1.2 eq), potassium carbonate (6.21 g, 2.5 eq) were added into 100 ml three-necked flask, stirred for 10 minutes and then added with compound C2 (hydrazide) (6.0 g, 1.1 eq), stirred overnight at room temperature, the reaction was monitored by TLC until completion. The resultant was diluted with water, the formed precipitate was filtered off and dried, the crude compound was purified by reverse phase HPLC without additional treatment with the eluent methanol-water, the selected fractions were combined and concentrated to obtain the target product PXG7.

Method 2:

(1) Preparation of compound B2: 10 g of compound A2, 100 ml of absolute ethanol, 28.7 ml (2 eq) of 10% NaOH was first added into 100 ml three-necked flask, heated to reflux for 5 hours, the reaction was completely cooled, and was adjusted to pH=2-3 with 10% hydrochloric acid, filtered by suction to obtain 6.8 g of compound B2, yield 70%.

(2) Compound B2 (carboxylic acid) (7.0 g, 1 eq), DMF 10 ml, EDCI (5.75 g, 1.2 eq), potassium carbonate (8.63 g, 2.5 eq) were added into 100 ml three-necked flask, stirred for 10 minutes and then added with compound G7 (hydrazide) (3.48 g, 1.1 eq), stirred overnight at room temperature, the reaction was monitored by TLC until completion. The resultant was diluted with water, the formed precipitate was filtered off and dried, the crude compound was purified by reverse phase HPLC without additional treatment with the eluent methanol-water, the selected fractions were combined and concentrated to obtain the target product PXG7.

Figure 10:
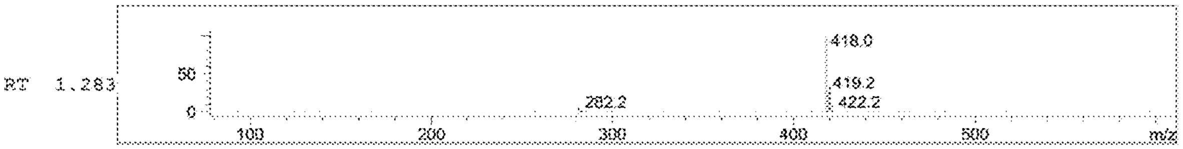
FIG. 10 is the mass spectrogram of the compound PXG7 prepared in the present invention.

MS(ES-API) cacld. for $C_{22}H_{16}ClN_5O_2$ found 418.0[M+1]$^+$. (FIG. 10)

Preparation Example 8 Preparation of Compound PXG8

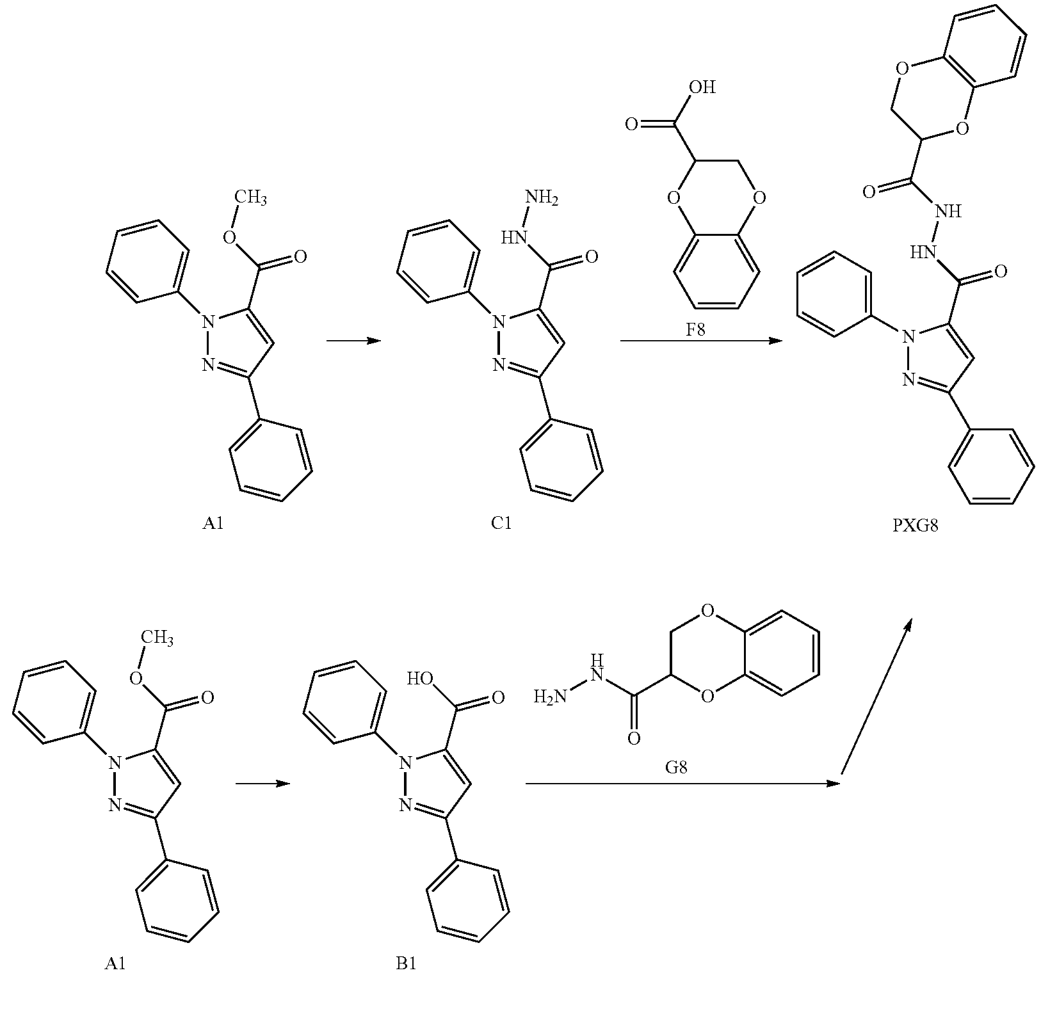

Method 1: Compound PXG8 was prepared using the same method and steps as in Preparation Example 1, except that compound F8 (carboxylic acid) (3.24 g, 1 eq) was added into the 100 ml three-neck flask in step (2).

Method 2: Compound PXG8 was prepared using the same method and steps as in Preparation Example 1, except that compound G8 (hydrazide) (5.34 g, 1.1 eq) was added after stirring for 10 minutes in step (2).

Figure 11:
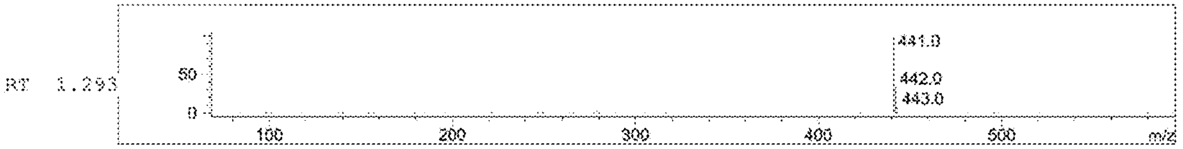
FIG. 11 is the mass spectrogram of the compound PXG8 prepared in the present invention.

MS(ES-API) cacld. for $C_{25}H_{20}N_4O_4$ found 441.0[M+1]$^+$. (FIG. 11)

Preparation Example 9 Preparation of Compound PXG9

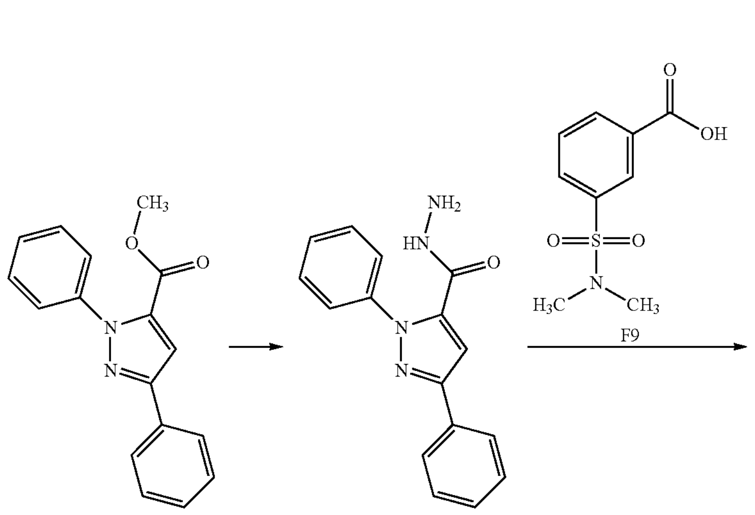

A1 C1 F9 PXG9

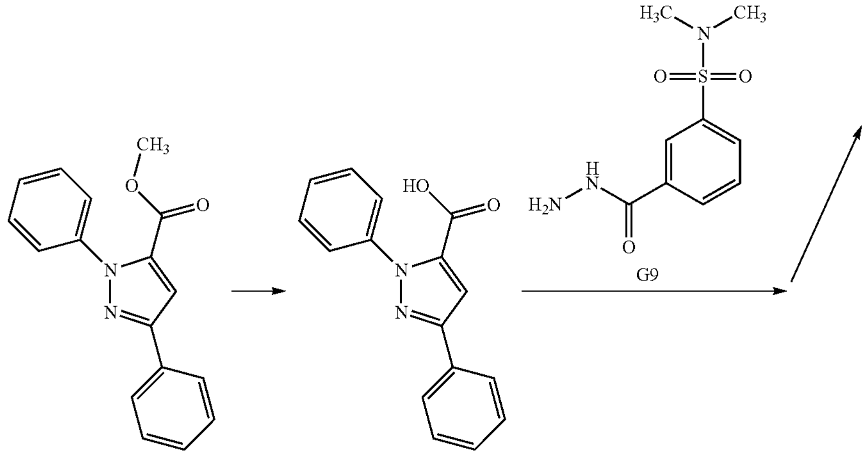

A1 B1 G9

Method 1: Compound PXG9 was prepared using the same method and steps as in Preparation Example 1, except that compound F9 (carboxylic acid) (4.12 g, 1 eq) was added into the 100 ml three-neck flask in step (2). Or Method 2: Compound PXG9 was prepared using the same method and steps as in Preparation Example 1, except that compound G9 (hydrazide) (6.68 g, 1.1 eq) was added after stirring for 10 minutes in step (2).

Figure 12:
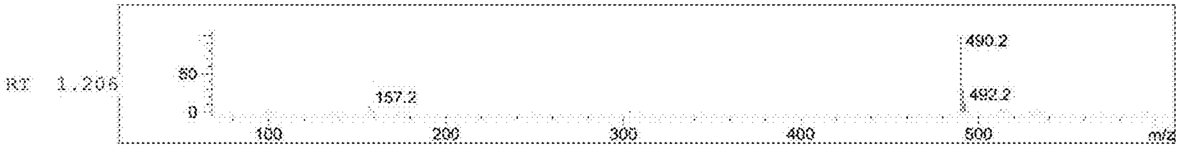
FIG. 12 is the mass spectrogram of the compound PXG9 prepared in the present invention.

MS(ES-API) cacld. for $C_{25}H_{23}N_5O_4S$ found 490.2[M+1]$^+$. (FIG. 12)

Preparation Example 10 Preparation of Compound PXG10

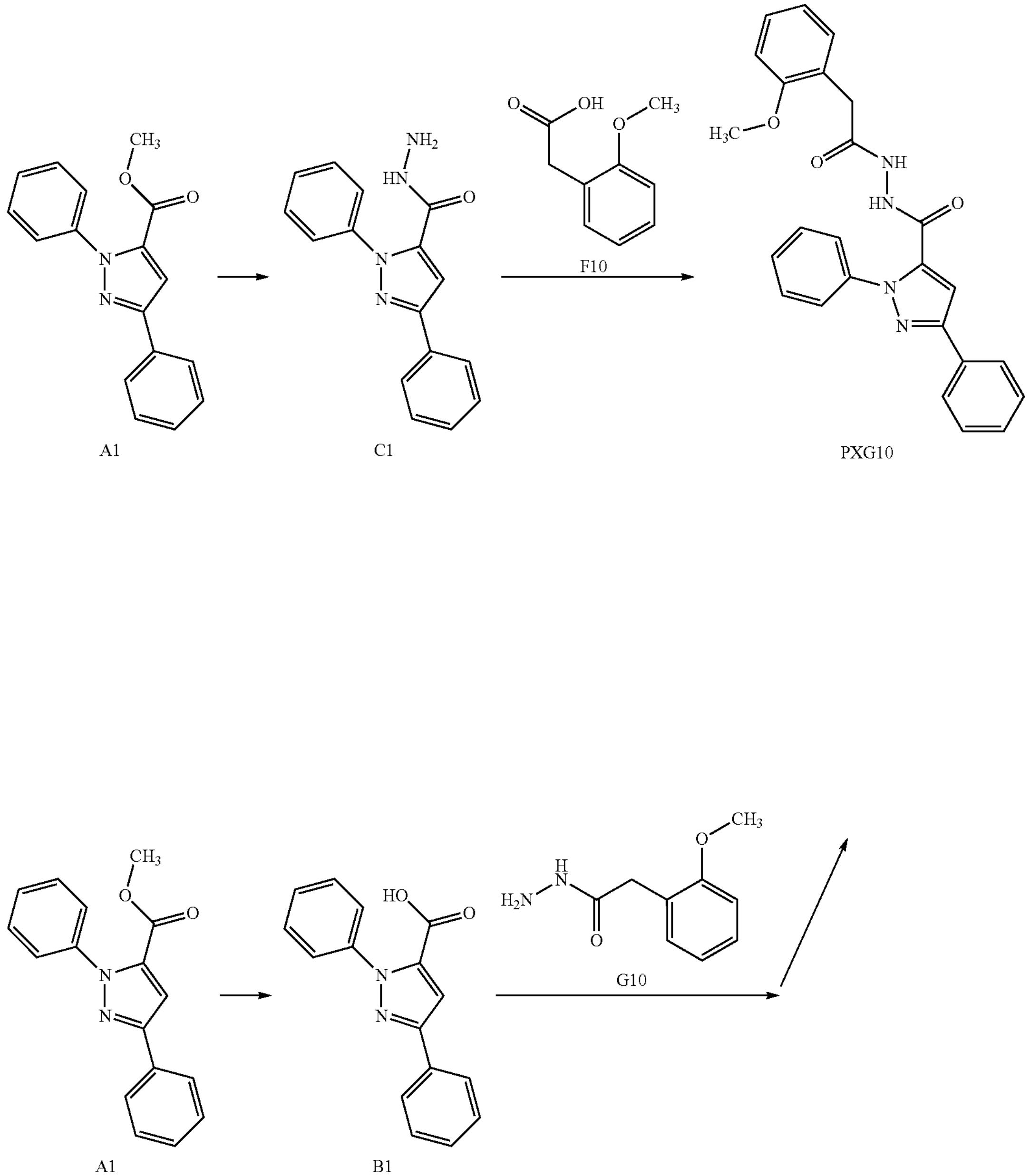

A1 C1 PXG10

A1 B1

Method 1: Compound PXG10 was prepared using the same method and steps as in Preparation Example 1, except that compound F10 (carboxylic acid) (3.00 g, 1 eq) was added into the 100 ml three-neck flask in step (2).

Method 2: Compound PXG10 was prepared using the same method and steps as in Preparation Example 1, except that compound G10 (hydrazide) (4.95 g, 1.1 eq) was added after stirring for 10 minutes in step (2).

Figure 13:
FIG. 13 is the mass spectrogram of the compound PXG10 prepared in the present invention.
Figure 14:
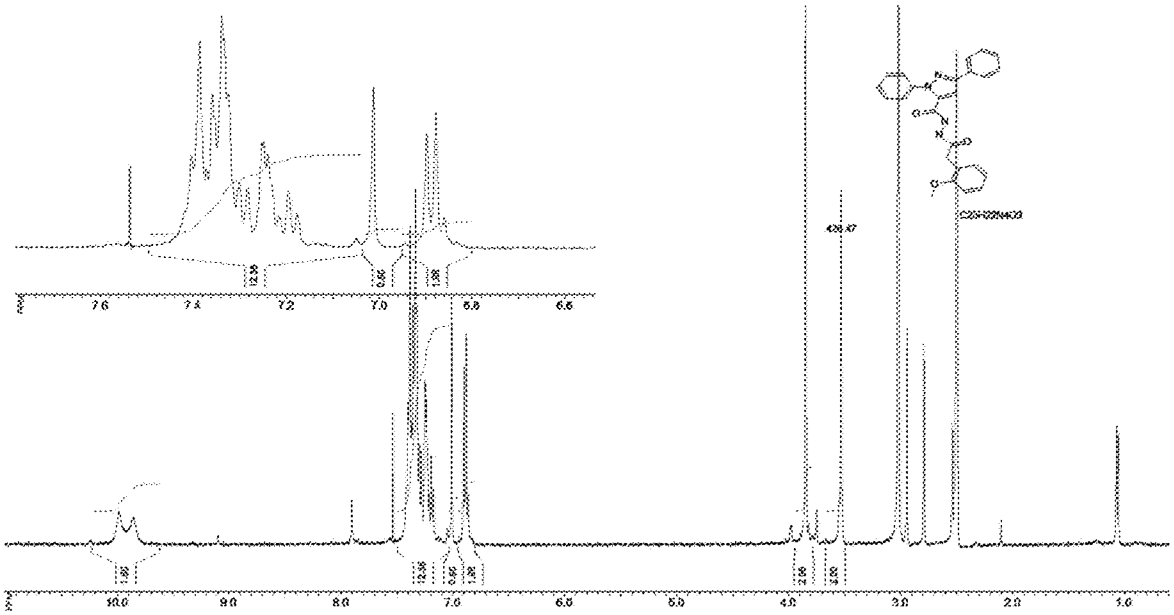
FIG. 14 is the $^1$H-NMR spectrogram of the compound PXG10 prepared in the present invention dissolved in deuterated DMSO.

MS(ES-API) cacld. for $C_{25}H_{22}N_4O_3$ found 427.2[M+1]$^+$. (FIG. 13); HNMR (400 MHz, DMSO): δ 3.5 (s, 2H), 3.8 (s, 3H), 6.8 (m, 2H), 7.05 (s, 1H), 7.2-7.6 (m, 12H), 10.0 (dd, 2H). (FIG. 14)

Preparation Example 11 Preparation of Compound PXG11

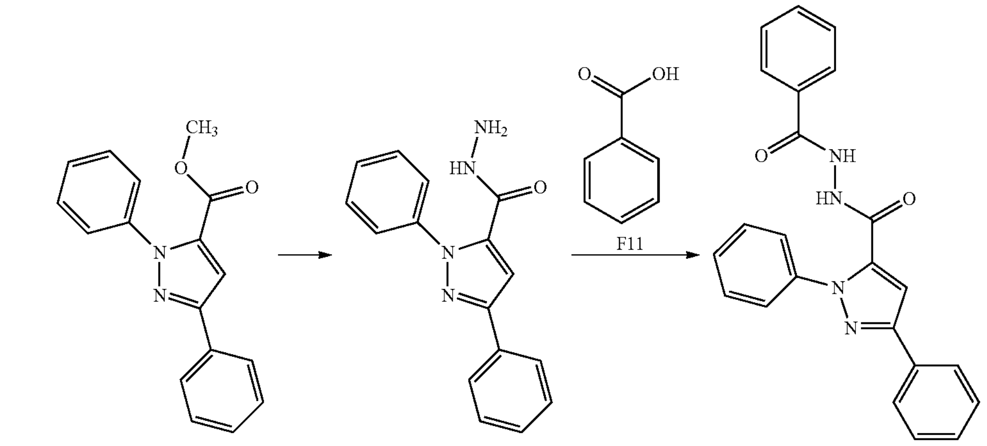

A1 C2 PXG11

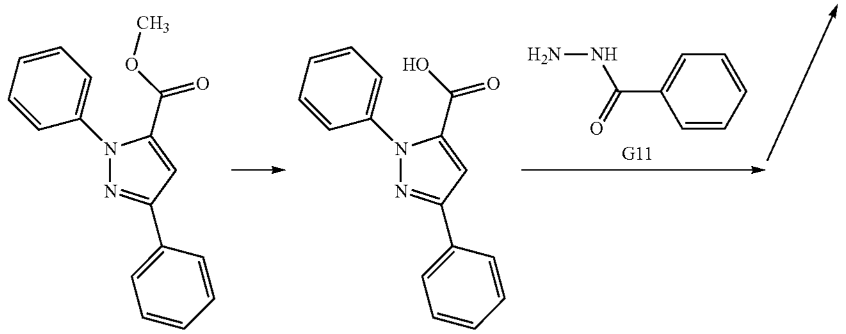

A1 B1

Method 1: Compound PXG11 was prepared using the same method and steps as in Preparation Example 1, except that compound F11 (carboxylic acid) (2.20 g, 1 eq) was added into the 100 ml three-neck flask in step (2). Or Method 2: Compound PXG11 was prepared using the same method and steps as in Preparation Example 1, except that compound G11 (hydrazide) (3.74 g, 1.1 eq) was added after stirring for 10 minutes in step (2).

Figure 15:
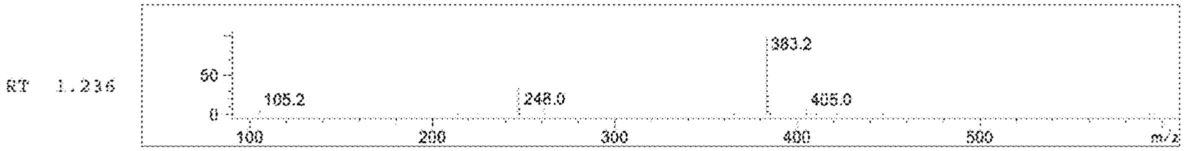
FIG. 15 is the mass spectrogram of the compound PXG11 prepared in the present invention.
Figure 16:
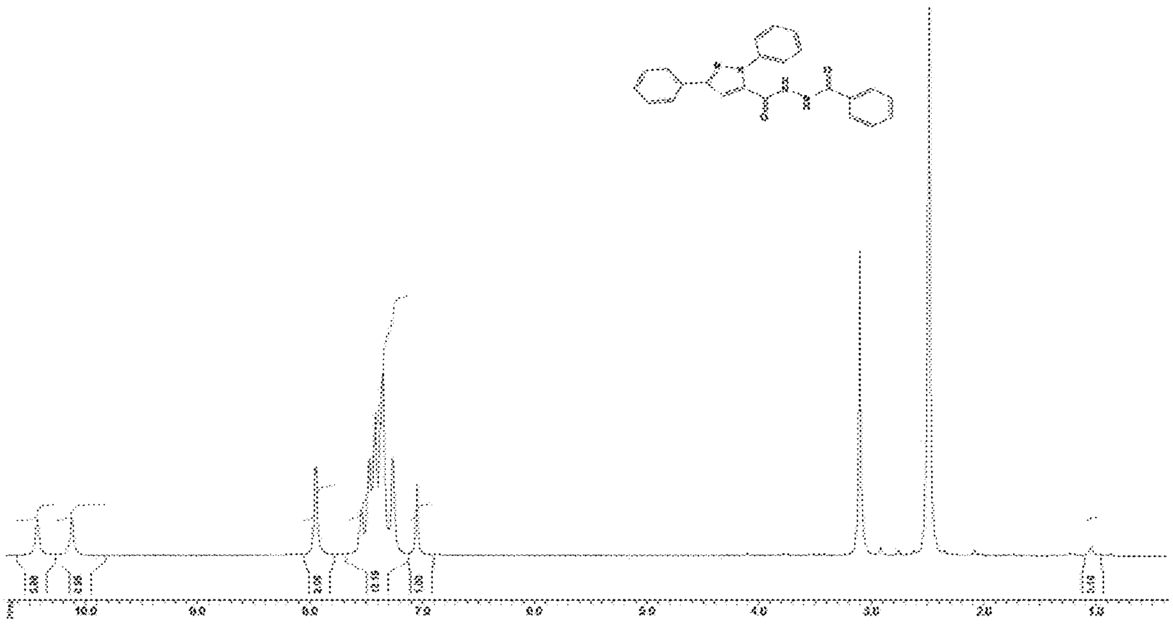
FIG. 16 is the $^1$H-NMR spectrogram of the compound PXG11 prepared in the present invention dissolved in deuterated DMSO.

MS(ES-API) cacld. for $C_{23}H_{18}N_4O_2$ found 383.2[M+1]$^+$. (FIG. 15); HNMR (400 MHz, DMSO): δ 7.05 (s, 1H), 7.2-7.6 (m, 13H), 7.95 (s, 2H), 10.05 (s, 1H), 10.45 (s, 1H). (FIG. 16)

Preparation Example 12 Preparation of Compound PXG12

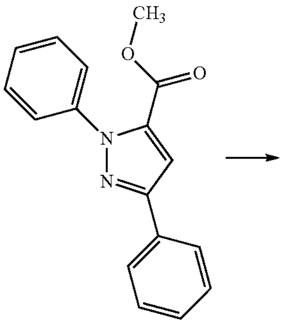

A1

-continued

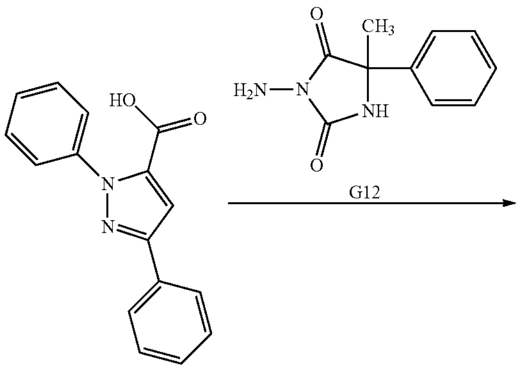

B1

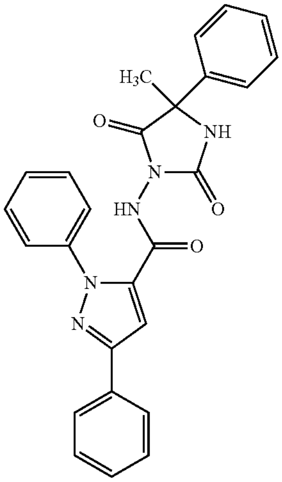

PXG12

Method 1: Compound PXG12 was prepared using the same method and steps as in Preparation Example 1, except that compound G12 (hydrazide) (5.64 g, 1 eq) was added into the 100 ml three-neck flask in step (2).

Figure 17:
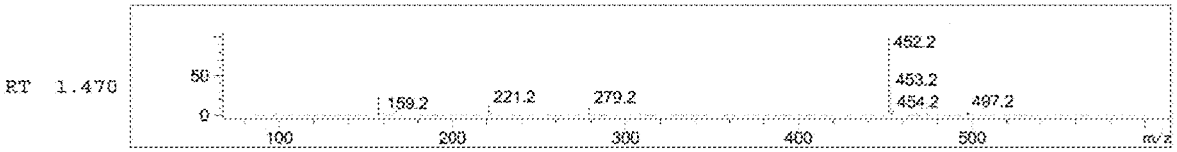
FIG. 17 is the mass spectrogram of the compound PXG12 prepared in the present invention.

MS(ES-API) cacld. for $C_{26}H_{21}N_5O_3$ found 452.2[M+1]$^+$. (FIG. 17)

Preparation Example 13 Preparation of Compound PXG13

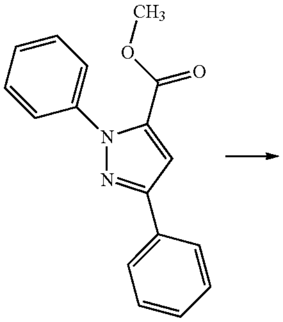

A1

-continued

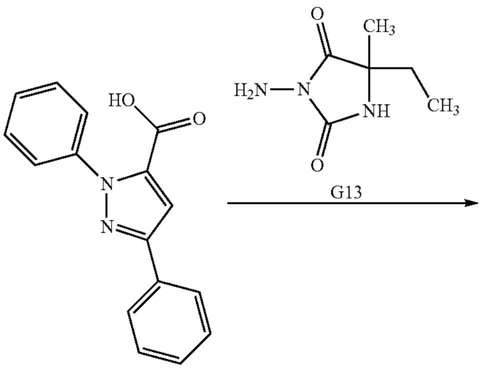

B1

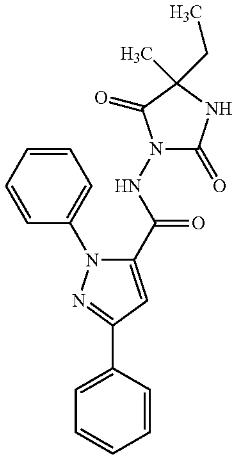

PXG13

Method 1: Compound PXG13 was prepared using the same method and steps as in Preparation Example 1, except that compound G13 (hydrazide) (4.32 g, 1 eq) was added into the 100 ml three-neck flask in step (2).

Figure 18:
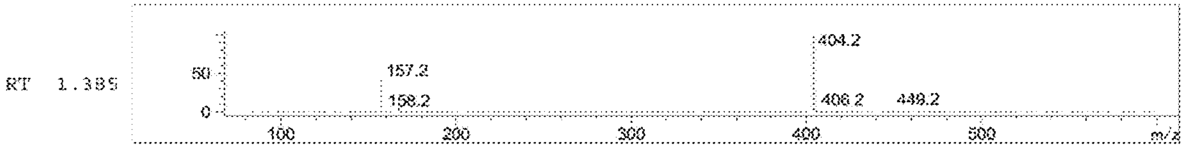
FIG. 18 is the mass spectrogram of the compound PXG13 prepared in the present invention.

MS(ES-API) cacld. for $C_{22}H_{21}N_5O_3$ found 404.2[M+1]$^+$. (FIG. 18)

Preparation Example 14 Preparation of Compound PXG14

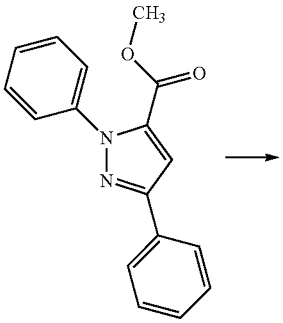

A1

-continued

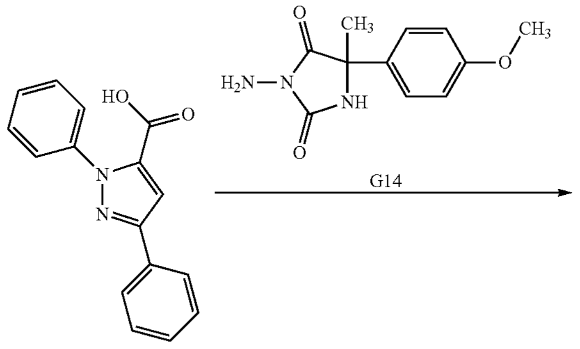

B1

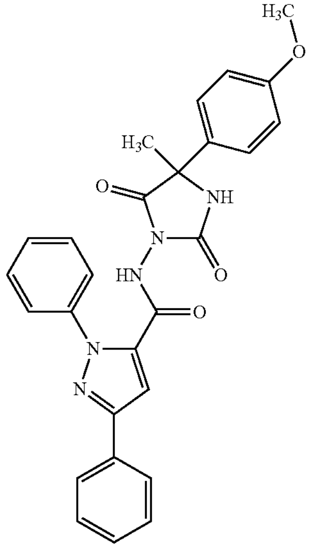

PXG14

Method 1: Compound PXG14 was prepared using the same method and steps as in Preparation Example 1, except that compound G14 (hydrazide) (6.47 g, 1 eq) was added into the 100 ml three-neck flask in step (2).

Figure 19:
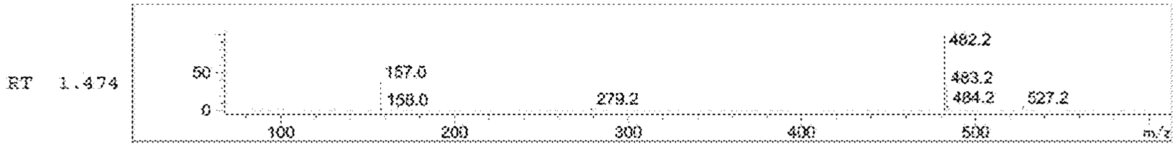
FIG. 19 is the mass spectrogram of the compound PXG14 prepared in the present invention.

MS(ES-API) cacld. for $C_{27}H_{23}N_5O_4$ found 482.2[M+1]$^+$. (FIG. 19)

Preparation Example 15 Preparation of Compound PXG15

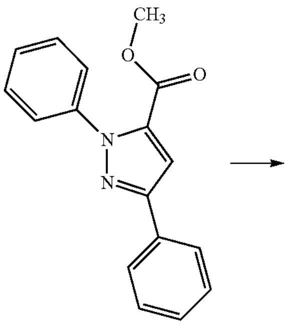

A1

-continued

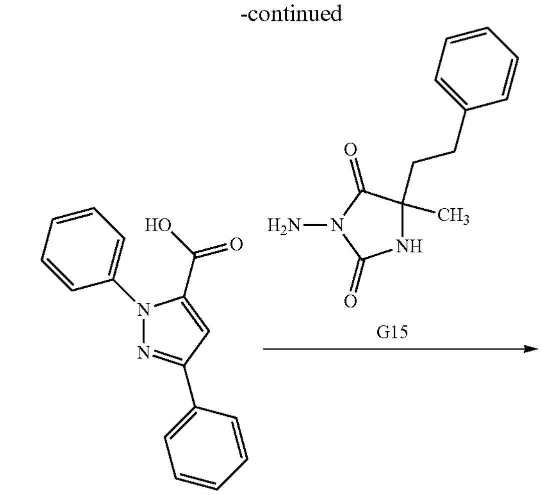

B1

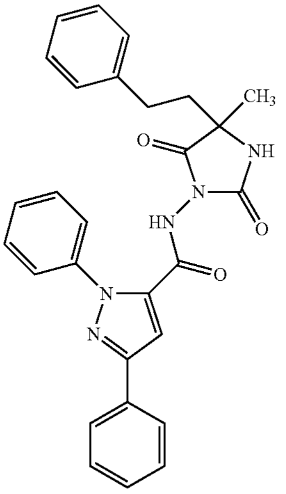

PXG15

Method 1: Compound PXG15 was prepared using the same method and steps as in Preparation Example 1, except that compound G15 (hydrazide) (6.41 g, 1 eq) was added into the 100 ml three-neck flask in step (2).

Figure 20:
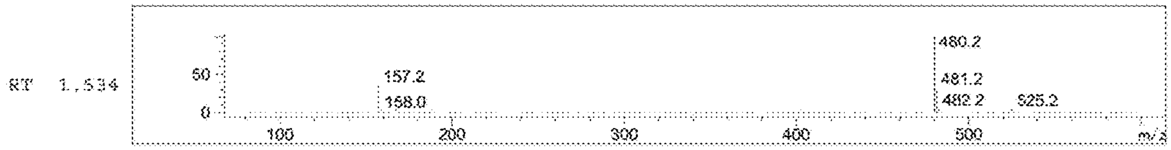
FIG. 20 is the mass spectrogram of the compound PXG15 prepared in the present invention.

MS(ES-API) cacld. for $C_{28}H_{25}N_5O_3$ found 480.2[M+1]+. (FIG. 20)

Preparation Example 16 Preparation of Compound PXG16

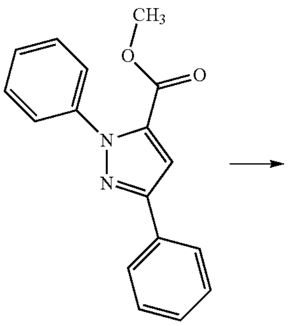

A1

-continued

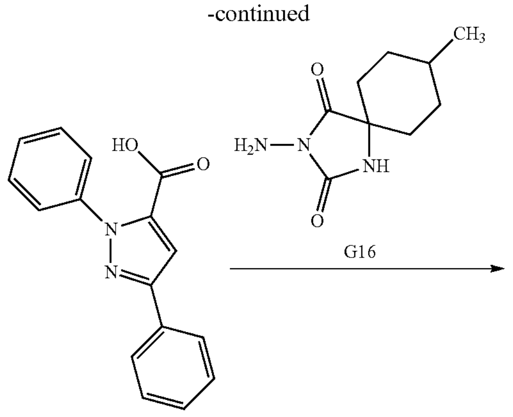

B1

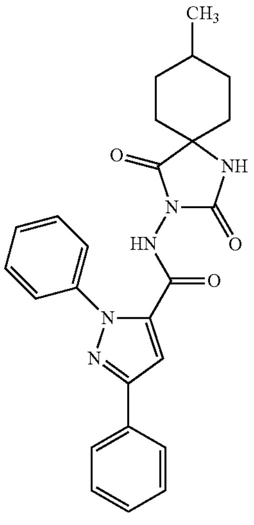

PXG16

Method 1: Compound PXG16 was prepared using the same method and steps as in Preparation Example 1, except that compound G16 (hydrazide) (5.42 g, 1 eq) was added into the 100 ml three-neck flask in step (2).

Figure 21:
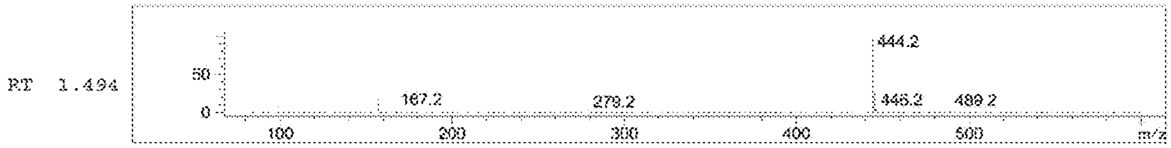
FIG. 21 is the mass spectrogram of the compound PXG16 prepared in the present invention.
Figure 22:
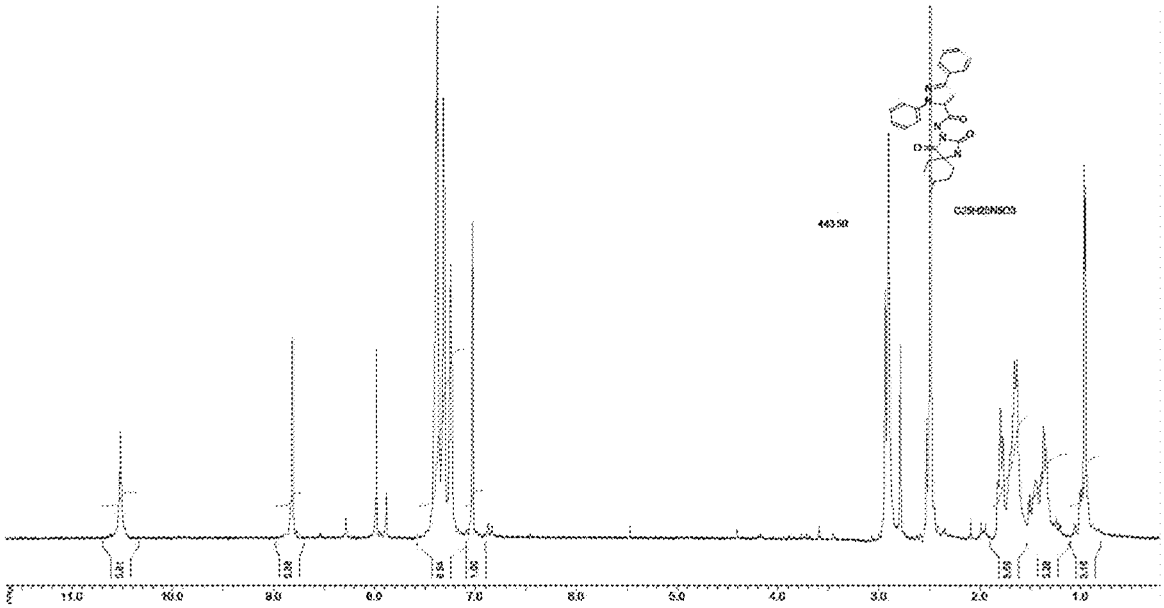
FIG. 22 is the $^1$H-NMR spectrogram of the compound PXG16 prepared in the present invention dissolved in deuterated DMSO.

MS(ES-API) cacld. for $C_{25}H_{25}N_5O_3$ found 444.2[M+1]$^+$. (FIG. 21); HNMR (400 MHz, DMSO): δ 1.0 (s, 3H), 1.1-1.8 (m, 8H), 7.05 (s, 1H), 7.2-7.4 (m, 10H), 9.05 (s, 1H), 10.5 (s, 1H). (FIG. 22)

Preparation Example 17 Preparation of Compound PXG17

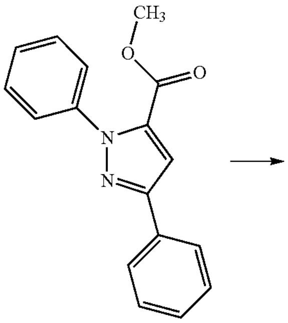

A1

-continued

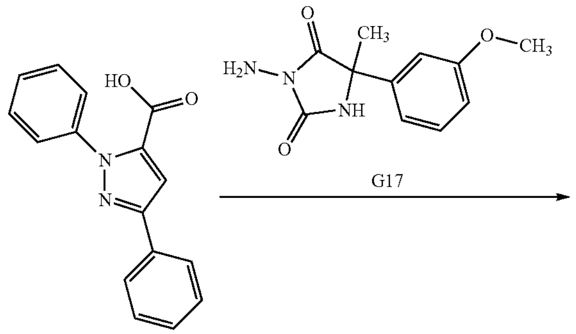

B1

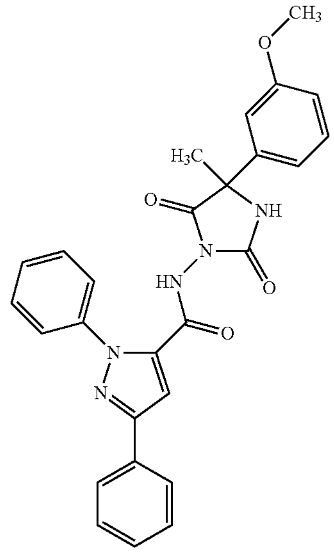

PXG17

Method 1: Compound PXG17 was prepared using the same method and steps as in Preparation Example 1, except that compound G17 (hydrazide) (6.47 g, 1 eq) was added into the 100 ml three-neck flask in step (2).

Figure 23:
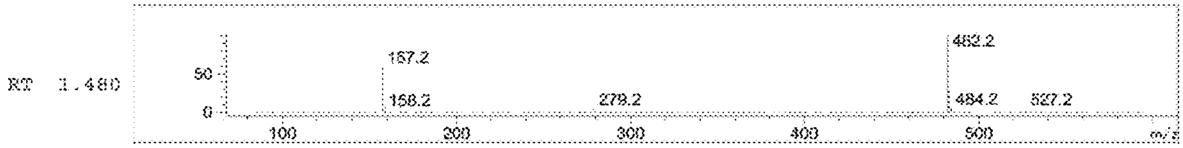
FIG. 23 is the mass spectrogram of the compound PXG17 prepared in the present invention.

MS(ES-API) cacld. for $C_{27}H_{23}N_5O_4$ found 482.2[M+1]$^+$. (FIG. 23)

Preparation Example 18 Preparation of Compound PXG18

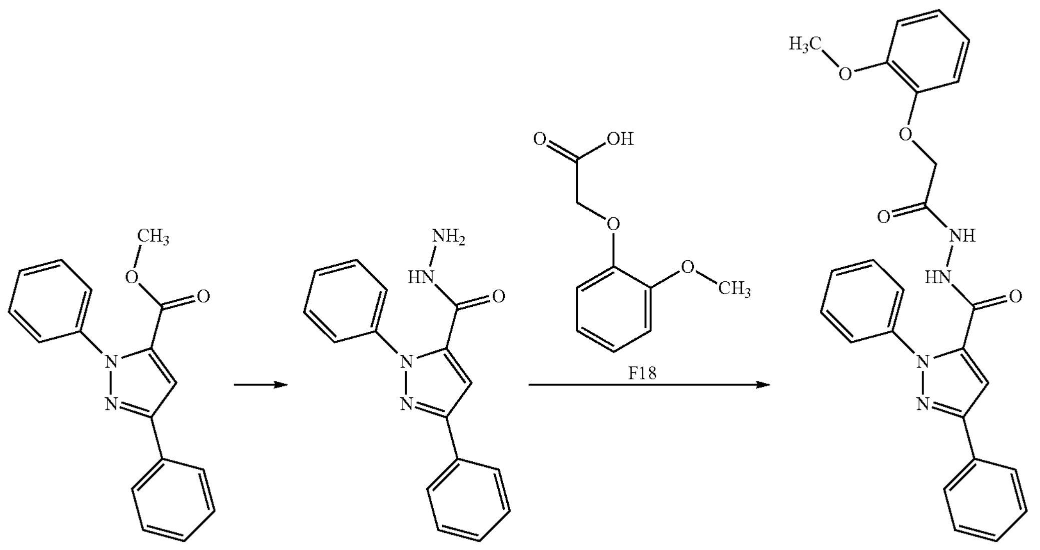

A1 C1 PXG18

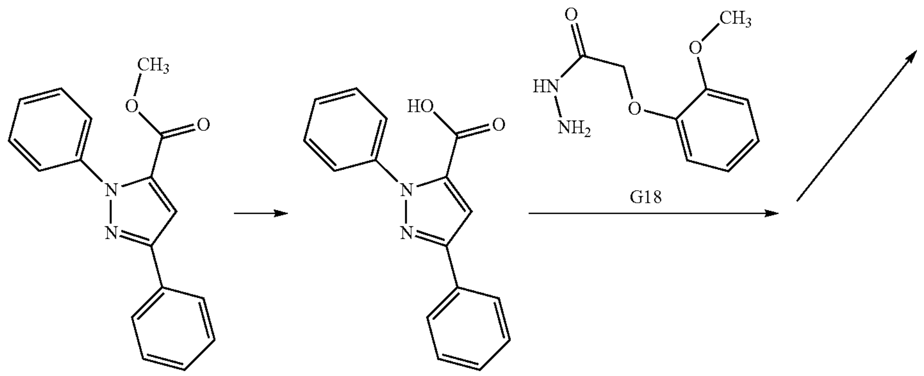

A1 B1

Method 1: Compound PXG18 was prepared using the same method and steps as in Preparation Example 1, except that compound F18 (carboxylic acid) (3.28 g, 1 eq) was added into the 100 ml three-neck flask in step (2). Or Method 2: Compound PXG18 was prepared using the same method and steps as in Preparation Example 1, except that compound G18 (hydrazide) (5.39 g, 1.1 eq) added put after stirring for 10 minutes in step (21.

Figure 24:
FIG. 24 is the mass spectrogram of the compound PXG18 prepared in the present invention.
Figure 25:
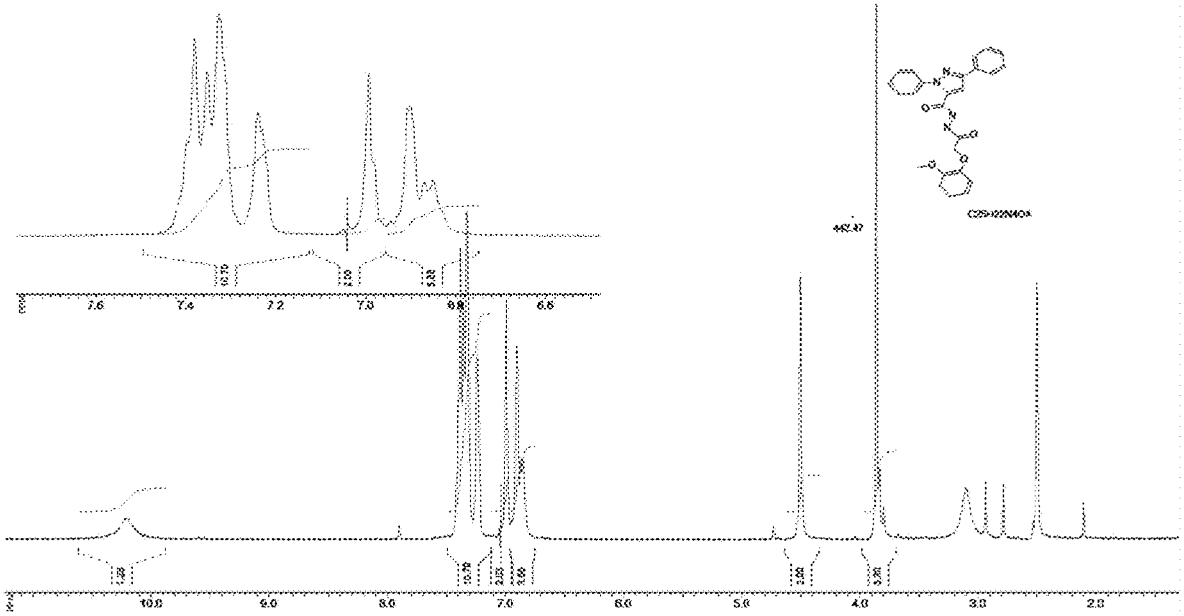
FIG. 25 is the $^1$H-NMR spectrogram of the compound PXG18 prepared in the present invention dissolved in deuterated DMSO.

MS(ES-API) cacld. for $C_{25}H_{22}N_4O_4$ found 443.2[M+1]$^+$. (FIG. 24); HNMR (400 MHz, DMSO): δ 3.85 (s, 3H), 4.45 (s, 2H), 6.8-7.25 (m, 5H), 7.2-7.5 (m, 10H), 8.05 (s, 1H), 10.25 (s, 1H). (FIG. 25)

Preparation Example 19 Preparation of Compound PXG19

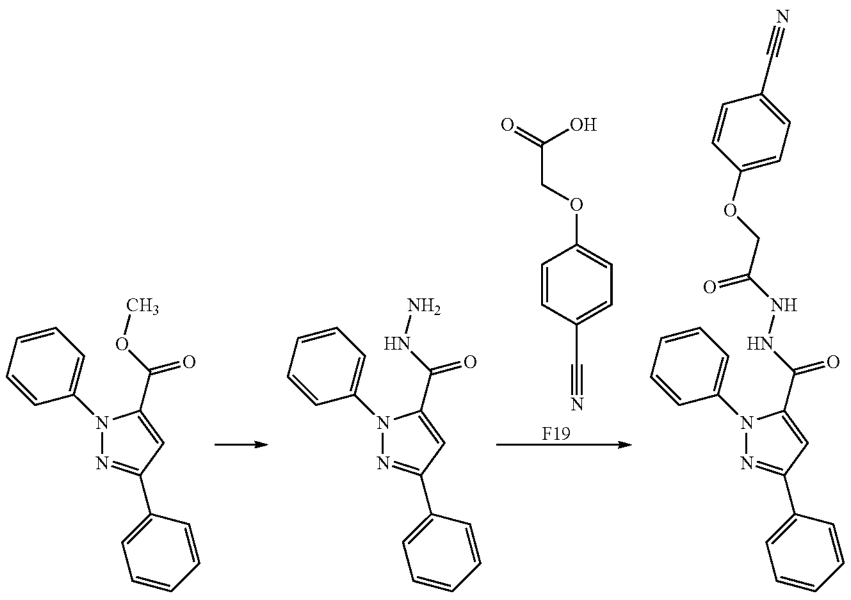

A1 C1 PXG19

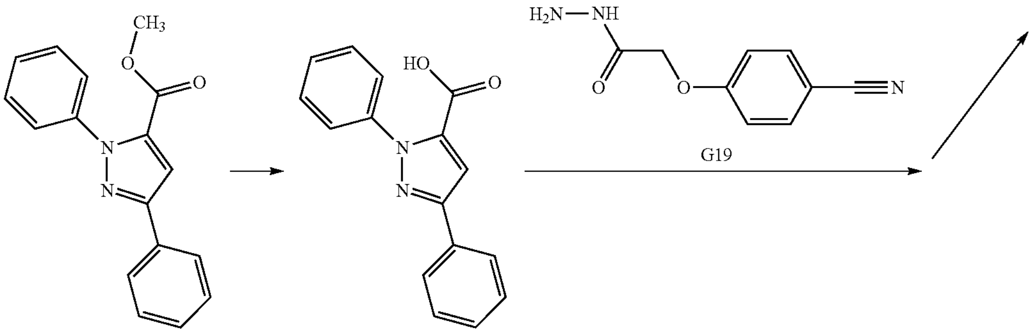

A1 B1

Method 1: Compound PXG19 was prepared using the same method and steps as in Preparation Example 1, except that compound F19 (carboxylic acid) (3.19 g, 1 eq) was added into the 100 ml three-neck flask in step (2). Or Method 2: Compound PXG19 was prepared using the same method and steps as in Preparation Example 1, except that compound G19 (hydrazide) (5.25 g, 1.1 eq) was added after stirring for 10 minutes in step (2).

Figure 26:
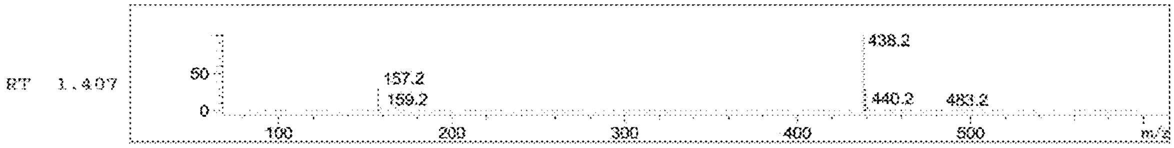
FIG. 26 is the mass spectrogram of the compound PXG19 prepared in the present invention.
Figure 27:
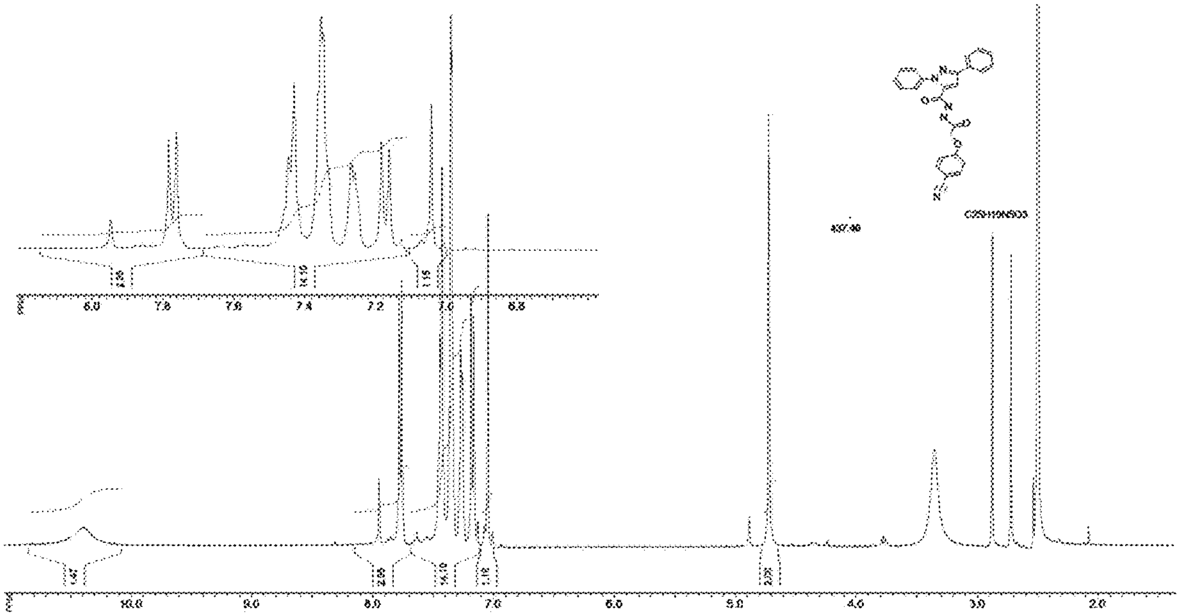
FIG. 27 is the $^1$H-NMR spectrogram of the compound PXG19 prepared in the present invention dissolved in deuterated DMSO.

MS(ES-API) cacld. for $C_{25}H_{19}N_5O_3$ found 438.2[M+1]+. (FIG. 26); HNMR (400 MHz, DMSO): δ 4.75 (s, 2H), 7.05-7.5 (m, 15H), 7.8 (dd, 2H), 8.05 (s, 1H), 10.5 (s, 1H). (FIG. 27)

Preparation Example 20 Preparation of Compound PXG20

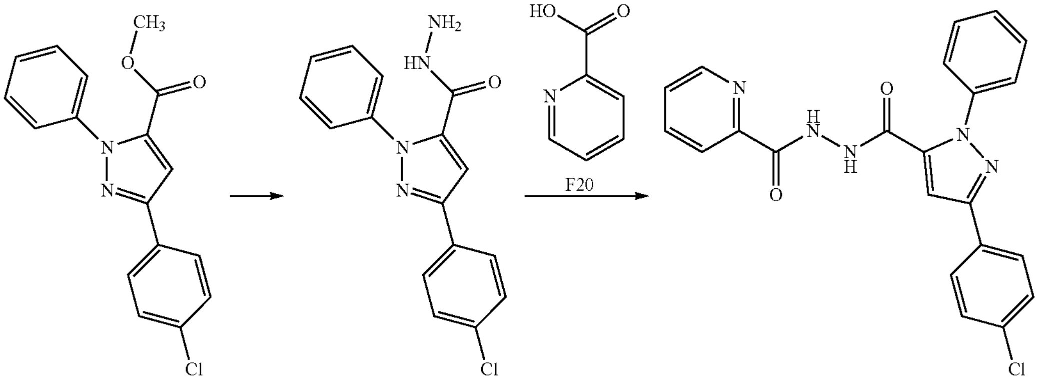

A1′ C1 PXG20

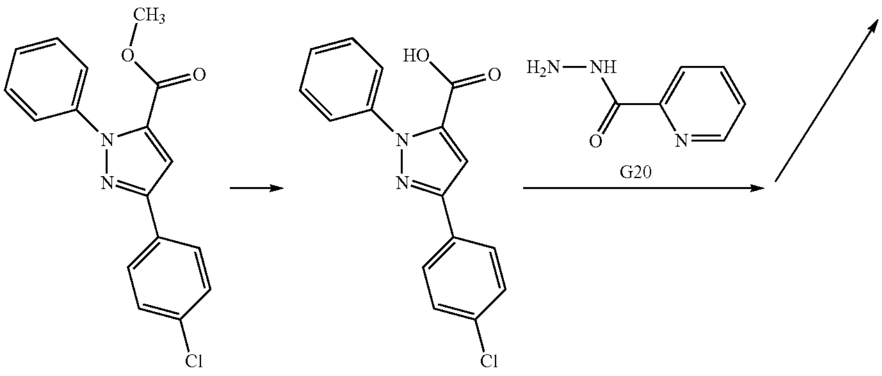

A1′ B2

Method 1: Compound PXG20 was prepared using the same method and steps as in Preparation Example 7, except that compound F20 (carboxylic acid) (2.09 g, 1 eq) was added into the 100 ml three-neck flask in step (2). Or Method 2: Compound PXG20 was prepared using the same method and steps as in Preparation Example 7, except that compound G20 (hydrazide) (3.47 g, 1.1 eq) was added after stirring for 10 minutes in step (2).

Figure 28:
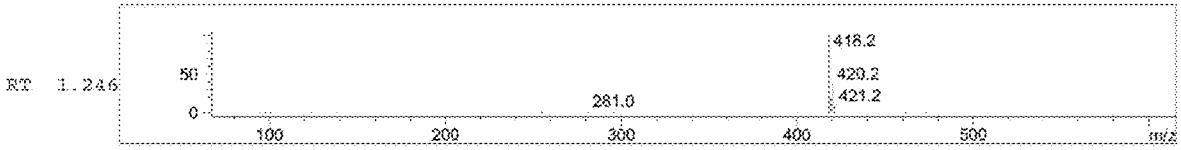
FIG. 28 is the mass spectrogram of the compound PXG20 prepared in the present invention.

MS(ES-API) cacld. for $C_{22}H_{16}ClN_5O_2$ found 418.2[M+1]$^+$. (FIG. 28)

Preparation Example 21 Preparation of Compound PXG21

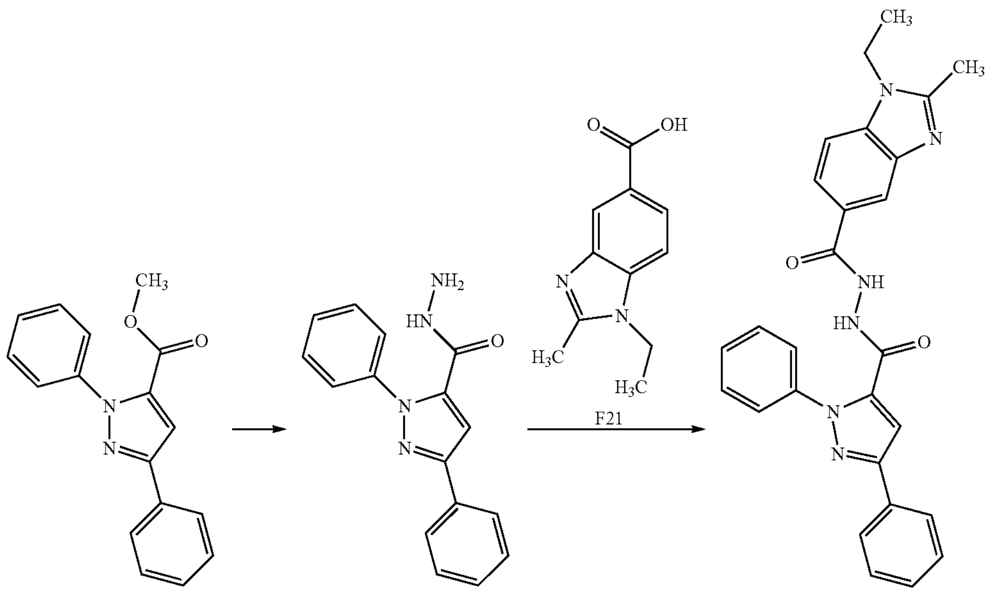

A1 C1 F21 PXG21

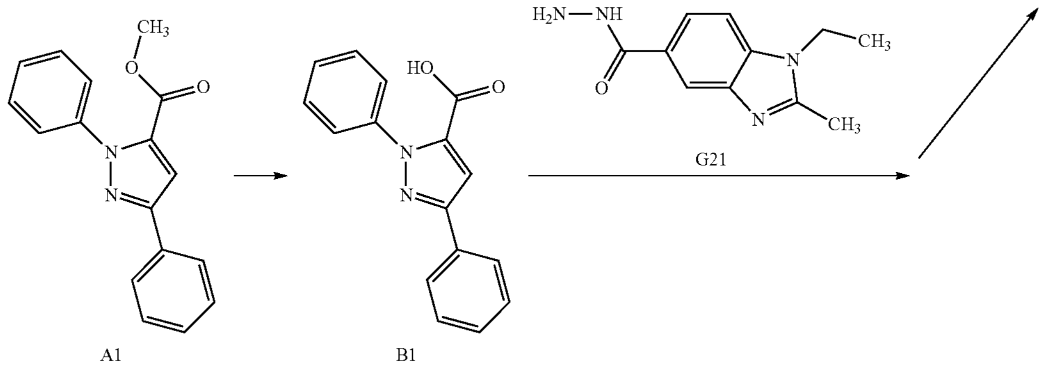

A1 B1 G21

Method 1: Compound PXG21 was prepared using the same method and steps as in Preparation Example 1, except that compound F21 (carboxylic acid) (3.67 g, 1 eq) was added into the 100 ml three-neck flask in step (2). Or Method 2: Compound PXG21 was prepared using the same method and steps as in Preparation Example 1, except that compound G21 (hydrazide) (6.00 g, 1.1 eq) was added after stirring for 10 minutes in step (2).

Figure 29:
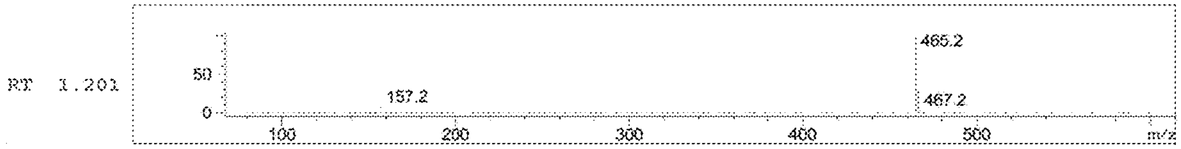
FIG. 29 is the mass spectrogram of the compound PXG21 prepared in the present invention.

MS(ES-API) cacld. for $C_{22}H_{16}ClN_5O_2$ found 465.2[M+1]$^+$. (FIG. 29)

Preparation Example 22 Preparation of Compound PXG22

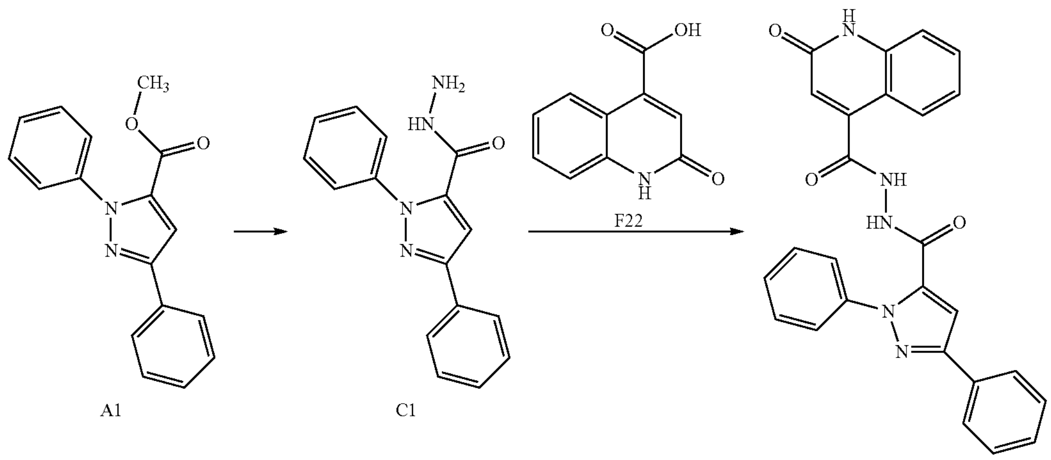

A1

C1

PXG22

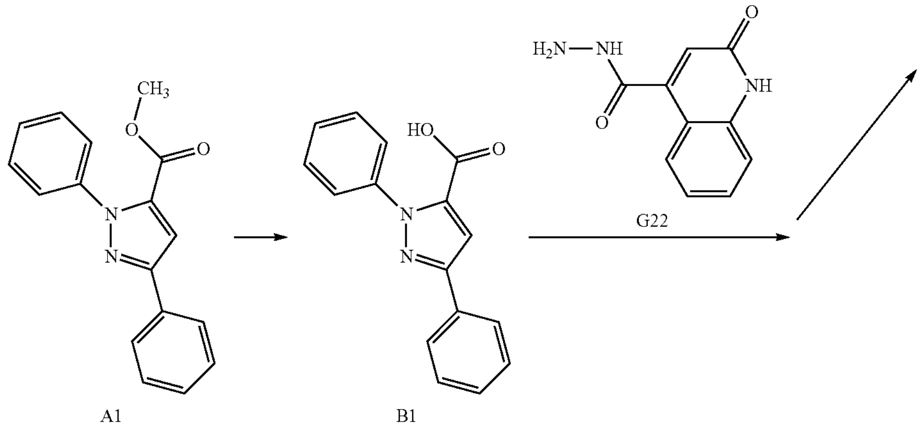

A1

B1

Method 1: Compound PXG22 was prepared using the same method and steps as in Preparation Example 1, except that compound F22 (carboxylic acid) (3.40 g, 1 eq) was added into the 100 ml three-neck flask in step (2). Or Method 2: Compound PXG22 was prepared using the same method and steps as in Preparation Example 1, except that compound G22 (hydrazide) (5.58 g, 1.1 eq) was added after stirring for 10 minutes in step (2).

Figure 30:
FIG. 30 is the mass spectrogram of the compound PXG22 prepared in the present invention.
Figure 31:
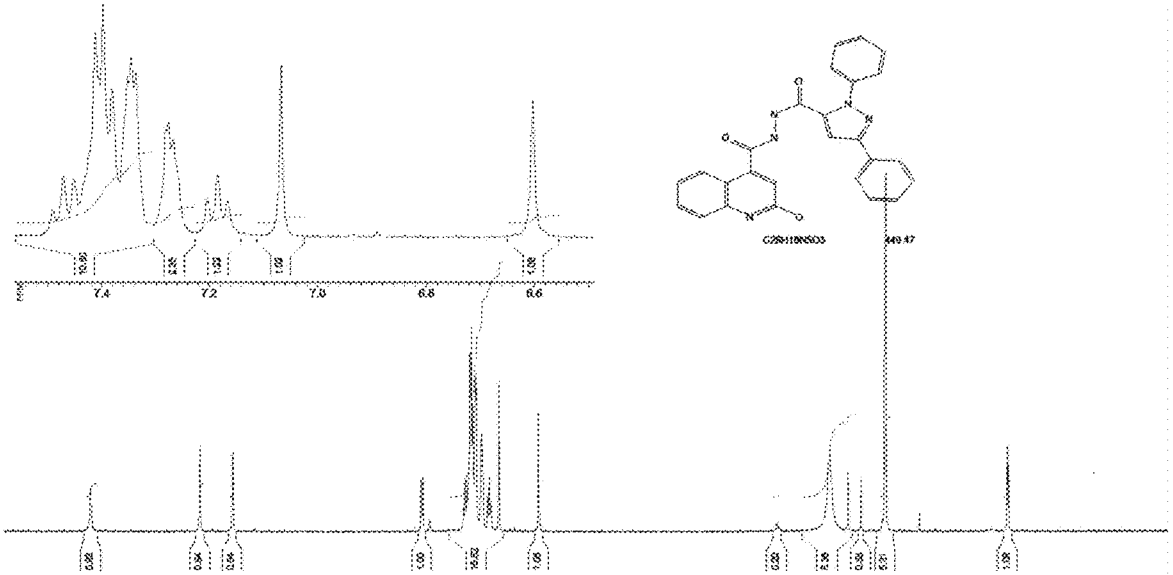
FIG. 31 is the $^1$H-NMR spectrogram of the compound PXG22 prepared in the present invention dissolved in deuterated DMSO.

MS(ES-API) cacld. for $C_{26}H_{19}N_5O_3$ found 450.2[M+1]$^+$. (FIG. 30); HNMR (400 MHz, DMSO): δ 1.05 (s, 1H), 2.45 (m, 5H), 3.2 (s, 5H), 6.6 (s, 1H), 7.05-7.5 (m, 15H), 8.05 (s, 1H), 10.0 (s, 1H), 10.4 (s, 1H), 12.05 (s, 1H). (FIG. 31)

Preparation Example 23 Preparation of Compound PXG23

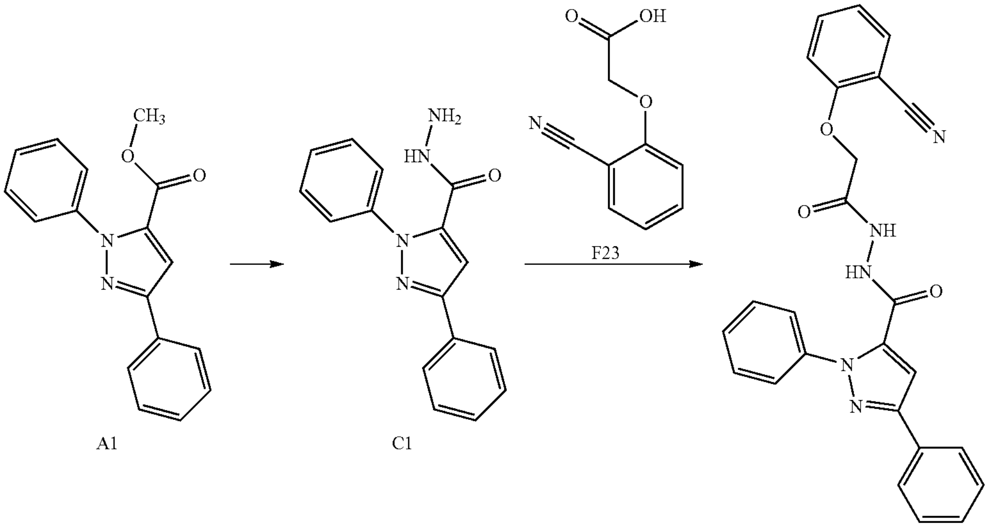

A1 C1 PXG23

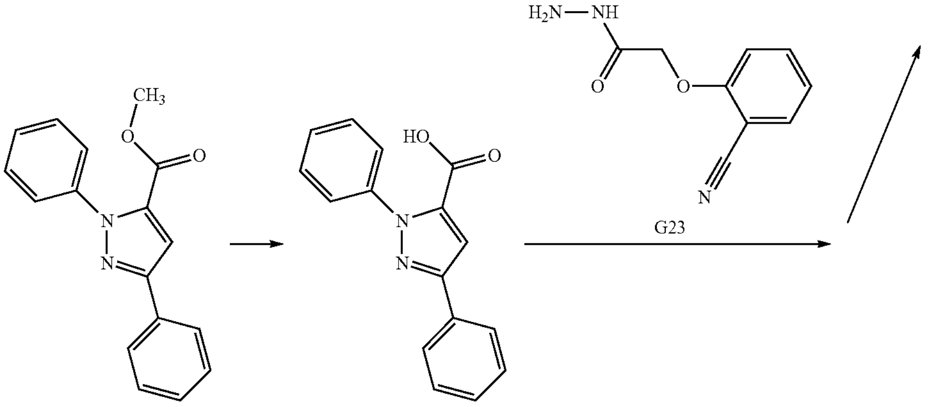

A1 B1

Method 1: Compound PXG23 was prepared using the same method and steps as in Preparation Example 1, except that compound F23 (carboxylic acid) (3.19 g, 1 eq) was added into the 100 ml three-neck flask in step (2). Or Method 2: Compound PXG23 was prepared using the same method and steps as in Preparation Example 1, except that compound G23 (hydrazide) (5.25 g, 1.1 eq) was added after stirring for 10 minutes in step (2).

Figure 32:
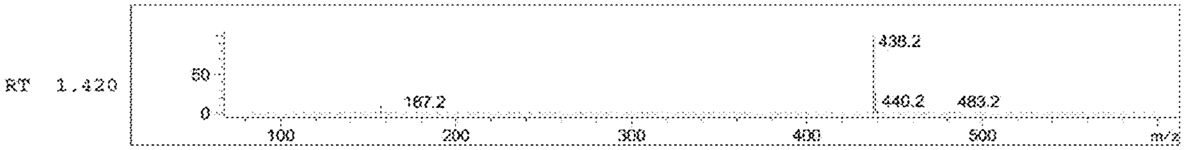
FIG. 32 is the mass spectrogram of the compound PXG23 prepared in the present invention.
Figure 33:
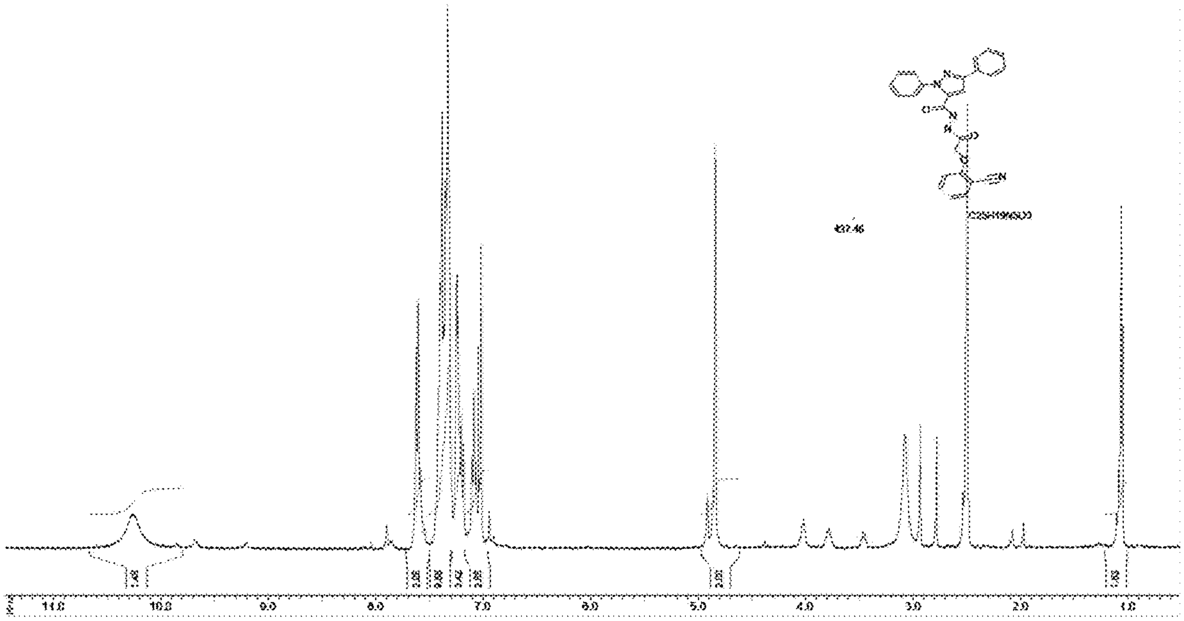
FIG. 33 is the $^1$H-NMR spectrogram of the compound PXG23 prepared in the present invention dissolved in deuterated DMSO.

MS(ES-API) cacld. for $C_{25}H_{19}N_5O_3$ found 438.2[M+1]$^+$. (FIG. 32); HNMR (400 MHz, DMSO): δ 4.8 (s, 2H), 7.05-7.8 (m, 17H), 10.3 (s, 1H). (FIG. 33)

Preparation Example 24 Preparation of Compound PXG24

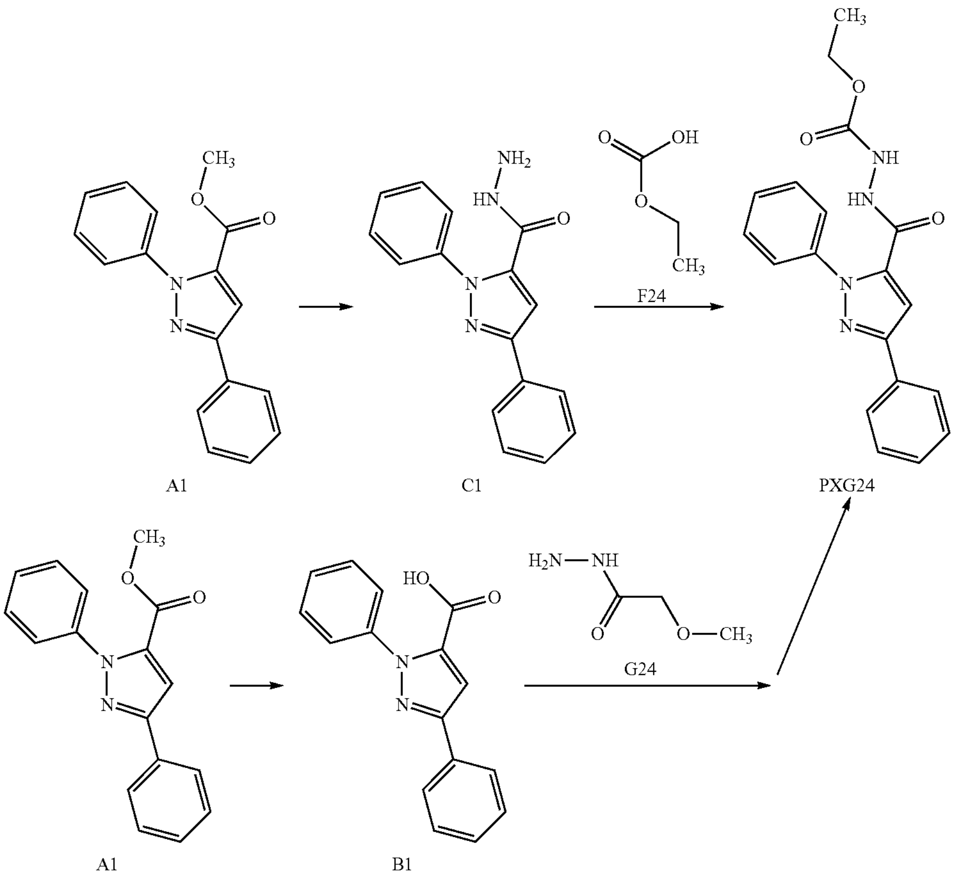

Method 1: Compound PXG24 was prepared using the same method and steps as in Preparation Example 1, except that compound F24 (carboxylic acid) (1.62 g, 1 eq) was added into the 100 ml three-neck flask in step (2). Or Method 2: Compound PXG24 was prepared using the same method and steps as in Preparation Example 1, except that compound G24 (hydrazide) (2.86 g, 1.1 eq) was added after stirring for 10 minutes in step (2).

Figure 34:
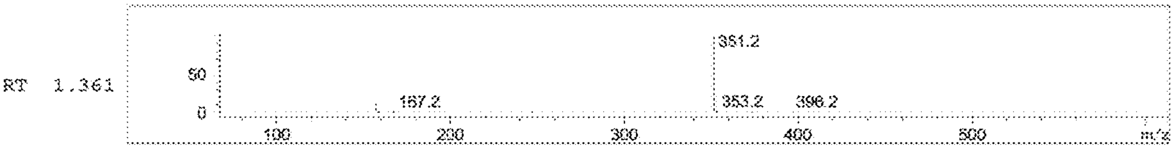
FIG. 34 is the mass spectrogram of the compound PXG24 prepared in the present invention.
Figure 35:
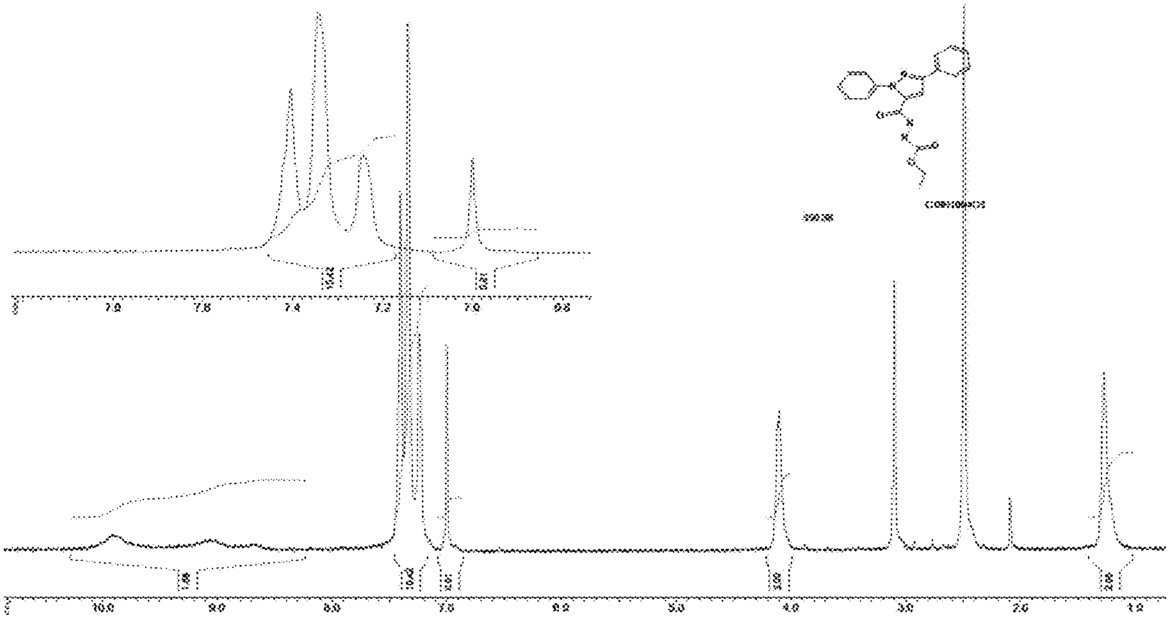
FIG. 35 is the $^1$H-NMR spectrogram of the compound PXG24 prepared in the present invention dissolved in deuterated DMSO.

MS(ES-API) cacld. for $C_{19}H_{18}N_4O_3$ found 351.2[M+1]$^+$. (FIG. 34); HNMR (400 MHz, DMSO): δ 1.25 (s, 3H), 4.05 (s, 2H), 7.05 (s, 1H), 7.2-7.4 (in, 10H). (FIG. 35)

Preparation Example 25 Preparation of Compound PXG25

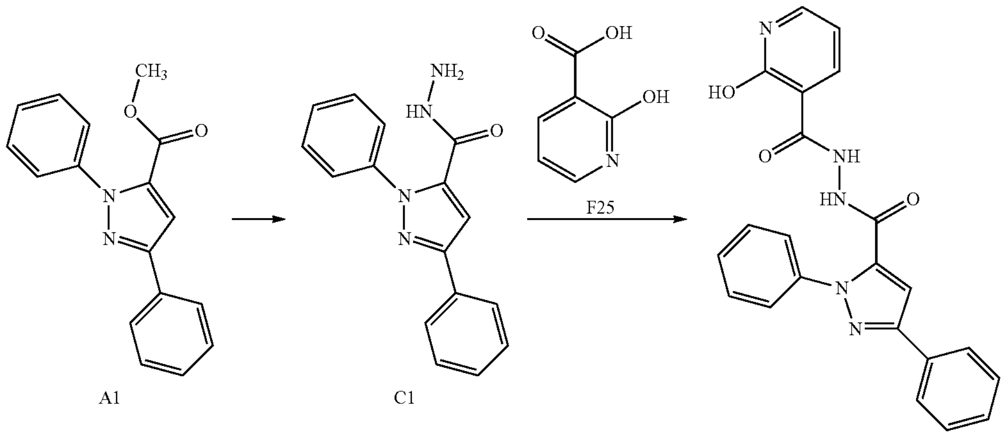

PXG25

-continued

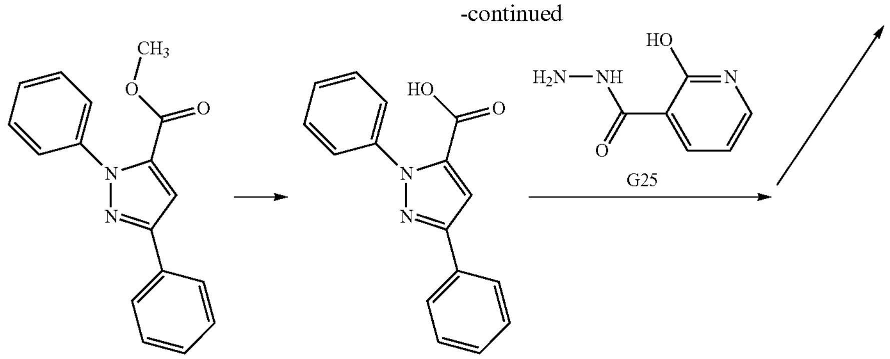

A1 B1

Method 1: Compound PXG25 was prepared using the same method and steps as in Preparation Example 1, except that compound F25 (carboxylic acid) (2.50 g, 1 eq) was added into the 100 ml three-neck flask in step (2). Or Method 2: Compound PXG25 was prepared using the same method and steps as in Preparation Example 1, except that compound G25 (hydrazide) (4.21 g, 1.1 eq) was added after stirring for 10 minutes in step (2).

Figure 36:
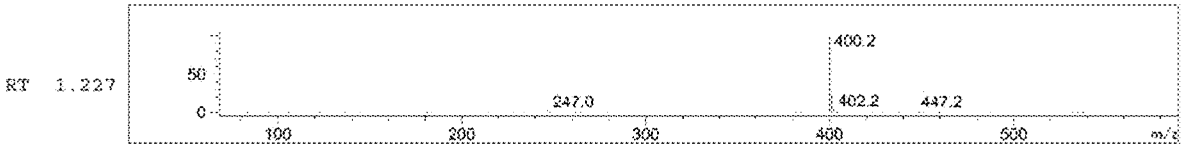
FIG. 36 is the mass spectrogram of the compound PXG25 prepared in the present invention.

MS(ES-API) cacld. for $C_{22}H_{17}N_5O_3$ found 400.2[M+1]$^+$. (FIG. 36)

Preparation Example 26 Preparation of Compound PXG26

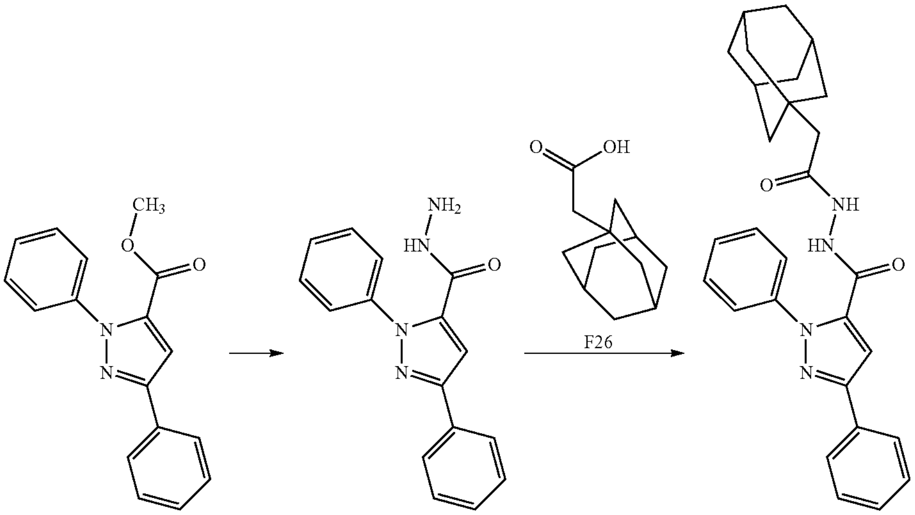

A1 C1 PXG26

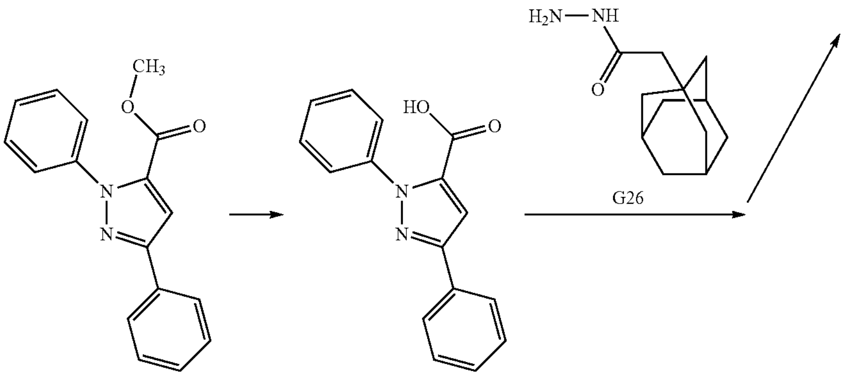

A1 B1

Method 1: Compound PXG26 was prepared using the same method and steps as in Preparation Example 1, except that compound F26 (carboxylic acid) (3.49 g, 1 eq) was added into the 100 ml three-neck flask in step (2). Or Method 2: Compound PXG26 was prepared using the same method and steps as in Preparation Example 1, except that compound G26 (hydrazide) (5.72 g, 1.1 eq) was added after stirring for 10 minutes in step (2).

Figure 37:
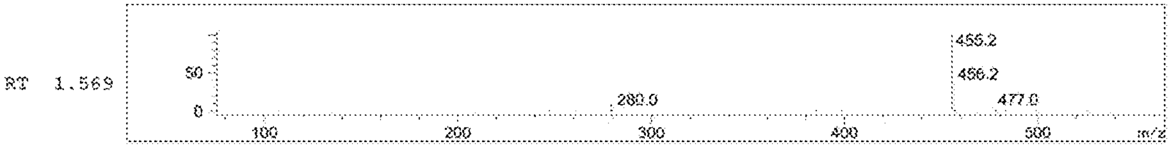
FIG. 37 is the mass spectrogram of the compound PXG26 prepared in the present invention.
Figure 38:
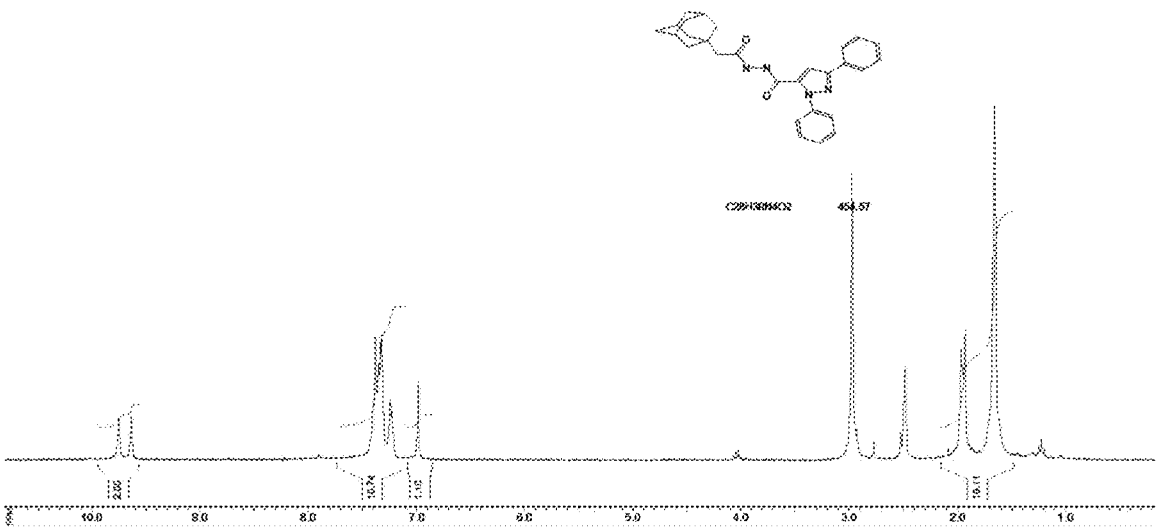
FIG. 38 is the $^1$H-NMR spectrogram of the compound PXG26 prepared in the present invention dissolved in deuterated DMSO.

MS(ES-API) cacld. for $C_{28}H_{30}N_4O_2$ found 455.2[M+1]$^+$. (FIG. 37); HNMR (400 MHz, DMSO): δ 1.6-2.0 (m, 19H), 7.1 (s, 1H), 7.2-7.4 (m, 10H), 9.6 (d, 2H). (FIG. 38)

Preparation Example 27 Preparation of Compound PXG27

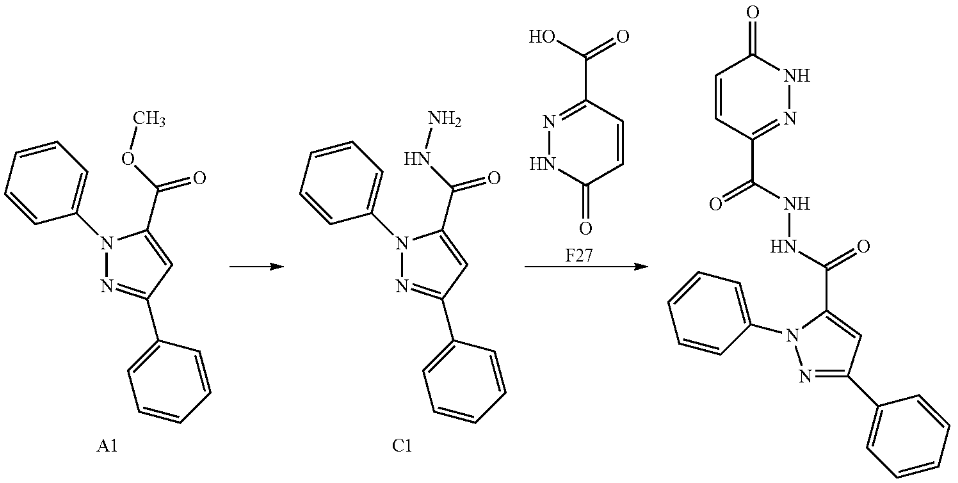

A1 C1 F27 PXG27

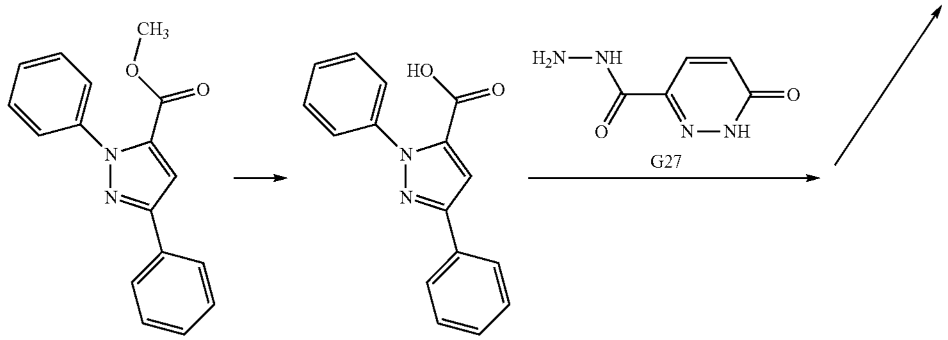

A1 B1 G27

Method 1: Compound PXG27 was prepared using the same method and steps as in Preparation Example 1, except that compound F27 (carboxylic acid) (2.52 g, 1 eq) was added into the 100 ml three-neck flask in step (2). Or Method 2: Compound PXG27 was prepared using the same method and steps as in Preparation Example 1, except that compound G27 (hydrazide) (4.24 g, 1.1 eq) was added after stirring for 10 minutes in step (2).

Figure 39:
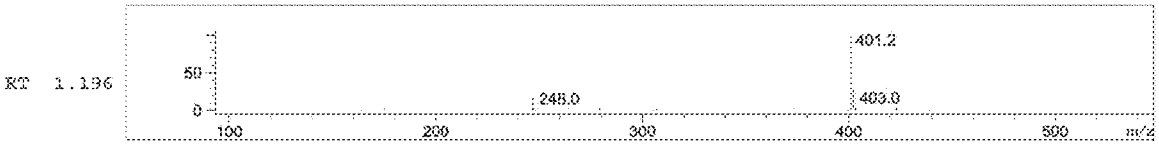
FIG. 39 is the mass spectrogram of the compound PXG27 prepared in the present invention.
Figure 40:
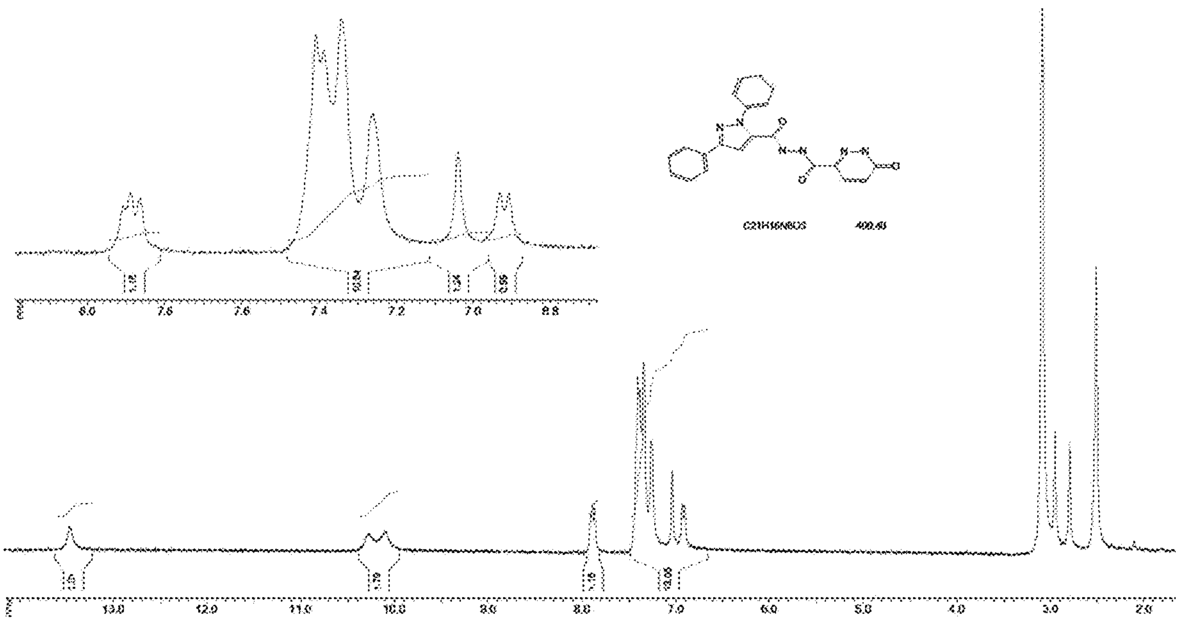
FIG. 40 is the $^1$H-NMR spectrogram of the compound PXG27 prepared in the present invention dissolved in deuterated DMSO.

MS(ES-API) cacld. for $C_{21}H_{16}N_6O_3$ found 455.2[M+1]+. (FIG. 39); HNMR (400 MHz, DMSO): δ 6.8-7.3 (m, 13H), 7.8 (m, 1H), 10.2 (m, 2H), 13.5 (s, 1H). (FIG. 40)

Preparation Example 28 Preparation of Compound PXG28

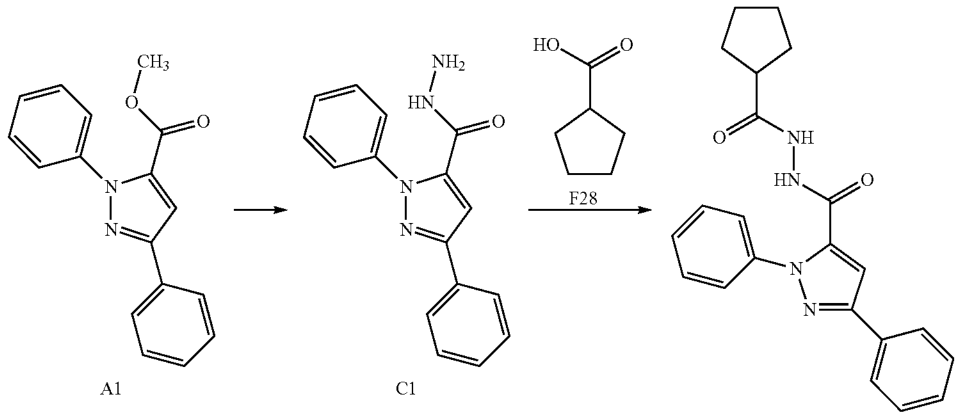

A1 C1 PXG28

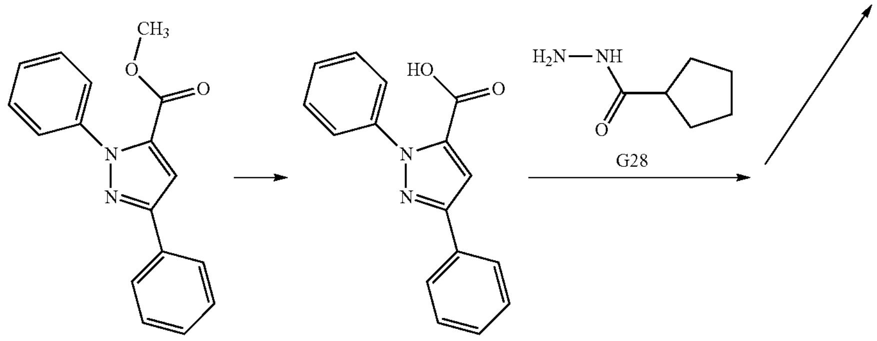

A1 B1

Method 1: Compound PXG28 was prepared using the same method and steps as in Preparation Example 1, except that compound F28 (carboxylic acid) (2.05 g, 1 eq) was added into the 100 ml three-neck flask in step (2). Or Method 2: Compound PXG28 was prepared using the same method and steps as in Preparation Example 1, except that compound G28 (hydrazide) (3.52 g, 1.1 eq) was added after stirring for 10 minutes in step (2).

Figure 41:
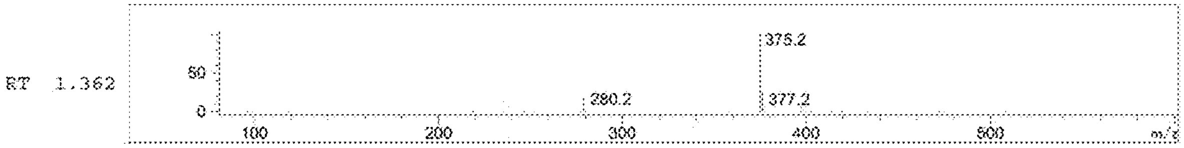
FIG. 41 is the mass spectrogram of the compound PXG28 prepared in the present invention.

MS(ES-API) cacld. for $C_{22}H_{22}N_4O_2$ found 375.2 $[M+1]^+$. (FIG. 41)

Preparation Example 29 Preparation of Compound PXG29

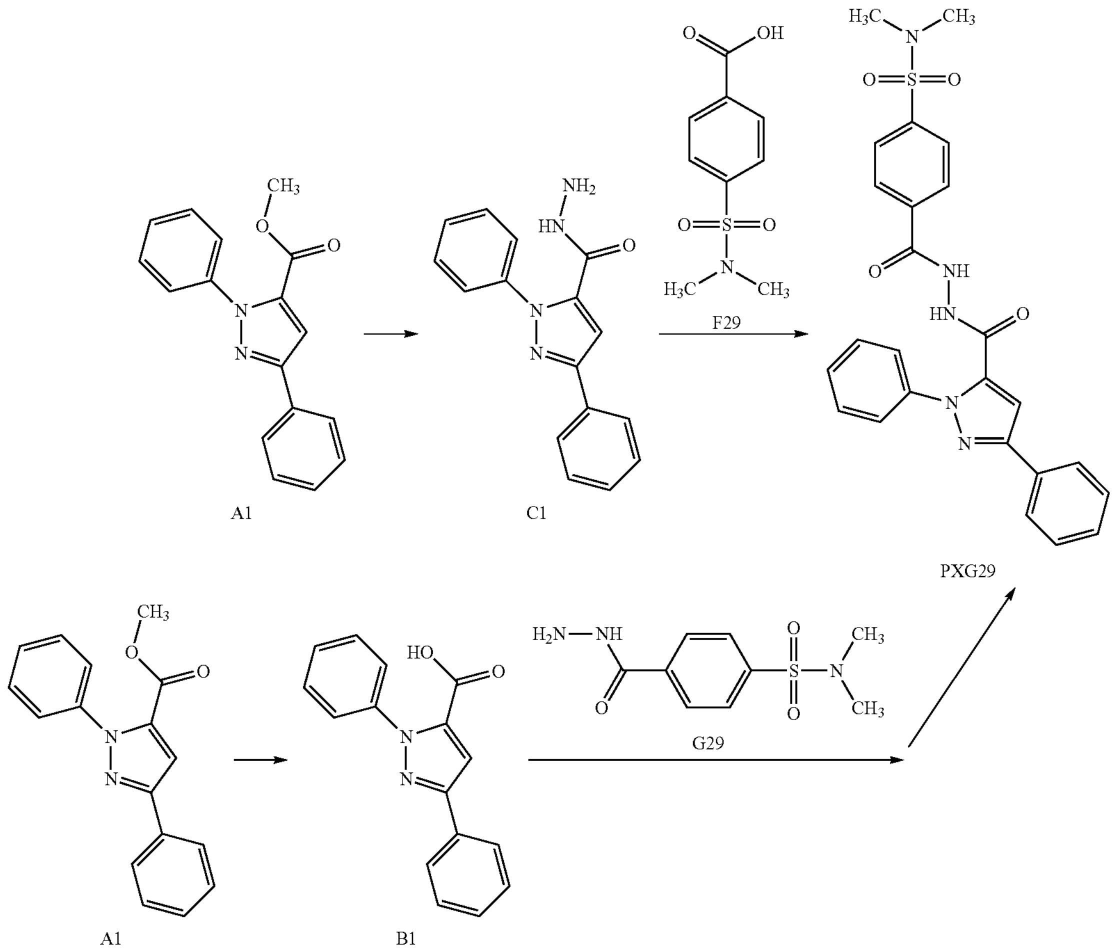

A1 C1 PXG29 A1 B1

Method 1: Compound PXG29 was prepared using the same method and steps as in Preparation Example 1, except that compound F29 (carboxylic acid) (4.12 g, 1 eq) was added into the 100 ml three-neck flask in step (2). Or Method 2: Compound PXG29 was prepared using the same method and steps as in Preparation Example 1, except that compound G29 (hydrazide) (6.68 g, 1.1 eq) was added after stirring for 10 minutes in step (2).

Figure 42:
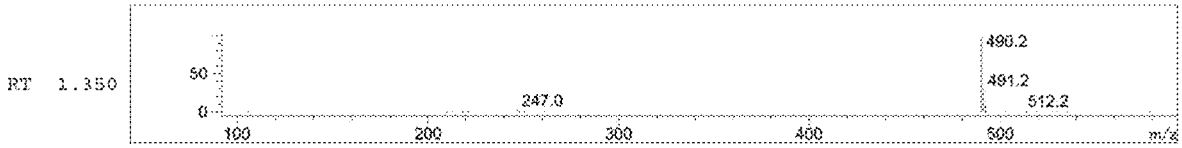
FIG. 42 is the mass spectrogram of the compound PXG29 prepared in the present invention.
Figure 43A:
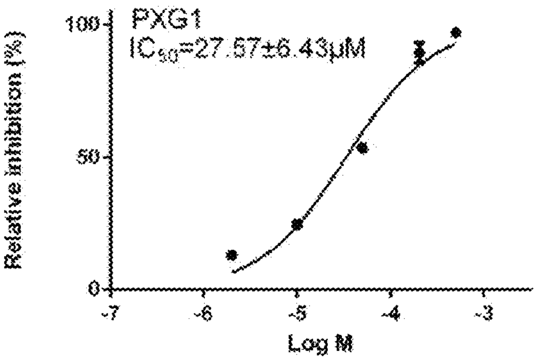
FIGS. 43A-43D are the inhibition curve of some compounds of the present invention against total enzymes of GSTs of *Plutella xylostella.*
Figure 43B:
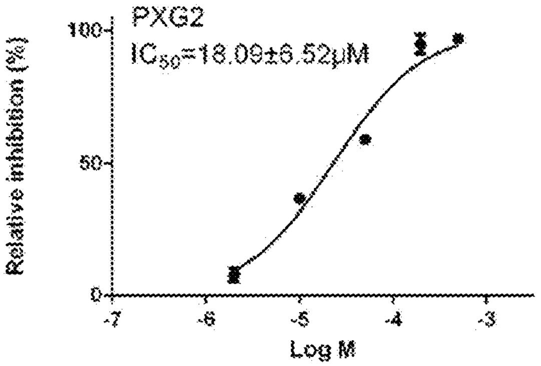
Figure 43C:
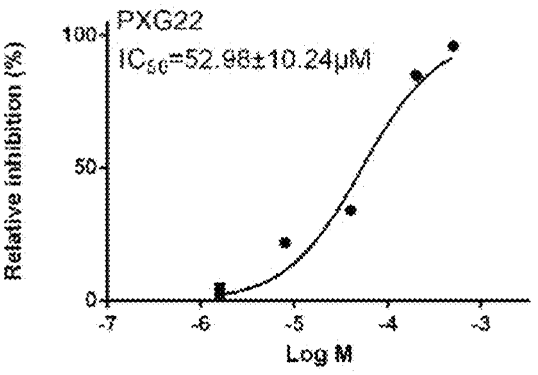
Figure 43D:
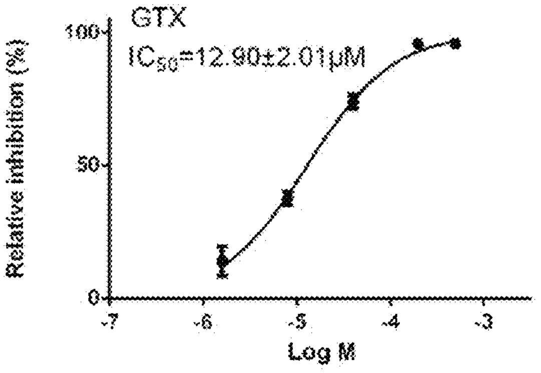
Figure 44A:
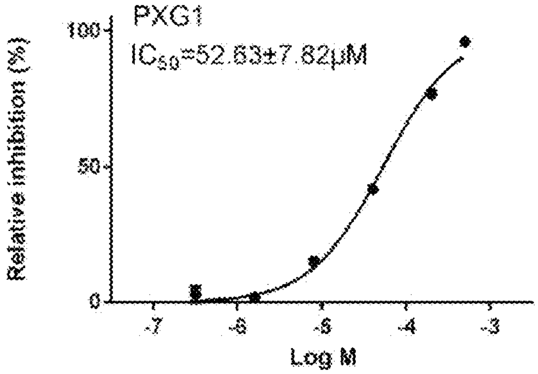
FIGS. 44A-44B are the inhibition curve of some compounds of the present invention against total enzymes of GSTs of *Carposina sasakii.*
Figure 44B:
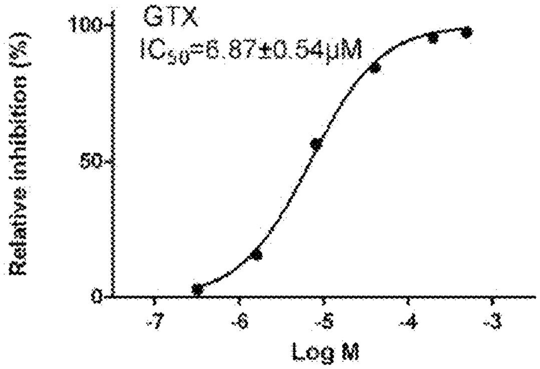
Figure 45A:
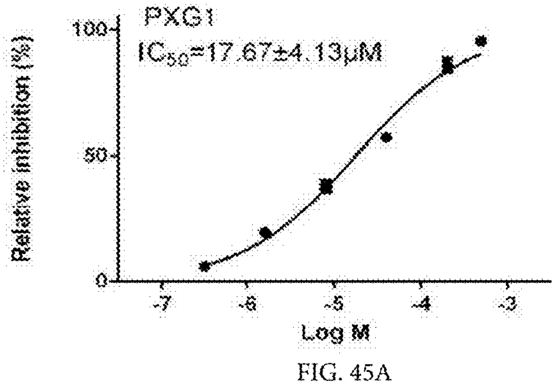
FIGS. 45A-45C are the inhibition curve of some compounds of the present invention against total enzymes of GSTs of *Spodoptera litura.*
Figure 45B:
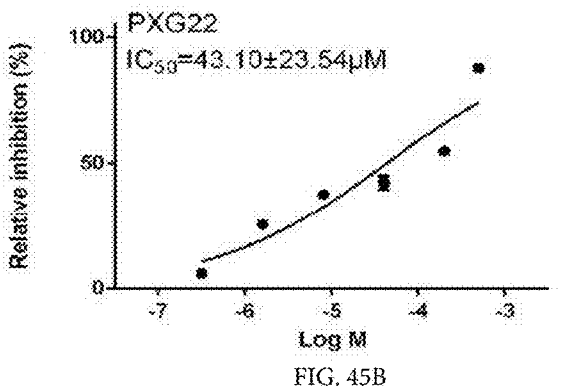
Figure 45C:
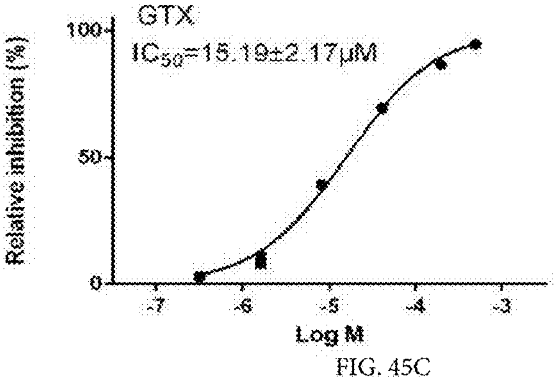
Figure 46A:
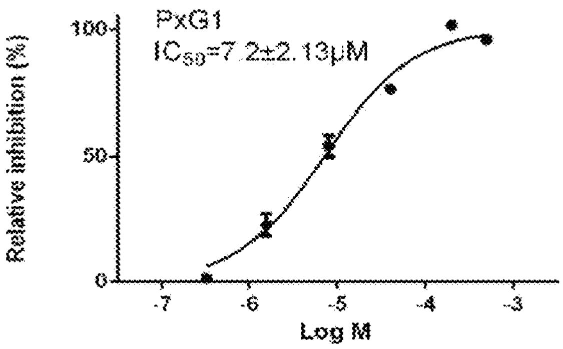
FIGS. 46A-46E are the inhibition curve of some compounds of the present invention against total enzymes of GSTs of *Mythimna separata.*
Figure 46B:
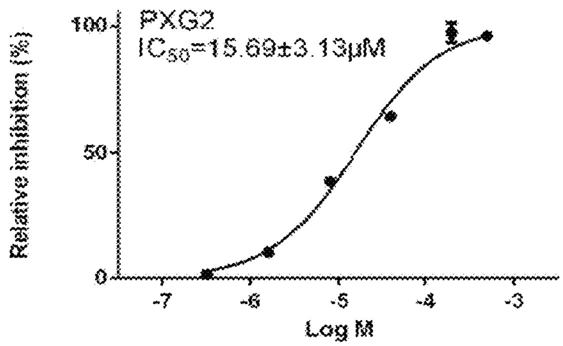
Figure 46C:
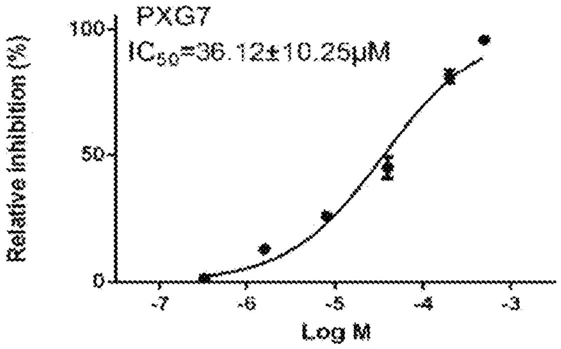
Figure 46D:
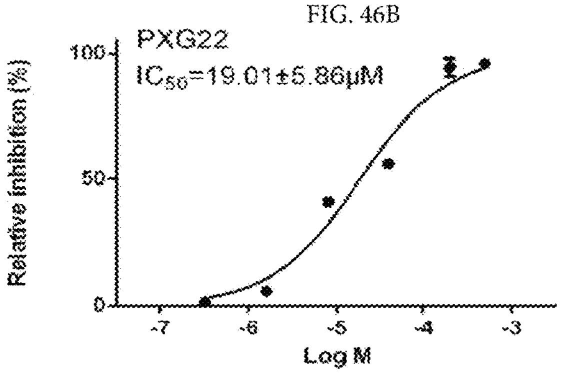
Figure 46E:
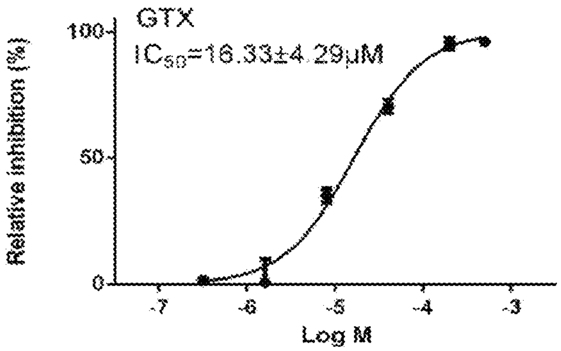
Figure 47A:
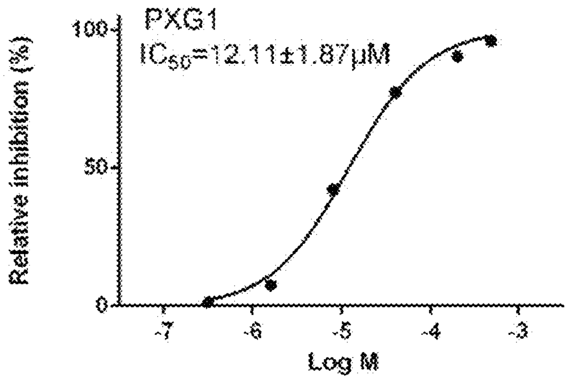
FIGS. 47A-47D are the inhibition curve of some compounds of the present invention against GSTs total enzymes of *Pyrausta nubilalis.*
Figure 47B:
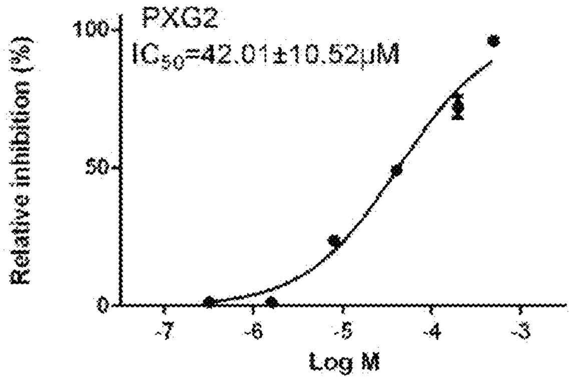
Figure 47C:
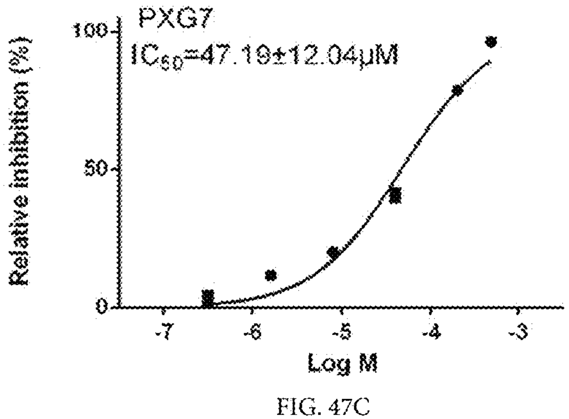
Figure 47D:
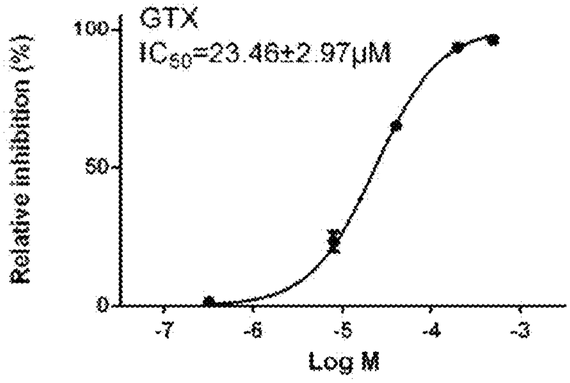
Figure 48A:
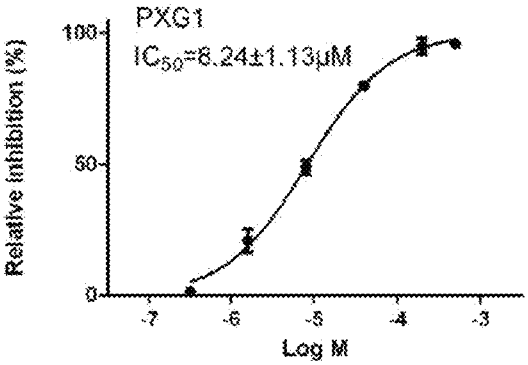
FIGS. 48A-48G are the inhibition curve of some compounds of the present invention against GSTs total enzymes of *Chilo suppressalis.*
Figure 48B:
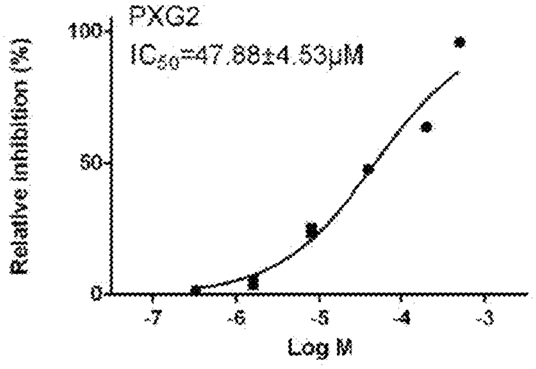
Figure 48C:
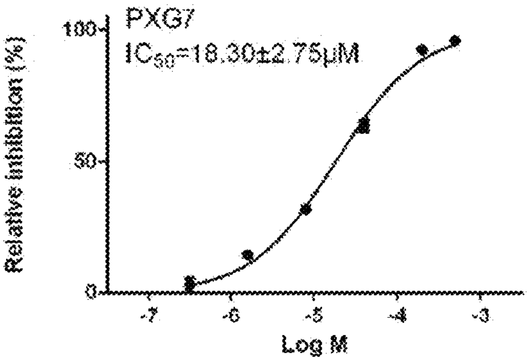
Figure 48D:
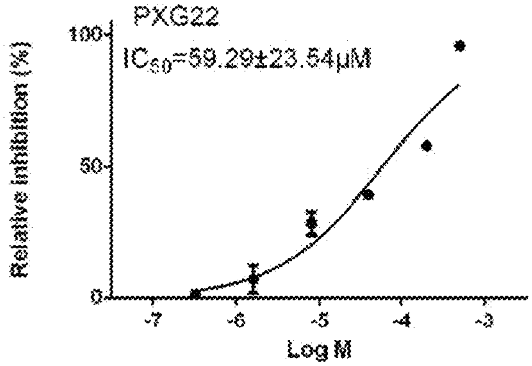
Figure 48E:
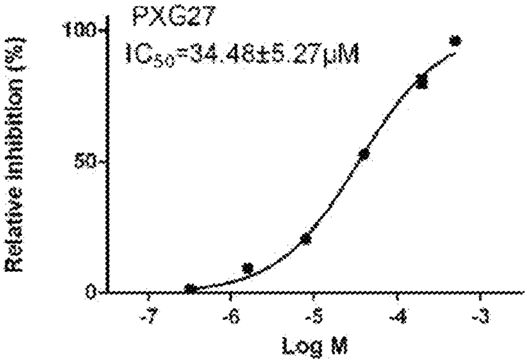
Figure 48F:
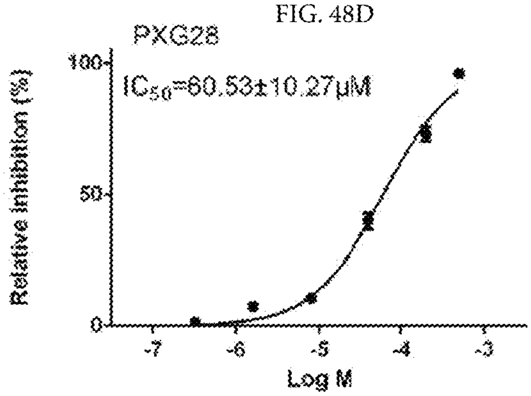
Figure 48G:
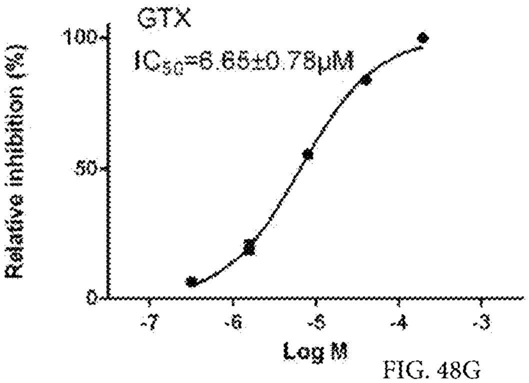
Figure 49A:
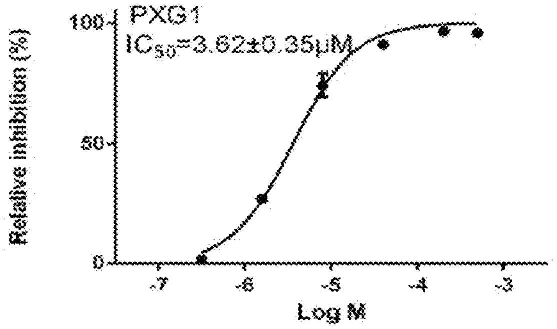
FIGS. 49A-49E are the inhibition curve of some compounds of the present invention against GSTs total enzymes of *Nilaparvata lugens.*
Figure 49B:
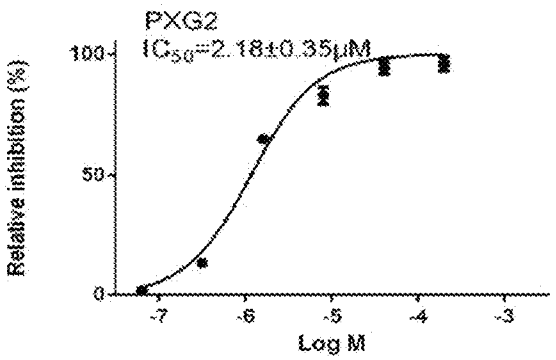
Figure 49C:
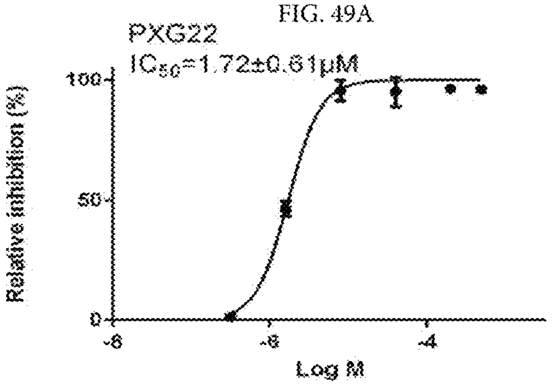
Figure 49D:
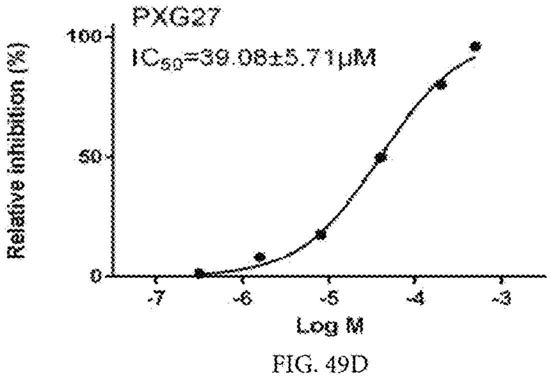
Figure 49E:
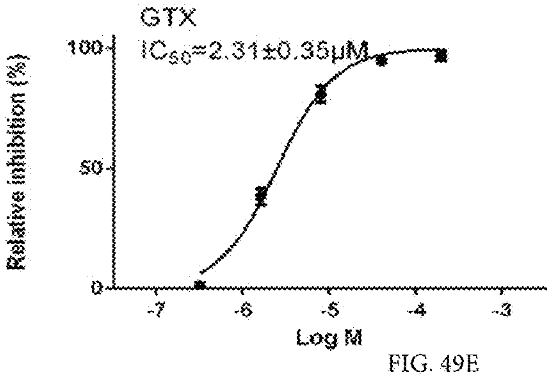
Figure 50A:
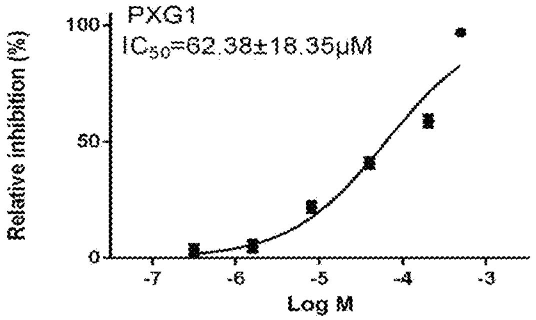
FIGS. 50A-50D are the inhibition curve of some compounds of the present invention against GSTs total enzymes of *Spodoptera frugiperda.*
Figure 50B:
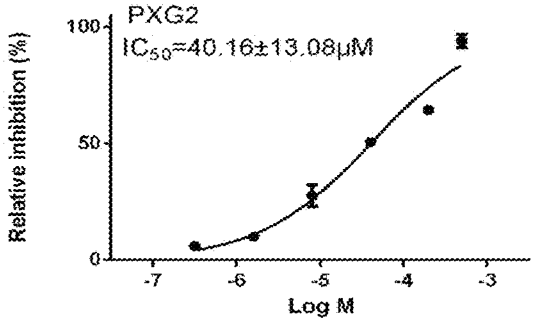
Figure 50C:
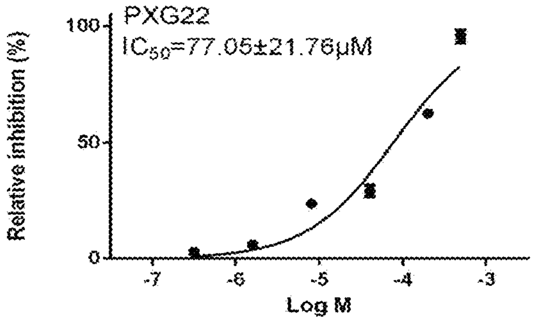
Figure 50D:
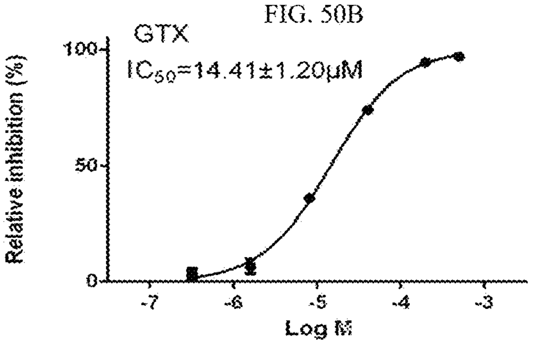
Figure 51A:
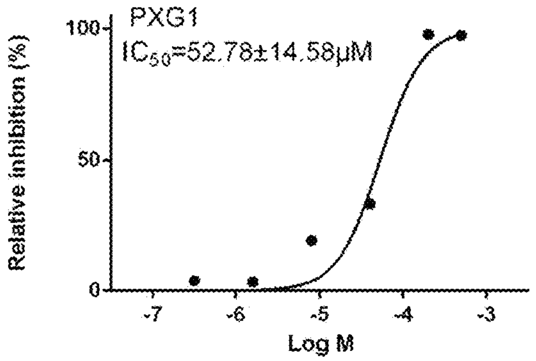
FIGS. 51A-51D are the inhibition curve of some compounds of the present invention against GSTs total enzymes of *Helicoverpa armigera.*
Figure 51B:
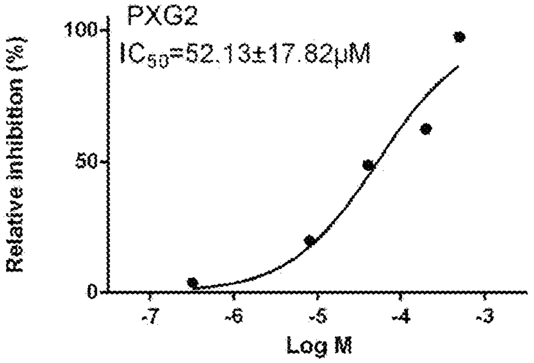
Figure 51C:
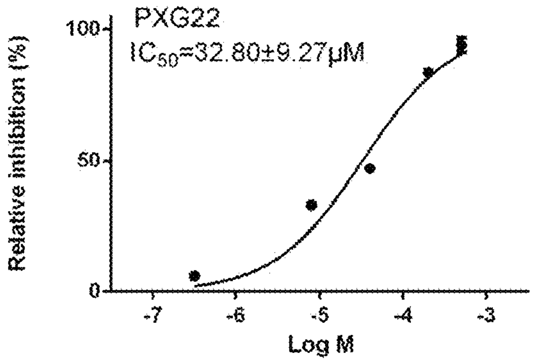
Figure 51D:
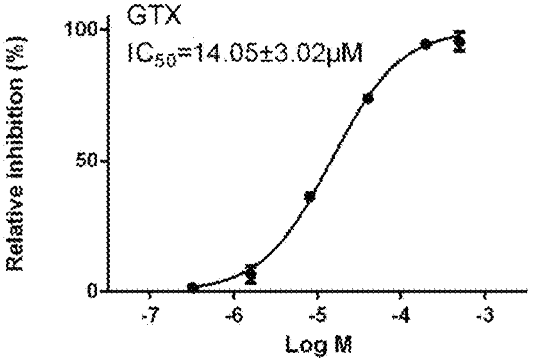
Figure 52A:
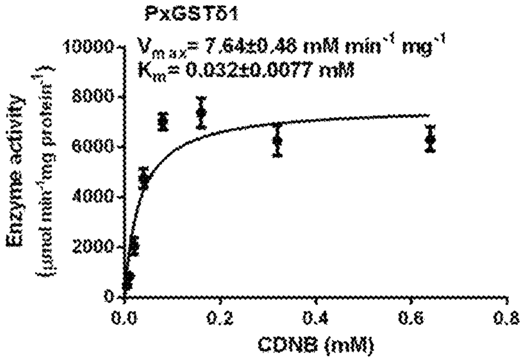
FIGS. 52A-52D are the enzyme kinetics curve of *Pxlutella xylostella* PxGSTs recombinant protein.
Figure 52B:
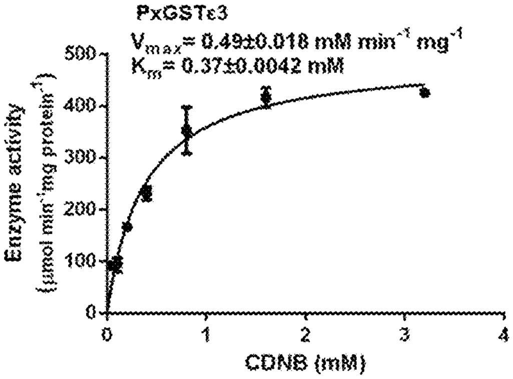
Figure 52C:
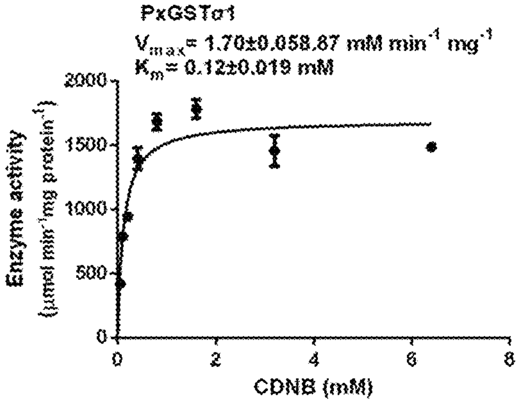
Figure 52D:
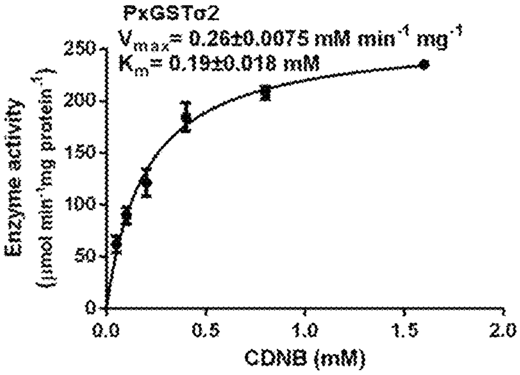
Figure 53A:
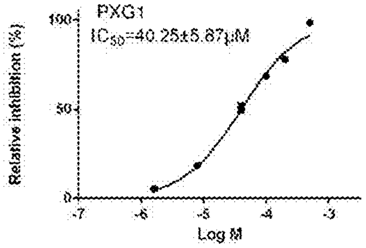
FIGS. 53A-53N are the inhibition curve of some compounds of the present invention against PxGSTδ1.
Figure 53B:
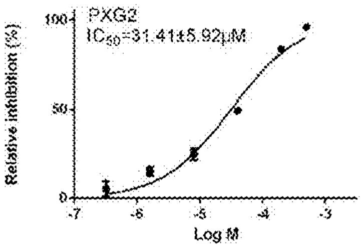
Figure 53C:
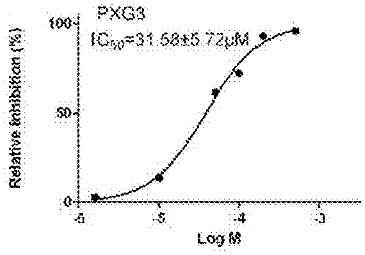
Figure 53D:
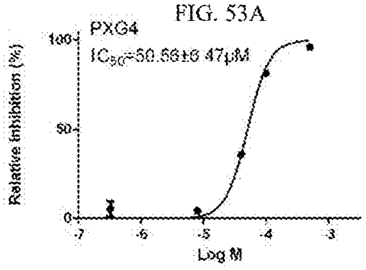
Figure 53E:
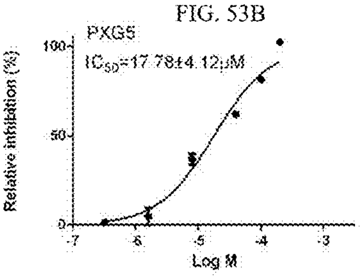
Figure 53F:
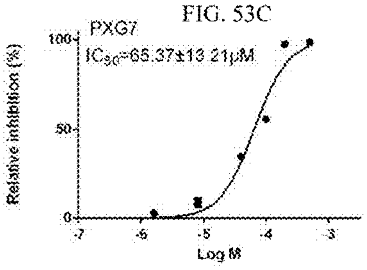
Figure 53G:
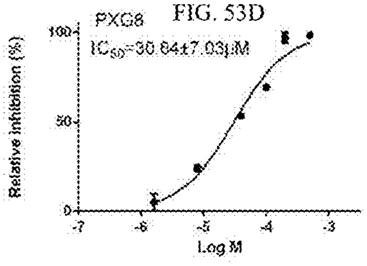
Figure 53H:
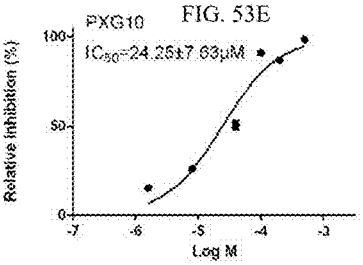
Figure 53I:
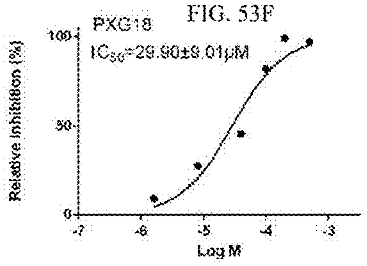
Figure 53J:
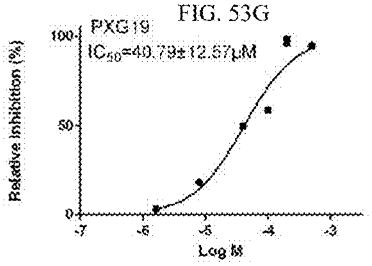
Figure 53K:
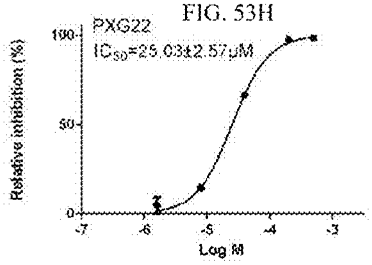
Figure 53L:
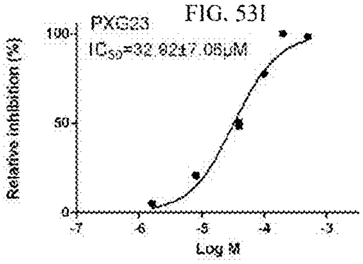
Figure 53M:
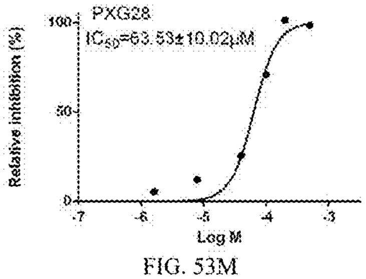
Figure 53N:
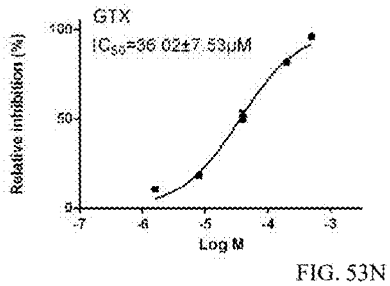
Figure 54A:
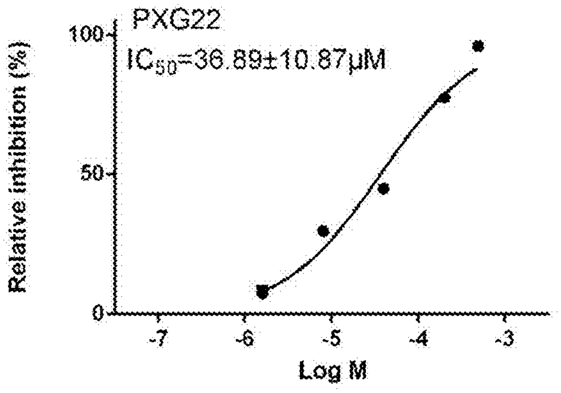
FIGS. 54A-54B are the inhibition curve of some compounds of the present invention against PxGSTε3.
Figure 54B:
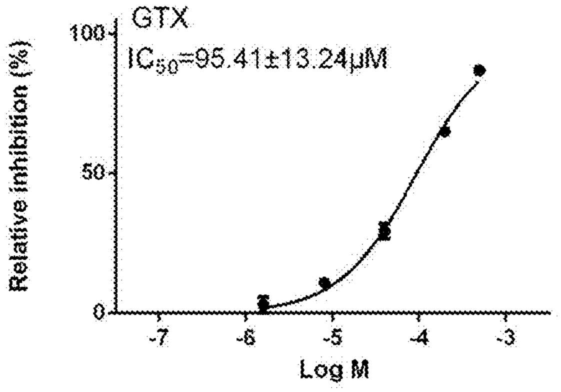
Figure 55A:
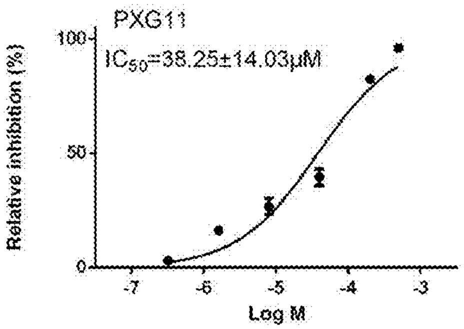
FIGS. 55A-55I are the inhibition curve of some compounds of the present invention against PxGSTσ1.
Figure 55B:
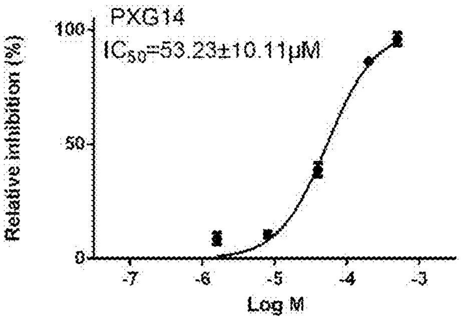
Figure 55C:
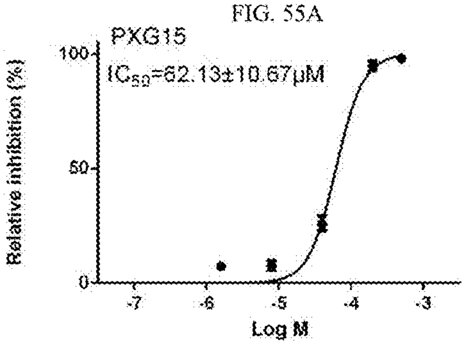
Figure 55D:
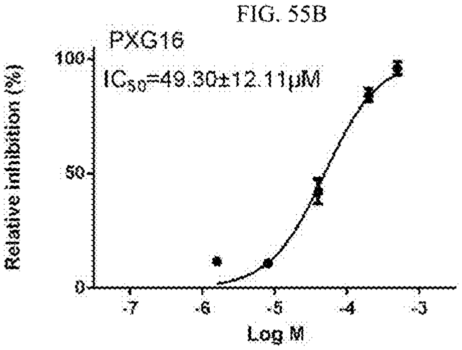
Figure 55E:
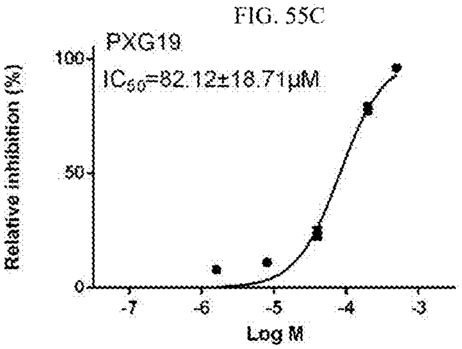
Figure 55F:
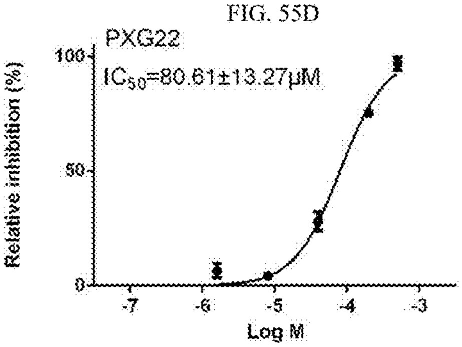
Figure 55G:
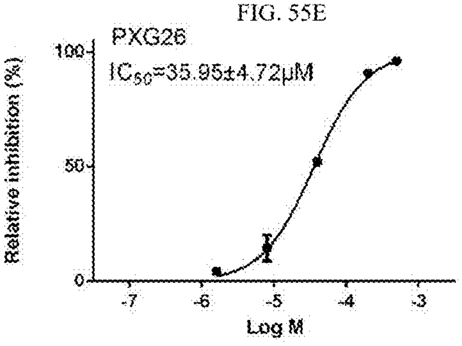
Figure 55H:
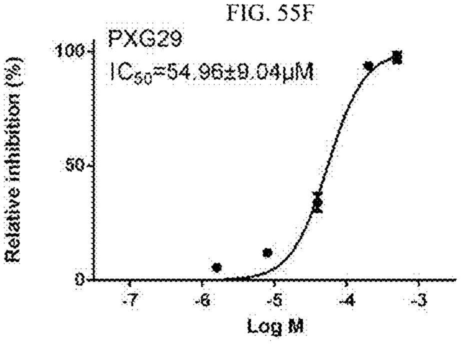
Figure 55I:
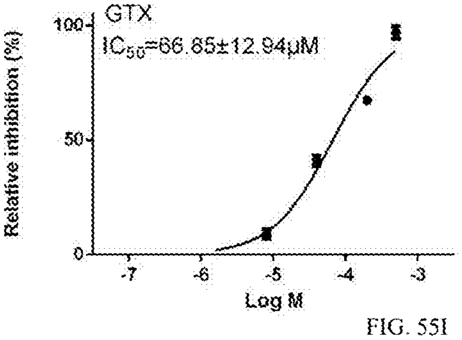
Figure 56A:
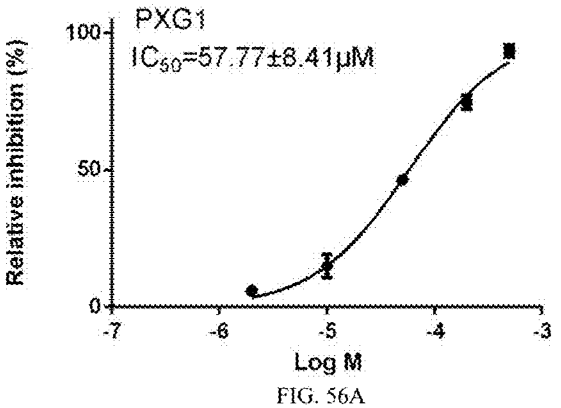
FIGS. 56A-56C are the inhibition curve of some compounds of the present invention against PxGSTσ2.
Figure 56B:
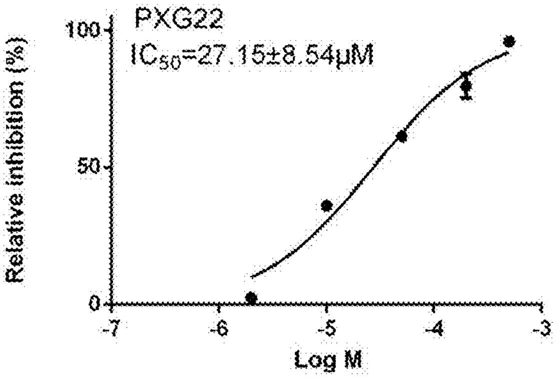
Figure 56C:
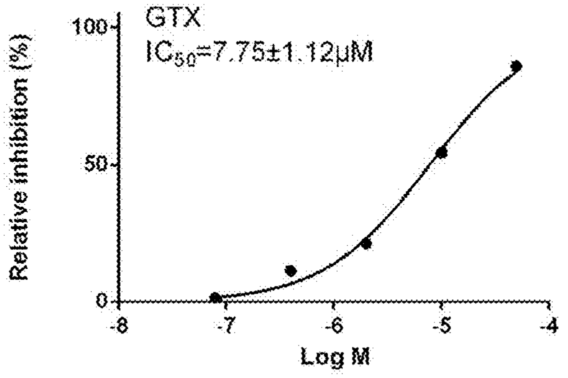

MS(ES-API) cacld. for $C_{25}H_{23}N_5O_4S$ found 490.2[M+1]$^+$. (FIG. 42)

Experimental Example 1: Inhibitory Activity Assay of the Compounds PXG1-PXG29 (29 Compounds) of the Present Invention Against the Total GSTs Enzyme of 6 Kinds of Field Crop Pests and 3 Kinds of Economic Crop Pests Experiment: About 50 mg of larvae/nymphs of nine major pests such as *Plutella xylostella, Mythimna separata, Pyrausta nubilalis, Chilo suppressalis, Nilaparvata lugens, Spodoptera frugiperda, Helicoverpa armigera, Carposina sasakii, Spodoptera litura* were taken, grounded in a mortar pre-cooled at −80° C., and then 1 mL of 100 mM sodium phosphate buffer (1 mM EDTA, pH 7.2) was added and fully homogenized. The homogenate was transferred to a 1.5 mL centrifuge tube at 4° C., and centrifuged at 14,000 g for 30 minutes, and the supernatant was transferred to a new centrifuge tube as the GSTs total enzyme. The protein concentrations of the above total enzymes were determined using the BCA method.

100 μL of PBS buffer (100 mM, pH 7.2) containing 1 mM GSH was taken and placed in a 96-well plate, 5 μg of insect total GSTs enzymes and an appropriate concentration of compounds PXG1-PXG29 (29 compounds) of the present invention were added to each well, after uniformly mixing, and allowed to stand at 30° C. for 10 min. Then 100 μL of PBS buffer (100 mM, pH 7.2) containing 1 mM CDNB was added to each well. Immediately after mixing, the mixture was placed in a microplate reader to measure the absorbance at a wavelength of 340 nm (A 340) once every 1 min, the measurement was carried out continuously for 5 min, the light absorption values of each measuring point were recorded and the inhibition rate in vitro of the compounds with different concentrations against insects total GSTs enzymes were calculated. Each group of assays was repeated three times, and total GSTs enzymes inactivated at 100° C. for 5 min were used as negative controls, and GTX was used as positive controls. GraphPad Prism 5 software was used for analysis and calculation of $IC_{50}$. Relative inhibition was calculated using the following formula:

$$\text{Relative inhibition (\%)} = \frac{\Delta A_{340c} - \Delta A_{340t}}{\Delta OD_{340c}} \times 100$$

wherein, $A_{340}$ is the change of $A_{340}$ within 5 minutes for the control group, and $A_{340t}$ is the change of $A_{340}$ within 5 minutes for the experimental group.

Results: The experimental results are shown in Table 1, Table 2, and FIGS. 43 to 51. The compounds PXG1-PXG29 (29 compounds) of the present invention have a certain inhibitory activity on the total GSTs enzymes of field crop pests and economic crop pests. Among them, $IC_{50}$ of the compound PXG1 of the present invention on the total GSTs enzymes of field crop pests including *Mythimna separata, Pyrausta nubilalis, Chilo suppressalis, Nilaparvata lugens, Spodoptera frugiperda* and *Helicoverpa armigera*, and economic crop pests such as *Plutella xylostella, Carposina sasakii* and *Spodoptera litura* is 27.57 µM, 7.2 µM, 12.11 µM, 8.24 µM, 3.62 µM, 62.38 µM, 52.78 µM, 52.63 µM, 17.67 µM, respectively; $IC_{50}$ of the compound PXG2 of the present invention on the total GSTs enzymes of field crop pests such as *Mythimna separata, Pyrausta nubilalis, Chilo suppressalis, Nilaparvata lugens, Spodoptera frugiperda* and *Helicoverpa armigera*, and economic crop pests such as *Plutella xylostella* is 18.09 µM, 15.69 µM, 42.01 µM, 47.88 µM, 2.18 µM, 40.16 µM and 52.13 µM, respectively. $IC_{50}$ of the compound PXG2 of the present invention on the total GSTs enzyme of economic crop pests such as *Carposina sasakii* and *Spodoptera litura* is greater than 100 µM, and the inhibitory rates at 100 µM are respectively 35.12% and 57.13%; $IC_{50}$ of the compound PXG22 of the present invention on the total GSTs enzyme of field crop pests such as *Mythimna separata, Chilo suppressalis, Nilaparvata lugens, Spodoptera frugiperda* and *Helicoverpa armigera*, and economic crop pests such as *Plutella xylostella* and *Spodoptera litura* is 52.98 µM, 19.01 µM, 59.29 µM, 1.72 µM, 77.05 µM, 32.8 µM, 43.1 µM, respectively. $IC_{50}$ of the compound PXG22 of the present invention on the total GSTs enzyme of field crop pests *Pyrausta nubilalis*, and economic crop pests such as *Carposina sasakii* are greater than 100 µM, and the inhibitory rates at 100 µM are respectively 42.38% and 42.76%; $IC_{50}$ of the positive control GSTs inhibitor GTX (S-Hexylglutathione) on the total GSTs enzymes of field crop pests such as *Mythimna separata, Pyrausta nubilalis, Chilo suppressalis, Nilaparvata lugens, Spodoptera frugiperda* and *Helicoverpa armigera*, and economic crop pests such as *Plutella xylostella, Carposina sasakii* and *Spodoptera litura* is 12.9 µM, 16.33 µM, 23.46 µM, 6.65 µM, 2.31 µM, 14.41 µM, 14.05 µM, 6.87 µM, 15.19 µM, respectively.

TABLE 1

The inhibitory effect of compounds PXG1-PXG29 of the present invention on the total GSTs enzymes of 3 kinds of economic crop pests

| Index | *Plutella xylostella* GSTs 100 µM Inhibition rate % | *Plutella xylostella* GSTs $IC_{50}$ (µM) | *Carposina sasakii* GSTs 100 µM Inhibition rate % | *Carposina sasakii* GSTs $IC_{50}$ (µM) | *Spodoptera litura* GSTs 100 µM Inhibition rate % | *Spodoptera litura* GSTs $IC_{50}$ (µM) |
|---|---|---|---|---|---|---|
| PXG1 | 70.90 | 27.57 | 71.91 | 52.63 | 80.06 | 17.67 |
| PXG2 | 69.27 | 18.09 | 35.12 | >100 | 57.13 | >100 |
| PXG3 | 25.47 | >100 | 23.07 | >100 | 17.09 | >100 |
| PXG4 | −10.64 | >100 | 2.34 | >100 | −17.52 | >100 |
| PXG5 | 11.58 | >100 | 23.22 | >100 | 37.80 | >100 |
| PXG6 | 21.15 | >100 | 18.21 | >100 | 6.90 | >100 |
| PXG7 | 15.46 | >100 | 48.15 | >100 | 57.87 | >100 |
| PXG8 | 35.73 | >100 | 19.83 | >100 | 44.25 | >100 |
| PXG9 | 3.94 | >100 | 12.55 | >100 | 12.58 | >100 |
| PXG10 | −17.71 | >100 | 32.54 | >100 | 3.87 | >100 |
| PXG11 | 22.90 | >100 | 76.09 | >100 | 24.52 | >100 |
| PXG12 | 15.08 | >100 | 17.94 | >100 | 4.60 | >100 |
| PXG13 | 26.60 | >100 | 25.90 | >100 | 9.91 | >100 |
| PXG14 | 10.33 | >100 | 20.64 | >100 | 2.49 | >100 |
| PXG15 | 16.83 | >100 | 17.01 | >100 | −5.22 | >100 |
| PXG16 | 8.64 | >100 | 6.98 | >100 | −0.15 | >100 |
| PXG17 | −1.63 | >100 | 12.40 | >100 | −4.14 | >100 |
| PXG18 | 32.94 | >100 | 13.69 | >100 | 7.95 | >100 |
| PXG19 | 23.03 | >100 | 19.42 | >100 | 31.70 | >100 |
| PXG20 | −1.50 | >100 | 10.99 | >100 | 7.09 | >100 |
| PXG21 | 16.96 | >100 | 35.52 | >100 | 5.00 | >100 |
| PXG22 | 60.50 | 52.98 | 42.77 | >100 | 56.09 | 43.1 |
| PXG23 | 26.35 | >100 | 19.76 | >100 | 12.89 | >100 |
| PXG24 | 29.72 | >100 | 22.33 | >100 | 28.38 | >100 |
| PXG25 | 31.66 | >100 | 48.54 | >100 | 22.37 | >100 |
| PXG26 | 25.09 | >100 | 18.11 | >100 | 15.89 | >100 |
| PXG27 | 42.68 | >100 | 43.24 | >100 | 45.08 | >100 |
| PXG28 | 22.40 | >100 | 49.51 | >100 | 46.09 | >100 |
| PXG29 | 9.32 | >100 | 33.57 | >100 | 4.60 | >100 |
| GTX | 73.72 | 12.9 | 95.39 | 6.87 | 85.61 | 15.19 |

TABLE 2

The inhibitory effect of compounds PXG1-PXG29 of the present invention on the total GSTs enzymes of 9 kinds of field crop pests

| | *Mythimna separata* GSTs | | *Pyrausta nubilalis* GSTs | | *Chilo suppressalis* GSTs | | *Nilaparvata lugens* GSTs | | *Spodoptera frugiperda* GSTs | | *Helicoverpa armigera* GSTs | |
|---|---|---|---|---|---|---|---|---|---|---|---|---|
| Index | 100 μM Inhibition rate % | $IC_{50}$ (μM) | 100 μM Inhibition rate % | $IC_{50}$ (μM) | 100 μM Inhibition rate % | $IC_{50}$ (μM) | 100 μM Inhibition rate % | $IC_{50}$ (μM) | 100 μM Inhibition rate % | $IC_{50}$ (μM) | 100 μM Inhibition rate % | $IC_{50}$ (μM) |
| PXG1 | 95.19 | 7.20 | 87.80 | 12.11 | 92.32 | 8.24 | 100.60 | 3.62 | 58.40 | 62.38 | 77.22 | 52.78 |
| PXG2 | 90.46 | 15.69 | 64.92 | 42.01 | 52.60 | 47.88 | 91.51 | 2.18 | 64.72 | 40.16 | 57.53 | 52.13 |
| PXG3 | 42.96 | >100 | 17.35 | >100 | 26.63 | >100 | 35.05 | >100 | 35.46 | >100 | 20.74 | >100 |
| PXG4 | 0.00 | >100 | −7.23 | >100 | −10.90 | >100 | −5.99 | >100 | −7.57 | >100 | 4.07 | >100 |
| PXG5 | 47.24 | >100 | 14.08 | >100 | 28.17 | >100 | 23.90 | >100 | 31.42 | >100 | 9.57 | >100 |
| PXG6 | 38.85 | >100 | 13.70 | >100 | 15.98 | >100 | −1.46 | >100 | 11.37 | >100 | 23.21 | >100 |
| PXG7 | 61.50 | 36.12 | 63.59 | 47.19 | 70.09 | 18.3 | 25.89 | >100 | 45.78 | >100 | 46.85 | >100 |
| PXG8 | 38.06 | >100 | 14.10 | >100 | 29.11 | >100 | 53.31 | >100 | 35.01 | >100 | 24.81 | >100 |
| PXG9 | 2.72 | >100 | 5.71 | >100 | 34.79 | >100 | −10.48 | >100 | 5.56 | >100 | 5.25 | >100 |
| PXG10 | −2.50 | >100 | −3.85 | >100 | 5.85 | >100 | 19.24 | >100 | 20.93 | >100 | 9.75 | >100 |
| PXG11 | 31.76 | >100 | 23.84 | >100 | 54.79 | >100 | 8.16 | >100 | 20.95 | >100 | 8.09 | >100 |
| PXG12 | 19.42 | >100 | 19.48 | >100 | 29.54 | >100 | −3.30 | >100 | 12.52 | >100 | −5.00 | >100 |
| PXG13 | 40.68 | >100 | 34.93 | >100 | 46.18 | >100 | 22.14 | >100 | 19.41 | >100 | 0.86 | >100 |
| PXG14 | 13.21 | >100 | 10.91 | >100 | 28.65 | >100 | −17.12 | >100 | 9.38 | >100 | 12.41 | >100 |
| PXG15 | 4.29 | >100 | 4.69 | >100 | 18.72 | >100 | 2.97 | >100 | 0.41 | >100 | −1.48 | >100 |
| PXG16 | 10.50 | >100 | 0.41 | >100 | 10.53 | >100 | −1.00 | >100 | −1.72 | >100 | 2.28 | >100 |
| PXG17 | −4.94 | >100 | 12.14 | >100 | −5.11 | >100 | −16.13 | >100 | 2.26 | >100 | −9.63 | >100 |
| PXG18 | −2.16 | >100 | 23.84 | >100 | 23.00 | >100 | 45.31 | >100 | 28.67 | >100 | −3.02 | >100 |
| PXG19 | 47.16 | >100 | 15.64 | >100 | 22.03 | >100 | 10.00 | >100 | 19.64 | >100 | 6.30 | >100 |
| PXG20 | 30.36 | >100 | 41.65 | >100 | 25.43 | >100 | −19.64 | >100 | 32.18 | >100 | −2.90 | >100 |
| PXG21 | 18.46 | >100 | 17.75 | >100 | 11.87 | >100 | −32.48 | >100 | 0.49 | >100 | 5.68 | >100 |
| PXG22 | 60.97 | 19.01 | 42.38 | >100 | 58.55 | 59.29 | 95.14 | 1.72 | 62.87 | 77.05 | 84.32 | 32.8 |
| PXG23 | 22.92 | >100 | 15.55 | >100 | 22.83 | >100 | 24.74 | >100 | 22.33 | >100 | 0.43 | >100 |
| PXG24 | 35.70 | >100 | 44.66 | >100 | 41.15 | >100 | 42.77 | >100 | 19.70 | >100 | 35.93 | >100 |
| PXG25 | 31.23 | >100 | 36.57 | >100 | 51.03 | >100 | 41.85 | >100 | 15.80 | >100 | 33.02 | >100 |
| PXG26 | 42.48 | >100 | −0.99 | >100 | 17.07 | >100 | 28.56 | >100 | 16.01 | >100 | 24.75 | >100 |
| PXG27 | 45.15 | >100 | 46.93 | >100 | 68.13 | 34.48 | 66.99 | 39.08 | 46.58 | >100 | 44.63 | >100 |
| PXG28 | 55.24 | >100 | 55.49 | >100 | 58.02 | 60.53 | 45.44 | >100 | 45.15 | >100 | 23.64 | >100 |
| PXG29 | 4.90 | >100 | 10.83 | >100 | 13.81 | >100 | −10.71 | >100 | 4.82 | >100 | 10.99 | >100 |
| GTX | 87.20 | 16.33 | 86.35 | 23.46 | 99.97 | 6.65 | 95.14 | 2.31 | 95.20 | 14.41 | 96.30 | 14.05 |

Conclusion: the compounds PXG1, PXG2 and PXG22 of the present invention have obvious inhibitory activity on the total GSTs enzymes of various field crop pests and economic crop pests, and can reduce metabolic activity towards insecticides of the total GSTs enzymes of field crop pests such as *Mythimna separata, Pyrausta nubilalis, Chilo suppressalis, Nilaparvata lugens, Spodoptera frugiperda* and *Helicoverpa armigera*, and economic crop pests such as *Plutella xylostella, Carposina sasakii* and *Spodoptera litura.*

Experimental Example 2: Enzyme Kinetic Assay of 8 Kinds of Known GSTs Recombinant Proteins in *Plutella xylostella*

Experiment: There are currently 8 known *Plutella xylostella* GSTs (PxGSTs), namely PxGSTδ1, PxGSTε3, PxGSTσ1, PxGSTσ2, PxGSTω4, PxGSTθ1, PxGSTζ1 and PxGSTμ1. The recombinant proteins of the 8 PxGSTs were obtained by prokaryotic expression, and the enzyme kinetics of the recombinant PxGSTs proteins were determined by the CDNB method. 1 μg of PxGST recombinant protein was added to 200 μL of PBS buffer (100 mM, pH 7.2) containing gradient concentrations of CDNB (0.05-1.60 mM) and 1 mM GSH. The absorbance at a wavelength of 340 nm ($A_{340}$) was measured in every 1 min at 30° C. using a microplate reader, and the measurement was continued for 5 min. The obtained light absorption value was converted into molar CDNB conjugated/min/mg, and the extinction coefficient ε340=9600 $M^{-1}$ $cm^{-1}$. Michaelis-Menten plots were generated according to different concentrations of CDNB to obtain enzyme kinetic parameters.

Results: By deterring the enzyme kinetics of the recombinant protein with CDNB as substrate, it was found that only PxGSTδ1, PxGSTσ1, PxGSTσ2 and PxGSTε3 have catalytic activity on CDNB, and the remaining four PxGSTs (PxGSTω4, PxGSTθ1, PxGSTζ1 and PxGSTμ1) have no catalytic activity on CDNB. The experimental results are shown in Table 3 and FIG. 52. The $K_m$ of the recombinant proteins of PxGSTδ1, PxGSTε3, PxGSTσ1 and PxGSTσ2 are 0.032 mM, 0.37 mM, 0.12 mM and 0.19 mM, respectively, $V_{max}$ is 7.64 mM/min/mg, 0.49 mM/min/mg, 1.70 mM/min/mg and 0.26 mM/min/mg, respectively.

TABLE 3

Kinetic parameters of *Pxlutella xylostella* PxGSTs recombinant protease

| PxGSTs recombinant protein | $K_m$ (mM) | $V_{max}$ (μmol $min^{-1}mg^{-1}$) |
|---|---|---|
| PxGSTδ1 | 0.032 | 7.64 |
| PxGSTε3 | 0.37 | 0.49 |
| PxGSTσ1 | 0.12 | 1.7 |
| PxGSTσ2 | 0.19 | 0.26 |
| PxGSTo4 | N/A | N/A |
| PxGSTθ1 | N/A | N/A |
| PxGSTu1 | N/A | N/A |

Conclusion: Among the 8 kinds of PxGSTs, only 4 kinds of PxGSTs of PxGSTδ1, PxGSTσ1, PxGSTσ2 and PxGSTε3 have GSH binding sites, which belong to the GST type with insecticide metabolic activity in *Plutella xylostella*.

Experimental Example 3: Inhibitory Activity Assay of Compound PXG1-PXG29 of the Present Invention to 4 Kinds of GSTs Having GSH Binding Site of *Plutella xylostella*

Experiment: 100 μL of PBS buffer (100 mM, pH 7.2) was taken and added to a 96-well plate, 1 μg of PxGSTs recombinant protein and an appropriate concentration of the compounds PXG1-PXG29 of the present invention were added to each well, after uniformly mixing, and allowed to stand at 30° C. for 10 min. Then 100 μL of PBS buffer (100 mM, pH 7.2) containing 1 mM CDNB and 1 mM GSH was successively added to each well. Immediately after mixing, the mixture was placed in a microplate reader to measure the absorbance at a wavelength of 340 nm ($A_{340}$) once every 1 min, the measurement was continued for 5 min, the light absorption values of each measuring point were recorded and the inhibition rate in vitro of the compounds PXG1-PXG29 of the present invention with different concentrations against PxGSTs recombinant protein were calculated. Each group of assays was repeated three times, and PxGSTs recombinant protein inactivated at 100° C. for 5 min was used as negative control, and GTX was used as positive control. GraphPad Prism 5 software was used for analysis and calculation of $IC_{50}$. Relative inhibition was calculated using the following formula:

$$\text{Relative inhibition (\%)} = \frac{\Delta A_{340c} - \Delta A_{340t}}{\Delta OD_{340c}} \times 100$$

wherein, $A_{340c}$ is the change of $A_{340}$ within minutes or the control group, an $A_{340t}$ is the change of $A_{340}$ within 5 minutes for the experimental group.

Results: The experimental results are shown in Table 4 and FIG. 53 to FIG. 56. The $IC_{50}$ of compounds PXG1, PXG2, PXG3, PXG4, PXG5, PXG7, PXG8, PXG10, PXG18, PXG20, PXG22, PXG23 and PXG28 of the present invention against the PxGSTδ1 recombinant protein of *Plutella xylostella* is 40.25 μM, 31.41 μM, 31.58 μM, 50.56 μM, 17.78 μM, 65.37 μM, 30.64 μM, 24.25 μM, 29.9 μM, 40.79 μM, 25.03 μM, 32.92 μM and 63.53 μM, respectively, and the $IC_{50}$ of the other compounds of the present invention against PxGSTδ1 recombinant protein are all greater than 100 μM; the $IC_{50}$ of compounds PXG11, PXG14, PXG15, PXG16, PXG19, PXG22, PXG26 and PXG29 of the present invention against the PxGSTσ1 recombinant protein of *Plutella xylostella* are 38.25 μM, 53.23 μM, 62.13 μM, 49.3 μM, 82.12 μM, 80.61 μM, 35.95 μM and 54.96 μM, respectively, and the $IC_{50}$ of the other compounds of the present invention against PxGSTσ1 recombinant protein are all greater than 100 μM; The $IC_{50}$ of compounds PXG1 and PXG22 of the present invention against the PxGSTσ2 recombinant protein of *Plutella xylostella* are 57.77 μM and 27.15 μM, respectively, and the $IC_{50}$ of the other compounds of the present invention against PxGSTσ2 recombinant protein are all greater than 100 μM; The $IC_{50}$ of compound PXG22 of the present invention against the PxGSTε3 recombinant protein of *Plutella xylostella* is 36.89 μM, and the $IC_{50}$ of the other compounds of the present invention to PxGSTε3 recombinant protein are all greater than 100 μM. The $IC_{50}$ of the positive control GSTs inhibitor GTX against PxGSTδ1, PxGSTσ1, PxGSTσ2 and PxGSTε3 recombinant proteins are 36.02 μM, 66.85 μM, 7.75 μM and 95.41 μM, respectively.

TABLE 4

The inhibitory effect of compounds PXG1-PXG29 of the present invention on 4 kinds of PxGSTs recombinant protein

| | PxGSTδ1 | | PxGSTσ1 | | PxGSTσ2 | | PxGSTε3 | |
|---|---|---|---|---|---|---|---|---|
| Index | 100 μM Inhibition rate % | $IC_{50}$ (μM) | 100 μM Inhibition rate % | $IC_{50}$ (μM) | 100 μM Inhibition rate % | $IC_{50}$ (μM) | 100 μM Inhibition rate % | $IC_{50}$ (μM) |
| PXG1 | 68.91 | 40.25 | 25.54 | >100 | 58.07 | 57.77 | 17.64 | >100 |
| PXG2 | 87.75 | 31.41 | 25.12 | >100 | 14.56 | >100 | −4.00 | >100 |
| PXG3 | 72.39 | 31.58 | 36.06 | >100 | 27.59 | >100 | −1.11 | >100 |
| PXG4 | 18.41 | 50.56 | 43.63 | >100 | 21.57 | >100 | 8.88 | >100 |
| PXG5 | 81.66 | 17.78 | 35.57 | >100 | 24.51 | >100 | −2.97 | >100 |
| PXG6 | 12.21 | >100 | 49.08 | >100 | 33.65 | >100 | 4.85 | >100 |
| PXG7 | 55.74 | 65.37 | 35.15 | >100 | 20.06 | >100 | 5.93 | >100 |
| PXG8 | 69.47 | 30.64 | 37.78 | >100 | 42.39 | >100 | −3.30 | >100 |
| PXG9 | 30.42 | >100 | 28.59 | >100 | 31.45 | >100 | −3.88 | >100 |
| PXG10 | 91.02 | 24.25 | 29.36 | >100 | 19.17 | >100 | 2.03 | >100 |
| PXG11 | 35.34 | >100 | 60.66 | 38.25 | 22.64 | >100 | −7.28 | >100 |
| PXG12 | 40.17 | >100 | 48.30 | >100 | 33.65 | >100 | 10.90 | >100 |
| PXG13 | 14.11 | >100 | 34.22 | >100 | 22.76 | >100 | 18.43 | >100 |
| PXG14 | 14.93 | >100 | 52.24 | 53.23 | 36.41 | >100 | 15.32 | >100 |
| PXG15 | 7.86 | >100 | 42.48 | 62.13 | 25.58 | >100 | 4.62 | >100 |
| PXG16 | 5.35 | >100 | 70.49 | 49.3 | 39.29 | >100 | 4.12 | >100 |
| PXG17 | 2.22 | >100 | 48.92 | >100 | 43.85 | >100 | 4.43 | >100 |
| PXG18 | 82.05 | 29.9 | 31.74 | >100 | 13.48 | >100 | −2.47 | >100 |
| PXG19 | 58.74 | 40.79 | 45.88 | 82.12 | 32.46 | >100 | 5.57 | >100 |
| PXG20 | 23.01 | >100 | 71.80 | >100 | 29.56 | >100 | −15.67 | >100 |
| PXG21 | 7.82 | >100 | 44.93 | >100 | 11.65 | >100 | −2.67 | >100 |
| PXG22 | 78.78 | 25.03 | 45.71 | 80.61 | 76.68 | 27.15 | 65.84 | 36.89 |
| PXG23 | 77.66 | 32.92 | 35.86 | >100 | 26.95 | >100 | 6.04 | >100 |
| PXG24 | 23.09 | >100 | 14.94 | >100 | 19.66 | >100 | 28.32 | >100 |
| PXG25 | 23.75 | >100 | −1.47 | >100 | 15.27 | >100 | 2.07 | >100 |
| PXG26 | 21.58 | >100 | 67.92 | 35.95 | 24.71 | >100 | 7.12 | >100 |

TABLE 4-continued

The inhibitory effect of compounds PXG1-PXG29 of the present invention on 4 kinds of PxGSTs recombinant protein

| | PxGSTδ1 | | PxGSTσ1 | | PxGSTσ2 | | PxGSTε3 | |
|---|---|---|---|---|---|---|---|---|
| Index | 100 μM Inhibition rate % | $IC_{50}$ (μM) | 100 μM Inhibition rate % | $IC_{50}$ (μM) | 100 μM Inhibition rate % | $IC_{50}$ (μM) | 100 μM Inhibition rate % | $IC_{50}$ (μM) |
| PXG27 | 41.66 | >100 | 25.10 | >100 | 42.39 | >100 | 17.56 | >100 |
| PXG28 | 70.89 | 63.53 | 19.53 | >100 | 23.38 | >100 | 0.96 | >100 |
| PXG29 | 16.73 | >100 | 53.27 | 54.96 | 44.66 | >100 | 0.03 | >100 |
| GTX | 66.50 | 36.02 | 67.29 | 66.85 | 84.82 | 7.75 | 50.71 | 95.41 |

Conclusion: The compound PXG22 of the present invention has obvious inhibitory activity against 4 kinds of PxGSTs recombinant proteins with GSH binding sites, wherein the inhibitory activity of the compound PXG22 of the present invention against PxGSTδ1 and PxGSTε3 recombinant proteins exceeds the inhibitory activity of the positive control GSTs inhibitor GTX. The remaining compounds of the present invention have different degrees of inhibitory activity against PxGSTδ1 and PxGSTσ1 recombinant proteins, and only the compound PXG1 of the present invention has obvious inhibitory activity against PxGSTσ2 recombinant protein.

Experimental Example 4: Insecticidal Synergistic Activity Assay of the Compound PXG22 of the Present Invention with Chlorantraniliprole Experiment: 96% chlorantraniliprole (Chl) original drug was prepared into mother liquor with a concentration of 50000 mg/L. During the test, 6 treatment solutions with concentrations of 500, 250, 125, 62.5, 31.25 and 15.63 mg/L were prepared. 200 mg/L of the compound PXG22 of the present invention was added to each treatment solution, 200 mg/L of diethyl maleate (DEM) was used as the control synergist, and water was used as another control. The *Plutella xylostella* (Linnaeus) larvae was collected from a vegetable field in Yunnan Province. Healthy 3rd instar larvae of the same age were selected for indoor biological activity assay.

Clean wild cabbage leaves were cut into discs with a diameter of 6.5 cm (avoiding main veins). The leaves were soaked in the pesticide solution for 10 seconds, then taken out, dried at 25° C., and placed in a petri dish with a diameter of 6.5 cm. 10 larvae of the resistant strains of *Plutella xylostella* at the early stage of 3rd instar were placed in each petri dish, which was covered with double-layer absorbent roll paper, and covered by the upper cover of the petri dish. It was placed face up in an incubator at a temperature of 25±1° C., a relative humidity of 65%-70%, and a light ratio (L:D) of 16: 8 h. Each treatment was replicated 4 times with 10 larvae per replicate. After 48 hours, mortality was checked, and the $LC_{50}$ and resistance ratio were calculated. During observation, the worm body was gently touched with a small brush or sharp tweezers, if the worm body did not respond or could not coordinate movements, it was considered dead. The test process is strictly in accordance with the standard: NY/T 1154.7-2006.

Experimental data analysis was carried out using practical statistical analysis and its computer processing platform (DPS) (TANG Qiyi et al., 1997). The toxicity regression equation of each agent was established, $LC_{50}$ value and 95% confidence limit were calculated.

Results: The experimental results are shown in Table 5. After the addition of the compound PXG22 of the present invention, the $LC_{50}$ of the chlorantraniliprole solution to the resistant strains of *Plutella xylostella* decreases from 110.17 mg/L to 14.04 mg/L, and the resistance ratio of resistant strains of *Plutella xylostella* to chlorantraniliprole falls from 479 to 61.04. For the chlorantraniliprole solution added with the control synergist DEM, its $LC_{50}$ and resistance ratio decreases to 50.02 mg/L and 217.48, respectively.

TABLE 5

Synergistic effect of compounds of the present invention and DEM with chlorantraniliprole

| treatment group | regression equation | $LC_{50}$ (mg/L) | confidence interval | Correlation coefficient $R^2$ | Resistance ratio |
|---|---|---|---|---|---|
| Chl | $Y = 0.95X - 1.94$ | 110.17 | 67.72-172.48 | 0.927 | 479 |
| Chl + DEM | $Y = 1.15X - 1.95$ | 50.02 | 34.53-75.11 | 0.984 | 217.48 |
| Chl + PXG22 | $Y = 1.75X - 2.01$ | 14.04 | 0.45-22.73 | 0.881 | 61.04 |

Note:
Chl: Chlorantraniliprole

Conclusion: The compound PXG22 of the present invention has obvious insecticidal synergistic activity with chlorantraniliprole, and its synergistic activity exceeds that of the control synergist DEM.

Experimental Example 5: Insecticidal Synergistic Activity Assay of the Compounds PXG1, PXG2 and PXG22 of the Present Invention with Indoxacarb Experiment: 95% indoxacarb (Ind) original drug was prepared into mother liquor with a concentration of 50000 mg/L. During the test, 6 treatment solutions with concentrations of 500, 250, 125, 62.5, 31.25 and 15.63 mg/L were prepared. 200 mg/L of the compounds PXG1, PXG2 and- PXG22 of the present invention were added to each treatment solution, 200 mg/L of diethyl maleate (DEM) was used as the control synergist, and water was used as another control. The *Plutella xylostella* (Linnaeus) larvae was collected from a vegetable field in Huizhou city, Guangdong Province. Healthy 3rd instar larvae of the same age were selected for indoor biological activity assay.

Clean wild cabbage leaves were cut into discs with a diameter of 6.5 cm (avoiding main veins). The leaves were soaked in the pesticide solution for 10 seconds, then taken out, dried at 25° C., and placed in a petri dish with a diameter of 6.5 cm. 10 larvae of the resistant strains of *Plutella xylostella* at the early stage of 3rd instar were placed in each petri dish, which was covered with double-layer absorbent roll paper, and covered by the upper cover of the petri dish. It was placed face up in an incubator at a temperature of 25±1° C., a relative humidity of 65%-70%, and a light ratio (L:D) of 16: 8 h. Each treatment was replicated 4 times with 10 larvae per replicate. After 48 hours, mortality was checked, and the $LC_{50}$ and resistance ratio were calculated. During observation, the worm body was gently touched with a small brush or sharp tweezers, if the worm body did not respond or could not coordinate movements, it was considered dead. The test process is strictly in accordance with the standard: NY/T 1154.7-2006.

Experimental data analysis was carried out using practical statistical analysis and its computer processing platform (DPS) (TANG Qiyi et al., 1997). The toxicity regression equation of each agent was established, $LC_{50}$ value and 95% confidence limit were calculated.

Results: The experimental results are shown in Table 6. After the addition of the compound PXG1 of the present invention, the $LC_{50}$ of the indoxacarb to the resistant strains of *Plutella xylostella* decreases from 74.72 mg/L to 59.13 mg/L, and the resistance ratio of resistant strains of *Plutella xylostella* to indoxacarb falls from 143.70 to 113.71; After the addition of the compound PXG2 of the present invention, the $LC_{50}$ of the indoxacarb to the resistant strains of *Plutella xylostella* decreases from 74.72 mg/L to 39.93 mg/L, and the resistance ratio of resistant strains of *Plutella xylostella* to indoxacarb falls from 143.70 to 76.78; After the addition of the compound PXG22 of the present invention, the $LC_{50}$ of the indoxacarb to the resistant strains of *Plutella xylostella* decreases from 74.72 mg/L to 51.21 mg/L, and the resistance ratio of resistant strains of *Plutella xylostella* to indoxacarb falls from 143.70 to 98.48; For the indoxacarb solution added with the control synergist DEM, its $LC_{50}$ and resistance ratio decrease to 54.11 mg/L and 104.06, respectively.

TABLE 6

Synergistic effect of compounds of the present invention and DEM with indoxacarb

| treatment group | regression equation | $LC_{50}$ (mg/L) | confidence interval | Correlation coefficient $R^2$ | Resistance ratio |
|---|---|---|---|---|---|
| Ind | Y = 1.32X − 2.47 | 74.72 | 48.82-106.92 | 0.860 | 143.70 |
| Ind + DEM | Y = 1.16X − 2.01 | 54.11 | 29.03-79.18 | 0.903 | 104.06 |
| Ind + PXG1 | Y = 1.111X − 1.97 | 59.13 | 32.67-86.20 | 0.955 | 113.71 |
| Ind + PXG2 | Y = 1.17X − 1.88 | 39.93 | 18.05-61.39 | 0.997 | 76.78 |
| Ind + PXG22 | Y = 1.14X − 1.94 | 51.21 | 26.43-76.19 | 0.948 | 98.48 |

Note:
Ind: Indoxacarb

Conclusion: tresistance ratiohe compounds PX1, PXG2 and PXG22 of the present invention have obvious synergistic activity with indoxacarb, and PXG2 and PXG22 have significant effects, which can make the resistance of resistant strains of *Plutella xylostella* to indoxacarb from high resistance to moderate resistance.

Experimental Example 6: Insecticidal Synergistic Activity Assay of the Compound PXG22 of the Present Invention with Chlorantraniliprole Using the Ultra-High Resistant Strains of *Plutella xylostella* (Huizhou Insect Source) as the Tested Insect Experiment: The method was the same as in Experimental Example 4. The tested *Plutella xylostella* was ultra-high resistance strains to chlorantraniliprole (Huizhou insect source). The compound PXG22 of the present invention was added at a concentration of 200 mg/L. The control synergist diethyl maleate (DEM) was added at a concentration of 200 mg/L.

Results: The experimental results are shown in Table 7. After the addition of compound PXG22 of the present invention, the $LC_{50}$ of the chlorantraniliprole solution to the ultra-high resistant strains of *Plutella xylostella* (Huizhou insect source) decreases from 503.38 mg/L to 148.45 mg/L, and the resistance ratio of ultra-high resistant strains of *Plutella xylostella* (Huizhou insect source) to chlorantraniliprole falls from 2188.61 to 645.43. For the chlorantraniliprole solution added with the control synergist DEM, its $LC_{50}$ and resistance ratio decrease to 442.81 mg/L and 1925.26, respectively.

TABLE 7

Synergistic effect of compound PXG22 of the present invention and DEM with chlorantraniliprole

| treatment group | regression equation | $LC_{50}$ (mg/L) | confidence interval | Correlation coefficient $R^2$ | Resistance ratio |
|---|---|---|---|---|---|
| Chl | Y = 2.39X − 6.46 | 503.38 | 375.19-719.83 | 0.860 | 2188.61 |
| Chl + DEM | Y = 2.87X − 7.86 | 442.81 | 369.82-540.47 | 0.903 | 1925.26 |
| Chl + PXG22 | Y = 1.53X − 3.33 | 148.45 | 72.60-235.24 | 0.918 | 645.43 |

Note:
Chl: Chlorantraniliprole

Conclusion: The compound PXG22 of the present invention significantly enhances the insecticidal activity of chlorantraniliprole to ultra-high resistant strains of *Plutella xylostella* (Huizhou insect source), and its synergistic activity with chlorantraniliprole is significantly higher than that of the control synergist DEM.

Experimental Example 7: Insecticidal Synergistic Activity Assay of the Compound PXG22 of the Present Invention Having Different Concentrations with Chlorantraniliprole Using the High Resistant Strains I of *Plutella xylostella* (Lianzhou Insect Source) as the Tested Insect Experiment: The method was the same as in Experimental example 4, and the tested *Plutella xylostella* was the high resistant strains I against chlorantraniliprole (Lianzhou source). The added concentrations of the compound PXG22 of the present invention were 200 mg/L, 100 mg/L and 50 mg/L, and the added concentration of diethyl maleate (DEM) of the control synergist was maintained at 200 mg/L.

Results: The experimental results are shown in Table 8. After the addition of 200 mg/L, 100 mg/L and 50 mg/L of the compound PXG22 of the present invention, the $LC_{50}$ of the chlorantraniliprole solution to the high resistant strains I of *Plutella xylostella* (Lianzhou insect source) decreases from 134.26 mg/L to 40.44 mg/L, 21.16 mg/L and 49.89 mg/L, respectively, and the resistance ratio of high resistant strains I of *Plutella xylostella* (Lianzhou insect source) to chlorantraniliprole falls from 583.74 to 175.82, 92 and 216.91 respectively. For the chlorantraniliprole solution added with the control synergist DEM, its $LC_{50}$ and resistance ratio decrease to 53.36 mg/L and 232, respectively.

TABLE 8

Synergistic effect of compound PXG22 of the present invention and DEM with chlorantraniliprole

| treatment group | regression equation | $LC_{50}$ (mg/L) | confidence interval | Correlation coefficient $R^2$ | Resistance ratio |
|---|---|---|---|---|---|
| Chl | Y = 0.99X − 2.10 | 134.26 | 69.30-208.45 | 0.983 | 583.74 |
| Chl + 200 mg/L PXG22 | Y = 1.26X − 2.03 | 40.44 | 6.45-75.75 | 0.989 | 175.82 |
| Chl + 100 mg/L PXG22 | Y = 1.04X − 1.38 | 21.16 | 8.37-33.80 | 0.979 | 92 |
| Chl + 50 mg/L PXG22 | Y = 1.30X − 2.20 | 49.89 | 28.11-71.00 | 0.901 | 216.91 |
| Chl + DEM | Y = 0.79X − 1.36 | 53.36 | 16.57-95.03 | 0.967 | 232 |

Note:
Chl: Chlorantraniliprole

Conclusion: The compound PXG22 of the present invention significantly enhances the insecticidal activity of chlorantraniliprole against high resistant strains I of *Plutella xylostella* (Lianzhou insect source), and when the compound PXG22 of the present invention is added with a concentration of 100 mg/L, its synergistic activity with chlorantraniliprole is the strongest, which is significantly higher than that of the control synergist DEM.

Experimental Example 8: Insecticidal Synergistic Activity Assay of the Compound PXG22 of the Present Invention Having Different Concentrations with Chlorantraniliprole Using the High Resistant Strains II of *Plutella xylostella* (Lianzhou Insect Source) as the Tested Insect Experiment: The method was the same as in Experimental example 4, and the tested *Plutella xylostella* was the high resistant strains II against chlorantraniliprole (Lianzhou source). The added concentrations of the compound PXG22 of the present invention were 200 mg/L, 100 mg/L, 50 mg/L and 25 mg/L, and the added concentration of diethyl maleate (DEM) of the control synergist was maintained at 200 mg/L.

Results: The experimental results are shown in Table 9. After the addition of 200 mg/L, 100 mg/L, 50 mg/L and 25 mg/L of the compound PXG22 of the present invention, the $LC_{50}$ of the chlorantraniliprole solution to the high resistant strains II of *Plutella xylostella* (Lianzhou insect source) decrease from 145.19 mg/L to 55.92 mg/L, 44.86 mg/L, 71.88 mg/L and 78.54 mg/L, respectively, and the resistance ratio of high resistant strains II of *Plutella xylostella* (Lianzhou insect source) to chlorantraniliprole fall from 631.26 to 243.13, 195.04, 312.52 and 341.48 respectively. For the chlorantraniliprole solution added with the control synergist DEM, its $LC_{50}$ and resistance ratio decrease to 107.99 mg/L and 469.52, respectively.

TABLE 9

Synergistic effect of compound PXG22 of the present invention and DEM with chlorantraniliprole

| treatment group | regression equation | $LC_{50}$ (mg/L) | confidence interval | Correlation coefficient $R^2$ | Resistance ratio |
|---|---|---|---|---|---|
| Chl | Y = 1.54X − 3.33 | 145.19 | 111.97-192.13 | 0.940 | 631.26 |
| Chl + 200 mg/L PXG22 | Y = 1.67X − 2.91 | 55.92 | 38.60-73.32 | 0.964 | 243.13 |
| Chl + 100 mg/L PXG22 | Y = 1.56X − 2.58 | 44.86 | 27.78-61.46 | 0.984 | 195.04 |
| Chl + 50 mg/L PXG22 | Y = 1.76X − 3.26 | 71.88 | 48.99-95.51 | 0.993 | 312.52 |
| Chl + 25 mg/L PXG22 | Y = 1.31X − 2.47 | 78.54 | 48.23-111.47 | 0.958 | 341.48 |
| Chl + DEM | Y = 1.49x − 3.032 | 107.99 | 82.46-140.86 | 0.932 | 469.52 |

Note:
Chl: Chlorantraniliprole

Conclusion: The compound PXG22 of the present invention significantly enhances the insecticidal activity of chlorantraniliprole against high resistant strains II of *Plutella xylostella* (Lianzhou insect source), and when the compound PXG22 of the present invention is added with a concentration of 100 mg/L, its synergistic activity with chlorantraniliprole is the strongest, which is significantly higher than that of the control synergist DEM.

Based on the above description of the summary of the invention, those skilled in the art will be able fully apply the present invention, and all the same principles or similar modifications should be considered to be within the scope of the present invention.

The invention claimed is:

1. A method of inhibiting glutathione S-transferases (GSTs) in pests, comprising applying a diphenylpyrazole-based compound of following formula (I), or its pesticidally acceptable salts to the pests or their habitat, Formula (I)

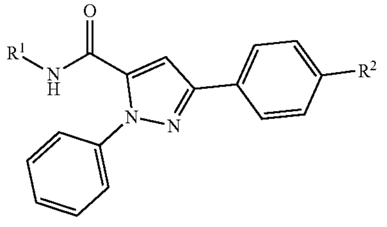

wherein $R^1$ is:

(1) an amido group —NH—CH(O) which is unsubstituted or substituted by one or more of the following substituents;

(a) —$C_{1-6}$ alkyl-$R^3$, —$C_{3-8}$ cycloalkyl-$R^3$, —$C_{2-6}$ alkenyl-$R^3$, —$C_{2-6}$ alkynyl-$R^3$, —NH—$R^3$, —N($R^3$)$_2$, —C(O)—$R^3$, —NH—$C_{1-6}$ alkyl-$R^3$, —$C_{1-6}$ alkyl-NH—$R^3$, —$C_{1-6}$ alkyl-N($R^3$)$_2$, —$C_{1-6}$ alkyl-O$R^3$, —$C_{3-8}$ cycloalkyl-O$R^3$, —O$C_{1-6}$ alkyl-$R^3$, —$C_{1-6}$ alkyl-O$C_{1-6}$ alkyl-$R^3$, —C(O)—NH—$R^3$, —C(O)—N($R^3$)$_2$, —NH—C(O)—$R^3$, —$C_{1-6}$ alkyl-NH—C(O)—$R^3$, —$C_{1-6}$ alkyl-NH—C(O)—O$R^3$, —NH—C(O)—$C_{1-6}$ alkyl-$R^3$, —NH—C(O)—$C_{1-6}$ alkyl-O$R^3$, —C(O)—NH—$C_{1-6}$ alkyl-$R^3$ or —$C_{1-6}$ alkyl-S$R^3$;

$R^3$ is each independently selected from: H, O, S, =NH, amino, halogen, cyano, —$C_{1-6}$ alkyl, —$C_{3-8}$ cycloalkyl, —S—$C_{1-6}$ alkyl, —S—OH, —$SO_2$—$C_{1-6}$ alkyl, -6-14 membered aryl, -5-14 membered heterocyclic group, -5-14 membered heteroaryl and -adamantyl;

$R^3$ is unsubstituted or substituted by one or more of the following substituents: O, —OH, halogen, cyano, nitro, —CH(O), amino, —$C_{1-6}$ alkyl, —$C_{2-6}$ alkenyl, —$C_{2-6}$ alkynyl, —O$C_{1-6}$ alkyl, sulfonic acid group, —$C_{1-6}$ alkyl-halogen, —$C_{1-6}$ alkyl-HS, —$C_{1-6}$ alkyl-$NH_3^+$, —$C_{1-6}$ alkyl-OH, —$C_{1-6}$ alkyl-NH—$C_{1-6}$ alkyl, or —$C_{1-6}$ alkyl-N($C_{1-6}$ alkyl)$_2$;

(b) -6-14 membered aryl, -5-14 membered heterocyclic group or -5-14 membered heteroaryl;

the 6-14 membered aryl, the 5-14 membered heterocyclic group or the 5-14 membered heteroaryl is unsubstituted or substituted by one or more of the following substituents: O, —OH, halogen, cyano, nitro, —CH(O), amino, —$C_{1-6}$ alkyl, —O$C_{1-6}$ alkyl, —$C_{1-6}$ alkyl-NH—$C_{1-6}$ alkyl, —$C_{1-6}$ alkyl-N($C_{1-6}$ alkyl)$_2$, —C(O)—O$C_{1-6}$ alkyl, —NH—C(O)—$C_{1-6}$ alkyl, —$SO_2$—$C_{1-6}$ alkyl, —$SO_2$—$NH_2$, —$SO_2$—NH—$C_{1-6}$ alkyl, —$SO_2$—N($C_{1-6}$ alkyl)$_2$, -6-14 membered aryl, -5-14 membered heterocyclic group, or -5-14 membered heteroaryl;

(2) N atom and C atom of the amido group —NH—CH(O) are connected to form a ring structure via —$C_{3-6}$ alkylene-, —NH—$C_{2-6}$ alkylene-, —NH—C(O)—$C_{1-6}$ alkylene-, —$C_{1-6}$ alkylene-NH—C(O)—, —NH—$C_{1-6}$ alkylene-C(O)— or —$C_{1-6}$ alkylene-C(O)—; the ring structure is optionally substituted by the following substituents: —$C_{1-6}$ alkyl, —$C_{3-8}$ cycloalkyl, —$C_{3-8}$ cycloalkyl-$C_{1-6}$ alkyl, —O$C_{1-6}$ alkyl, -6-14 membered aryl, -5-14 membered heterocyclic group, -5-14 membered heteroaryl, —$C_{1-6}$ alkyl-6-14 membered aryl, —$C_{1-6}$ alkyl-5-14 membered heterocyclic group, —$C_{1-6}$ alkyl-5-14 membered heteroaryl or trifluoroethyl; the 6-14 membered aryl, the 5-14 membered heterocyclic group and the 5-14 membered heteroaryl are optionally substituted by —O$C_{1-6}$ alkyl; or, the ring structure is further combined with 5-8 membered aryl, 5-8 membered heterocyclic group or 5-8 membered heteroaryl to fuse into a fused ring;

the heterocyclic group contains 1-4 heteroatoms selected from N, S and O; the heteroaryl contains 1-4 heteroatoms selected from N, S and O;

$R^2$ is selected from: —H, -halogen, -amino, —$NO_2$, —$CF_3$, —$C_{1-6}$ alkyl, —$C_{1-6}$ alkyl-OH, —O—$R^4$, —C(O)—$R^4$, —C(O)—$NH_2$, —NH—C(O)—$R^4$, —C(O)—O—$R^4$ or —C(O)—O—N($R^4$)$_2$; $R^4$ is selected from: H or $C_{1-6}$ alkyl.

2. The method according to claim 1, wherein $R^1$ is:

(1) an amido group —NH—CH(O) which is substituted by one or more of the following substituents, (a) —$C_{1-3}$ alkyl-$R^3$, —$C_{3-6}$ cycloalkyl-$R^3$, —$C_{2-5}$ alkenyl-$R^3$, —$C_{1-3}$ alkyl-NH—$R^3$, —$C_{1-3}$ alkyl-O—$R^3$ or —O—$C_{1-3}$ alkyl-$R^3$; $R^3$ are each independently selected from: H, O, S, ═NH, amino, halogen, cyano, —$C_{1-3}$ alkyl, —$C_{3-6}$ cycloalkyl, -6-14 membered aryl, -5-14 membered heterocyclic group or -5-14 membered heteroaryl; $R^3$ is unsubstituted or substituted by one or more of the following substituents: O, —OH, halogen, cyano, nitro, —CH(O), —S—OH, amino, —$C_{1-3}$ alkyl, —$C_{2-5}$ alkenyl, —$C_{2-5}$ alkynyl, —$OC_{1-3}$ alkyl, sulfonic acid group, —$C_{1-3}$ alkyl-halogen or —$C_{1-3}$ alkyl-OH;

(b) -6-14 membered aryl, -5-14 membered heterocyclic group or -5-14 membered heteroaryl; the 6-14 membered aryl, the 5-14 membered heterocyclic group or the 5-14 membered heteroaryl is unsubstituted or substituted by one or more of the following substituents: 0, —OH, halogen, cyano, nitro, —CH(O), amino, —$C_{1-3}$ alkyl, —$OC_{1-3}$ alkyl, —$C_{1-3}$ alkyl-NH—$C_{1-3}$ alkyl, —$C_{1-3}$ alkyl-N($C_{1-3}$ alkyl)$_2$, —C(O)—$OC_{1-3}$ alkyl, —NH—C(O)—$C_{1-3}$ alkyl, —$SO_2$—$C_{1-3}$ alkyl, —$SO_2$—$NH_2$, —$SO_2$—NH—$C_{1-3}$ alkyl or —$SO_2$—N($C_{1-3}$ alkyl)$_2$;

(2) N atom and C atom of the amido group —NH—CH (O) are connected to form a ring structure via —$C_{3-6}$ alkylene-, —NH—$C_{2-4}$ alkylene-, —NH—C(O)—$C_{1-3}$ alkylene-, —$C_{1-3}$ alkylene-NH—C(O)—, —NH—$C_{1-3}$ alkylene-C(O)— or —$C_{1-3}$ alkylene-C(O)—; the ring structure is optionally substituted by the following substituents: —$C_{1-3}$ alkyl, —$C_{3-6}$ cycloalkyl, —$C_{3-6}$ cycloalkyl-$C_{1-3}$ alkyl, -6-14 membered aryl, -5-14 membered heterocyclic group, -5-14 membered heteroaryl, —$C_{1-3}$ alkyl-6-14 membered aryl, —$C_{1-3}$ alkyl-5-14 membered heterocyclic group, —$C_{1-3}$ alkyl-5-14 membered heteroaryl or trifluoroethyl; the 6-14 membered aryl, the 5-14 membered heterocyclic group and the 5-14 membered heteroaryl are optionally substituted by —$OC_{1-3}$ alkyl;

the heterocyclic group contains 1-3 heteroatoms selected from N, S and O; the heteroaryl contains 1-3 heteroatoms selected from N, S and O;

$R^2$ is: —H or halogen.

3. The method according to claim 1, wherein $R^1$ is:

(1) —NH—C(O)—$C_{1-3}$ alkyl-$R^3$; $R^3$ is selected from: -6-10 membered aryl, -5-10 membered heterocyclic group, -5-10 membered heteroaryl; $R^3$ is unsubstituted or substituted by one or more of the following substituents: O, —OH, halogen, cyano, nitro, —CH(O), —S—OH, amino, —$C_{1-3}$ alkyl, —$OC_{1-3}$ alkyl, sulfonic acid group, —$C_{1-3}$ alkyl-halogen, —$C_{1-3}$ alkyl-HS, —$C_{1-3}$ alkyl-$NH_3^+$ or —$C_{1-3}$ alkyl-OH;

(2) —NH—C(O)-6-10 membered aryl, —NH—C(O)-5-10 membered heterocyclic group or —NH—C(O)-5-10 membered heteroaryl; the 6-10-membered aryl, the 5-10-membered heterocyclic group or the 5-10-membered heteroaryl is unsubstituted or substituted by one or more of the following substituents: O, —OH, halogen, cyano, nitro, —CH(O), amino, —$C_{1-3}$ alkyl or —$OC_{1-3}$ alkyl;

the heterocyclic group contains 1-3 heteroatoms selected from N, S and O; the heteroaryl contains 1-3 heteroatoms selected from N, S and O;

$R^2$ is —H.

4. The method according to claim 1, wherein $R^1$ is selected from:

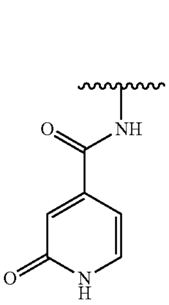
,
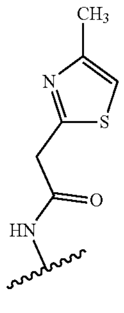
and
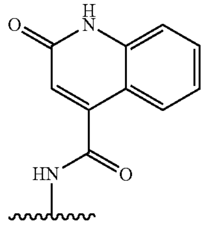
.

5. The method according to claim 1, wherein the diphenylpyrazole-based compound of formula (I) or its pesticidally acceptable salts is following compound or its pesticidally acceptable salts:

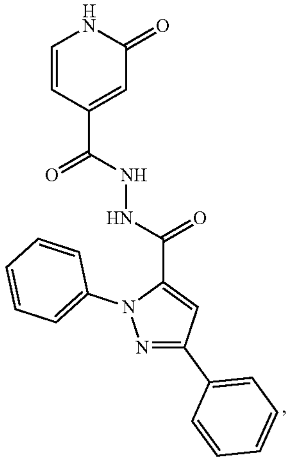
,
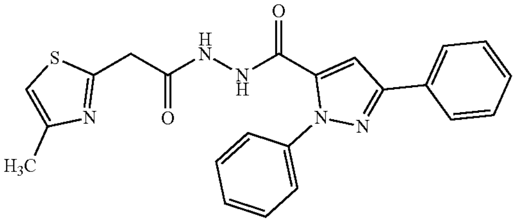
,
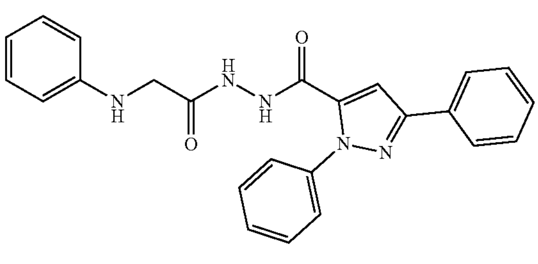
,

-continued
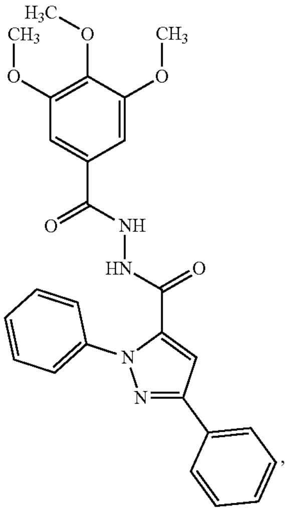
,
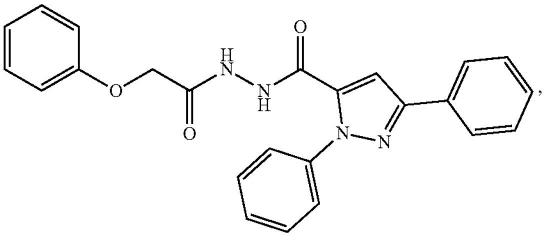
,
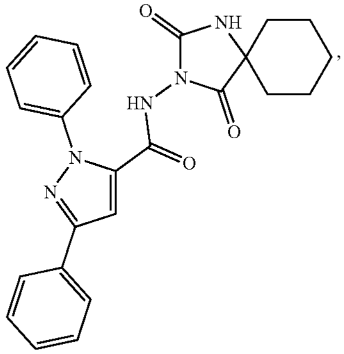
,
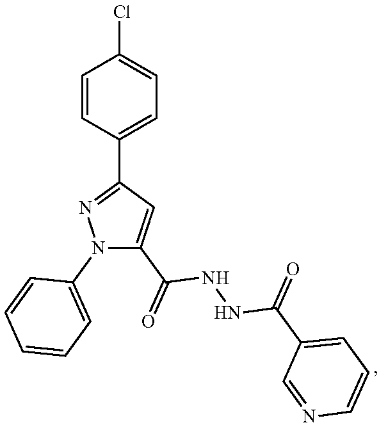
,
-continued
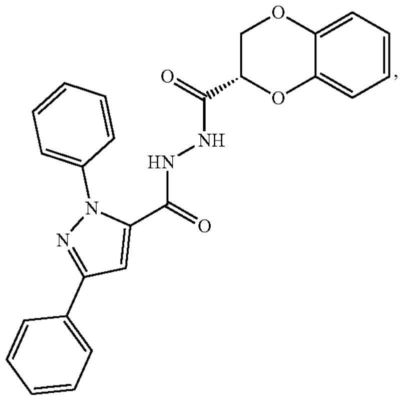
,
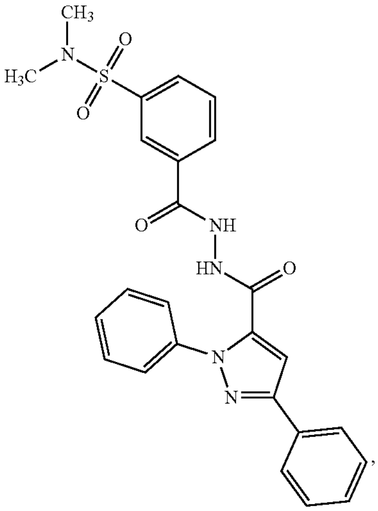
,
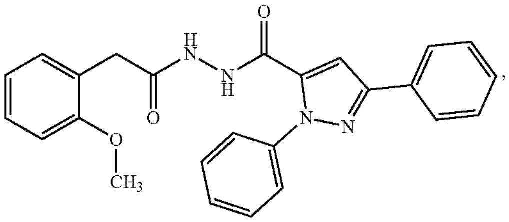
,
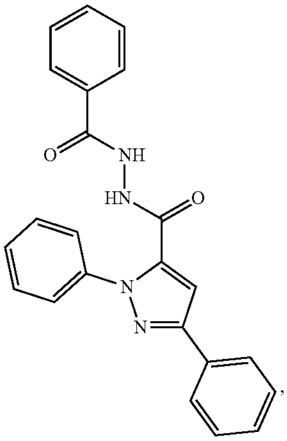
, -continued
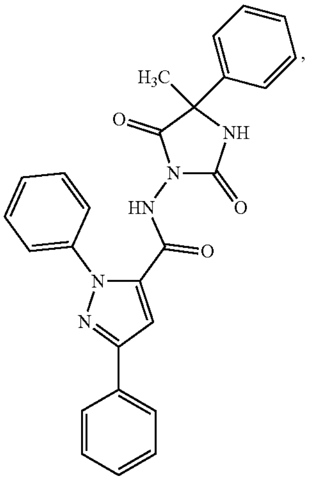
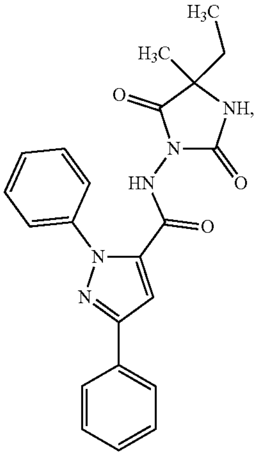
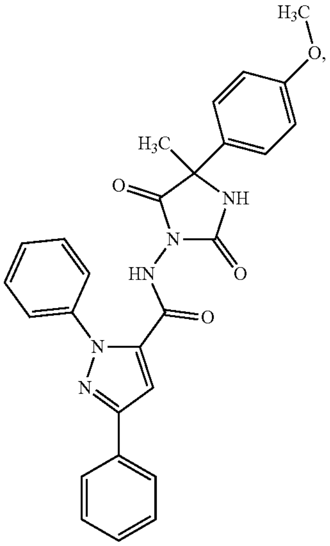
-continued
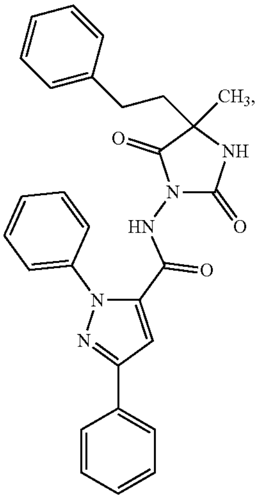
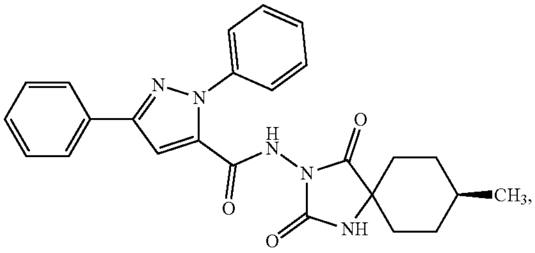
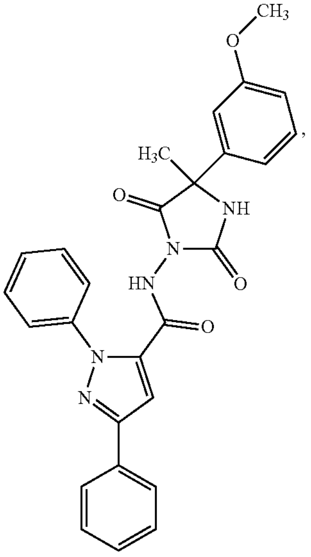
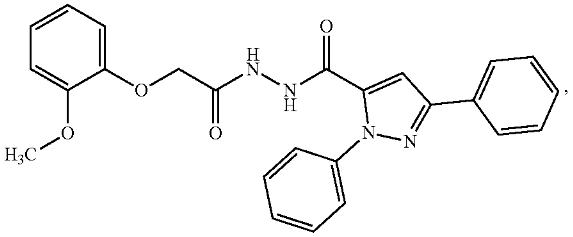

-continued
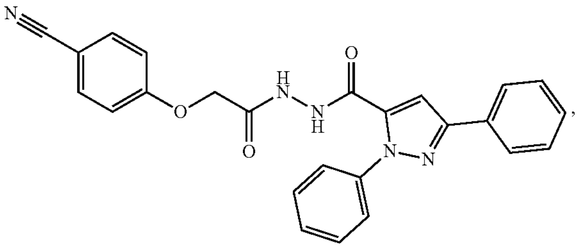
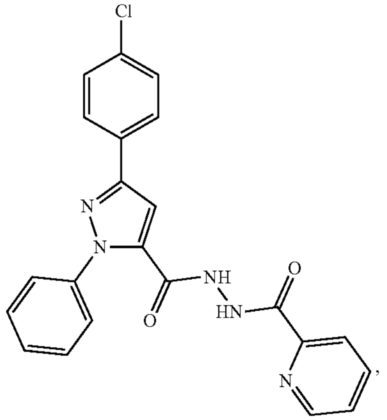
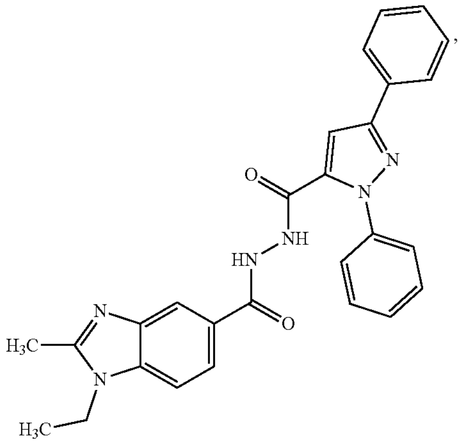
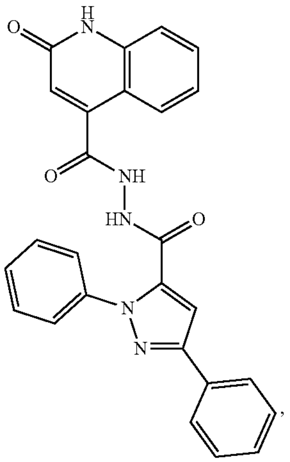
-continued
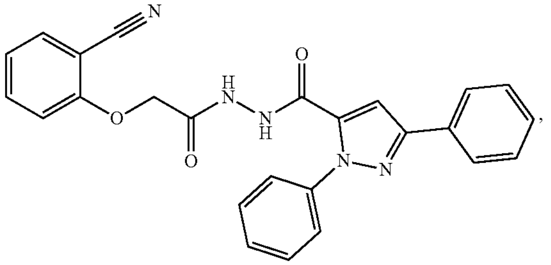
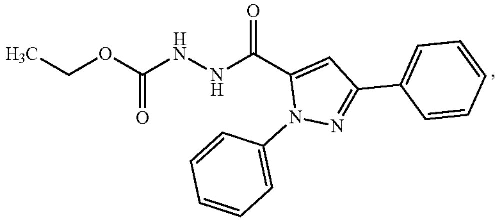
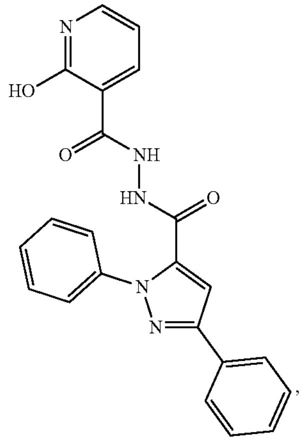
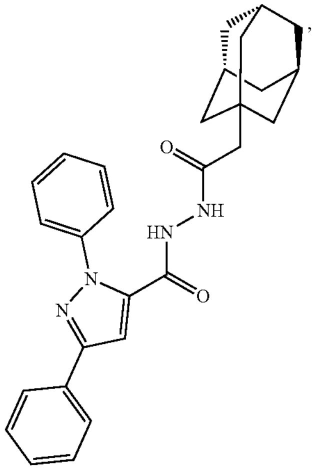

-continued

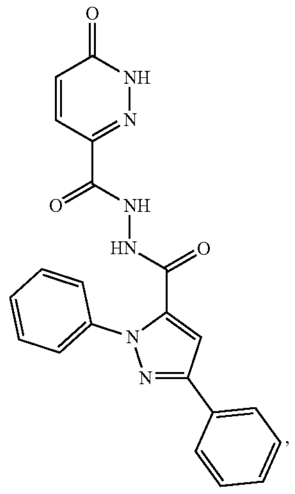

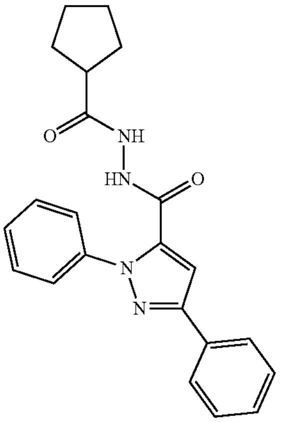

or

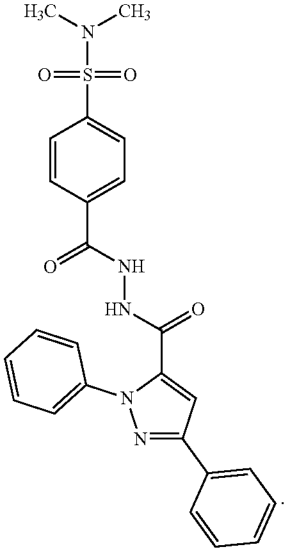

6. The method according to claim 1, wherein the diphenylpyrazole-based compound of formula (I) or its pesticidally acceptable salts is following compound or its pesticidally acceptable salts:

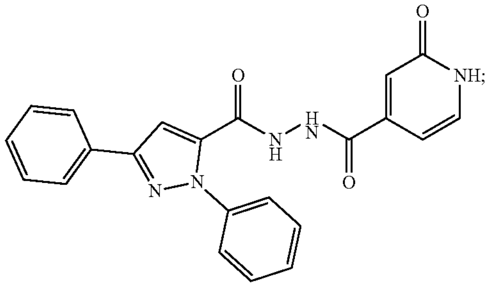

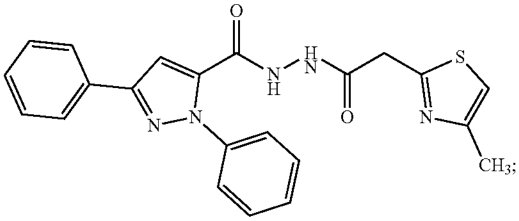

or

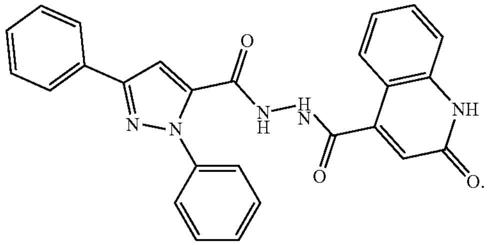

7. The method according to claim 1, wherein the diphenylpyrazole-based compound of formula (I), or its pesticidally acceptable salts is provided in combination with pesticidally acceptable excipients.

8. The method according to claim 7, wherein the diphenylpyrazole-based compound of formula (I), or its pesticidally acceptable salts is provided in combination with one or more other insecticides.

9. The method according to claim 1, wherein the GSTs include PxGSTδ1, PxGSTε3, PxGSTσ1, PxGSTσ2, PxGSTω4, PxGSTθ1, PxGSTζ1 and PxGSTμ1.

10. The method according to claim 1, wherein the GSTs include PxGSTδ1, PxGSTσ1, PxGSTσ2 and PxGSTε3.

11. The method according to claim 1, wherein the GSTs include PxGSTδ1 and PxGSTε3.

12. A method of preparing a pesticidal composition, comprising mixing of the diphenylpyrazole-based compound of formula (I), or its pesticidally acceptable salts of claim 1, with a pesticidally acceptable excipient.

13. A method of controlling pests, comprising applying a synergistic pesticidal composition to the pests or their habitat, wherein, the composition comprises the diphenylpyrazole-based compound of formula (I), or its pesticidally acceptable salts of claim 1, and other insecticides.

14. The method according to claim 13, wherein the composition delays or reduces the resistance of pests to insecticides.

15. The method according to claim 13, wherein the other insecticides include ryanodine receptor modulator insecticides and voltage-dependent sodium ion channel blocker insecticides.

16. The method according to claim 13, wherein the other insecticides include diamide insecticides and oxadiazine insecticides.

17. The method according to claim 13, wherein the other insecticides include chlorantraniliprole and indoxacarb.

18. The method according to claim 13, wherein the pests include field crop pests and economic crop pests.

19. The method according to claim 13, wherein the pests include *Plutella xylostella, Mythimna separata, Pyrausta nubilalis, Chilo suppressalis, Nilaparvata lugens, Spodoptera frugiperda, Helicoverpa armigera, Carposina sasakii* and *Spodoptera litura*.

20. The method according to claim 12, wherein the diphenylpyrazole-based compound of formula (I), or its pesticidally acceptable salts inhibits GSTs.

* * * * *